US010981905B2

(12) United States Patent
Andrez et al.

(10) Patent No.: US 10,981,905 B2
(45) Date of Patent: Apr. 20, 2021

(54) HETEROARYL-SUBSTITUTED SULFONAMIDE COMPOUNDS AND THEIR USE AS THERAPEUTIC AGENTS

(71) Applicant: Xenon Pharmaceuticals Inc., Burnaby (CA)

(72) Inventors: Jean-Christophe Andrez, Vancouver (CA); Kristen Nicole Burford, Burnaby (CA); Christoph Martin Dehnhardt, Burnaby (CA); Thilo Focken, Burnaby (CA); Michael Edward Grimwood, North Vancouver (CA); Qi Jia, Burnaby (CA); Verner Alexander Lofstrand, Burnaby (CA); Shaoyi Sun, Coquitlam (CA); Steven Sigmund Wesolowski, Natick, MA (US); Michael Scott Wilson, Burnaby (CA); Alla Yurevna Zenova, Vancouver (CA)

(73) Assignee: Xenon Pharmaceuticals Inc., Burnaby (CA)

(*) Notice: Subject to any disclaimer, the term of this patent is extended or adjusted under 35 U.S.C. 154(b) by 0 days.

(21) Appl. No.: 16/556,055

(22) Filed: Aug. 29, 2019

(65) Prior Publication Data

US 2020/0157089 A1    May 21, 2020

Related U.S. Application Data

(60) Provisional application No. 62/725,956, filed on Aug. 31, 2018.

(51) Int. Cl.
| | |
|---|---|
| *C07D 471/04* | (2006.01) |
| *A61K 31/437* | (2006.01) |
| *C07D 417/14* | (2006.01) |
| *C07D 401/12* | (2006.01) |
| *C07D 401/14* | (2006.01) |
| *C07D 409/12* | (2006.01) |
| *C07D 413/12* | (2006.01) |
| *C07D 417/12* | (2006.01) |
| *C07D 487/08* | (2006.01) |

(52) U.S. Cl.
CPC ......... *C07D 417/14* (2013.01); *C07D 401/12* (2013.01); *C07D 401/14* (2013.01); *C07D 409/12* (2013.01); *C07D 413/12* (2013.01); *C07D 417/12* (2013.01); *C07D 471/04* (2013.01); *C07D 487/08* (2013.01)

(58) Field of Classification Search
CPC .. C07D 471/04; C07D 401/14; C07D 417/12; A61K 31/437; A61K 31/444; A61K 31/4436; A61P 25/08
USPC .................. 546/122, 256, 269.7, 280.4, 121; 514/300, 333, 342
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 5,877,193 | A | 3/1999 | Cesura et al. |
| 5,958,910 | A | 9/1999 | Cesura et al. |
| 8,222,281 | B2 | 7/2012 | Toda et al. |
| 9,156,811 | B2 | 10/2015 | Brand et al. |
| 9,481,677 | B2 | 11/2016 | Liu et al. |
| 10,246,453 | B2 | 4/2019 | Andrez et al. |
| 2009/0023740 | A1 | 1/2009 | Fulp et al. |
| 2010/0267782 | A1 | 10/2010 | Beaudoin et al. |
| 2014/0045862 | A1 | 2/2014 | Shinozuka et al. |
| 2014/0256736 | A1 | 9/2014 | Liu et al. |
| 2014/0315878 | A1 | 10/2014 | Storer et al. |
| 2014/0315933 | A1 | 10/2014 | Owen et al. |
| 2018/0162868 | A1 | 6/2018 | Andrez et al. |
| 2019/0194184 | A1 | 6/2019 | Andrez et al. |

FOREIGN PATENT DOCUMENTS

| | | |
|---|---|---|
| EP | 2 813 491 A1 | 12/2014 |
| WO | WO 98/50016 A2 | 11/1998 |
| WO | WO 00/42003 A1 | 7/2000 |
| WO | WO 01/05393 A2 | 1/2001 |
| WO | WO 01/40222 A1 | 6/2001 |
| WO | WO 03/076406 A1 | 9/2003 |
| WO | WO 2004/002481 A1 | 1/2004 |
| WO | WO 2005/021536 A2 | 3/2004 |
| WO | WO 2004/092123 A2 | 10/2004 |
| WO | WO 2005/000309 A2 | 1/2005 |
| WO | WO 2005/005421 A1 | 1/2005 |
| WO | WO 2005/013914 A2 | 2/2005 |
| WO | WO 2006/066109 A2 | 6/2006 |
| WO | WO 2006/129199 A1 | 12/2006 |
| WO | WO 2007/039171 A1 | 4/2007 |
| WO | WO 2007/075895 A2 | 7/2007 |
| WO | WO 2008/019967 A2 | 2/2008 |
| WO | WO 2008/051494 A1 | 5/2008 |
| WO | WO 2009/012242 A2 | 1/2009 |
| WO | WO 2009/013171 A2 | 1/2009 |
| WO | WO 2009/157418 A1 | 12/2009 |

(Continued)

OTHER PUBLICATIONS

Cymerman-craig et al., "794. Potential thiophen chemotherapeutics. Part V. Preparation and proof of structure of some substituted 5-aminothiophen-2-sulphonamides," Journal of the Chemical Society, Jan. 1956, 4114-8.

Paola Ciapetti and Bruno Giethlen, "Chapter 15—Molecular Variations Based on Isosteric Replacements,"The Practice of Medicinal Chemistry, 2008, 290-342.

PubChem Database, CID=24248930, "6-{[(4-Methylphenyl)methyl]amino}-N-(pyridin-2-yl)pyridine-3-sulfonamide," dated Feb. 29, 2008, 2 pages.

(Continued)

*Primary Examiner* — Charanjit Aulakh
(74) *Attorney, Agent, or Firm* — Fish & Richardson P.C.

(57) ABSTRACT

This invention is directed to benzenesulfonamide compounds, as stereoisomers, enantiomers, tautomers thereof or mixtures thereof; or pharmaceutically acceptable salts, solvates or prodrugs thereof, for the treatment of diseases or conditions associated with voltage-gated sodium channels, such as epilepsy and/or epileptic seizure disorders.

54 Claims, No Drawings

(56) References Cited

FOREIGN PATENT DOCUMENTS

| WO | WO 2010/002956 A2 | 1/2010 |
|---|---|---|
| WO | WO 2010/029300 A1 | 3/2010 |
| WO | WO 2010/079443 A1 | 7/2010 |
| WO | WO 2012/004743 A1 | 1/2012 |
| WO | WO 2012/022265 A1 | 2/2012 |
| WO | WO 2013/025883 A1 | 2/2013 |
| WO | WO 2013/063459 A1 | 5/2013 |
| WO | WO 2013/064983 A1 | 5/2013 |
| WO | WO 2013/122897 A1 | 8/2013 |
| WO | WO 2014/061970 A1 | 4/2014 |
| WO | WO 2014/066490 A1 | 5/2014 |
| WO | WO 2014/066491 A1 | 5/2014 |
| WO | WO 2014/170793 A1 | 10/2014 |
| WO | WO 2014/198849 A1 | 12/2014 |
| WO | WO 2014/201206 A1 | 12/2014 |
| WO | WO 2015/035278 A1 | 3/2015 |
| WO | WO 2015/038533 A2 | 3/2015 |
| WO | WO 2015/077905 A1 | 6/2015 |
| WO | WO 2015/080988 A1 | 6/2015 |
| WO | WO 2015/099841 A1 | 7/2015 |
| WO | WO 2016/177340 A1 | 11/2016 |
| WO | WO 2017/106409 A1 | 6/2017 |
| WO | WO 2017/201468 A1 | 11/2017 |
| WO | WO 2018/093694 A1 | 5/2018 |
| WO | WO 2018/106284 A1 | 6/2018 |

OTHER PUBLICATIONS

U.S. Appl. No. 16/440,459, filed Jun. 13, 2019, Burford et al.
U.S. Appl. No. 16/555,983, filed Aug. 29, 2019, Andrez et al.
Barton et al., "Pharmacological characterization of the 6 Hz psychomotor seizure model of partial epilepsy," *Epilepsy Research* 47: 217-227, 2001.
Bean et al., "Lidocaine Block of Cardiac Sodium Channels," *J. Gen. Physiol.* 81: 613-642, May 1983.
Boerma et al., "Remarkable Phenytoin Sensitivity in 4 Children with SCN8A-related Epilepsy: A Molecular Neuropharmacological Approach," *Neurotherapeutics* 13: 192-197, 2016.
Bordwell et al., "The Reduction of Sulfones to Sulfides," *JACS* 73: 2251-2253, May 1951.
Burgess et al., "Mutation of a new sodium channel gene, Scn8a, in the mouse mutant 'motor endplate disease'," *Nature Genetics* 10: 461-465, Aug. 1995.
Carroll et al., "Mutation screening of SCN2A in schizophrenia and identification of a novel loss-of-function mutation," *Psychiatr. Genet.* 26: 60-65, 2016.
Catterall, "Sodium Channels, Inherited Epilepsy, and Antiepileptic Drugs," *Annu. Rev. Pharmacol. Toxicol.* 54: 317-338, 2014.
Cestèle et al., "Molecular mechanisms of neurotoxin action on voltage-gated sodium channels," *Biochimie* 82: 883-892, 2000.
Cheah et al., "Correlations in timing of sodium channel expression, epilepsy, and sudden death in Dravet syndrome," *Channels* 7(6): 468-472, Nov./Dec. 2013.
Cojocariu et al., "Sinteza unor $N^4$-(2-hidroxi-4-clorbenzoil)-sulfamide cu activitate antimicotica potentiala," *Revista de Chimie* 30(12): C-1261, 1979 (3 pages).
De Kovel et al., "Characterization of a de novo SCN8A mutation in a patient with epileptic encephalopathy," *Epilepsy Research* 108: 1511-1518, 2014.
Dravet et al., *Handbook of Clinical Neurology, vol. 111($3^{rd\ series}$)—Pediatric Neurology Part 1*, Elsevier B.V., Amsterdam, Netherlands, 2013, Chapter 65, "Dravet syndrome (severe myoclonic epilepsy in infancy)," pp. 627-633.
Dutton et al., "Preferential inactivation of Scn1a in parvalbumin interneurons increases seizure susceptibility," *Neurobiology of Disease* 49: 211-220, 2013.
Estacion et al., "A novel de novo mutation of SCN8A ($Na_v1.6$) with enhanced channel activation in a child with epileptic encephalopathy," *Neurobiology of Disease* 69: 117-123, 2014.
Focken et al., "Discovery of Aryl Sulfonamides as Isoform-Selective Inhibitors of Nav1.7 with Efficacy in Rodent Pain Models," *ACS Med.Chem. Lett.* 7: 277-282, 2016.
Fukasawa et al., "A case of recurrent encephalopathy with SCN2A missense mutation," *Brain &Development* 37: 631-634, 2015.
Gardner et al., "A Facile Reduction of Sulfones to Sulfides," *Can. J. Chem.* 51: 1419-1421, 1973.
Hadži et al., "The Role of Hydrogen Bonding in Drug-Receptor Interactions," *Journal of Molecular Structure* 237: 139-150, 1990.
Hawkins et al., Hlf is a genetic modifier of epilepsy caused by voltage-gated sodium channel mutations, *Epilepsy Research* 119: 20-23, 2016.
Hawkins et al., "Neuronal voltage-gated ion channels are genetic modifiers of generalized epilepsy with febrile seizures plus," *Neurobiology of Disease* 41: 655-660, 2011.
Helbig, "Genetic Causes of Generalized Epilepsies," *Semin. Neurol.* 35: 288-292, 2015.
Hille, "Local Anesthetics: Hydrophilic and Hydrophobic Pathways for the Drug-Receptor Reaction," *The Journal of General Physiology* 69: 497-515, 1977.
Hitchcock et al., "Perspective: Structure—Brain Exposure Relationships," *Journal of Medicinal Chemistry* 49(26): 7559-7583, Dec. 28, 2006.
Hossfeld, "Paper Partition Chromatography of Simple Phenols," *J. Am. Chem. Soc.* 73: 852-854, 1951.
Howell et al., "SCN2A encephalopathy: A major cause of epilepsy of infancy with migrating focal seizures," *Neurology* 85: 958-966, 2015.
Hu et al., "Distinct contributions of $NA_v1.6$ and $Na_v1.2$ in action potential initiation and backpropagation," *Nature Neuroscience* 12(8): 996-1002, Aug. 2009 (9 pages).
James et al., "A modular, gold-catalysed approach to the synthesis of lead-like piperazine scaffolds," *Org. Lett.* 15(23): 6094-6097, 2013.
Kearney et al., "A Gain-of-Function Mutation in the Sodium Channel Gene Scn2a Results in Seizures and Behavioral Abnormalities," *Neuroscience* 102(2): 307-317, 2001.
Kong et al., "SCN8A mutations in Chinese children with early onset epilepsy and intellectual disability," *Epilepsia* 56(3): 431-438, 2015.
Kuzma et al., "Progress in the Development of Ultra-Long-Acting Local Anesthetics," *Regional Anesthesia* 22(6): 543-551, 1997.
Larsen et al., "The phenotypic spectrum of SCN8A encephalopathy," *Neurology* 84: 480-489, 2015.
Leuwer et al., "An improved model for the binding of lidocaine and structurally related local anaesthetics to fast-inactivated voltage-operated sodium channels, showing evidence of cooperativity," *British Journal of Pharmacology* 141: 47-54, 2004.
Liu et al., "Mutations in Cardiac Sodium Channels: Clinical Implications," *Am. J. Pharmacogenomics* 3(3): 173-179, 2003.
Löscher et al., "Which animal models should be used in the search for new antiepileptic drugs? A proposal based on experimental and clinical considerations," *Epilepsy Res.* 2: 145-181, 1988.
Luci et al., "Synthesis and Structure—Activity Relationship Studies of 4-((2-Hydroxy-3-methoxybenzyl)amino)benzenesulfonamide Derivatives as Potent and Selective Inhibitors of 12-Lipoxygenase," *J. Med. Chem.* 57: 495-506, 2014.
Makinson et al., "An Scn1a epilepsy mutation in Scn8a alters seizure susceptibility and behavior," *Experimental Neurology.* 275: 46-58, 2016.
Makinson et al., "Role of the hippocampus in $Na_v1.6$ (Scn8a) mediated seizure resistance," *Neurobiology of Disease* 68: 16-25, 2014.
Martin et al., "The voltage-gated sodium channel Scn8a is a genetic modifier of severe myoclonic epilepsy of infancy," *Human Molecular Genetics* 16(23): 2892-2899, 2007.
Martin et al., "Altered Function of the SCN1A Voltage-gated Sodium Channel Leads to γ-Aminobutyric Acid-ergic (GABAergic) Interneuron Abnormalities," *The Journal of Biological Chemistry* 285(13): 9823-9834, Mar. 26, 2010.
Massey et al., "Mechanisms of sudden unexpected death in epilepsy: the pathway to prevention," *Nature Reviews Neurology* 10: 271-282, May 2014.

(56) References Cited

OTHER PUBLICATIONS

Matsukawa et al., "Studies on Chemotherapeutics. XII. Syntheses of p-Hydroxybenezenesulfonamide Derivatives," *Yakugaku Zasshi* 70(10): 557-561, 1950.

McKusik et al., Epileptic Encephalopathy, Early Infantile 6; EIEE6, Online Mendelian Inheritance in Man: John Hopkins University, 2012, 12 pages, URL=http:omin.org/entry/607208, download date Sep. 6, 2017.

Miller et al., "Mapping genetic modifiers of survival in a mouse model of Dravet syndrome," *Genes, Brain and Behavior* 13: 163-172, 2014.

Mistry et al., "Strain- and age-dependent hippocampal neuron sodium currents correlate with epilepsy severity in Dravet syndrome mice," *Neurobiology of Disease* 65: 1-11, 2014.

Norinder et al., "QSAR investigation of NaV1.7 active compounds using the SVM/Signature approach and the Bioclipse Modeling platform," *Bioorganic &Medicinal Chemistry Letters* 23: 261-263, 2013.

Ogiwara et al., "$Na_v1.1$ Localizes to Axons of Parvalbumin-Positive Inhibitory Interneurons: A Circuit Basis for Epileptic Seizures in Mice Carrying an Scn1a Gene Mutation," *The Journal of Neuroscience* 27(22): 5903-5914, May 30, 2007.

Ohba et al., "Early onset epileptic encephalopathy caused by de novo Scn8A mutations," *Epilepsia* 55(7): 994-1000, 2014.

Patani et al., "Bioisosterism: A Rational Approach in Drug Design," *Chem. Rev.* 96: 3147-3176, 1996.

Payne et al., "Identification of KD5170: A novel mercaptoketone-based histone deacetylase inhibitor," *Bioorganic &Medicinal Chemistry Letters* 18: 6093-6096, 2008.

Piredda et al., "Effect of Stimulus Intensity on the Profile of Anticonvulsant Activity of Phenytoin, Ethosuximide and Valproate," *The Journal of Pharmacology and Experimental Therapeutics* 232(3): 741-745, 1985.

Prasanthy et al., "Synthesis and Biological Evaluation of 1-Substituted Imidazole Derivatives," *Int. J. Pharma* 1(2): 92-99, 2011.

Raymond et al., "Expression of Alternatively Spliced Sodium Channel α-Subunit Genes," *Journal of Biological Chemistry* 279(44): 46234-46241, Oct. 29, 2004.

Rogers et al., "Characterization of Endogenous Sodium Channels in the ND7-23 Neuroblastoma Cell Line: Implications for Use as a Heterologous Ion Channel Expression System Suitable for Automated Patch Clamp Screening," *Assay and Drug Development Technologies* 14(2): 109-130, Mar. 2016.

Royeck et al., "Role of Axonal $Na_v1.6$ Sodium Channels in Action Potential Initiation of CA1 Pyramidal Neurons," *J. Neurophysiol.* 100: 2361-2380, 2008.

Saitoh et al., "Missense mutations in sodium channel SCN1A and SCN2A predispose children to encephalopathy with severe febrile seizures," *Epilepsy Research* 117: 1-6, 2015.

Samanta et al., "De novo R853Q mutation of SCN2A gene and West syndrome," *Acta Neurol. Belg.* 115: 773-776, 2015.

Schwarz et al., "Mutations in the sodium channel gene SCN2A cause neonatal epilepsy with late-onset episodic ataxia," *J. Neurol.* 263: 334-343, 2016.

Stumpf et al., "Development of an Expedient Process for the Multi-Kilogram Synthesis of Chk1 Inhibitor GDC-0425," *Org. Process Res. Dev.* 19: 661-672, 2015.

Suzuki et al., "Morphogenetic Effect of Kainate on Adult Hippocampal Neurons Associated with a Prolonged Expression of Brain-derived Neurotrophic Factor," *Neuroscience* 64(3): 665-674, 1995.

Toman et al., "Properties of Maximal Seizures, and Their Alteration by Anticonvulsant Drugs and Other Agents," *J. Neurophysiol.* 9: 231-239, 1946.

Trudeau et al., "Heterozygosity for a protein truncation mutation of sodium channel SCN8A in a patient with cerebellar atrophy, ataxia, and mental retardation," *J. Med. Genet.* 43: 527-530, 2006.

Tuncer et al., "A clinical variant in SCN1A inherited from a mosaic father cosegregates with a novel variant to cause Dravet syndrome in a consanguineous family," *Epilepsy Research* 113: 5-10, 2015.

Vaher et al., "De Novo SCN8A Mutation Identified by Whole-Exome Sequencing in a Boy With Neonatal Epileptic Encephalopathy, Multiple Congenital Anomalies, and Movement Disorders," *Journal of Child Neurology* 29(12): NP202-NP206, 2014.

Veeramah et al., "De Novo Pathogenic SCN8A Mutation Identified by Whole-Genome Sequencing of a Family Quartet Affected by Infantile Epileptic Encephalopathy and SUDEP," *The American Journal of Human Genetics* 90: 502-510, Mar. 9, 2012.

Vega et al., "Reduced expression of $Na_v1.6$ sodium channels and compensation of $Na_v1.2$ channels in mice heterozygous for a null mutation in Scn8a," *Neuroscience Letters* 442: 69-73, 2008.

Wagnon et al., "Convulsive seizures and SUDEP in a mouse model of SCN8A epileptic encephalopathy," *Human Molecular Genetics* 24(2): 506-515, 2015.

Ward, "Chiral Separations," *Anal. Chem.* 74: 2863-2872, 2002.

White et al., "The early identification of anticonvulsant activity: role of the maximal electroshock and subcutaneous pentylenetetrazol seizure models," *Ital. J. Neurol. Sci* 16: 73-77, 1995.

Wilmshurst et al., Summary of recommendations for the management of infantile seizures: Task Force Report for the ILAE Commission of Pediatrics, *Epilepsia* 56(8): 1185-1197, 2015.

Wu et al., "Development of New Benzenesulfonamides As Potent and Selective $Na_v1.7$ Inhibitors for the Treatment of Pain," *J. Med. Chem.* 60: 2513-2525, 2017.

Yu et al., "Reduced sodium current in GABAergic interneurons in a mouse model of severe myoclonic epilepsy in infancy," *Nature Neuroscience* 9(9): 1142-1149, Sep. 2006.

Zerem et al., "Paternal germline mosaicism of a SCN2A mutation results in Ohtahara syndrome in half siblings," *European Journal of Paediatric Neurology* 18: 567-571, 2014.

International Search Report and Written Opinion, dated Sep. 25, 2017, for International Application No. PCT/US2017/033666, 30 pages.

International Preliminary Report on Patentability, dated Jun. 11, 2019, for International Application No. PCT/US2017/033666, 20 pages.

International Search Report and Written Opinion, dated Jul. 4, 2017, for International Application No. PCT/US2017/033634, 13 pages.

International Preliminary Report on Patentability, dated Nov. 20, 2018, for International Application No. PCT/US2017/033634, 7 pages.

International Search Report and Written Opinion, dated Sep. 11, 2019, for International Application No. PCT/US2019/037011, 13 pages.

HETEROARYL-SUBSTITUTED SULFONAMIDE COMPOUNDS AND THEIR USE AS THERAPEUTIC AGENTS

CROSS-REFERENCE TO RELATED APPLICATION

This application claims the benefit under 35 U.S.C. § 119(e) of U.S. Provisional Patent Application No. 62/725,956, filed Aug. 31, 2018, which is incorporated herein by reference in its entirety.

FIELD OF THE INVENTION

The present invention is directed to heteroaryl-substituted sulfonamide compounds and pharmaceutical compositions comprising the compounds and methods of using the compounds and the pharmaceutical compositions in treating sodium channel-mediated diseases or conditions, such as epilepsy and/or epileptic seizure disorder, as well as other diseases and conditions associated with the mediation of sodium channels.

BACKGROUND OF THE INVENTION

Voltage gated sodium channels ($Na_v$'s) are critical determinants of cellular excitability in muscle and nerve (Hille, B, *Ion Channels of Excitable Membranes* (2001), Sunderland, Mass., Sinauer Associates, Inc.). Four isoforms in particular, $Na_v1.1$, $Na_v1.2$, $Na_v1.3$, and $Na_v1.6$, account for the majority of sodium current in the neurons of the central nervous system. $Na_v1.3$ is primarily expressed embryonically. Beyond the neonatal stage, $Na_v1.1$, $Na_v1.2$, and $Na_v1.6$ are the critical isoforms that regulate neuronal signaling in the brain (Catterall, W. A., *Annual Review of Pharmacology and Toxicology* (2014), Vol. 54, pp. 317-338).

$Na_v1.5$ is expressed mainly in cardiac myocytes (Raymond, C. K. et al., *J. Biol. Chem.* (2004), Vol. 279, No. 44, pp. 46234-41), including atria, ventricles, the sino-atrial node, atrio-ventricular node and cardiac Purkinje fibers. Mutations in human $Na_v1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H., et al., *Am. J. Pharmacogenomics* (2003), Vol. 3, No. 3, pp. 173-9). Sodium channel blocker therapy has been used extensively in treating cardiac arrhythmias.

Epilepsy is a condition characterized by excessive synchronous excitability in the brain that arises when the delicate balance of excitatory and inhibitory signals in the brain fall out of equilibrium. This can happen either due to an excess of excitation, or a deficiency of inhibition. Mutations in the genes encoding $Na_v$ channels have been linked to both types of disequilibrium.

$Na_v1.1$ has been identified as the primary $Na_v$ isoform of inhibitory interneurons (Yu, F. H. et al., *Nat. Neurosci.* (2006), Vol. 9, pp. 1142-1149). These interneurons synapse on many other neurons, including excitatory glutamatergic neurons. Action potentials in the interneurons induce the release of the neurotransmitter GABA onto other neurons, hyperpolarizing them and thus dampening excitation. This results in a negative feedback that enables controlled signaling and prevents local signals from expanding into waves of excitation that spread across large brain regions. Because of this critical role in inhibitory interneurons, mutations that impair $Na_v1.1$ channel function can lead to a failure of those neurons to activate and release GABA (Ogiwara, I. et al., *J. Neurosci.* (2007), Vol. 27, pp. 5903-5914; Martin, M. S. et al., *J. Biol. Chem.* (2010), Vol. 285, pp. 9823-9834; Cheah, C. S. et al., *Channels (Austin)* (2013), Vol. 7, pp. 468-472; and Dutton, S. B., et al., (2013), Vol. 49, pp. 211-220). The result is a loss in the inhibitory tone of the brain and a failure to contain the excitability of the glutamatergic neurons. This failure of the inhibitory interneurons can result in aberrant wide-scale synchronous firing of neurons across regions of the brain (epilepsy).

Mutations in the gene encoding $Na_v1.1$ (SCN1A) fall into two broad classes, those that cause generalized epilepsy with febrile seizures plus (GEFS+) and those that cause severe myoclonic epilepsy of infancy (SMEI), also known as Dravet Syndrome or early infantile epileptic encephalopathy 6 (EIEE6) (McKusik, V. K. et al., A Epileptic Encephalopathy, Early Infantile 6, EIEE6 (2012), Online Mendelian Inheritance in Man: John Hopkins University). SMEI mutations are heterozygous autosomal dominant mutations and are often caused by a gene deletion or truncation that leads to a channel with little or no function. The mutations arise de novo, or in a few cases have been shown to arise in asymptomatic mosaic parents (Tuncer, F. N. et al., *Epilepsy Research* (2015), Vol. 113, pp. 5-10). Patients are born phenotypically normal and meet developmental milestones until the onset of seizures, typically between the age of 6 months and 1 year. This time of onset is believed to be a consequence of the normal decrease in the expression of the embryonic isoform $Na_v1.3$ and the coincident rise of $Na_v1.1$. When the $Na_v1.1$ channels fail to reach normal levels, the phenotype is revealed (Cheah, C. S. et al., *Channels (Austin)* (2013), Vol. 7, pp. 468-472). The initial seizure is often triggered by a febrile episode and can manifest as status epilepticus. Seizures continue and increase in frequency and severity for the first several years of life and can reach frequencies of over 100 episodes per day. Seizures may be triggered by fever or may arise spontaneously without apparent cause. After seizure onset patients begin to miss developmental milestones and significant cognitive and behavioral deficits accrue (Dravet, C. and Oguni, H., *Handbook of Clinical Neurology* (2013), Vol. 111, pp. 627-633). 80 to 85% of phenotypically diagnosed Dravet syndrome patients are believed to have a responsible mutation in SCN1A, while the other 15-20% of patients have other mutations or are of unknown etiology. There is a high rate of sudden unexplained death in epilepsy (SUDEP) in SMEI patients, with an estimated 37% of patients dying by SUDEP, but the mechanism for this catastrophic outcome remains unclear (Massey, C. A., et al., *Nature Reviews Neurology* (2014), Vol. 10, pp. 271-282). Clinically useful anti-epileptic drugs that target voltage-gated sodium channels non-selectively, like carbamazepine and phenytoin, are contra-indicated for SMEI patients as they can exacerbate seizures in these patients (Wilmshurst, J. M. et al., *Epilepsia* (2015), Vol. 56, pp. 1185-1197). This is presumed to be because patients cannot tolerate further reductions in $Na_v1.1$ function.

GEFS+ is often caused by missense SCN1A mutations that induce relatively mild channel dysfunction, consistent with the relatively milder seizure phenotype. A large and growing number of mutations have been identified, and both the severity and the penetrance of the phenotype varies considerably. Many GEFS+ patients outgrow the seizure phenotype, however not all do, and GEFS+ patients with childhood epilepsy are considerably more prone to have epilepsy as adults than are the general population. Mutations that cause deficits in other genes involved with GABA-ergic signaling, like SCN1B that encodes the sodium channel auxiliary subunit and GABRG2 that encodes a subunit of $GABA_A$ receptors can also give rise to GEFS+ (Helbig, I., *Seminars in Neurology* (2015) Vol. 35, pp. 288-292).

Transgenic mice have been developed that harbor the same mutations identified in SMEI and GEFS+ patients. In both cases the mice replicate the human phenotype well, though the penetrance of the phenotype can be significantly impacted by the genetic background. Some mouse strains tolerate the mutations relatively well, while in other strains the same mutations can cause drastic seizure phenotypes. These differences are presumed to be due to differing levels of expression of other genes that modulate the excitation phenotype (Miller, A. R. et al., *Genes, Brain, and Behavior* (2014), Vol. 13, pp. 163-172; Mistry, A. M. et al., *Neurobiology of Disease* (2014), Vol. 65, pp. 1-11; and Hawkins, N. A. et al., *Epilepsy Research* (2016), Vol. 119, pp. 20-23).

In the brain, $Na_v1.2$ and $Na_v1.6$ are primarily expressed in excitatory glutamatergic neurons. Both channels are especially dense in the action initial segment (AIS), a region of the neuron adjacent to the neuronal soma that acts to integrate inputs and initiates action potential propagation to the soma and the distal dendrites (Royeck, M. et al., *J. Neurophysiol.* (2008), Vol. 100, pp. 2361-2380; Vega, A. V. et al., *Neurosci. Lett.* (2008), Vol. 442, pp. 69-73; and Hu, W. et al., *Nat. Neurosci.* (2009), Vol. 12, pp. 996-1002). $Na_v1.6$ tends to be especially densely localized the early AIS (distal from the soma) where it is thought to act to trigger action potential initiation. $Na_v1.2$ is more highly localized to the segment of the AIS most proximal to the soma. Mutations in both SCN2A ($Na_v1.2$) and SCN8A ($Na_v1.6$) have been linked to epilepsy and cognitive delay. The effects of the mutations are diverse both at the level of the impact on channel function, and on the patient phenotype. Both $Na_v1.2$ and $Na_v1.6$ are also expressed in peripheral neurons. $Na_v1.6$ is especially dense at the nodes of Ranvier of myelinated neurons, where it is critical for maintaining salutatory conduction and high speed neuronal signaling.

Only a handful of $Na_v1.2$ mutations have been described, but they are primarily linked with central nervous system pathologies, especially epilepsy (Kearney, J. A. et al., *Neuroscience* (2001), Vol. 102, pp. 307-317; Zerem, A. et al., *European Journal of Paediatric Neurology: EJPN: Official Journal of the European Paediatric Neurology Society* (2014), Vol. 18, pp. 567-571; Fukasawa, T. et al., *Brain & Development* (2015), Vol. 37, pp. 631-634; Howell, K. B. et al., *Neurology* (2015), Vol. 85, pp. 958-966; Saitoh, M. et al., *Epilepsy Research* (2015), Vol. 117, pp. 1-6; Samanta, D. et al., *Acta Neurologica Belgica* (2015), Vol. 115, pp. 773-776; Carroll, L. S. et al., *Psychiatric Genetics* (2016), Vol. 26, pp. 60-65; and Schwarz, N. et al., *Journal of Neurology* (2016), Vol. 263, pp. 334-343). The epilepsy mutations are presumed to be primarily gain of function mutations, meaning that they lead to an increase in the amount of sodium current and thereby increasing excitability. Establishing the impact on channel function in vivo beyond reasonable doubt is challenging and some of these mutations may yet lead to loss of function phenotypes.

Mutations in SCN8A have likewise been reported to show a range of gain and loss of function effects on the $Na_v1.6$ channel though, for $Na_v1.6$, most mutations examined have been associated with gain of function phenotypes. Mutations in $Na_v1.6$ have been linked with epilepsy and autism spectrum disorders (Trudeau, M. M. et al., *Journal of Medical Genetics* (2006), Vol. 43, pp. 527-530; Veeramah, K. R. et al., *Am. J. Hum. Genet.* (2012), Vol. 90, pp. 502-510; Vaher, U. et al., *Journal of Child Neurology* (2013); de Kovel, C. G. et al., *Epilepsy Research* (2014); Estacion, M. et al., *Neurobiology of Disease* (2014), Vol. 69, pp. 117-123; Ohba, C. et al., *Epilepsia* (2014), Vol. 55, pp. 994-1000; Wagnon, J. L. et al., *Human Molecular Genetics* (2014); Kong, W. et al., *Epilepsia* (2015), Vol. 56, pp. 431-438; and Larsen, J. et al., *Neurology* (2015), Vol. 84, pp. 480-489). The best described SCN8A mutant patients have a syndrome known as early infantile epileptic encephalopathy, 13 (EIEE13). Over 100 EIEE13 patients have been identified. Patients typically present with intractable seizures between birth and 18 months of age. Patients have developmental and cognitive delay, and motor impairment often associated with chronic muscular hypotonia. The most severely impacted patients never gain sufficient motor control to walk. Many are not verbal. Less severe phenotypes learn to walk and talk but are motor-impaired and miss cognitive and social milestones. Most of the identified mutations are missense mutations, and it is assumed that the specific functional impact of the mutation contributes to the variability in the phenotype, though genetic background is also likely involved (Larsen, J. et al., *Neurology* (2015), Vol. 84, pp. 480-489). In contrast to SMEI patients, anecdotal evidence suggests that antiepileptic drugs that target voltage-gated sodium channels non-selectively can ameliorate symptoms in EIEE13 patients, though no controlled clinical trials have been completed (Boerma, R. S. et al., *Neurotherapeutics: The Journal of the American Society for Experimental Neuro-Therapeutics* (2016), Vol. 13, pp. 192-197). While phenytoin does seem to provide efficacy for EIEE13 patients, it does so at a cost. Efficacy is only achieved at very high doses where the significant adverse effects are tolerated only because the patients are in such dire need. Adverse effects commonly associated with phenytoin therapy include hepatic necrosis, hypertrichosis, nervousness, tremor of hands, numbness, dizziness, drowsiness, tremor, depression, confusion, fatigue, constipation, vertigo, ataxia, mental status changes, myasthenia, mood changes, restlessness, irritability, and excitement. It seems likely that a drug that selectively targets $Na_v1.6$ would retain efficacy while reducing its adverse event burden.

Loss of function mutations in SCN8A in mice lead to a phenotype known as motor endplate disease (med) and multiple mutations and phenotypes were linked to the med gene region prior to the identification of the SCN8A gene (Burgess, D. L. et al., *Nat. Genet.* (1995), Vol. 10, pp. 461-465). Mice with $SCN8A^{med}$ mutations have varying degrees of muscle hypotonia, consistent with the degree of dysfunction of the $Na_v1.6$ function. Mice with the $SCN8A^{med/jo}$ have $Na_v1.6$ channels that have a loss of function, but not null, phenotype. $SCN8A^{med}$ and $SCN8A^{med/jo}$ mice are resistant to seizures induced by chemical insult (flurothyl, kainic acid, and picrotoxin) (Martin, M. S. et al., *Human Molecular Genetics* (2007), Vol. 16, pp. 2892-2899; Hawkins, N. A. et al., *Neurobiology of Disease* (2011), Vol. 41, pp. 655-660; and Makinson, C. D. et al., *Neurobiology of Disease* (2014), Vol. 68, pp. 16-25). Curiously, when $SCN8A^{med/jo}$ mice are crossed with $SCN1A^{null}$ mutant mice to produce a mouse that is heterozygous for both the $SCN1A^{null}$ allele and the $SCN8A^{med/jo}$ allele the double mutant mice have a much improved seizure and cognitive phenotype than those with only an $SCN1A^{null}$ mutation (Martin, M. S. et al., *Human Molecular Genetics* (2007), Vol. 16, pp. 2892-2899). Such mice have a spontaneous seizure and death rate similar to wild type mice and their seizure threshold after chemical insult is also increased. A similar result occurs upon crossing mice with missense mutations of SCN1A (a model for GEFS+) and mice with SCN8A loss of function mutations. Having a single allele of SCN8A$^{med/jo}$ protected the GEFS+ model mice from seizures and premature death (Hawkins, N. A. et al., *Neurobiology of Disease* (2011), Vol. 41, pp. 655-660). The ability of SCN8A knock down to improve seizure resistance is not limited to knockouts where the gene is globally absent throughout animal development. Knock down of SCN8A in adult mice either globally or specifically in the hippocampus via a CRE-LOX inducible knockout approach also improved resistance to electrically and chemically induced seizures Makinson, C. D. et al., *Neurobiology of Disease* (2014), Vol. 68, pp. 16-25). These data suggest that the suppression of inhibitory signaling caused by decreased $Na_v1.1$ current can be offset, at least in part, by suppressing excitatory signaling via decreased in $Na_v1.6$ current.

Voltage-gated sodium channel antagonism is the most common mechanism of widely prescribed antiepileptic drugs (AED's) (Ochoa, J. R. et al., *Sodium Channel Blockers. In: Antiepileptic Drugs* (2016), Vol. (Benbadis, S., ed) Medscape News & Perspectives). Carbamazepine, Eslicarbazepine, Oxcarbazepine, Lacosamide, Lamotrigine, Phenytoin, Rufinamide and Zonisamide are all believed to act primarily by blocking that function of $Na_v$ channels. Despite the presumed mechanism of action, these drugs are relatively promiscuous. They block all $Na_v$ channel isoforms indiscriminately, thus block of $Na_v1.1$ would be expected to proconvulsant. Block of $Na_v1.6$, and perhaps $Na_v1.2$, would be anticonvulsant. In addition to sodium channels, these compounds also block other targets, including voltage-gated calcium channels. Selective $Na_v$ antagonists that spare $Na_v1.1$ and other off-target receptors are expected to have both improved efficacy and therapeutic index relative to the currently available $Na_v$ blocking drugs.

There is therefore an unmet medical need to treat epilepsy and other $Na_v1.6$ associated pathological states effectively and without adverse side effects due to the blocking of other sodium channels, such as $Na_v1.1$ and/or $Na_v1.5$. The present invention provides methods to meet these critical needs.

SUMMARY OF THE INVENTION

The present invention is directed to heteroaryl-substituted sulfonamide compounds and pharmaceutical compositions comprising the compounds and methods of using the compounds and the pharmaceutical compositions of the invention for the treatment of diseases or conditions associated with the activity of voltage-gated sodium channels, particularly, $Na_v1.6$ activity, such as epilepsy and/or epileptic seizure disorder.

Accordingly, in one aspect, this invention is directed to heteroaryl-substituted sulfonamide compounds of formula (I):

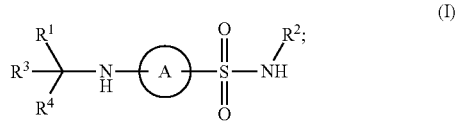

wherein:

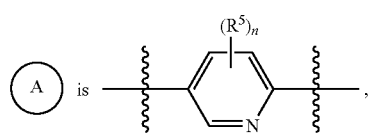

-continued

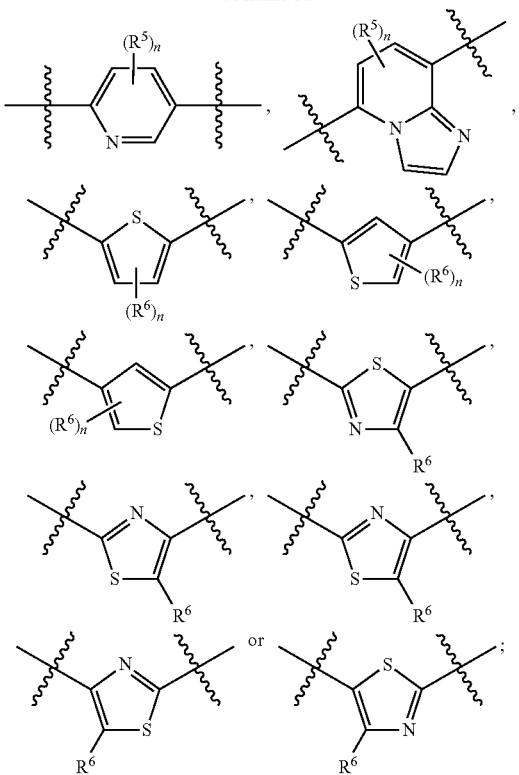

each n is 1 or 2;
$R^1$ is an optionally substituted aryl, an optionally substituted monocyclic heteroaryl or an optionally substituted bicyclic heteroaryl;
$R^2$ is an optionally substituted 5-membered N-heteroaryl or an optionally substituted 6-membered N-heteroaryl;
$R^3$ and $R^4$ are each independently hydrogen or alkyl;
each $R^5$ and $R^6$ is independently hydrogen, alkyl, halo, haloalkyl, optionally substituted cycloalkyl, cyano or $-OR^7$;
$R^7$ is hydrogen, alkyl or haloalkyl;
as an individual stereoisomer, enantiomer or tautomer thereof or a mixture thereof;
or a pharmaceutically acceptable salt, solvate or prodrug thereof.

The compounds of the invention, which are compounds of formula (I) as described above, as individual stereoisomers, enantiomers or tautomers thereof or mixtures thereof; or as pharmaceutically acceptable salts, solvates or prodrugs thereof, are useful in treating diseases or conditions associated with voltage-gated sodium channels, preferably $Na_v1.6$. Preferably, the compounds of the invention are $Na_v1.6$ inhibitors. More preferably, the compounds of the invention show selectivity of inhibiting $Na_v1.6$ as compared with inhibiting $Na_v1.5$ and/or $Na_v1.1$. Without wishing to be bound by theory, such selectivity is thought to advantageously reduce any side effects which may be associated with the inhibition of $Na_v1.5$ and/or $Na_v1.1$.

In another aspect, the invention provides pharmaceutical compositions comprising a pharmaceutically acceptable excipient and a compound of formula (I), as described above, as a stereoisomer, enantiomer or tautomer thereof or mixtures thereof; or a pharmaceutically acceptable salt, solvate or prodrug thereof.

In another aspect, the invention provides methods for the treatment of a sodium channel-mediated disease or condition in a mammal, wherein the methods comprise administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods for the treatment of epilepsy and/or epileptic seizure disorder in a mammal, preferably a human, wherein the methods comprise administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the present invention provides a method for treating or lessening the severity of a disease, condition, or disorder in a mammal where activation or hyperactivity of $Na_v1.6$ is implicated in the disease, condition or disorder, wherein the method comprises administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or ameliorating, but not preventing, epilepsy and/or epileptic seizure disorder in a mammal, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of preparing a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed herein.

In another aspect, this invention is directed to methods of selectively inhibiting a first voltage-gated sodium channel in a mammal over a second voltage-gated sodium channel, wherein the method comprises administering to the mammal a inhibitory amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a inhibitory amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, this invention is directed to the use of the compounds of the invention, as set forth above, as a stereoisomer, enantiomer or tautomer thereof or mixtures thereof, or a pharmaceutically acceptable salt, solvate or prodrug thereof, or the use of a pharmaceutical composition comprising a pharmaceutically acceptable excipient and a compound of the invention, as set forth above, as a stereoisomer, enantiomer or tautomer thereof or mixtures thereof, or a pharmaceutically acceptable salt, solvate or prodrug thereof, in the preparation of a medicament for the treatment of a disease or condition associated with the activity of a voltage-gated sodium channel, preferably $Na_v1.6$, in a mammal and preferably wherein the disease or condition is epilepsy and/or epileptic seizure disorder.

DETAILED DESCRIPTION OF THE INVENTION

Definitions

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, $-OR^{20}$, $-OC(O)-R^{20}$, $-N(R^{20})_2$, $-C(O)R^{20}$, $-C(O)OR^{20}$, $-C(O)N(R^{20})_2$, $-N(R^{20})C(O)OR^{22}$, $-N(R^{20})C(O)R^{22}$, $-N(R^{20})S(O)R^{22}$ (where p is 1 to 2), $-S(O)_pOR^{22}$ (where p is 1 to 2), $-S(O)_tR^{22}$ (where t is 0 to 2), and $-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: halo, cyano, nitro, aryl, cycloalkyl, heterocyclyl, heteroaryl, oxo, trimethylsilanyl, $-OR^{20}$, $-OC(O)-R^{20}$, $-N(R^{20})_2$, $-C(O)R^{20}$, $-C(O)OR^{20}$, $-C(O)N(R^{20})_2$, $-N(R^{20})C(O)OR^{22}$, $-N(R^{20})C(O)R^{22}$, $-N(R^{20})S(O)R^{22}$ (where p is 1 to 2), $-S(O)_pOR^{22}$ (where p is 1 to 2), $-S(O)_tR^{22}$ (where t is 0 to 2), and $-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. When specifically stated in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, $-OR^{20}$, $-OC(O)-R^{20}$, $-N(R^{20})_2$, $-C(O)R^{20}$, $-C(O)OR^{20}$, $-C(O)N(R^{20})_2$, $-N(R^{20})C(O)OR^{22}$, $-N(R^{20})C(O)R^{22}$, $-N(R^{20})S(O)R^{22}$ (where p is 1 to 2), $-S(O)_pOR^{22}$ (where p is 1 to 2), $-S(O)_tR^{22}$ (where t is 0 to 2), and $-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Preferably, an aryl group for $R^1$ is phenyl. When specifically stated in the specification, an aryl group may be optionally substituted by one or more substituents independently selected from the group consisting of alkyl, alkenyl, halo, haloalkyl, haloalkenyl, cyano, nitro, aryl, aralkyl, optionally substituted cycloalkyl, optionally substituted cycloalkylalkyl, optionally substituted heterocyclyl, optionally substituted heterocyclylalkyl, optionally substituted N-heterocyclylalkyl, optionally substituted heteroaryl, optionally substituted heteroarylalkyl, $-R^{21}-OR^{20}$, $-R^{21}-OC(O)-R^{20}$, $-R^{21}-N(R^{20})_2$, $-R^{21}-N(R^{20})-R^{23}-OR^{20}$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)R^{22}$ (where p is 1 to 2), $-R^{21}-N=C(OR^{20})R^{20}$, $-R^{21}-S(O)OR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain. Preferably, the optional substituents on an optionally substituted aryl group for $R^1$ herein are alkyl, optionally substituted cycloalkyl, halo, haloalkyl, cyano, optionally substituted heterocyclyl, optionally substituted N-heterocyclylalkyl, optionally substituted heteroaryl, $-R^{21}-OR^{20}$ and $-R^{21}-N(R^{20})_2$, (where $R^{20}$ and $R^{21}$ are as defined above).

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}N(R^{20})-R^{23}-OR^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)R^{22}$ (where p is 1 to 2), $-R^{21}-N=C(OR^{20})R^{20}$, $-R^{21}-S(O)OR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain.

"Cycloalkylalkyl" refers to a radical of the formula $-R_bR_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused, bridged and spiro ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, 3-azabicyclo[3.1.0]hexan-3-yl, 1-azaspiro[3.3]heptan-1-yl, 5-azaspiro[2.3]hexan-5-yl, 2-oxa-6-azaspiro[3.3]heptan-6-yl, 1-oxa-6-azaspiro[3.4]octan-6-yl, 1-oxa-6-azaspiro[3.3]heptan-6-yl, 6-oxa-1-azaspiro[3.3]heptan-1-yl, 6-azaspiro[3.4]octan-6-yl, 7-oxa-2-azaspiro[3.5]nonan-2-yl, 2,6-diazaspiro[3.3]heptan-2-yl, (1s,4s)-7-azabicyclo[2.2.1]heptanyl, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})-R^{23}-OR^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain.

"N-heterocyclyl" refers to a heterocyclyl radical as defined above containing at least one nitrogen. The point of attachment of the N-heterocyclyl to the rest of the molecule can be through a nitrogen atom or a carbon atom in the N-heterocyclyl. When specifically stated in the specification, an N-heteroaryl radical may be optionally substituted as described above for an optionally substituted heterocyclyl radical.

"Heterocyclylalkyl" refers to a radical of the formula $-R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkylene chain. When specifically stated in the specification, the heterocyclyl part of the heterocyclylalkyl radical may be optionally substituted as defined above for an optionally substituted heterocyclyl group.

"N-heterocyclylalkyl" refers to a heterocyclylalkyl radical as defined above containing at least one nitrogen. When specifically stated in the specification, the alkylene chain of the N-heterocyclylalkyl radical may be optionally substituted as defined above for an optionally substituted alkylene chain. When specifically stated in the specification, the N-heterocyclyl part of the N-heterocyclylalkyl radical may be optionally substituted as defined above for an optionally substituted heterocyclyl group. Preferably the optional substituents on the N-heterocyclyl part of the N-heterocyclylalkyl radical are alkyl and halo.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e., thienyl). When specifically stated in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})-R^{23}-OR^{20}$, $-R^{21}-N(R^{20})_2$, $-R^{21}-C(O)R^{20}$, $-R^{21}-C(O)OR^{20}$, —$R^{21}$—C(O)N($R^{20}$)$_2$, —$R^{21}$—N($R^{20}$)C(O)O$R^{22}$, —$R^{21}$—N($R^{20}$)C(O)$R^{22}$, —$R^{21}$—N($R^{20}$)S(O)$R^{22}$ (where p is 1 to 2), —$R^{21}$—N=C(O$R^{20}$)$R^{20}$, —$R^{21}$—S(O)O$R^{22}$ (where p is 1 to 2), —$R^{21}$—S(O)$_t R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain. Preferably, the optional substituents on an optionally substituted bicyclic heteroaryl group for $R^1$ herein are halo. Preferably, the optional substituents on an optionally substituted monocyclic heteroaryl group for $R^1$ herein are alkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical. Preferably the optional substituents on the optionally substituted 5-membered N-heteroaryl group for $R^2$ herein are alkyl and halo. Preferably the optional substituents on the optionally substituted 6-membered N-heteroaryl group for $R^2$ herein are alkyl, halo, and haloalkyl.

"Heteroarylalkyl" refers to a radical of the formula —$R_b R_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of formula (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. In one embodiment of the invention, the compounds of formula (I) are enriched with deuterium. Such deuterated compounds can be achieved by methods known to one skilled in the art, such as exchanging protons with deuterium or by synthesizing the molecule with enriched starting materials.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples and Preparations as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a sodium channel-mediated disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, e.g., relieving epilepsy without addressing the underlying disease or condition.

As defined herein, a sodium channel-mediated disease or condition is a disease or condition ameliorated or prevented by modulation of sodium channels and includes without limitation central nervous conditions such as epilepsy, depression and anxiety; neuromuscular conditions such as muscle paralysis, Amyotrophic Lateral Sclerosis (ALS) and restless leg syndrome; pain; chemotherapy-induced peripheral neuropathy; cardiovascular conditions such as atrial fibrillation and ventricular fibrillation; neuroprotection against multiple sclerosis, neural trauma and stroke; and dermatological conditions such as pruritus.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)-for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure,* 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

The chemical naming protocol and structure diagrams used herein are a modified form of the I.U.P.A.C. nomenclature system, using ChemDraw Professional Version 17.0 software program, wherein the compounds of the invention are named herein as derivatives of a central core structure, e.g., the heteroaryl-substituted sulfonamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

"Enantiomers" refer to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions).

The designations, "R" and "S", for the absolute configuration of an enantiomer of the invention may appear as a prefix or as a suffix in the name of the compound; they may or may not be separated from the enantiomer name by a hyphen; they may or may not be hyphenated; and they may or may not be surrounded by parentheses.

Following the standard chemical literature description practice and as used in this specification, a solid full bond, as illustrated above in Structure (A) and a dashed full bond, as illustrated by the exemplary structure (A) below, means that the substituents are in a trans-configuration with respect to the plane of the ring:

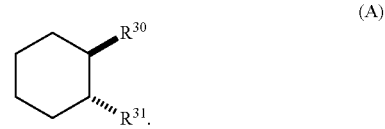

(A)

In the same manner, the bonds in the following exemplary structures (Aa) and (Ab) are in a cis-configuration with respect to the plane of the ring:

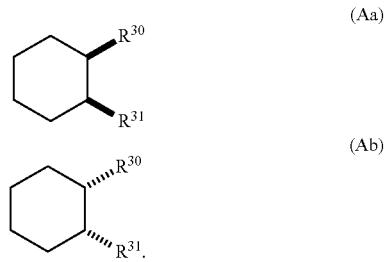

(Aa)

(Ab)

Following the standard chemical literature description practice and as used in this specification, a full wedge bond, as illustrated below in structure (B), means that the substituent bonded to the ring by this bond, in this case the $R^{30}$ substituent, is above the ring plane as illustrated on the page in a two dimensional representation, and a dashed wedge bond, as illustrated below in Structure (B), means that the substituent bonded to the ring by this bond, in this case the $R^{31}$ substituent, is below the ring plane as shown on the page in a two dimensional representation;

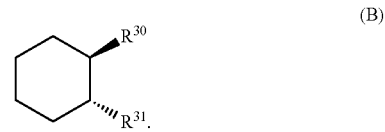

(B)

Following the standard chemical literature description practice and as used in this specification, a wavy bond, as illustrated below in structure (C), indicates that the substituent, in this case the $R^{30}$ substituent, is either below the plane of the ring or above the plane of the ring:

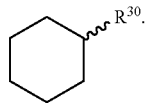
(C)

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, in the following structure (D), the bond attaching the $R^{30}$ substituent can be on any of the carbons, including the carbon to which the $R^{31}$ is attached, provided that the valency allows for such an attachment:

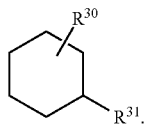
(D)

"Resolution" or "resolving" when used in reference to a racemic compound or a racemic mixture of a compound of the invention refers to the separation of the racemic compound or a racemic mixture into its two enantiomeric forms (i.e., (+) and (−); (R) and (S) forms).

"Enantiomeric excess" or "ee" as used herein refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this invention, the (S)-enantiomer of a compound prepared by the methods disclosed herein is considered to be "substantially free" of the corresponding (R)-enantiomer when the (S)-enantiomer is present in enantiomeric excess of greater than 80%, preferably greater than 90%, more preferably greater than 95% and most preferably greater than 99%.

The chemical naming protocol and structure diagrams used herein are a modified form of the I.U.P.A.C. nomenclature system, using, for example, ChemBioDraw Ultra Version 14.0 software program, wherein the compounds of the invention are named herein as derivatives of a central core structure, e.g., the benzenesulfonamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Accordingly, a compound of formula (I), as set forth above in the Summary of the Invention, wherein

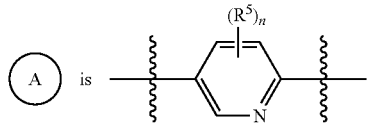

where n is 1 and $R^5$ is methyl, $R^1$ is ((2,2-dimethylazetidin-1-yl)methyl)-6-fluorophenyl, $R^2$ is thiazolyl, and $R^3$ and $R^4$ are both hydrogen, i.e. a compound of the following structure:

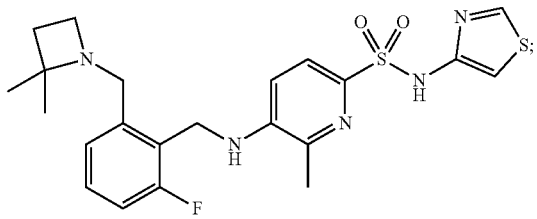 [SMILES: Cc1nc(S(=O)(=O)Nc2cscn2)ccc1NCc1c(F)cccc1CN1CCC1(C)C]

is named herein as 5-((2-((2,2-dimethylazetidin-1-yl)methyl)-6-fluorobenzyl)amino)-6-methyl-N-(thiazol-4-yl)pyridine-2-sulfonamide.

EMBODIMENTS OF THE INVENTION

One aspect of the invention are compounds of formula (I), as set forth above in the Summary of the Invention, as an individual stereoisomer, enantiomer or tautomer thereof or a mixture thereof; or a pharmaceutically acceptable salt, solvate or prodrug thereof.

In one embodiment of this aspect, the compounds of formula (I) are compounds of formula (I) wherein:

is as defined above in the Summary of the Invention for compounds of formula (I);
n is as defined above in the Summary of the Invention for compounds of formula (I);
$R^1$ is aryl optionally substituted by one or more substituents selected from alkyl, halo, haloalkyl, $-R^8-N(R^9)R^{10}$ and optionally substituted N-heterocyclylalkyl;
$R^2$ is as defined above in the Summary of the Invention for compounds of formula (I);
$R^3$ and $R^4$ are each hydrogen or alkyl;
$R^5$, $R^6$ and $R^7$ are each as defined above in the Summary of the Invention for compounds of formula (I);
$R^8$ is a direct bond or an optionally substituted straight or branched alkylene chain; and
$R^9$ and $R^{10}$ are each independently hydrogen, alkyl, haloalkyl, optionally substituted cycloalkyl, optionally substituted cycloalkylalkyl, optionally substituted heterocyclyl, optionally substituted heterocyclylalkyl.

In another embodiment of this aspect, the compounds of formula (I) are compounds of formula (I) wherein:

is as defined above in the Summary of the Invention for compounds of formula (I);

n is as defined above in the Summary of the Invention for compounds of formula (I);
$R^1$ is phenyl optionally substituted by one or more substituents selected from halo, $-R^8-N(R^9)R^{10}$ or optionally substituted N-heterocyclylalkyl;
$R^2$ is as defined above in the Summary of the Invention for compounds of formula (I);
$R^3$ and $R^4$ are each hydrogen or alkyl;
$R^5$, $R^6$ and $R^7$ are as defined above in the Summary of the Invention for compounds of formula (I);
$R^8$ is an optionally straight or branched alkylene chain;
$R^9$ is hydrogen or alkyl; and
$R^{10}$ is hydrogen or alkyl.

In another embodiment of this aspect, the compounds of formula (I) are compounds of formula (I) wherein:

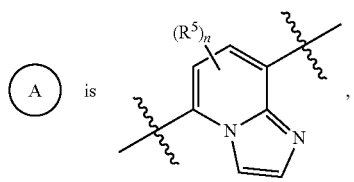

wherein the compound has the following formula (Ia):

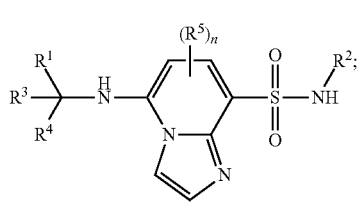

(Ia)

n is as defined above in the Summary of the Invention for compounds of formula (I);
$R^1$ is phenyl optionally substituted by one or more substituents selected from halo, $-R^8-N(R^9)R^{10}$ or optionally substituted N-heterocyclylalkyl;
$R^2$ is as defined above in the Summary of the Invention for compounds of formula (I);
$R^3$ and $R^4$ are each hydrogen or alkyl;
$R^5$ and $R^7$ independently as defined above in the Summary of the Invention for compounds of formula (I);
$R^8$ is an optionally straight or branched alkylene chain;
$R^9$ is hydrogen or alkyl; and
$R^{10}$ is hydrogen or alkyl.

Of this embodiment, a preferred embodiment is 5-((3,6-difluoro-2-(pyrrolidin-1-ylmethyl)benzyl)amino)-N-(thiazol-4-yl)imidazo[1,2-a]pyridine-8-sulfonamide, as an individual stereoisomer, enantiomer or tautomer thereof or a mixture thereof; or a pharmaceutically acceptable salt, solvate or prodrug thereof.

In another embodiment of this aspect, the compounds of formula (I) are compounds of formula (I) wherein:

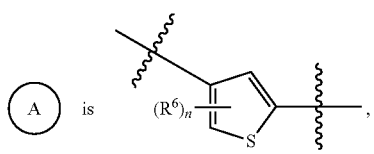

wherein the compound has the following formula (Ia):

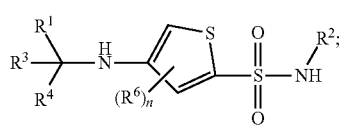

(Ib)

wherein:
n is as defined above in the Summary of the Invention for compounds of formula (I);
$R^1$ is phenyl optionally substituted by one or more substituents selected from halo, $-R^8-N(R^9)R^{10}$ or optionally substituted N-heterocyclylalkyl;
$R^2$ is as defined above in the Summary of the Invention for compounds of formula (I);
$R^3$ and $R^4$ are each hydrogen or alkyl;
$R^6$ and $R^7$ are independently as defined above in the Summary of the Invention for compounds of formula (I);
$R^8$ is an optionally straight or branched alkylene chain;
$R^9$ is hydrogen or alkyl; and
$R^{10}$ is hydrogen or alkyl.

Of this embodiment, a preferred embodiment is 4-((2-bromo-6-fluorobenzyl)amino)-N-(6-fluoropyridin-2-yl)-5-methylthiophene-2-sulfonamide, as an individual stereoisomer, enantiomer or tautomer thereof or a mixture thereof; or a pharmaceutically acceptable salt, solvate or prodrug thereof.

In another embodiment of this aspect, the compounds of formula (I) are compounds of formula (I) wherein:

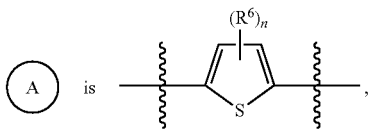

wherein the compound has the following formula (Ic):

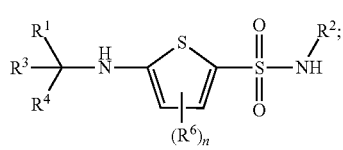

(Ic)

wherein:
n is as defined above in the Summary of the Invention for compounds of formula (I);
$R^1$ is phenyl optionally substituted by one or more substituents selected from halo, $-R^8-N(R^9)R^{10}$ or optionally substituted N-heterocyclylalkyl;
$R^2$ is as defined above in the Summary of the Invention for compounds of formula (I);
$R^3$ and $R^4$ are each hydrogen or alkyl;
$R^6$ and $R^7$ are independently as defined above in the Summary of the Invention for compounds of formula (I); and
$R^8$ is an optionally straight or branched alkylene chain;
$R^9$ is hydrogen or alkyl; and
$R^{10}$ is hydrogen or alkyl.

Of this embodiment, a preferred embodiment is 5-((2-fluoro-6-(pyrrolidin-1-ylmethyl)benzyl)amino)-N-(6-fluoropyridin-2-yl)-4-methylthiophene-2-sulfonamide, as an individual stereoisomer, enantiomer or tautomer thereof or a mixture thereof; or a pharmaceutically acceptable salt, solvate or prodrug thereof.

In another embodiment of this aspect, the compounds of formula (I) are compounds of formula (I) wherein:

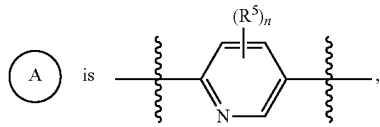

wherein the compound has the following formula (Id):

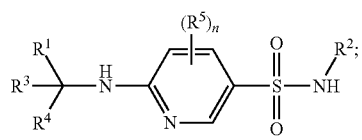

wherein:
n is as defined above in the Summary of the Invention for compounds of formula (I);
$R^1$ is phenyl optionally substituted by one or more substituents selected from halo, $—R^8—N(R^9)R^{10}$ or optionally substituted N-heterocyclylalkyl;
$R^2$ is as defined above in the Summary of the Invention for compounds of formula (I);
$R^3$ and $R^4$ are each hydrogen or alkyl;
$R^5$ and $R^7$ are independently as defined above in the Summary of the Invention for compounds of formula (I); and
$R^8$ is an optionally straight or branched alkylene chain;
$R^9$ is hydrogen or alkyl; and
$R^{10}$ is hydrogen or alkyl.

Of this embodiment, a preferred embodiment are compounds of formula (Id) where $R^2$ is an optionally substituted 5-membered N-heteroaryl.

Of this preferred embodiment, one embodiment are compounds of formula (Id) wherein:
$R^2$ is

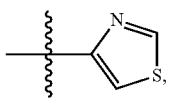

wherein the compound has the following structure (Id1):

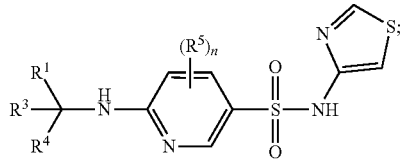

wherein:
n is as defined above in the Summary of the Invention for compounds of formula (I);
$R^1$ is phenyl optionally substituted by one or more substituents selected from halo, $—R^8—N(R^9)R^{10}$ or optionally substituted N-heterocyclylalkyl;
$R^2$ is as defined above in the Summary of the Invention for compounds of formula (I);
$R^3$ and $R^4$ are each hydrogen or alkyl;
$R^5$ and $R^7$ are independently as defined above in the Summary of the Invention for compounds of formula (I); and
$R^8$ is an optionally straight or branched alkylene chain;
$R^9$ is hydrogen or alkyl; and
$R^{10}$ is hydrogen or alkyl.

Of this embodiment, a preferred embodiment is a compound of formula (Id1) selected from:
(S)-5-chloro-6-((1-(5-chloro-2-fluorophenyl)ethyl)amino)-N-(thiazol-4-yl)pyridine-3-sulfonamide;
(S)-5-chloro-6-((1-(2-fluorophenyl)ethyl)amino)-N-(thiazol-4-yl)pyridine-3-sulfonamide;
6-((2-(azetidin-1-ylmethyl)-6-fluorobenzyl)amino)-N-(thiazol-4-yl)pyridine-3-sulfonamide;
6-((2-((tert-butyl(methyl)amino)methyl)-6-fluorobenzyl)amino)-2-methyl-N-(thiazol-4-yl)pyridine-3-sulfonamide;
6-((2-((tert-butyl(methyl)amino)methyl)-6-fluorobenzyl)amino)-5-methyl-N-(thiazol-4-yl)pyridine-3-sulfonamide;
6-((2-((tert-butyl(methyl)amino)methyl)-6-fluorobenzyl)amino)-5-chloro-N-(thiazol-4-yl)pyridine-3-sulfonamide; and
6-((2-fluoro-6-(pyrrolidin-1-ylmethyl)benzyl)amino)-2-methyl-N-(thiazol-4-yl)pyridine-3-sulfonamide;
as an individual stereoisomer, enantiomer or tautomer thereof or a mixture thereof;
or a pharmaceutically acceptable salt, solvate or prodrug thereof.

Of the embodiment above for compounds of formula (Id), a preferred embodiment are compounds of formula (Id) where $R^2$ is an optionally substituted 6-membered N-heteroaryl.

Of this preferred embodiment, one embodiment are compounds of formula (Id) wherein:
$R^2$ is

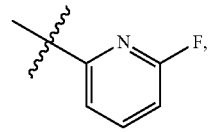

wherein the compound has the following structure (Id2):

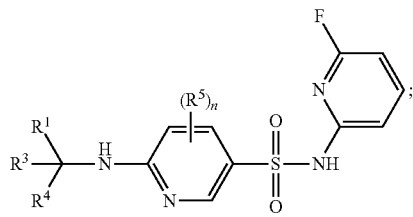

wherein:
n is as defined above in the Summary of the Invention for compounds of formula (I);
$R^1$ is phenyl optionally substituted by one or more substituents selected from halo, $—R^8—N(R^9)R^{10}$ or optionally substituted N-heterocyclylalkyl;
$R^2$ is as defined above in the Summary of the Invention for compounds of formula (I);
$R^3$ and $R^4$ are each hydrogen or alkyl;
$R^5$ and $R^7$ are independently as defined above in the Summary of the Invention for compounds of formula (I); and
$R^8$ is an optionally straight or branched alkylene chain;
$R^9$ is hydrogen or alkyl; and
$R^{10}$ is hydrogen or alkyl.

Of this embodiment, a preferred embodiment is a compound of formula (Id2) selected from:

6-((2-fluoro-6-(pyrrolidin-1-ylmethyl)benzyl)amino)-N-(6-fluoropyridin-2-yl)-2-methylpyridine-3-sulfonamide; and 5-chloro-6-((2-fluoro-6-(pyrrolidin-1-ylmethyl)benzyl)amino)-N-(6-fluoropyridin-2-yl)pyridine-3-sulfonamide;

as an individual stereoisomer, enantiomer or tautomer thereof or a mixture thereof;

or a pharmaceutically acceptable salt, solvate or prodrug thereof.

In another embodiment of this aspect, the compounds of formula (I) are compounds of formula (I) wherein:

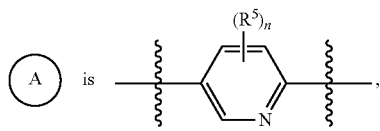

wherein the compound has the following formula (Ie):

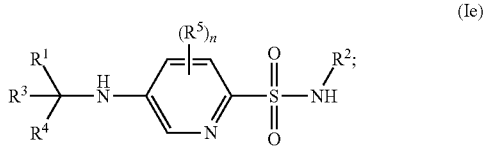

wherein:

n is as defined above in the Summary of the Invention for compounds of formula (I);

$R^1$ is phenyl optionally substituted by one or more substituents selected from halo, —$R^8$—$N(R^9)R^{10}$ or optionally substituted N-heterocyclylalkyl;

$R^2$ is as defined above in the Summary of the Invention for compounds of formula (I);

$R^3$ and $R^4$ are each hydrogen or alkyl;

$R^5$ and $R^7$ is as defined above in the Summary of the Invention for compounds of formula (I); and $R^8$ is an optionally straight or branched alkylene chain;

$R^9$ is hydrogen or alkyl; and $R^{10}$ is hydrogen or alkyl.

Of this embodiment, a preferred embodiment are compounds of formula (Ie) where $R^2$ is an optionally substituted 5-membered N-heteroaryl.

Of this preferred embodiment, one embodiment are compounds of formula (Ie) wherein:
$R^2$ is

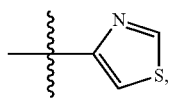

wherein the compound has the following structure (Ie1):

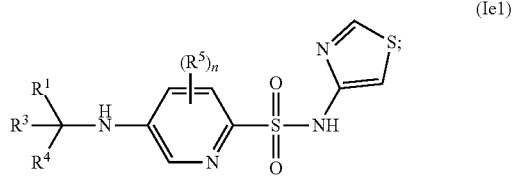

wherein:

n is as defined above in the Summary of the Invention for compounds of formula (I);

$R^1$ is phenyl optionally substituted by one or more substituents selected from halo, —$R^8$—$N(R^9)R^{10}$ or optionally substituted N-heterocyclylalkyl;

$R^3$ and $R^4$ are each hydrogen or alkyl;

$R^5$ and $R^7$ is as defined above in the Summary of the Invention for compounds of formula (I); and $R^8$ is an optionally straight or branched alkylene chain;

$R^9$ is hydrogen or alkyl; and $R^{10}$ is hydrogen or alkyl.

Of this embodiment, a preferred embodiment is a compound of formula (Ie1) selected from:

(S)-5-((1-(2-fluorophenyl)ethyl)amino)-6-methyl-N-(thiazol-4-yl)pyridine-2-sulfonamide;

5-((2-(azetidin-1-ylmethyl)-6-fluorobenzyl)amino)-6-methyl-N-(thiazol-4-yl)pyridine-2-sulfonamide;

5-((2-(azetidin-1-ylmethyl)-6-fluorobenzyl)amino)-4-methyl-N-(thiazol-4-yl)pyridi ne-2-sulfonamide;

5-((2-((tert-butyl(methyl)amino)methyl)-6-fluorobenzyl)amino)-6-methyl-N-(thiazol-4-yl)pyridine-2-sulfonamide;

5-((2-((2,2-dimethylazetidin-1-yl)methyl)-6-fluorobenzyl)amino)-6-methyl-N-(thiazol-4-yl)pyridine-2-sulfonamide;

5-((2-fluoro-6-((isopropyl(methyl)amino)methyl)benzyl)amino)-6-methyl-N-(thiazol-4-yl)pyridine-2-sulfonamide;

5-((2-(azetidin-1-ylmethyl)-3-fluorobenzyl)amino)-6-methyl-N-(thiazol-4-yl)pyridine-2-sulfonamide;

4-(difluoromethyl)-5-((2-fluoro-6-(pyrrolidin-1-ylmethyl)benzyl)amino)-N-(thiazol-4-yl)pyridine-2-sulfonamide;

6-(difluoromethyl)-5-((2-fluoro-6-(pyrrolidin-1-ylmethyl)benzyl)amino)-N-(thiazol-4-yl)pyridine-2-sulfonamide;

5-((2-fluoro-6-((3-methylazetidin-1-yl)methyl)benzyl)amino)-6-methyl-N-(thiazol-4-yl)pyridine-2-sulfonamide;

5-((2-((tert-butyl(methyl)amino)methyl)benzyl)amino)-6-methyl-N-(thiazol-4-yl)pyridine-2-sulfonamide;

5-((2-(azetidin-1-ylmethyl)benzyl)amino)-6-methyl-N-(thiazol-4-yl)pyridine-2-sulfonamide;

5-((2-fluoro-6-(pyrrolidin-1-ylmethyl)benzyl)amino)-6-methyl-N-(thiazol-4-yl)pyridine-2-sulfonamide;

5-((2-(((cyclopropylmethyl)(methyl)amino)methyl)-6-fluorobenzyl)amino)-6-methyl-N-(thiazol-4-yl)pyridine-2-sulfonamide;

5-((2-fluoro-6-((3-fluoro-3-methylazetidin-1-yl)methyl)benzyl)amino)-6-methyl-N-(thiazol-4-yl)pyridine-2-sulfonamide;

5-((2-((tert-butyl(methyl)amino)methyl)-3,6-difluorobenzyl)amino)-6-methyl-N-(thiazol-4-yl)pyridine-2-sulfonamide;

5-((2-(azetidin-1-ylmethyl)-6-fluorobenzyl)amino)-N-(thiazol-4-yl)-4-(trifluoromethyl)pyridine-2-sulfonamide;

5-((2-(((1s,4s)-7-azabicyclo[2.2.1]heptan-7-yl)methyl)-6-fluorobenzyl)amino)-6-methyl-N-(thiazol-4-yl)pyridine-2-sulfonamide;

5-((2-(((1s,4s)-7-azabicyclo[2.2.1]heptan-7-yl)methyl)-6-fluorobenzyl)amino)-3-fluoro-6-methyl-N-(thiazol-4-yl)pyridine-2-sulfonamide;

3-fluoro-5-((2-fluoro-6-((isopropyl(methyl)amino)methyl)benzyl)amino)-6-methyl-N-(thiazol-4-yl)pyridine-2-sulfonamide;

5-((2-((tert-butyl(methyl)amino)methyl)-6-fluorobenzyl)amino)-3-fluoro-6-methyl-N-(thiazol-4-yl)pyridine-2-sulfonamide;

5-((2-bromo-3,6-difluorobenzyl)amino)-3-fluoro-6-methyl-N-(thiazol-4-yl)pyridine-2-sulfonamide;

5-((2-((7-azabicyclo[2.2.1]heptan-7-yl)methyl)-3-(trifluoromethyl)benzyl)amino)-3-fluoro-6-methyl-N-(thiazol-4-yl)pyridine-2-sulfonamide;
5-((2-((7-azabicyclo[2.2.1]heptan-7-yl)methyl)-6-fluorobenzyl)amino)-N-(thiazol-4-yl)-6-(trifluoromethyl)pyridine-2-sulfonamide;
5-((2-((tert-butyl(methyl)amino)methyl)benzyl)amino)-3-fluoro-6-methyl-N-(thiazol-4-yl)pyridine-2-sulfonamide; and
5-((2-((tert-butyl(methyl)amino)methyl)-6-fluorobenzyl)amino)-6-cyclopropyl-3-fluoro-N-(thiazol-4-yl)pyridine-2-sulfonamide;
as an individual stereoisomer, enantiomer or tautomer thereof or a mixture thereof;
or a pharmaceutically acceptable salt, solvate or prodrug thereof.

Of the preferred embodiment above of the compounds of formula (Ie) where $R^2$ is an optionally substituted 5-membered N-heteroaryl, another preferred embodiment are compounds wherein:
$R^2$ is

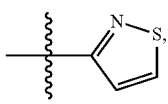

wherein the compound has the following structure (Ie2):

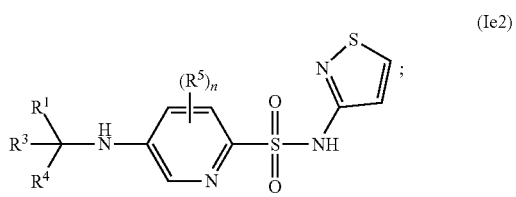

(Ie2)

wherein:
n is as defined above in the Summary of the Invention for compounds of formula (I);
$R^1$ is phenyl optionally substituted by one or more substituents selected from halo, —$R^8$—$N(R^9)R^{10}$ or optionally substituted N-heterocyclylalkyl;
$R^3$ and $R^4$ are each hydrogen or alkyl;
$R^5$ and $R^7$ is as defined above in the Summary of the Invention for compounds of formula (I); and
$R^8$ is an optionally straight or branched alkylene chain;
$R^9$ is hydrogen or alkyl; and
$R^{10}$ is hydrogen or alkyl.

Of this embodiment, a preferred embodiment is a compound of formula (Ie2) selected from:
5-((2-(azetidin-1-ylmethyl)-6-fluorobenzyl)amino)-N-(isothiazol-3-yl)-4-methylpyridine-2-sulfonamide;
5-((2-(azetidin-1-ylmethyl)-6-fluorobenzyl)amino)-N-(isothiazol-3-yl)-6-methylpyridine-2-sulfonamide; and
5-((2-((tert-butyl(methyl)amino)methyl)-6-fluorobenzyl)amino)-N-(isothiazol-3-yl)-6-methylpyridine-2-sulfonamide;
as an individual stereoisomer, enantiomer or tautomer thereof or a mixture thereof;
or a pharmaceutically acceptable salt, solvate or prodrug thereof.

Of the preferred embodiment above of the compounds of formula (Ie) where $R^2$ is an optionally substituted 5-membered N-heteroaryl, another preferred embodiment are compounds wherein:

$R^2$ is

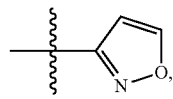

wherein the compound has the following structure (Ie3):

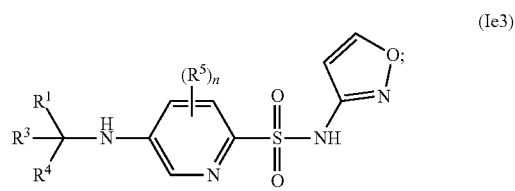

(Ie3)

wherein:
n is as defined above in the Summary of the Invention for compounds of formula (I);
$R^1$ is phenyl optionally substituted by one or more substituents selected from halo, —$R^8$—$N(R^9)R^{10}$ or optionally substituted N-heterocyclylalkyl;
$R^3$ and $R^4$ are each hydrogen or alkyl;
$R^5$ and $R^7$ is as defined above in the Summary of the Invention for compounds of formula (I); and
$R^8$ is an optionally straight or branched alkylene chain;
$R^9$ is hydrogen or alkyl; and
$R^{10}$ is hydrogen or alkyl.

Of this embodiment, a preferred embodiment is a compound of formula (Ie3) which is 5-((2-((tert-butyl(methyl)amino)methyl)benzyl)amino)-3-fluoro-N-(isoxazol-3-yl)-6-methylpyridine-2-sulfonamide; as an individual stereoisomer, enantiomer or tautomer thereof or a mixture thereof; or a pharmaceutically acceptable salt, solvate or prodrug thereof.

Of the embodiment above for compounds of formula (Ie), another preferred embodiment are compounds of formula (Ie) where $R^2$ is an optionally substituted 5-membered N-heteroaryl.

Of this preferred embodiment, one embodiment are compounds of formula (Ie) wherein:
$R^2$ is

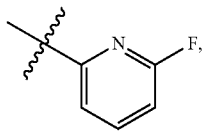 [SMILES: *c1cccc(F)n1]

wherein the compound has the following structure (Ie4):

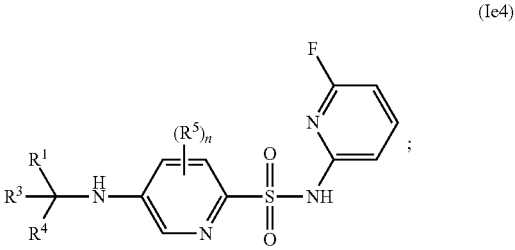

(Ie4)

wherein:
n is as defined above in the Summary of the Invention for compounds of formula (I);

$R^1$ is phenyl optionally substituted by one or more substituents selected from halo, $-R^8-N(R^9)R^{10}$ or optionally substituted N-heterocyclylalkyl;

$R^3$ and $R^4$ are each hydrogen or alkyl;

$R^5$ and $R^7$ is as defined above in the Summary of the Invention for compounds of formula (I); and $R^8$ is an optionally straight or branched alkylene chain;

$R^9$ is hydrogen or alkyl; and $R^{10}$ is hydrogen or alkyl.

Of this embodiment, a preferred embodiment is a compound of formula (Ie3) selected from:

5-((2-(azetidin-1-ylmethyl)-6-fluorobenzyl)amino)-N-(6-fluoropyridin-2-yl)-4-methylpyridine-2-sulfonamide;

5-((2-fluoro-6-(pyrrolidin-1-ylmethyl)benzyl)amino)-N-(6-fluoropyridin-2-yl)-4-methylpyridine-2-sulfonamide;

5-((2-fluoro-6-(pyrrolidin-1-ylmethyl)benzyl)amino)-N-(6-fluoropyridin-2-yl)-6-methylpyridine-2-sulfonamide;

5-((2-((tert-butyl(methyl)amino)methyl)-6-fluorobenzyl)amino)-N-(6-fluoropyridin-2-yl)-6-methylpyridine-2-sulfonamide;

5-((2-((tert-butyl(methyl)amino)methyl)benzyl)amino)-3-fluoro-N-(6-fluoropyridin-2-yl)-6-methylpyridine-2-sulfonamide; and 3-fluoro-5-((2-fluoro-6-((isopropyl(methyl)amino)methyl)benzyl)amino)-N-(6-fluoropyridin-2-yl)-4-methylpyridine-2-sulfonamide;

as an individual stereoisomer, enantiomer or tautomer thereof or a mixture thereof;

or a pharmaceutically acceptable salt, solvate or prodrug thereof.

In another embodiment of this aspect, the compounds of formula (I) are compounds of formula (I) wherein:

(A)

is as defined above in the Summary of the Invention for compounds of formula (I).

n is as defined above in the Summary of the Invention for compounds of formula (I);

$R^1$ is a bicyclic heteroaryl optionally substituted by one or more substituents selected from alkyl, halo, haloalkyl, $-R^8-N(R^9)R^{10}$ and optionally substituted N-heterocyclylalkyl;

$R^2$ is as defined above in the Summary of the Invention for compounds of formula (I);

$R^3$ and $R^4$ are each hydrogen or alkyl;

$R^5$, $R^6$ and $R^7$ are each as defined above in the Summary of the Invention for compounds of formula (I);

$R^8$ is a direct bond or an optionally substituted straight or branched alkylene chain; and $R^9$ and $R^{10}$ are each independently hydrogen, alkyl, haloalkyl, optionally substituted cycloalkyl, optionally substituted cycloalkylalkyl, optionally substituted heterocyclyl, optionally substituted heterocyclylalkyl.

In another embodiment of this aspect, the compounds of formula (I) are compounds of formula (I) wherein:

(A)

is as defined above in the Summary of the Invention for compounds of formula (I);

n is as defined above in the Summary of the Invention for compounds of formula (I);

$R^1$ is isoquinolinyl optionally substituted by one or more substituents selected from halo, $-R^8-N(R^9)R^{10}$ or optionally substituted N-heterocyclylalkyl;

$R^2$ is as defined above in the Summary of the Invention for compounds of formula (I);

$R^3$ and $R^4$ are each hydrogen or alkyl;

$R^5$, $R^6$ and $R^7$ is as defined above in the Summary of the Invention for compounds of formula (I);

$R^8$ is an optionally straight or branched alkylene chain;

$R^9$ is hydrogen or alkyl; and $R^{10}$ is hydrogen or alkyl.

In another embodiment of this aspect, the compounds of formula (I) are compounds of formula (I) wherein:

(A) is [structure with $(R^5)_n$ on pyridine ring], wherein the compound has the following formula (Ie):

(Ie)
[structure showing $R^1$, $R^3$, $R^4$ attached to CH-NH linked to pyridine with $(R^5)_n$, sulfonamide $SO_2$-NH-$R^2$]

wherein:

n is as defined above in the Summary of the Invention for compounds of formula (I);

$R^1$ is isoquinolinyl optionally substituted by one or more substituents selected from halo, $-R^8-N(R^9)R^{10}$ or optionally substituted N-heterocyclylalkyl;

$R^2$ is as defined above in the Summary of the Invention for compounds of formula (I);

$R^3$ and $R^4$ are each hydrogen or alkyl;

$R^5$, $R^6$ and $R^7$ is as defined above in the Summary of the Invention for compounds of formula (I);

$R^8$ is an optionally straight or branched alkylene chain;

$R^9$ is hydrogen or alkyl; and $R^{10}$ is hydrogen or alkyl.

Of this embodiment, a preferred embodiment are compounds of formula (Ie) where $R^2$ is an optionally substituted 5-membered N-heteroaryl.

Of this preferred embodiment, one embodiment are compounds of formula (Ie) wherein:

$R^2$ is

[thiazole structure]

wherein the compound has the following structure (Ie1):

(Ie1)
[structure showing $R^1$, $R^3$, $R^4$ attached to CH-NH linked to pyridine with $(R^5)_n$, sulfonamide $SO_2$-NH-thiazole]

wherein n is as defined above in the Summary of the Invention for compounds of formula (I);

$R^1$ is isoquinolinyl optionally substituted by one or more substituents selected from halo, $—R^8—N(R^9)R^{10}$ or optionally substituted N-heterocyclylalkyl;

$R^2$ is as defined above in the Summary of the Invention for compounds of formula (I);

$R^3$ and $R^4$ are each hydrogen or alkyl;

$R^5$, $R^6$ and $R^7$ is as defined above in the Summary of the Invention for compounds of formula (I);

$R^8$ is an optionally straight or branched alkylene chain;

$R^9$ is hydrogen or alkyl; and $R^{10}$ is hydrogen or alkyl.

Of this embodiment, a preferred embodiment is 5-((isoquinolin-8-ylmethyl)amino)-6-methyl-N-(thiazol-4-yl)pyridine-2-sulfonamide; as an individual stereoisomer, enantiomer or tautomer thereof or a mixture thereof; or a pharmaceutically acceptable salt, solvate or prodrug thereof.

Another embodiment of the invention are compounds of formula (I) wherein $R^1$ is aryl, preferably phenyl, optionally substituted by one or more substituents selected from halo, $—R^8—N(R^9)R^{10}$ or optionally substituted N-heterocyclylalkyl. Of these optional substituents, preferred substituents are bromo, chloro, fluoro, (dialkylamino)methyl, azetidin-1-ylmethyl, pyrrolidin-1-ylmethyl, 2,2-dimethylazetidin-1-ylmethyl, 3-methylazetidin-1-yl, ((cycloalkylmethyl)(alkyl)amino)methyl, 3-fluoro-3-methylazetidin-1-yl, and (7-azabicyclo[2.2.1]heptanyl)methyl.

Of this embodiment, the optional substituents are in the ortho and/or meta position on the aryl relative to the bond to the carbon to which $R^3$ and $R^4$ are attached.

Another embodiment of the invention are compounds of formula (I) wherein n is 1 or 2 and $R^5$ is selected from fluoro, chloro, methyl, difluoromethyl and trifluoromethyl.

Another embodiment of the invention are compounds of formula (I) wherein $R^2$ is a 5-membered N-heteroaryl or a 6-membered N-heteroaryl optionally substituted with halo, preferably fluoro.

It is understood that any embodiment of the compounds of the invention, as set forth above, and any specific substituent set forth herein for a particular (A), n, $R^1$, $R^2$, $R^3$, $R^4$, $R^5$, $R^6$, $R^7$, $R^8$, $R^9$ and $R^{10}$ group in the compounds of the invention, as set forth above, may be independently combined with other embodiments and/or substituents of compounds of the invention to form embodiments of the inventions not specifically set forth above. In addition, in the event that a list of substituents is disclosed for any particular (A), n, $R^1$, $R^2$, $R^3$, $R^4$, $R^5$, $R^6$, $R^7$, $R^8$, $R^9$ and $R^{10}$ group in a particular embodiment and/or claim, it is understood that one or more substituents may be deleted from the list and that the remaining list of substituents will be considered to be an embodiment of the invention.

Another embodiment of the invention is a method of using the compounds of formula (I) as standards or controls in in vitro or in vivo assays in determining the efficacy of test compounds in modulating voltage-dependent sodium channels.

Another aspect of the invention is a pharmaceutical composition comprising a pharmaceutically acceptable excipient and a compound of the invention, as described above, as a stereoisomer, enantiomer or tautomer thereof or a mixture thereof; or a pharmaceutically acceptable salt, solvate or prodrug thereof.

Another aspect of the invention is a method of treating a sodium channel-mediated disease or condition in a mammal wherein the sodium channel-mediated disease or condition is selected from epilepsy, depression and anxiety; neuromuscular conditions such as muscle paralysis, Amyotrophic Lateral Sclerosis (ALS) and restless leg syndrome; pain; chemotherapy-induced peripheral neuropathy; cardiovascular conditions such as atrial fibrillation and ventricular fibrillation; neuroprotection against multiple sclerosis, neural trauma and stroke; and dermatological conditions such as pruritus and wherein the method comprises administering to the mammal in need thereof a therapeutically effective amount of a compound of the invention, as described above, as a stereoisomer, enantiomer or tautomer thereof or a mixture thereof; or a pharmaceutically acceptable salt, solvate or prodrug thereof.

Another aspect of the invention is a method of treating a disease or a condition associated with $Na_v1.6$ activity in a mammal wherein the disease or condition is epilepsy and/or epileptic seizure disorder and wherein the method comprises administering to the mammal in need thereof a therapeutically effective amount of a compound of the invention, as described above, as a stereoisomer, enantiomer or tautomer thereof or a mixture thereof; or a pharmaceutically acceptable salt, solvate or prodrug thereof.

In one embodiment of this aspect, the epilepsy or epileptic seizure disorder is selected from photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia.

In one embodiment of this embodiment, the epilepsy or epileptic seizure disorder is selected from Dravet syndrome, infantile spasms/West's syndrome, temporal lobe epilepsy, Lennox-Gastaut syndrome (LGS), generalized epilepsy with febrile seizures+ and early infantile epileptic encephalopathy.

Another aspect of the invention is a method of decreasing ion flux through $Na_v1.6$ in a mammalian cell, wherein the method comprises contacting the cell with a compound of the invention, as described above, as a stereoisomer, enantiomer or tautomer thereof or a mixture thereof; or a pharmaceutically acceptable salt, solvate or prodrug thereof.

Another aspect of the invention is a method of selectively inhibiting a first voltage-gated sodium channel over a second voltage-gated sodium channel in a mammal, wherein the method comprises administering to the mammal a modulating amount of a compound of the invention, as described above, as a stereoisomer, enantiomer or tautomer thereof or a mixture thereof; or a pharmaceutically acceptable salt, solvate or prodrug thereof.

In one embodiment of this aspect, the first voltage-gated sodium channel is $Na_v1.6$.

In another embodiment of this aspect, the first voltage-gated sodium channel is $Na_v1.6$ and the second voltage-gated sodium channel is $Na_v1.5$.

In another embodiment of this aspect, the first voltage-gated sodium channel is $Na_v1.6$ and the second voltage-gated sodium channel is $Na_v1.1$.

Specific embodiments of the compounds of the invention are described in more detail below in the Preparation of the Compounds of the Invention and in the Examples.

UTILITY AND TESTING OF THE COMPOUNDS OF THE INVENTION

The compounds of the invention modulate, preferably inhibit, ion flux through a voltage-dependent sodium channel, preferably $Na_v1.6$, in a mammal, especially in a human. Any such modulation, whether it be partial or complete inhibition or prevention of ion flux, is sometimes referred to herein as "blocking" and corresponding compounds as "blockers" or "inhibitors". In general, the compounds of the invention modulate the activity of a voltage-gated sodium channel downwards by inhibiting the voltage-dependent activity of the sodium channel, and/or reduce or prevent sodium ion flux across a cell membrane by preventing sodium channel activity such as ion flux.

The compounds of the invention inhibit the ion flux through a voltage-dependent sodium channel, preferably $Na_v1.6$. The compounds of the invention are state or frequency dependent modifiers of the sodium channel, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestele, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention are voltage-gated sodium channel inhibitors, preferably $Na_v1.6$ inhibitors, and are therefore useful for treating diseases and conditions, preferably epilepsy and/or epileptic seizure disorder, in mammals, preferably humans, and other organisms, including all those human diseases and conditions which are the result of aberrant voltage-dependent sodium channel biological activity, preferably aberrant $Na_v1.6$ activity, or which may be ameliorated by modulation of voltage-dependent sodium channel biological activity. In particular, the compounds of the invention, i.e., the compounds of formula (I), as set forth above in the Summary of the Invention, as individual stereoisomers, enantiomers or tautomers thereof or mixtures thereof; or as pharmaceutically acceptable salts, solvates or prodrugs thereof, are useful for treating diseases and conditions in mammals, preferably humans, which are the result of aberrant voltage-dependent $Na_v1.6$ biological activity or which may be ameliorated by the modulation, preferably the inhibition, of $Na_v1.6$ biological activity. Preferably the compounds of the invention selectively inhibit $Na_v1.6$ over $Na_v1.5$ and/or $Na_v1.1$.

As defined herein, a disease, disorder or condition associated with $Na_v1.6$ activity includes, but is not limited to, epilepsy and/or epileptic seizure disorder. Such epilepsy and/or epileptic seizure disorders include, but are not limited to, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia.

The present invention therefore relates to compounds, pharmaceutical compositions and methods of using the compounds and pharmaceutical compositions for the treatment of diseases or conditions associated by the activity of $Na_v1.6$ in a mammal, preferably a human, by administering to the mammal, preferably the human, in need of such treatment an effective amount of a compound of the invention or an pharmaceutical composition comprising a compound of the invention.

The general value of the compounds of the invention in inhibiting the $Na_v1.6$ ion flux can be determined using the assays described below in the Biological Assays section. Alternatively, the general value of the compounds in treating conditions and diseases in humans may be established in industry standard animal models for demonstrating the efficacy of compounds in treating epilepsy and/or epileptic seizure disorder. Animal models of human epileptic conditions have been developed that result in reproducible sensory deficits over a sustained period of time that can be evaluated by sensory testing.

For example, many rodent models have been developed to assess the propensity for seizures or epileptiform activity (Klein, B. R. et al., (2016), "Models Currently in Active Use. In: Epilepsy Therapy Screening Program", Vol. 2016, National Institute of Neurological Disorders and Stroke). These include acute chemical or electrical insults that induce seizures, as well as chronic chemical or genetic insults that create seizure prone animals. These models can be used to determine the relative ability of a compound to promote or prevent seizure activity. The maximal electroshock seizure (MES) assay and the 6 hertz psychomotor seizure test (6 Hz) are two examples of acute insult seizure assays used to evaluate anticonvulsive interventions (Suzuki, F. et al., *Neuroscience* (1995), Vo. 64, pp. 665-674; Barton, M. E. et al., *Epilepsy Research* (2001), Vol. 47, pp. 217-227). Both assays involve an electrical insult applied with electrodes placed on the corneas or ears in order to provoke an acute seizure. Acute seizures may also be induced chemically, for instance by administration of the proconvulsant ether compound flurothyl (Makinson, C. D. et al., *Exp. Neurol.* (2016), Vol. 275, Pt 1, pp. 46-58).

Genetic epilepsies have been linked to many distinct genes, including multiple voltage gated sodium channel genes. Genetically modified mice can be created that harbor mutations identified in human patients. In some cases these genetic modifications result in animals that behave much like the human patients in whom the genetic variations were initially identified. Mutant mice can be used to test anticonvulsant interventions. Such experiments can involve prevention of spontaneous seizures, or may make use of similar seizure provoking stimuli as those employed in wild type mice. Animal models of early infantile epileptic encephalopathy 6 (EIEE6), also known as severe myoclonic epilepsy of infancy or Dravet syndrome, have been created by mutating the SCN1A gene that encodes the $Na_v1.1$ voltage gated sodium channel (Yu, F. H. et al., *Nat. Neurosci.* (2006), Vol. 9, pp. 1142-1149). Models of EIEE13 have likewise been created by mutating the SCN6A gene that encodes the $Na_v1.6$ voltage gated sodium channel (Wagnon, J. L. et al., Human Molecular Genetics (2014)). Both of these mouse strains provide the opportunity to evaluate potential therapeutic interventions that might prove useful in clinical patient populations (Martin, M. S. et al., *J. Biol. Chem.* (2010), Vol. 285, pp. 9823-9834; and Martin, M. S. et al., *Human Molecular Genetics* (2007), Vol. 16, pp. 2892-2899).

The present invention readily affords many different means for identification of $Na_v1.6$ inhibitory agents that are useful as therapeutic agents. Identification of $Na_v1.6$ inhibitors can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., *J. General Physiology* (1983), 83:613-642, and Leuwer, M., et al., *Br. J. Pharmacol* (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they are useful in treating the disease or condition associated with the activity of the sodium channel of interest, preferably $Na_v1.6$, with minimal adverse events. The assays described below in the Biological Assays Section are useful in assessing the biological activity of the instant compounds.

Typically, the efficacy of a compound of the invention is expressed by its $IC_{50}$ value ("Inhibitory Concentration—50%"), which is the measure of the amount of compound required to achieve 50% inhibition of the activity of the target sodium channel over a specific time period. For example, representative compounds of the present invention have demonstrated $IC_{50}$'s ranging from less than 100 nanomolar to less than 10 micromolar in the patch voltage clamp $Na_v1.6$ electrophysiology assay described herein.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_v1.6$ activity in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_v1.6$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention, as set forth above in the Summary of the Invention, as stereoisomers, enantiomers, tautomers thereof or mixtures thereof, or pharmaceutically acceptable salts, solvates or prodrugs thereof, and/or the pharmaceutical compositions described herein which comprise a pharmaceutically acceptable excipient and one or more compounds of the invention, as set forth above in the Summary of the Invention, as a stereoisomer, enantiomer or tautomer thereof or mixtures thereof, or a pharmaceutically acceptable salt, solvate or prodrug thereof, can be used in the preparation of a medicament for the treatment of diseases or conditions associated with voltage-gated sodium channel activity, preferably $Na_v1.6$ activity, in a mammal.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier, excipient or diluent and in an amount effective to modulate, preferably inhibit, ion flux through a voltage-dependent sodium channel to treat sodium channel mediated diseases, such as epilepsy and/or epileptic seizure disorder, when administered to an animal, preferably a mammal, most preferably a human patient.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts (see, e.g., Berkow et al., eds., *The Merck Manual*, 19$^{th}$ edition, Merck and Co., Rahway, N.J., 2011; Brunton et al. eds., *Goodman and Cilman's The Pharmacological Basis of Therapeutics*, 12$^{th}$ edition, McGraw-Hill 2011; Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985); Osolci al., eds., *Remington's Pharmaceutical Sciences*, current edition, Mack Publishing Co., Easton, Pa.; Katzung, *Basic and Clinical Pharmacology*, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats and hamsters), Lagamorpha (including rabbits) and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the compound for safe and effective intraocular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the invention may be usefully combined with one or more other compounds of the invention or one or more other therapeutic agent or as any combination thereof, in the treatment of diseases and conditions associated with voltage-gated sodium channel activity. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetaminophen, salicylates (e.g., aspirin);

nonsteroidal anti-inflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (αR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT$_3$ antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressants such as mirtazapine, topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotinic) analgesics;

alpha-2-delta ligands;

prostaglandin E2 subtype antagonists;

leukotriene B4 antagonists;

5-lipoxygenase inhibitors; and

5-HT$_3$ antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

Kits-of-Parts

The present invention also provides kits that contain a pharmaceutical composition which includes one or more compounds of the invention. The kit also includes instructions for the use of the pharmaceutical composition for inhibiting the activity of voltage-gated sodium channels, preferably Na$_v$1.6, for the treatment of epilepsy, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds of the Invention

The following Reaction Schemes illustrate methods to make compounds of this invention, i.e., compounds of formula (I), as individual stereoisomers, enantiomers or tautomers thereof or mixtures thereof; or as pharmaceutically acceptable salts, solvates or prodrugs thereof It is also understood that one skilled in the art would be able to make the compounds of the invention by similar methods or by methods known to one skilled in the art. It is also understood that one skilled in the art would be able to make in a similar manner as described below other compounds of the invention not specifically illustrated below by using the appropriate starting components and modifying the parameters of the synthesis as needed. It is also understood that simple functional group transformations (see, e.g., Larock, R. C. *Comprehensive Organic Transformations*, 2$^{nd}$ edition (Wiley, 1999) can be effected by methods known to one skilled in the art. In general, starting components may be obtained from sources such as Sigma Aldrich, Combi-Blocks, Oakwood Chemicals, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure*, 6th edition (Wiley, 2007)) or prepared as described herein.

It is also understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Greene's Protective Groups in Organic Synthesis* (latest edition), Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The compounds of formula (I) may contain at least one asymmetric carbon atom and thus can exist as racemates, enantiomers and/or diastereoisomers. Specific enantiomers or diastereoisomers may be prepared by utilizing the appropriate chiral starting material. Alternatively, diastereoisomeric mixtures or racemic mixtures of compounds of formula (I) may be resolved into their respective enantiomers or diastereoisomers. Methods for resolution of diastereoisomeric mixtures or racemic mixtures of the compounds of formula (I), as described herein, or intermediates prepared herein, are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g., preferential crystallization, preferential crystallization in the presence of additives), asymmetric transformation of racemates, chemical separation (e.g., formation and separation of diastereomers such as diastereomeric salt mixtures or the use of other resolving agents; separation via complexes and inclusion compounds), kinetic resolution (e.g., with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, *Analytical Chemistry*, 2002, 2863-2872).

Preparation of Compounds of Formula (I)

In general, compounds of formula (I), as described above in the Summary of the Invention, can be synthesized following the general procedure described below in Reaction Scheme 1 where

$R^1$, $R^2$, $R^3$ and $R^4$ are as described above in the Summary of the Invention for compounds of formula (I), $X^1$ and $X^2$ are, at each occurrence, independently bromo, chloro, or fluoro and $Z^1$ is hydrogen or a nitrogen protecting group, for example, but not limited to, tert-butyloxycarbonyl, 2,4-dimethoxybenzyl, or 4-methoxybenzyl:

REACTION SCHEME 1

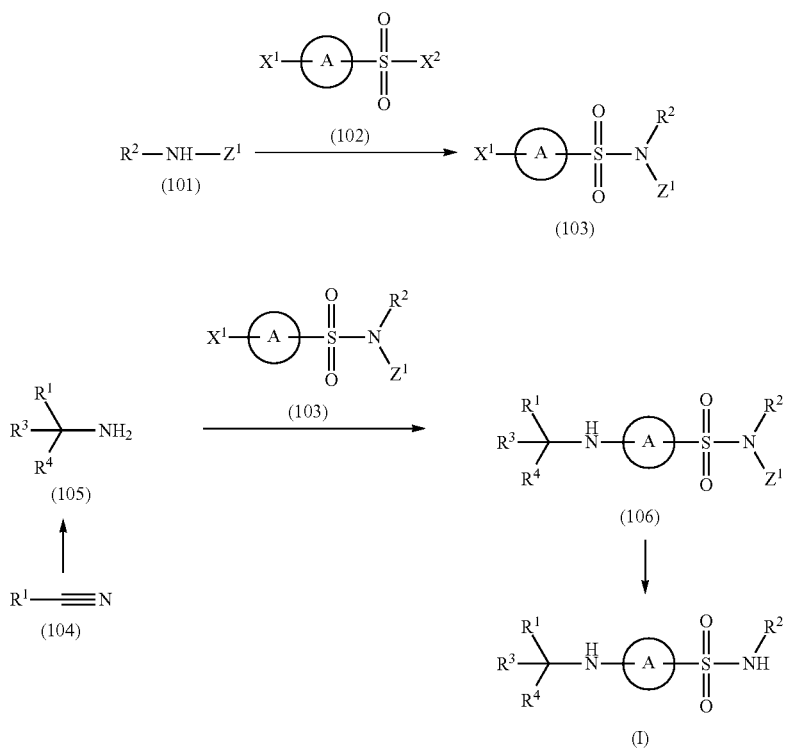

Compounds of formulae (101), (102), (103), (104), (105) and (106) are commercially available or can be prepared according to methods known to one skilled in the art or by methods disclosed herein. In general, the compounds of formula (I) are prepared as described above in Reaction Scheme 1 as follows:

The compound of formula (101) is reacted with sulfonyl halide compound of formula (102) under standard reaction conditions, such as, but not limited to, the use of a polar aprotic solvent, such as, but not limited to, tetrahydrofuran or N,N-dimethylformamide, in the presence of a base, such as, but not limited to, lithium bis(trimethylsilyl)amide or sodium hydride, at a temperature between about −78° C. and ambient temperature, for about 30 minutes to 18 hours to afford compound of formula (103).

Additionally, in the instance that $Z^1$ is an amine protecting group (e.g., tert-butyloxycarbonyl) and an alternative protecting group is desired, $Z^1$ can be removed using an acid, such as, but not limited to, trifluoroacetic acid in a polar aprotic solvent, such as, but not limited to, dichloromethane at a temperature of between 0° C. and ambient temperature for between 30 minutes and 5 hours. An alternative protecting group can then be added to the resultant compound by adding a polar aprotic solvent, such as, but not limited to, N,N-dimethylformamide or dimethyl sulfoxide in the presence of a base, such as, but not limited to, sodium bicarbonate and a suitable protecting group precursor, such as, but not limited to, 4-methoxybenzyl chloride at a temperature of between 0° C. and 65° C. for between 30 minutes and 5 hours. The resultant compound of formula (103) can be used in the next steps of the synthesis.

Compound of formula (103) is then coupled with amine compound (105) using a polar aprotic solvent, such as, but not limited to, dimethyl sulfoxide or N,N-dimethylformamide, using a base, such as, but not limited to, triethylamine, N,N-diisopropylethylamine or potassium bis(trimethylsilyl)amide or potassium carbonate, at a temperature of between 0° C. and 130° C., for about 30 minutes to 24 hours to afford compound of formula (106).

In parallel, and if necessary to synthesize compound of formula (105), nitrile compound (104) is converted to amine compound of formula (105) under standard catalytic hydrogenation reaction conditions, such as, but not limited to, using a polar solvent, such as, but not limited to, methanol, ethanol and/or water, in the presence of a basic solution, such as, but not limited to, concentrated ammonium hydroxide solution, using a catalyst, such as, but not limited to, Raney-Nickel, in the presence of a reductant, such as, but not limited to, $H_2$ gas at a temperature of between about 0° C. and ambient temperature for about 30 minutes to 72 hours. Alternatively, in certain instances, the catalytic hydrogenation can be carried out in the absence of the base.

Compound of formula (106) is treated with an acid, such as, but not limited to, trifluoroacetic acid or hydrochloric acid, in a polar aprotic solvent, such as, but not limited to, dichloromethane at a temperature of between about 0° C. and ambient temperature to generate a compound of formula (I), which can be isolated from the reaction mixture by standard techniques (e.g., HPLC, column chromatography).

Alternatively, compounds of formula (I), as described above in the Summary of the Invention, can be synthesized following the general procedure described below in Reaction Scheme 2 where

$R^1$, $R^2$, and $R^4$ are as described above in the Summary of the Invention for compounds of formula (I), $X^1$ is bromo, chloro, or iodo, $X^2$ and $X^3$ are, at each occurrence, independently bromo, chloro, or fluoro, $Z^1$ is hydrogen or a nitrogen protecting group, for example, but not limited to, tert-butyloxycarbonyl, 2,4-dimethoxybenzyl, or 4-methoxybenzyl and $Z^2$ is a thiol protecting group, for example, but not limited to, benzyl:

REACTION SCHEME 2

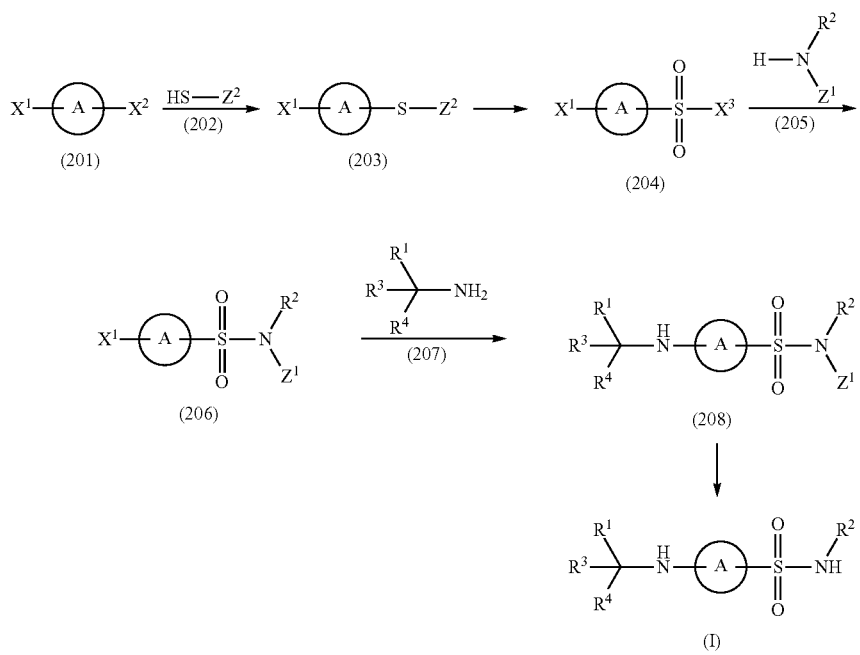

Compounds of formulae (201), (202), (203), (204), (205), (206), (207) and (208) are commercially available or can be prepared according to methods known to one skilled in the art or by methods disclosed herein. In general, the compounds of formula (I) are prepared as described above in Reaction Scheme 2 as follows:

The compound of formula (201) is reacted with thiol compound of formula (202) under standard thiol coupling reaction conditions, such as, but not limited to, the use of a polar aprotic solvent, such as, but not limited to, tetrahydrofuran, in the presence of a base, such as, but not limited to, sodium hydride, at a temperature of between about 0° C. and ambient temperature, for about 30 minutes to 12 hours to generate a compound of formula of formula (203).

The compound of formula of formula (203) can then be treated in a polar protic solvent or solvent system, such as, but not limited to, acetonitrile/water/acetic acid, using an oxidizer, such as, but limited to, 1,3-dichloro-5,5-dimethyl-imidazolidine-2,4-dione (or 1,3-dichloro-5,5-dimethyl-hydantoin) at a temperature of between about 0° C. and ambient temperature to generate compound of formula (204).

Compound of formula (204) is reacted with amine compound of formula (205) in a polar aprotic solvent, such as, but not limited to, N,N-dimethylformamide, using a base, such as, but not limited to, sodium hydride, at a temperature of between 0° C. to ambient temperature for between 30 minutes and 2 hours to generate compound of formula (206).

Compound of formula (206) is reacted with amine compound of formula (207) using a solvent such as, but not limited to, toluene, a base, such as, but not limited to, cesium carbonate, a palladium catalyst, such as, but not limited to, bis(dibenzylideneacetone)palladium(0), and an organophosphorous compound, such as, but not limited to, 4,5-bis(diphenylphosphino)-9,9-dimethylxanthene at a temperature of between ambient temperature and 100° C. for between 30 minutes and 12 hours.

The compound of formula (208) is treated with an acid, such as, but not limited to, hydrogen chloride or trifluoroacetic acid in a solvent, such as, but not limited to, ethyl acetate or dichloromethane at a temperature of between about 0° C. and ambient temperature to generate a compound of formula (I), which can be isolated from the reaction mixture by standard techniques (e.g., HPLC, column chromatography).

Alternatively, compounds of formula (I), as described above in the Summary of the Invention, can be synthesized following the general procedure described below in Reaction Scheme 3 where

, $R^1$, $R^2$, $R^3$ and $R^4$ are as described above in the Summary of the Invention for compounds of formula (I), $X^1$ is bromo, chloro, or iodo, and $Z^1$ is hydrogen or a nitrogen protecting group, for example, but not limited to, tert-butyloxycarbonyl, 2,4-dimethoxybenzyl, or 4-methoxybenzyl:

REACTION SCHEME 3

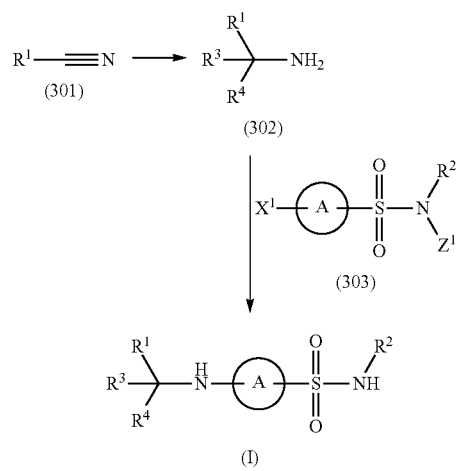

Compound of formulae (301), (302) and (303) can be prepared according to methods known to one skilled in the art or by methods disclosed herein. In general, the compounds of formula (I) are prepared as described above in Reaction Scheme 3 as follows:

The nitrile compound of formula (301) converted to amine compound of formula (302) under standard catalytic hydrogenation reaction conditions, such as, but not limited to, using a polar solvent, such as, but not limited to, methanol, in the presence of a basic solution, such as, but not limited to, concentrated ammonium hydroxide solution, using a catalyst, such as, but not limited to, Raney-Nickel, in the presence of a reductant, such as, but not limited to, $H_2$ gas at a temperature of between about 0° C. and ambient temperature for about 1 to 12 hours to afford a compound of formula (302).

The compound of formula (302) is reacted with the sulfonamide compound (303) in an anhydrous solvent such as, but not limited to, dioxane, 2-methylbutan-2-ol or tetrahydrofuran, using a catalyst, such as, but not limited to, chloro(2-dicyclohexylphosphino-2',6'-dimethoxy-1,1'-biphenyl)(2'-amino-1,1'-biphenyl-2-yl) palladium(II) or [(2-di-tert-butylphosphino-2',4',6'-triisopropyl-1,1'-biphenyl)-2-(2'-amino-1,1'-biphenyl)]palladium(II) methanesulfonate, in the presence of a base, such as, but not limited to, sodium tert-butoxide at a temperature of between ambient temperature and 90° C. for 30 minutes to 12 hours to generate a compound of formula (I), which can be isolated from the reaction mixture by standard techniques.

Alternatively, compounds of formula (I), as described above in the Summary of the Invention, can be synthesized following the general procedure described below in Reaction Scheme 4 where

, $R^1$, $R^2$, $R^3$ and $R^4$ are as described above in the Summary of the Invention for compounds of formula (I), $X^1$ is fluoro, chloro, or bromo, $X^2$ and $X^3$ are, at each occurrence, independently bromo, chloro, or iodo, $Z^1$ is hydrogen or a nitrogen protecting group, for example, but not limited to, tert-butyloxycarbonyl, 2,4-dimethoxybenzyl, or 4-methoxybenzyl, and $Z^2$ is a thiol protecting group, for example, but not limited to, benzyl:

N,N-dimethylformamide or dimethyl sulfoxide in the presence of a base, such as, but not limited to, sodium bicarbonate and a suitable protecting group precursor, such as,

REACTION SCHEME 4

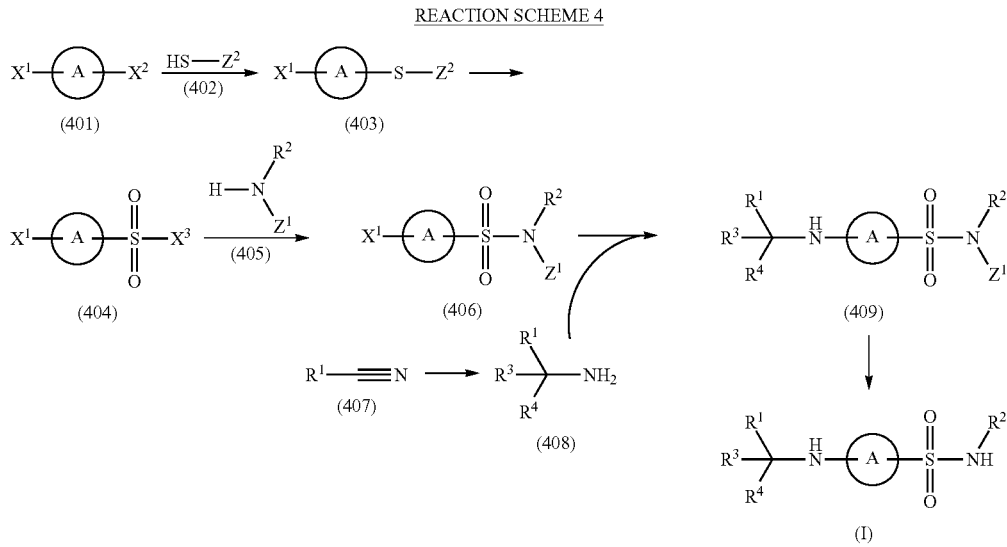

Compound of formulae (401), (402), (403), (404), (405), (406), (407), (408) and (409) can be prepared according to methods known to one skilled in the art or by methods disclosed herein. In general, the compounds of formula (I) are prepared as described above in Reaction Scheme 4 as follows:

Compound of formula (401) is reacted with thiol compound of formula (402) under standard reaction conditions, such as, but not limited to, the use of a polar aprotic solvent, such as, but not limited to, dioxane, in the presence of a base, such as, but not limited to, N,N-diisopropylethylamine, using an organophosphorus compound, such as, but not limited to, 4,5-bis(diphenylphosphino)-9,9-dimethylxanthene, and a palladium catalyst, such as, but not limited to, tris(dibenzylideneacetone)dipalladium(0) at a temperature of between about 0° C. and reflux, for about 30 minutes to 20 hours to generate compound of formula (403).

The compound of formula (403) can then be treated in a polar protic solvent or solvent system, such as, but not limited to, acetonitrile/water/acetic acid, using an oxidizer, such as, but limited to, 1,3-dichloro-5,5-dimethylimidazolidine-2,4-dione (or 1,3-dichloro-5,5-dimethylhydantoin) at a temperature of between about 0° C. and ambient temperature to generate compound of formula (404).

Compound of formula (404) is reacted with amine compound of formula (405) in a polar aprotic solvent, such as, but not limited to, tetrahydrofuran, using a base, such as, but not limited to, lithium bis(trimethylsilyl)amide, at a temperature of between −78° C. for between 30 minutes and 18 hours to generate compound of formula (406).

Additionally, in the instance that $Z^1$ is an amine protecting group (e.g., tert-butyloxycarbonyl) and an alternative protecting group is desired, $Z^1$ can be removed using an acid, such as, but not limited to, trifluoroacetic acid in a polar aprotic solvent, such as, but not limited to, dichloromethane at a temperature of between 0° C. and ambient temperature for between 30 minutes and 5 hours. An alternative protecting group can then be added to the resultant compound by adding a polar aprotic solvent, such as, but not limited to, but not limited to, 4-methoxybenzyl chloride at a temperature of between 0° C. and 65° C. for between 30 minutes and 5 hours. The resultant compound of formula (406) can be used in the next steps of the synthesis.

In parallel, and if necessary to synthesize compound of formula (408), nitrile compound of formula (407) is converted to amine compound of formula (408) under standard catalytic hydrogenation reaction conditions, such as, but not limited to, using a polar solvent, such as, but not limited to, methanol, ethanol and/or water, in the presence of a basic solution, such as, but not limited to, concentrated ammonium hydroxide solution, using a catalyst, such as, but not limited to, Raney-Nickel, in the presence of a reductant, such as, but not limited to, $H_2$ gas at a temperature of between about 0° C. and ambient temperature for about 30 minutes to 72 hours. Alternatively, in certain instances, the catalytic hydrogenation can be carried out in the absence of the base.

Compound of formula (406) is reacted with amine compound of formula (408) using a solvent such as, but not limited to, dimethyl sulfoxide or N,N-dimethylformamide and a base, such as, but not limited to, N,N-diisopropylethylamine or potassium carbonate at a temperature of between ambient temperature and 130° C. for between 30 minutes and 18 hours to afford compound of formula (409).

The compound (409) is treated with an acid, such as, but not limited to, trifluroroacetic acid in a solvent, such as, but not limited to, dichloromethane or 1,2-dichloroethane at a temperature of between about 0° C. and reflux for between 30 minutes and 18 hours to generate a compound of formula (I), which can be isolated from the reaction mixture by standard techniques.

Under certain conditions, the above cross coupling of of formulae (406) and (408) will afford a compound of formula (I) instead of a compound of formula (409). In these instances, the compound of formula (I) can be isolated from the reaction mixture by standard techniques.

Alternatively, compounds of formula (I), as described above in the Summary of the Invention, can be synthesized following the general procedure described below in Reaction Scheme 5 where

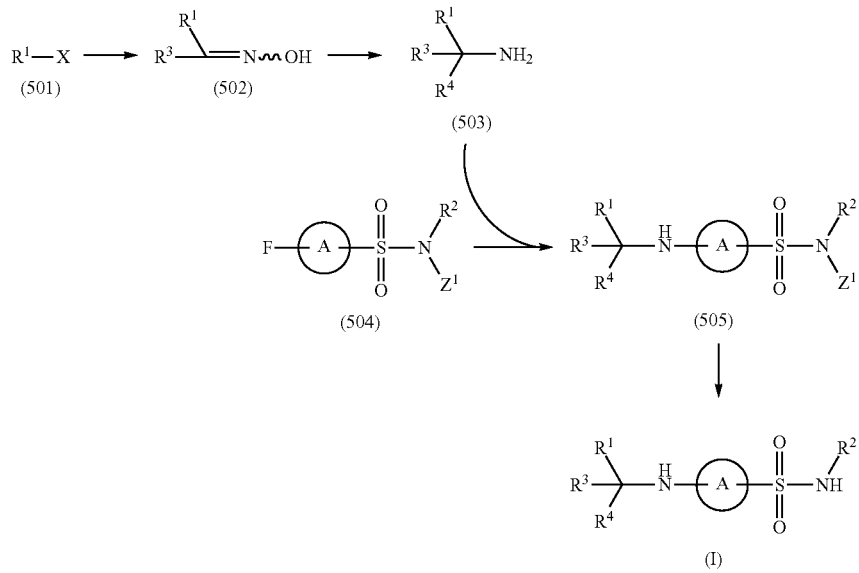, $R^1$, $R^2$, $R^3$ and $R^4$ are as described above in the Summary of the Invention for compounds of formula (I), X is bromo, chloro, or iodo and $Z^1$ is hydrogen or a nitrogen protecting group, for example, but not limited to, tert-butyloxycarbonyl, 2,4-dimethoxybenzyl, or 4-methoxybenzyl:

Compounds of formulae (501), (502), (503), (504) and (505) are commercially available or can be prepared according to methods known to one skilled in the art or by methods disclosed herein. In general, the compounds of formula (I) are prepared as described above in Reaction Scheme 5 as follows:

The compound of formula (501) converted to oxime compound of formula (502) under standard reaction conditions, such as, but not limited to, using a polar aprotic solvent, such as, but not limited to, tetrahydrofuran, a Grignard reagent, such as, but not limited to, isopropylmagnesium chloride lithium chloride, an aldehyde surrogate, such as, but not limited to, N,N-dimethylformamide, and an amine in a polar protic solvent, such as, but not limited to, hydroxylamine hydrochloride in water at a temperature of between about 0° C. and ambient temperature, for about 1 to 16 hours to afford a compound of formula (502).

The compound of formula (502) is reduced with a hydride such as, but not limited to, lithium aluminum hydride, using a solvent, such as, but not limited to, tetrahydrofuran at a temperature of between about 0° C. and ambient temperature, for about 30 minutes to 16 hours to generate a compound of formula (503).

The compound of formula (503) is reacted with the sulfonamide compound (504) in an anhydrous solvent such as, but not limited to, dimethyl sulfoxide or N,N-dimethylformamide, in the presence of a base, such as, but not limited to, N,N-diisopropylethylamine at a temperature of between ambient temperature and 130° C. for 30 minutes to 18 hours to generate a compound of formula (I), which can be isolated from the reaction mixture by standard techniques.

Alternatively, when $Z^1$ is an amine protecting group as shown in the compound of formula (505), the amine protecting group is treated with an acid, such as, but not limited to, trifluoroacetic acid or hydrochloric acid, in a polar aprotic solvent, such as, but not limited to, dichloromethane at a temperature of between about 0° C. and ambient temperature to generate a compound of formula (I), which can be isolated from the reaction mixture by standard techniques.

Alternatively, compounds of formula (I), as described above in the Summary of the Invention, can be synthesized following the general procedure described below in Reaction Scheme 6 where $R^3$ and $R^4$ are each hydrogen and

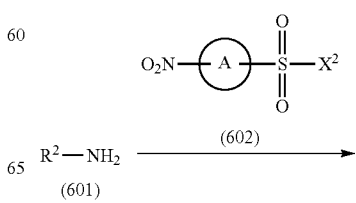, $R^1$ and $R^2$ are as described above in the Summary of the Invention for compounds of formula (I), $X^2$ is bromo, chloro, or iodo, $Z^1$ is a nitrogen protecting group, for example, but not limited to, tert-butyloxycarbonyl, 2,4-dimethoxybenzyl, or 4-methoxybenzyl:

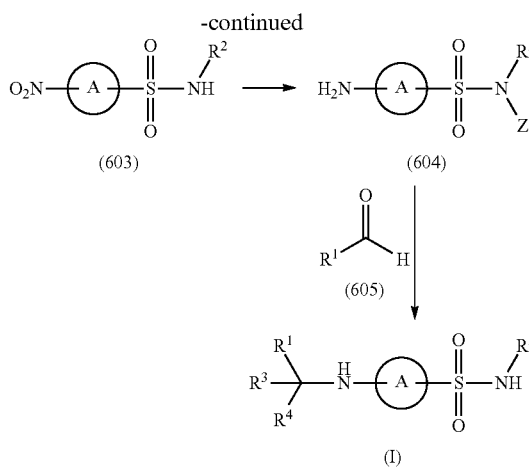

Compounds of formulae (601), (602), (603), (604) and (605) are commercially available or can be prepared according to methods known to one skilled in the art or by methods disclosed herein. In general, the compounds of formula (I) are prepared as described above in Reaction Scheme 6 as follows:

The compound of formula (601) is reacted with a sulfonyl halide compound of formula (602), under standard reaction conditions, such as, but not limited to, the use of a solvent, such as, but not limited to, dichloromethane, in the presence of a base, such as, but not limited to, pyridine, at a temperature of between about 0° C. and ambient temperature, for about 30 minutes to 72 hours to generate a compound of formula (603).

The compound of formula (603) can then be treated with for example, but not limited to, an acid, such as, but not limited to, acetic acid, and a reducing agent, such as, but not limited to, iron powder, at a temperature of between about ambient temperature and 60° C. to generate a compound of formula (604).

The resultant amine compound of formula (604) is reacted with the aldehyde compound of formula (605) under standard reductive amination conditions, such as, including but not limited to, use of an acid, such as, but not limited to, trifluoroacetic acid and a hydride, such as, but not limited to, sodium triacetoxyborohydride at about 0° C. to ambient temperature for between 30 minutes and 1 hour to generate a compound of formula (I), which can be isolated from the reaction mixture by standard techniques.

Compounds of formulae (Id) and (Ie), as described above in the Embodiments of the Invention, are compounds of formula (I), as described above in the Summary of the Invention, and can be synthesized following the general procedure described below in Reaction Scheme 7 where n is 1 or 2, m is 1, 2 or 3, $R^3$ and $R^4$ are each hydrogen, $R^1$ and $R^2$ are as described above in the Embodiments of the Invention for compounds of formulae (Id) and (Ie), $R^{5a}$ is alkyl, haloalkyl or optionally substituted cycloalkyl, $X^1$, $X^2$ and $X^3$ are, at each occurrence, independently bromo, chloro, or iodo, $Z^1$ is hydrogen or a nitrogen protecting group, for example, but not limited to, tert-butyloxycarbonyl, 2,4-dimethoxybenzyl, or 4-methoxybenzyl, and $Z^2$ is a thiol protecting group, for example, but not limited to, benzyl:

REACTION SCHEME 7

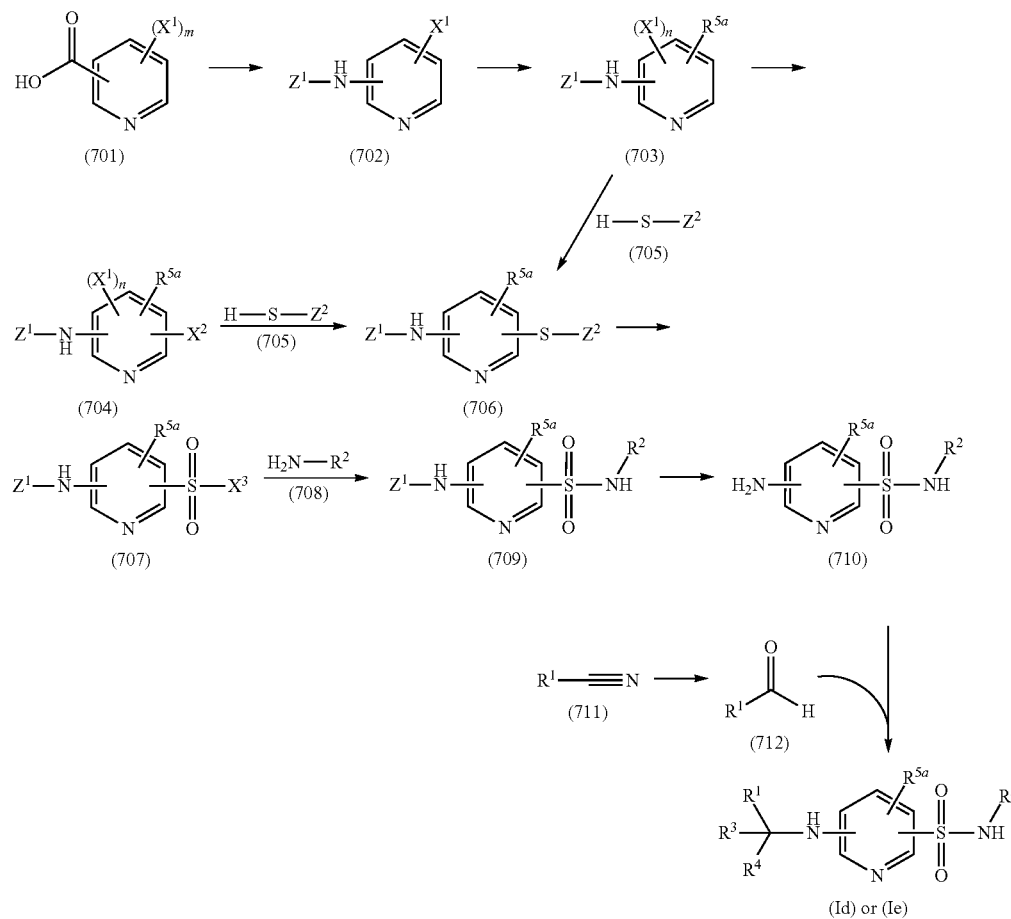

Compounds of formulae (701), (702), (703), (704), (705), (706), (707), (708), (709), (710), (711) and (712) are commercially available or can be prepared according to methods known to one skilled in the art or by methods disclosed herein. In general, the compounds of formula (I) are prepared as described above in Reaction Scheme 7 as follows:

The carboxylic acid compound of formula (701) is converted to the protected amine compound of formula (702) using a solvent mixture, such as, but not limited to, tert-butanol and toluene and an azide compound, such as, but not limited to, diphenylphosphoryl azide, at a temperature of between about ambient temperature and 90° C., for about 30 minutes to 4 hours to generate a compound of formula (702).

The compound of formula (702) can be converted under standard Suzuki-Miyaura cross-coupling conditions to a compound of formula (703) using a solvent mixture, such as, but not limited to, toluene and water, a boronic acid compound, such as, but not limited to, methylboronic acid and a base, such as, but not limited to, potassium phosphate tribasic in the presence of a palladium catalyst, such as, but not limited to, dichloro[1,1'-bis(diphenylphosphino)ferrocene]palladium (II) dichloromethane adduct, at a temperature of between about ambient temperature and 100° C., for about 30 minutes to 16 hours to generate a compound of formula (703).

Compound of (703) when n is 2 is reacted with thiol compound of formula (705) under standard reaction conditions, such as, but not limited to, the use of a polar aprotic solvent, such as, but not limited to, dioxane, in the presence of a base, such as, but not limited to, N,N-diisopropylethylamine, using an organophosphorus compound, such as, but not limited to, 4,5-bis(diphenylphosphino)-9,9-dimethylxanthene, and a palladium catalyst, such as, but not limited to, tris(dibenzylideneacetone)dipalladium(0) at a temperature of between about 0° C. and reflux, for about 30 minutes to 20 hours to generate compound of formula (706).

Alternatively, Compound of formula (703) when n is 1 is halogenated to afford reaction intermediate (704) using a solvent mixture, such as, but not limited to, acetonitrile and N,N-dimethylformamide, a bromo-compound, such as, but not limited to, N-bromosuccinimide, at a temperature of between about ambient temperature and 80° C., for about 30 minutes to 16 hours to generate a compound of formula (704), when can then be reacted with a compound of formula (705) as described above to generate a compound of formula (706).

The compound of formula of formula (706) can then be treated in a polar protic solvent or solvent system, such as, but not limited to, acetonitrile/water/acetic acid, using an oxidizer, such as, but not limited to, 1,3-dichloro-5,5-dimethyl-imidazolidine-2,4-dione (or 1,3-dichloro-5,5-dimethyl-hydantoin) at a temperature of between about 0° C. and ambient temperature to generate compound of formula (707).

The compound of formula (707) is reacted with amine compound of formula (708) using a basic solvent, such as, but not limited to, pyridine, at a temperature of between 0° C. and ambient temperature for between 30 minutes and 16 hours to generate compound of formula (709).

Compound of formula (709) is treated with an acid, such as, but not limited to, trifluroroacetic acid or hydrogen chloride in a solvent, such as, but not limited to, dioxane, dichloromethane or 1,2-dichloroethane at a temperature of between about 0° C. and reflux for between 30 minutes and 16 hours to generate a compound of formula (710).

In parallel, and if necessary to synthesize compound of formula (712), the nitrile compound of formula (711) is converted to the aldehyde compound of formula (712) using a polar aprotic solvent, such as, but not limited to, dichloromethane, in the presence of a hydride, such as, but not limited to, diisobutylaluminum hydride, at a temperature of between about −78° C. and ambient temperature for about 30 minutes to 6 hours.

Compound of formula (710) is reacted with aldehyde compound of formula (712) using a solvent such as, but not limited to, tetrahydrofuran and a reductant, such as, but not limited to, sodium cyanoborohydride and a titanium compound, such as, but not limited to, titanium (IV) isopropoxide at a temperature of between 0° C. and ambient temperature for between 30 minutes and 5 hours to generate a compound of formula (Id) or a compound of formula (Ie), both of which are compounds of formula (I), which can be isolated from the reaction mixture by standard techniques.

Compounds of formula (Ia), as described above in the Embodiments of the Invention, are compounds of formula (I), as described above in the Summary of the Invention, and can be synthesized following the general procedure described below in Reaction Scheme 8 where $R^1$, $R^2$, $R^3$ and $R^4$ are as described above in the Embodiments of the Invention for compounds of formula (Ia), $X^1$ and $X^2$ are, at each occurrence, independently fluoro, bromo, chloro, or iodo, and $Z^1$ and $Z^2$ are, at each occurrence, independently hydrogen or a nitrogen protecting group, for example, but not limited to, tert-butyloxycarbonyl, 2,4-dimethoxybenzyl, or 4-methoxybenzyl:

REACTION SCHEME 8

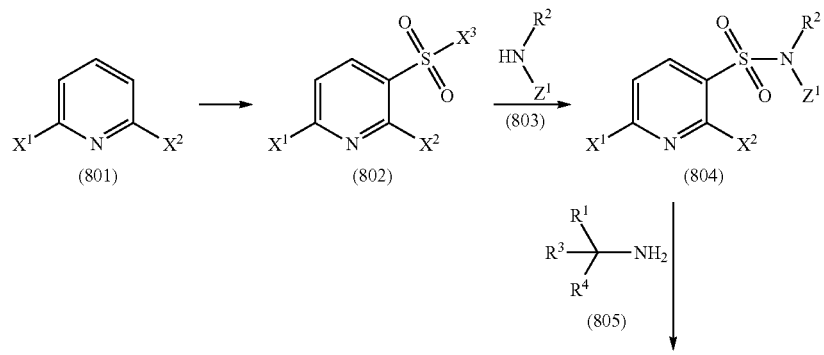

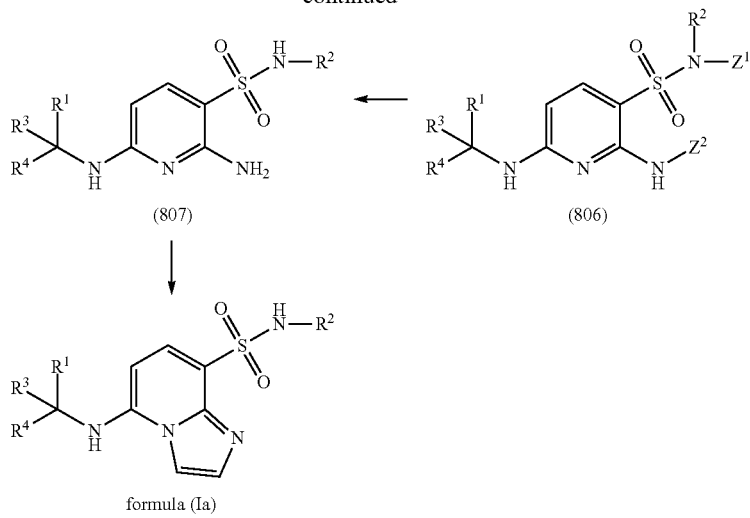

formula (Ia)

Compounds of formulae (801), (802), (803), (804), (805), (806), and (807) are commercially available or can be prepared according to methods known to one skilled in the art or by methods disclosed herein. In general, the compounds of formula (Ia) are prepared as described above in Reaction Scheme 8 as follows:

The compound of formula (801) is reacted with a lithium agent, for example, but not limited to, n-butyl lithium, in a polar aprotic solvent, such as, but not limited to, tetrahydrofuran and a sulfur reagent, such as, but not limited to sulfur dioxide gas and a halogenating reagent, such as, but not limited to, N-chlorosuccinimide at a temperature of about −78° C. to ambient temperature for about 1 to 20 hours, to generate a compound of formula (802).

The compound of formula (802) is then reacted with the amine compound of formula (803) using a polar aprotic solvent, such as, but not limited to, tetrahydrofuran in the presence of a base, such as, but not limited to, lithium bis(trimethylsilyl)amideat a temperature between about −78° C. and ambient temperature for 30 minutes to 16 hours to afford a compound of formula (804).

The compound of formula (804) was reacted with amine compound of formula (805) using a polar aprotic solvent, such as, but not limited to, dimethyl sulfoxide, using a base, such as, but not limited to, triethylamine as well as an amine compound, such as, but not limited to, 2,4-dimethoxybenzylamine at a temperature of between 0° C. and ambient temperature, for about 30 minutes to 16 hours to afford compound of formula (806).

The compound of formula (806) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (807).

The compound of formula (807) is reacted with an aldehyde, such as, but not limited to, chloroacetaldehyde in a solvent, such as, but not limited to, ethanol at a temperature of between ambient temperature and 90° C. for between 30 minutes and 16 hours to afford the compound of formula (Ia), which can be isolated from the reaction mixture by standard techniques.

It is understood that further modifications to the compounds of formula (I), (Ia), (Id) and (Ie), as prepared above in Reaction Schemes 1-8, can be made by methods known by one skilled in the art or by the methods disclosed herein to afford compounds of formula (I), (Ia), (Id) and (Ie) wherein $A$, $R^1$, $R^2$, $R^3$, $R^4$, $R^5$, $R^6$, $R^7$, $R^8$, $R^9$ and $R^{10}$ are as fully described above for compounds of formula (I) in the Summary of the Invention, or as fully described above for compounds of formula (Ia), (Id) and (Ie) in the Embodiments of the Invention. For example, but not limited to, a compound of formula (I) wherein $R^1$ is 2-bromo-6-fluorophenyl, may be treated with the appropriately substituted potassium trifluoroborate salt under standard Suzuki-Miyaura conditions to afford a compound of formula (I) where $R^1$ is 2-fluoro-6-(pyrrolidin-1-ylmethyl)phenyl).

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

The following Examples, which are directed to the synthesis of the compounds of the invention; and the following Biological Examples are provided as a guide to assist in the practice of the invention, and are not intended as a limitation on the scope of the invention.

In the Examples below, unless otherwise indicated all temperatures are set forth in degrees Celsius. Commercially available reagents were purchased from suppliers such as Aldrich Chemical Company, Combi-Blocks, TCI or Oakwood Chemicals and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Yields were not optimized. Melting points (m.p.) were determined on a Buchi hot-stage apparatus and are uncorrected. $^1$H NMR, $^{19}$F and $^{13}$C NMR data were obtained in deuterated CDCl$_3$, DMSO-d$_6$, CD$_3$OD, CD$_3$CN, or acetone-d$_6$ solvent solutions with chemical shifts (δ) reported in parts-per-million (ppm) relative to trimethylsilane (TMS) or the residual non-deuterated solvent peaks as the reference standard. Data are reported as follows, if applicable: chemical shift, multiplicity, coupling constant in Hz, and number of protons, fluorine or carbon atoms. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, are reported in Hz (Hertz).

Example 1

Synthesis of (S)-5-chloro-6-((1-(5-chloro-2-fluorophenyl)ethyl)amino)-N-(thiazol-4-yl)pyridine-3-sulfonamide

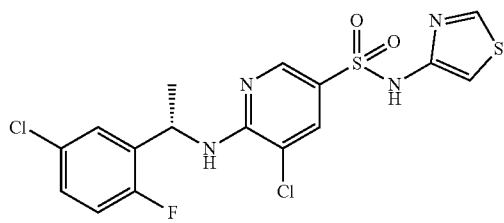 [SMILES: C[C@H](Nc1ncc(S(=O)(=O)Nc2cscn2)cc1Cl)c1cc(Cl)ccc1F]

Step 1. Preparation of tert-butyl ((5,6-dichloropyridin-3-yl)sulfonyl)(thiazol-4-yl)carbamate

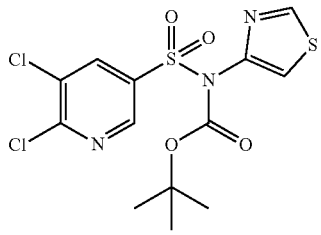 [SMILES: CC(C)(C)OC(=O)N(c1cscn1)S(=O)(=O)c1cnc(Cl)c(Cl)c1]

To a solution of tert-butyl thiazol-4-ylcarbamate (1.000 g, 4.06 mmol) in anhydrous tetrahydrofuran (13 mL) was added a 1 M solution of lithium bis(trimethylsilyl)amide in tetrahydrofuran (4.5 mL, 4.5 mmol) at −78° C. The reaction mixture was stirred at −78° C. for 30 minutes, allowed to warm to ambient temperature and stirred for 20 minutes. The reaction mixture was cooled to −78° C., and a solution of 5,6-dichloropyridine-3-sulfonyl chloride (0.894 g, 3.63 mmol) in anhydrous tetrahydrofuran (9 mL) was added to it. The reaction mixture was stirred at −78° C. for 30 minutes, allowed to warm to ambient temperature, and stirred for 4 hours. After addition of saturated aqueous ammonium chloride (20 mL), the mixture was extracted with ethyl acetate (3×20 mL). The combined organic phases were washed with brine (20 mL), dried over anhydrous sodium sulfate, and filtered. Concentration of the filtrate under reduced pressure gave a residue which was triturated with methanol (20 mL) to afford the title compound as a beige solid (1.13 g, 76% yield): $^1$H NMR (300 MHz, CDCl$_3$) δ 8.97 (d, J=2.2 Hz, 1H), 8.81 (d, J=2.3 Hz, 1H), 8.54 (d, J=2.2 Hz, 1H), 7.58 (d, J=2.3 Hz, 1H), 1.40 (s, 9H).

Step 2. Preparation of tert-butyl (S)-((5-chloro-6-((1-(5-chloro-2-fluorophenyl)ethyl)amino)pyridin-3-yl)sulfonyl)(thiazol-4-yl)carbamate

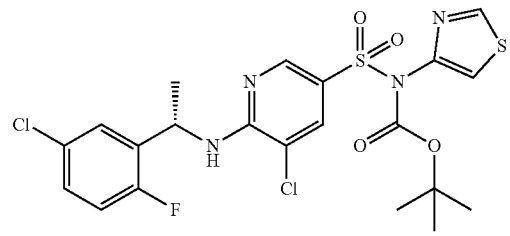 [SMILES: C[C@H](Nc1ncc(S(=O)(=O)N(C(=O)OC(C)(C)C)c2cscn2)cc1Cl)c1cc(Cl)ccc1F]

To a solution of tert-butyl ((5,6-dichloropyridin-3-yl)sulfonyl)(thiazol-4-yl)carbamate (0.20 g, 0.49 mmol) anhydrous dimethyl sulfoxide (5 mL) was added (S)-1-(5-chloro-2-fluorophenyl)ethan-1-amine hydrochloride (0.102 g, 0.49 mmol) and triethylamine (0.27 mL, 1.9 mmol) and the reaction mixture was at ambient temperature for 24 hours. Saturated aqueous ammonium chloride (5 mL) was added and the mixture extracted with ethyl acetate (3×5 mL). The combined organic phases were washed with brine (5 mL), dried over anhydrous sodium sulfate, and filtered. Concentration of the filtrate in vacuo and purification of the residue by column chromatography eluting with a gradient of 5 to 60% of ethyl acetate in hexanes afforded the title compound as a yellow oil (0.102 g, 38% yield): MS (ES+) m/z 447.1 (M−99), 449.3 (M−99).

Step 3. Preparation of (S)-5-chloro-6-((1-(5-chloro-2-fluorophenyl)ethyl)amino)-N-(thiazol-4-yl)pyridine-3-sulfonamide

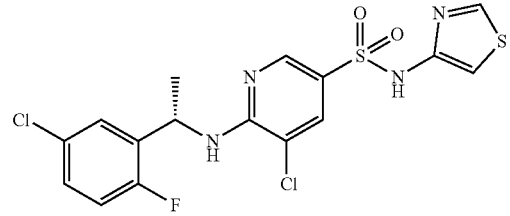 [SMILES: C[C@H](Nc1ncc(S(=O)(=O)Nc2cscn2)cc1Cl)c1cc(Cl)ccc1F]

To a solution of tert-butyl (S)-((5-chloro-6-((1-(5-chloro-2-fluorophenyl)ethyl)amino)pyridin-3-yl)sulfonyl)(thiazol-4-yl)carbamate (0.102 g, 0.186 mmol) in dichloromethane (5 mL) was added trifluoroacetic acid (1 mL) and the reaction mixture was stirred at ambient temperature for 1 hour. Methanol (5 mL) was added and the mixture concentrated in vacuo. Purification of the residue by column chromatography, eluting with a gradient of 20 to 80% of ethyl acetate (containing 10% isopropanol and 10% triethylamine) in hexanes to afford the title compound as a colorless solid (0.028 g, 33% yield): $^1$H NMR (300 MHz, DMSO-d$_6$) δ 11.06 (broad s, 1H), 8.84 (d, J=2.1 Hz, 1H), 8.27 (d, J=1.9 Hz, 1H), 7.88 (d, J=2.0 Hz, 1H), 7.65 (d, J=8.0 Hz, 1H), 7.50 (dd, J=6.5, 2.5 Hz, 1H), 7.35-7.29 (m, 1H), 7.21 (dd, J=9.3, 9.2 Hz, 1H), 6.95-6.93 (m, 1H), 5.56-5.51 (m, 1H), 1.51-1.48 (d, J=7.2 Hz, 3H); MS (ES+) m/z 447.0 (M+1), 449.0 (M+1).

Example 2

Synthesis of (S)-5-chloro-6-((1-(2-fluorophenyl)ethyl)amino)-N-(thiazol-4-yl)pyridine-3-sulfonamide

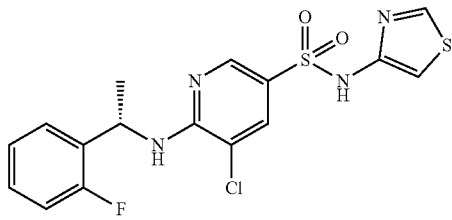 [SMILES: C[C@H](Nc1ncc(S(=O)(=O)Nc2cscn2)cc1Cl)c1ccccc1F]

Step 1. Preparation of tert-butyl (S)-((5-chloro-6-((1-(2-fluorophenyl)ethyl)amino)pyridin-3-yl)sulfonyl)(thiazol-4-yl)carbamate

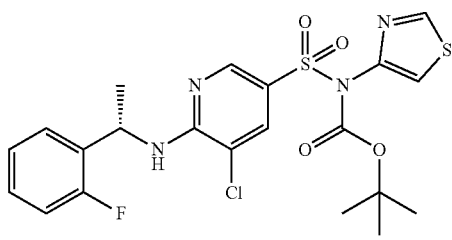 [SMILES: C[C@H](Nc1ncc(S(=O)(=O)N(C(=O)OC(C)(C)C)c2cscn2)cc1Cl)c1ccccc1F]

Following the procedure as described for EXAMPLE 1, Step 2 and making non-critical variations as required to replace (S)-1-(5-chloro-2-fluorophenyl)ethan-1-amine hydrochloride with (S)-1-(2-fluorophenyl)ethan-1-amine, the title compound was obtained as a colorless solid (0.233 g, 47% yield): MS (ES+) m/z 513.1 (M+1), 515.1 (M+1).

Step 2. Preparation of (S)-5-chloro-6-((1-(2-fluorophenyl)ethyl)amino)-N-(thiazol-4-yl)pyridine-3-sulfonamide

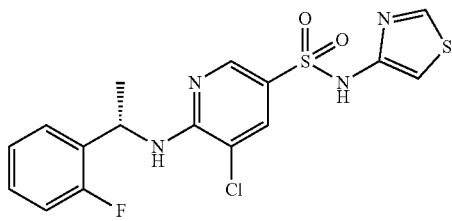 [SMILES: C[C@H](Nc1ncc(S(=O)(=O)Nc2cscn2)cc1Cl)c1ccccc1F]

Following the procedure as described for EXAMPLE 1, Step 3 and making non-critical variations as required to replace tert-butyl (S)-((5-chloro-6-((1-(5-chloro-2-fluorophenyl)ethyl)amino)pyridin-3-yl)sulfonyl)(thiazol-4-yl)carbamate with tert-butyl (S)-((5-chloro-6-((1-(2-fluorophenyl)ethyl)amino)pyridin-3-yl)sulfonyl)(thiazol-4-yl)carbamate, the title compound was obtained as a colorless solid (0.168 g, 90% yield): ¹H-NMR (300 MHz, DMSO-d₆) δ 10.95 (s, 1H), 8.88 (d, J=2.2 Hz, 1H), 8.27 (d, J=2.1 Hz, 1H), 7.88 (d, J=2.2 Hz, 1H), 7.68 (d, J=7.8 Hz, 1H), 7.45-7.39 (m, 1H), 7.29-7.21 (m, 1H), 7.16-7.09 (m, 2H), 7.08 (d, J=2.1 Hz, 1H), 5.59-5.52 (m, 1H), 1.50 (d, J=7.1 Hz, 3H); MS (ES+) m/z 413.1 (M+1), 415.1 (M+1).

Example 3

Synthesis of (S)-5-((1-(2-fluorophenyl)ethyl)amino)-6-methyl-N-(thiazol-4-yl)pyridine-2-sulfonamide

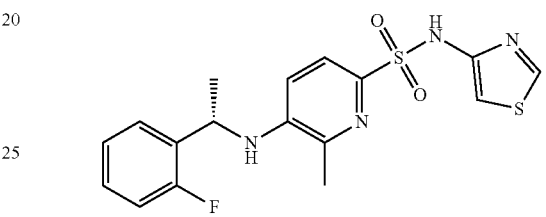

Step 1. Preparation of 6-(benzylthio)-3-bromo-2-methylpyridine

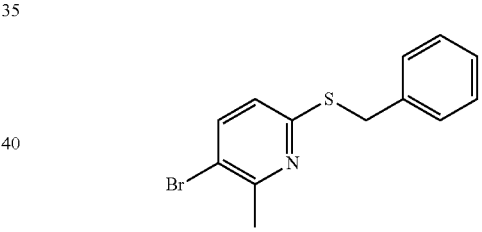

To a solution of benzyl mercaptan (3.69 g, 29.7 mmol) in anhydrous tetrahydrofuran (50 mL) was added sodium hydride (60% dispersion in mineral oil, 1.48 g, 37.1 mmol) in portions at 0° C. The reaction mixture was allowed to warm to ambient temperature and stirred for 1 hour. The reaction mixture was then cooled to 0° C. and a solution of 3-bromo-6-fluoro-2-methylpyridine (4.70 g, 24.7 mmol) in anhydrous tetrahydrofuran (25 mL) was added dropwise. The reaction mixture was allowed to warm to ambient temperature and stirred for 12 hours. After addition of water (200 mL), the mixture was extracted with ethyl acetate (3×200 mL). The combined organic layers were washed with brine (50 mL), dried over anhydrous sodium sulfate, and filtered. Concentration of the filtrate in vacuo and purification of the residue by column chromatography, eluting with petroleum ether, afforded the title compound as a red oil (7.0 g, 96% yield): ¹H NMR (400 MHz, CDCl₃) δ 11.06 (7.57 (d, J=8.2 Hz, 1H), 7.42 (d, J=7.2 Hz, 2H), 7.36-7.29 (m, 3H), 6.88 (d, J=8.2 Hz, 1H), 4.42 (s, 2H), 2.66 (s, 3H); MS (ES+) m/z 294.0 (M+1), 296.0 (M+1).

Step 2. Preparation of 5-bromo-6-methylpyridine-2-sulfonyl chloride

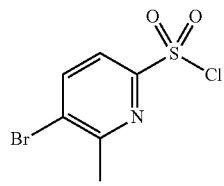

To a solution of 6-(benzylthio)-3-bromo-2-methylpyridine (5.20 g, 17.7 mmol) in a mixture of acetonitrile (50 mL), water (10 mL) and acetic acid (10 mL) was added 1,3-dichloro-5,5-dimethylimidazolidine-2,4-dione (6.96 g, 35.3 mmol) in portions at 0° C. The reaction mixture was stirred at 0° C. for 30 minutes. Saturated aqueous sodium bicarbonate solution (80 mL) was added to the mixture until pH 7 was reached, and the mixture was extracted with ethyl acetate (3×60 mL). The combined organic layers were washed with brine (20 mL), dried over anhydrous sodium sulfate, and filtered. Concentration of the filtrate in vacuo and purification of the residue by column chromatography, eluting with 1% of ethyl acetate in petroleum ether, afforded the title compound as a colorless solid (1.70 g, 36% yield): $^1$H NMR (400 MHz, CDCl$_3$) δ 8.15 (d, J=8.2 Hz, 1H), 7.82 (d, J=8.2 Hz, 1H), 2.83 (s, 3H); MS (ES+) m/z 269.8 (M+1), 271.9 (M+1).

Step 3. Preparation of tert-butyl ((5-bromo-6-methylpyridin-2-yl)sulfonyl)(thiazol-4-yl)carbamate

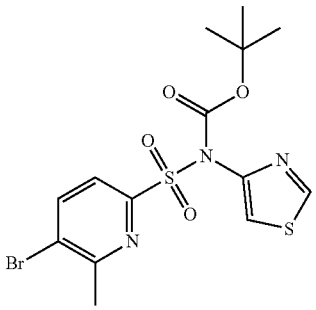 [SMILES: Cc1nc(S(=O)(=O)N(C(=O)OC(C)(C)C)c2cscn2)ccc1Br]

To a solution of tert-butyl thiazol-4-ylcarbamate (0.85 g, 4.24 mmol) in anhydrous N,N-dimethylformamide (20 mL) was added sodium hydride (60% dispersion in mineral oil, 0.20 g, 5.09 mmol) in portions at 0° C. The reaction mixture was stirred at 0° C. for 30 minutes, after which a solution of 5-bromo-6-methylpyridine-2-sulfonyl chloride (1.26 g, 4.66 mmol) in anhydrous N,N-dimethylformamide (8 mL) was added dropwise. The reaction mixture was allowed to warm to ambient temperature and stirred for 2 hours. The mixture was diluted with water (100 mL) and extracted with ethyl acetate (3×80 mL). The combined organic layers were washed with brine (50 mL), dried over anhydrous sodium sulfate, and filtered. Concentration of the filtrate in vacuo and purification of the residue by preparative thin layer chromatography, eluting with 30% of ethyl acetate in petroleum ether, provided the title compound as a colorless solid (0.35 g, 19% yield): $^1$H NMR (400 MHz, CDCl$_3$) δ 8.83 (d, J=2.0 Hz, 1H), 8.10 (d, J=8.2 Hz, 1H), 7.96 (d, J=8.2 Hz, 1H), 7.71 (d, J=2.0 Hz, 1H), 2.80 (s, 3H), 1.34 (s, 9H); MS (ES+) m/z 434.0 (M+1), 436.0 (M+1).

Step 4. Preparation of tert-butyl (S)-((5-((1-(2-fluorophenyl)ethyl)amino)-6-methylpyridin-2-yl)sulfonyl)(thiazol-4-yl)carbamate

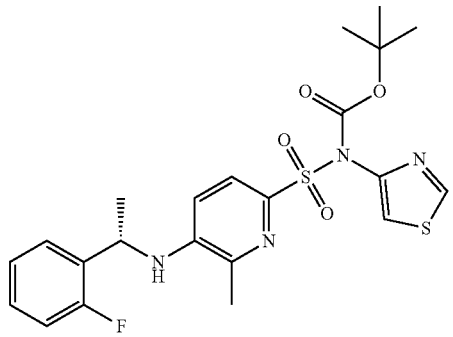 [SMILES: Cc1nc(S(=O)(=O)N(C(=O)OC(C)(C)C)c2cscn2)ccc1N[C@@H](C)c1ccccc1F]

To a solution of tert-butyl (5-bromo-6-methylpyridin-2-yl)sulfonyl(thiazol-4-yl)carbamate (0.15 g, 0.345 mmol), (S)-1-(2-fluorophenyl)ethanamine (0.096 g, 0.691 mmol) and cesium carbonate (0.45 g, 1.38 mmol) in anhydrous toluene (5 mL) was added bis(dibenzylideneacetone)palladium(0) (0.040 g, 0.069 mmol) and 4,5-bis(diphenylphosphino)-9,9-dimethylxanthene (0.040 g, 0.069 mmol). The reaction mixture was heated at 100° C. for 12 hours. After addition of water (30 mL), the reaction mixture was extracted with ethyl acetate (3×30 mL). The combined organic layers were washed brine (20 mL), dried over anhydrous sodium sulfate, and filtered. Concentration of the filtrate in vacuo and purification of the residue by preparative thin layer chromatography, eluting with 50% of ethyl acetate in petroleum ether, provided the title compound as a colorless solid (0.020 g, 12% yield): MS (ES+) m/z 493.2 (M+1).

Step 5. Preparation of (S)-5-((1-(2-fluorophenyl)ethyl)amino)-6-methyl-N-(thiazol-4-yl)pyridine-2-sulfonamide

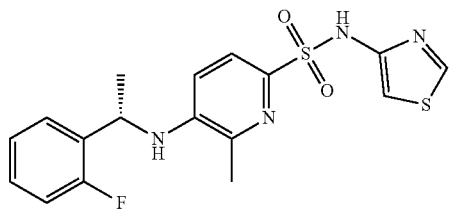 [SMILES: Cc1nc(S(=O)(=O)Nc2cscn2)ccc1N[C@@H](C)c1ccccc1F]

To (S)-tert-butyl(5-((1-(2-fluorophenyl)ethyl)amino)-6-methylpyridin-2-yl)sulfonyl(thiazol-4-yl)carbamate (0.035 g, 0.071 mmol) was added a 4 M solution of hydrogen chloride in ethyl acetate (14 mL), and the mixture was stirred at ambient temperature for 30 minutes. Concentration in vacuo and purification of the residue by preparative reverse phase HPLC using acetonitrile in water containing 0.2% formic acid as eluent to afford provided the title compound as a colorless solid (0.023 g, 73% yield): $^1$H NMR (400 MHz, CDCl$_3$) δ 9.20 (s, 1H), 8.64 (d, J=2.4 Hz, 1H), 7.59 (d, J=8.4 Hz, 1H), 7.28-7.18 (m, 2H), 7.12-7.06

(m, 2H), 7.02 (d, J=2.0 Hz, 1H), 6.53 (d, J=8.4 Hz, 1H), 4.82 (quin, J=6.4 Hz, 1H), 4.38 (br d, J=6.0 Hz, 1H), 2.43 (s, 3H), 1.64 (d, J=6.8 Hz, 3H); MS (ES+) m/z 393.1 (M+1).

Example 4

Synthesis of 5-((2-(azetidin-1-ylmethyl)-6-fluorobenzyl)amino)-6-methyl-N-(thiazol-4-yl)pyridine-2-sulfonamide

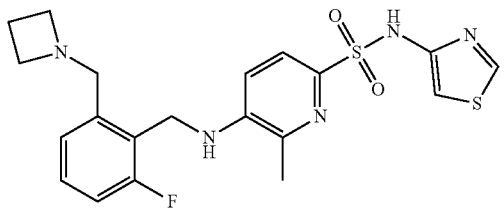 [SMILES: Cc1nc(S(=O)(=O)Nc2cscn2)ccc1NCc1c(F)cccc1CN1CCC1]

Step 1. Preparation of 2-(azetidin-1-ylmethyl)-6-fluorobenzonitrile

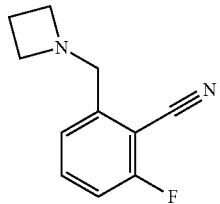 [SMILES: N#Cc1c(F)cccc1CN1CCC1]

To a solution of 2-(bromomethyl)-6-fluorobenzonitrile (11.50 g, 53.7 mmol) in anhydrous dichloromethane (150 mL) was added azetidine hydrochloride (6.03 g, 64.5 mmol) and N,N-diisopropylethylamine (20.83 g, 161.2 mmol) and the reaction mixture was stirred at ambient temperature for 2 hours. After addition of water (100 mL), the mixture was extracted with dichloromethane (2×100 mL). The combined organic layers were washed with brine (100 mL), dried over anhydrous sodium sulfate, and filtered. Concentration of the filtrate under reduced pressure and purification of the residue by column chromatography, eluting with a gradient of 17-33% of ethyl acetate in petroleum ether, provided the title compound as yellowish oil (6.00 g, 59% yield): ¹H NMR (400 MHz, CDCl₃) δ 7.47 (dt, J=5.8, 8.0 Hz, 1H), 7.25 (d, J=7.8 Hz, 1H), 7.01 (t, J=8.4 Hz, 1H), 3.70 (s, 2H), 3.24 (t, J=7.0 Hz, 4H), 2.06 (quin, J=7.0 Hz, 2H).

Step 2. Preparation of (2-(azetidin-1-ylmethyl)-6-fluorophenyl)methanamine

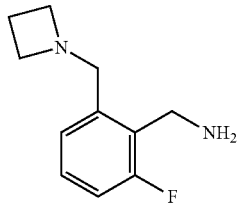 [SMILES: NCc1c(F)cccc1CN1CCC1]

To a mixture of 2-(azetidin-1-ylmethyl)-6-fluorobenzonitrile (6.00 g, 31.5 mmol) in methanol (100.00 mL) and concentrated ammonium hydroxide solution (20 mL) was added Raney-Nickel (0.594 g, 6.94 mmol). The suspension was degassed and purged with hydrogen three times. The reaction mixture was stirred under an atmosphere of hydrogen (50 psi) at ambient temperature 12 hours. Filtration of the reaction mixture and concentration of the filtrate under reduced pressure afforded the title compound as a yellow oil (6.00 g, 30.9 mmol, 98% yield): ¹H NMR (400 MHz, CDCl₃) δ 7.16 (dt, J=5.8, 7.8 Hz, 1H), 7.04-6.96 (m, 2H), 3.88 (br s, 2H), 3.63 (s, 2H), 3.19 (t, J=7.0 Hz, 4H), 2.11 (br s, 2H), 2.07-2.03 (m, 2H).

Step 3. Preparation of 5-((2-(azetidin-1-ylmethyl)-6-fluorobenzyl)amino)-6-methyl-N-(thiazol-4-yl)pyridine-2-sulfonamide

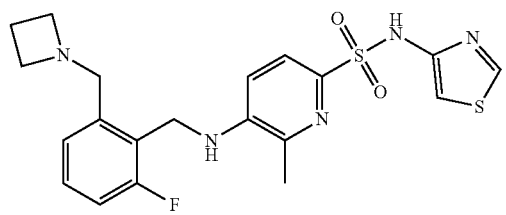 [SMILES: Cc1nc(S(=O)(=O)Nc2cscn2)ccc1NCc1c(F)cccc1CN1CCC1]

To a solution of tert-butyl (5-bromo-6-methylpyridin-2-yl)sulfonyl(thiazol-4-yl)carbamate (0.20 g, 0.46 mmol) and (2-(azetidin-1-ylmethyl)-6-fluorophenyl)methanamine (0.178 g, 0.92 mmol) in anhydrous 2-methylbutan-2-ol (5 mL) was added chloro(2-dicyclohexylphosphino-2',6'-dimethoxy-1,1'-biphenyl)(2'-amino-1,1'-biphenyl-2-yl) palladium(II) (0.033 g, 0.046 mmol) and sodium tert-butoxide (0.132 g, 1.38 mmol). The reaction mixture was degassed and heated to 90° C. for 12 hours. Filtration of the mixture and concentration of the filtrate under reduced pressure provided a residue which was purified by preparative reverse phase HPLC using acetonitrile in water containing 0.2% formic acid as eluent to give the title compound as a colorless solid (0.022 g, 10% yield): ¹H NMR (400 MHz, DMSO-d₆) δ 8.84 (d, J=2.4 Hz, 1H), 7.71 (d, J=8.4 Hz, 1H), 7.37-7.27 (m, 1H), 7.22-7.12 (m, 3H), 7.00 (br s, 1H), 6.93 (d, J=2.0 Hz, 1H), 4.40 (br s, 2H), 3.67 (s, 2H), 3.17 (t, J=7.0 Hz, 4H), 2.37 (s, 3H), 1.99 (quin, J=7.0 Hz, 2H), sulfonamide NH not observed; MS (ES+) m/z 448.3 (M+1).

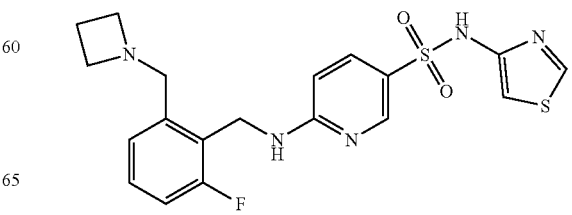

Step 1. Preparation of tert-butyl ((6-chloropyridin-3-yl)sulfonyl)(thiazol-4-yl)carbamate

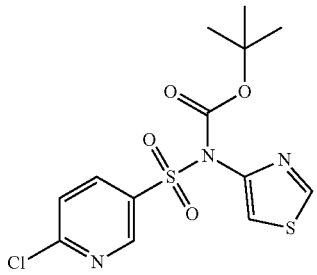 [SMILES: CC(C)(C)OC(=O)N(c1cscn1)S(=O)(=O)c1ccc(Cl)nc1]

To a solution of tert-butyl thiazol-4-ylcarbamate (2.00 g, 9.99 mmol) in anhydrous N,N-dimethylformamide (30 mL) was added sodium hydride (60% dispersion in mineral oil, 0.40 g, 9.99 mmol) at −10° C. The reaction mixture was warmed to 0° C. and stirred for 1 hour. The reaction mixture was cooled to −10° C. and to it was added 6-chloropyridine-3-sulfonyl chloride (2.54 g, 11.9 mmol). The reaction mixture was allowed to warm to ambient temperature and stirred for 2 hours. After addition of water (50 mL), the mixture was extracted with dichloromethane (3×50 mL).

The combined organic layers were washed with brine (3×50 mL), dried over anhydrous sodium sulfate, and filtered. Concentration of the filtrate in vacuo and purification of the residue by column chromatography, eluting with 25% of ethyl acetate in petroleum ether, afforded the title compound as a yellow solid (0.65 g, 17% yield): $^1$H NMR (400 MHz, CDCl$_3$) δ 9.07 (d, J=2.4 Hz, 1H), 8.78 (d, J=2.4 Hz, 1H), 8.42 (dd, J=2.6, 8.5 Hz, 1H), 7.56 (d, J=2.4 Hz, 1H), 7.54 (d, J=8.4 Hz, 1H), 1.37 (s, 9H); MS (ES+) m/z 275.5 (M−99).

Step 2. Preparation of 6-((2-(azetidin-1-ylmethyl)-6-fluorobenzyl)amino)-N-(thiazol-4-yl)pyridine-3-sulfonamide

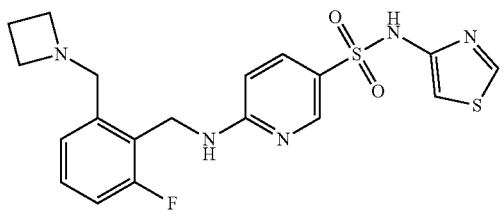 [SMILES: O=S(=O)(Nc1cscn1)c1ccc(NCc2c(F)cccc2CN2CCC2)nc1]

To a mixture of tert-butyl (6-chloropyridin-3-yl)sulfonyl (thiazol-4-yl)carbamate (0.10 g, 0.266 mmol), (2-(azetidin-1-ylmethyl)-6-fluorophenyl)methanamine (0.051 g, 0.266 mmol), sodium tert-butoxide (0.051 g, 0.532 mmol) in tert-amyl alcohol (5 mL) was added BrettPhos-Pd-G3 (0.048 g, 0.053 mmol) and the reaction mixture was heated to 90° C. for 12 hours. Filtration of the reaction mixture and concentration of the filtrate under reduced pressure afforded a residue which was purified by preparative reverse phase HPLC using acetonitrile in water containing 0.2% formic acid as eluent to give the title compound as a yellowish solid (0.026 g, 21% yield): $^1$H NMR (400 MHz, CDCl$_3$) δ 8.67 (d, J=2.2 Hz, 1H), 8.55 (d, J=2.4 Hz, 1H), 8.39 (s, 1H), 7.63 (dd, J=2.4, 8.8 Hz, 1H), 7.28-7.24 (m, 1H), 7.12-7.04 (m, 3H), 6.42 (d, J=9.0 Hz, 1H), 4.68 (s, 2H), 3.94 (s, 2H), 3.51 (t, J=7.2 Hz, 4H), 2.24 (quin, J=7.2 Hz, 2H), sulfonamide NH not observed; MS (ES+) m/z 433.9 (M+1).

Example 6

Synthesis of 5-((2-((tert-butyl(methyl)amino)methyl)-6-fluorobenzyl)amino)-6-methyl-N-(thiazol-4-yl)pyridine-2-sulfonamide formic acid salt

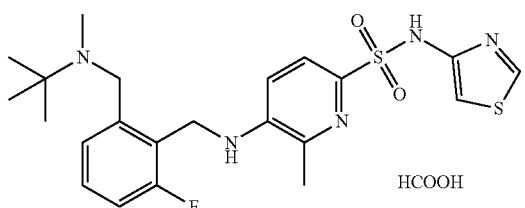

Step 1. Preparation of 2-((tert-Butyl(methyl)amino)methyl)-6-fluorobenzonitrile

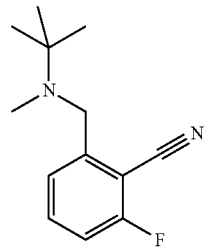 [SMILES: CN(Cc1cccc(F)c1C#N)C(C)(C)C]

To a suspension of 2-(bromomethyl)-6-fluorobenzonitrile (5.93 g, 27.7 mmol) and potassium carbonate (41.5 mmol, 5.73 g) in anhydrous acetonitrile (30 mL) was added N,2-dimethylpropan-2-amine (3.31 mL, 27.7 mmol) and the reaction mixture was heated to 60° C. for 16 hours. After cooling to ambient temperature, the reaction mixture was filtered over diatomaceous earth and the filter residue was rinsed with acetonitrile (3×15 mL). The filtrate was concentrated in vacuo to afford the title compound as a yellow oil (5.95 g, 98% yield): $^1$H NMR (300 MHz, CDCl$_3$) δ 7.58-7.48 (m, 2H), 7.07 (td, J=8.3, 1.5 Hz, 1H), 3.76 (s, 2H), 2.15 (s, 3H), 1.18 (s, 9H); MS (ES+) m/z 221.3 (M+1).

Step 2. Preparation of N-(2-(aminomethyl)-3-fluorobenzyl)-N,2-dimethylpropan-2-amine

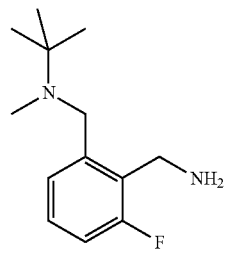 [SMILES: CN(Cc1cccc(F)c1CN)C(C)(C)C]

To a solution of 2-((tert-butyl(methyl)amino)methyl)-6-fluorobenzonitrile (10.6 g, 48.8 mmol) in methanol (60.0 ml)

was added Raney-Nickel (3 g, 50 mmol), previously washed with methanol (3×5 mL). The suspension was degassed and purged with hydrogen three times. The mixture was stirred under a hydrogen atmosphere (1 atm) at ambient temperature for 16 hours. The reaction mixture was filtered over diatomaceous earth and the filtrate concentrated under reduced pressure to afford the title compound as a yellow oil (10.7 g, 99% yield): $^1$H NMR (300 MHz, CDCl$_3$) δ 7.18-6.95 (m, 3H), 3.91 (dd, J=17.4, 1.9 Hz, 2H), 3.65 (d, J=8.0 Hz, 2H), 2.31 (br s, 2H), 2.03 (d, J=11.2 Hz, 3H), 1.18 (d, J=14.2 Hz, 9H); MS (ES+) m/z 225.3 (M+1).

Step 3. Preparation of 5-((2-((tert-butyl(methyl) amino)methyl)-6-fluorobenzyl)amino)-6-methyl-N-(thiazol-4-yl)pyridine-2-sulfonamide formate

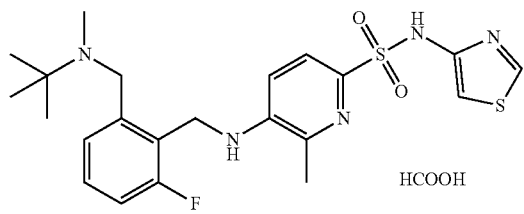 [SMILES: Cc1nc(S(=O)(=O)Nc2cscn2)ccc1NCc1c(F)cccc1CN(C)C(C)(C)C ; "HCOOH"]

To a solution of tert-butyl (5-bromo-6-methylpyridin-2-yl)sulfonyl(thiazol-4-yl)carbamate (0.30 g, 0.691 mmol) and N-(2-(aminomethyl)-3-fluorobenzyl)-N,2-dimethylpropan-2-amine (0.310 g, 1.38 mmol) in 2-methyl-2-butanol (2.0 mL) was added a 2M solution of sodium tert-butoxide solution in tetrahydrofuran (1.04 mL, 2.08 mmol) and chloro (2-dicyclohexylphosphino-2',6'-dimethoxy-1,1'-biphenyl) [2-(2'-amino-1,1'-biphenyl)] palladium(II) (0.050 g, 0.069 mmol). The mixture was degassed and heated to 90° C. for 12 hours. The mixture was diluted with water (100 mL) and extracted with ethyl acetate (3×100 mL). The combined organic layers were washed with brine (30 mL), dried over anhydrous sodium sulfate, and filtered. Concentration of the filtrate under reduced pressure and purification of the residue by preparative reverse phase HPLC using acetonitrile in water containing 0.2% formic acid as eluent provided the title compound as a colorless solid (0.016 g, 5% yield): $^1$H NMR (400 MHz, DMSO-d$_6$) δ 8.83 (d, J=1.6 Hz, 1H), 8.27 (s, 1H), 7.68 (d, J=8.4 Hz, 1H), 7.35-7.28 (m, 1H), 7.27-7.22 (m, 1H), 7.19 (d, J=8.4 Hz, 1H), 7.11 (t, J=9.2 Hz, 1H), 6.90 (d, J=1.6 Hz, 1H), 6.09 (br s, 1H), 4.43 (br s, 2H), 3.65 (s, 2H), 2.26 (s, 3H), 2.00 (s, 3H), 1.06 (s, 9H), NH and COOH not observed; MS (ES+) m/z 478.1 (M+1).

Example 7

Synthesis of 5-((2-(azetidin-1-ylmethyl)-6-fluorobenzyl)amino)-4-methyl-N-(thiazol-4-yl)pyridine-2-sulfonamide formic acid salt

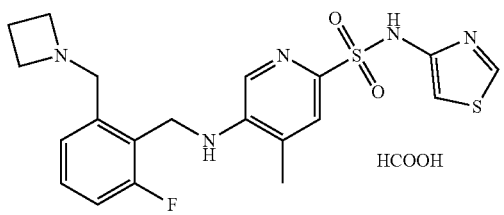 [SMILES: Cc1cc(S(=O)(=O)Nc2cscn2)ncc1NCc1c(F)cccc1CN1CCC1 ; "HCOOH"]

Step 1. Preparation of 2-(benzylthio)-5-bromo-4-methylpyridine

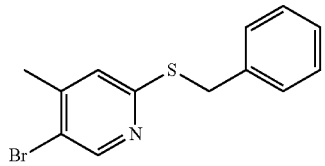 [SMILES: Cc1cc(SCc2ccccc2)ncc1Br]

To a solution of benzyl mercaptan (2.88 g, 23.1 mmol) in anhydrous tetrahydrofuran (100 mL) was added sodium hydride (60% dispersion in mineral oil, 1.68 g, 42.1 mmol) and 5-bromo-2-fluoro-4-methyl-pyridine (4.00 g, 21.0 mmol) at 0° C. The reaction mixture was allowed to warm to ambient temperature and stirred for 12 hours. After addition of saturated ammonium chloride solution (20 mL) and water (100 mL), the reaction mixture was extracted with ethyl acetate (3×100 mL). The combined organic layers were washed with brine (3×50 mL), dried over anhydrous sodium sulfate, and filtered. Concentration of the filtrate under reduced pressure and purification of the residue by column chromatography, eluting with 1% of ethyl acetate in petroleum ether, afforded the title compound as colorless oil (6.0 g, 96% yield): $^1$H NMR (400 MHz, CDCl$_3$) δ 8.52 (d, J=2.4 Hz, 1H), 7.43 (br d, J=7.6 Hz, 2H), 7.35-7.24 (m, 3H), 7.07 (s, 1H), 4.44 (d, J=2.6 Hz, 2H), 2.33 (s, 3H); MS (ES+) m/z 294.0 (M+1), 296.0 (M+3).

Step 2. Preparation of 5-bromo-4-methylpyridine-2-sulfonyl chloride

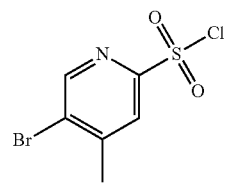

To a solution of 2-benzylsulfanyl-5-bromo-4-methyl-pyridine (5.00 g, 16.9 mmol) in a mixture of acetonitrile (40 mL) and water (6 mL) was added acetic acid (6.30 g, 104.8 mmol) at 0° C. followed by 1,3-dichloro-5,5-dimethyl-imidazolidine-2,4-dione (6.70 g, 33.9 mmol). The reaction mixture was stirred at 0° C. for 30 minutes, and then quenched by addition of saturated sodium bicarbonate solution until pH 7 was reached. The mixture was extracted with ethyl acetate (3×20 mL). The combined organic layers were washed with brine (20 mL), dried over anhydrous sodium sulfate, and filtered. Concentration of the filtrate under reduced pressure and purification of the residue by column chromatography, eluting with 1% of ethyl acetate in petroleum ether, afforded the title compound as colorless oil (4.20 g, 91% yield): $^1$H NMR (400 MHz, CDCl$_3$) δ 8.82 (s, 1H), 7.97 (s, 1H), 2.58 (s, 3H).

Step 3. Preparation of tert-butyl ((5-bromo-4-methylpyridin-2-yl)sulfonyl)(thiazol-4-yl)carbamate

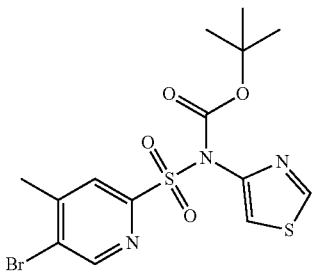 [SMILES: Cc1cc(S(=O)(=O)N(C(=O)OC(C)(C)C)c2cscn2)ncc1Br]

To a solution of tert-butyl N-thiazol-4-ylcarbamate (2.07 g, 10.3 mmol) in anhydrous N,N-dimethylformamide (20 mL) was added sodium hydride (60% dispersion in mineral oil, 0.496 g, 12.4 mmol) at 0° C. The reaction mixture was stirred at 0° C. for 1 h, and then 5-bromo-4-methyl-pyridine-2-sulfonyl chloride (4.20 g, 15.5 mmol) was added to it. The reaction mixture was allowed to warm to ambient temperature and stirred for 1 hour. After addition of water (50 mL), the mixture was extracted with ethyl acetate (3×50 mL). The combined organic layers were washed with brine (50 mL), dried over anhydrous sodium sulfate, and filtered. Concentration of the filtrate under reduced pressure and purification of the residue by column chromatography, eluting with 25% of ethyl acetate in petroleum ether, afforded the title compound as a yellow solid (0.370 g, 8% yield): $^1$H NMR (400 MHz, CDCl3) δ 8.74 (d, J=2.2 Hz, 1H), 8.71 (s, 1H), 8.05 (s, 1H), 7.60 (d, J=2.2 Hz, 1H), 2.47 (s, 3H), 1.24 (s, 9H); MS (ES+) m/z 333.9 (M−99) 335.9 (M−99).

Step 4. 5-((2-(azetidin-1-ylmethyl)-6-fluorobenzyl)amino)-4-methyl-N-(thiazol-4-yl)pyridine-2-sulfonamide formic acid salt

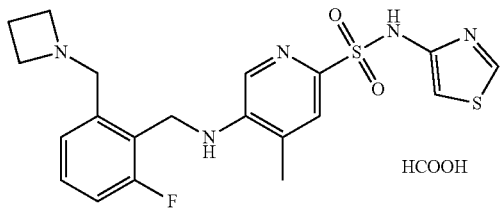 [SMILES: Cc1cc(S(=O)(=O)Nc2cscn2)ncc1NCc1c(F)cccc1CN1CCC1 ; "HCOOH"]

To a mixture of (2-(azetidin-1-ylmethyl)-6-fluorophenyl)methanamine (0.268 g, 1.38 mmol), tert-butyl (5-bromo-4-methylpyridin-2-yl)sulfonyl(thiazol-4-yl)carbamate (0.30 g, 0.690 mmol) and chloro(2-dicyclohexylphosphino-2',6'-dimethoxy-1,1'-biphenyl)[2-(2'-amino-1,1'-biphenyl)]palladium(II) (0.049 g, 0.069 mmol) in anhydrous 2-methylbutan-2-ol (5 mL) was added a 2 M solution of sodium tert-butoxide solution in tetrahydrofuran (1.04 mL, 2.08 mmol). The reaction mixture was degassed and heated to 90° C. for 12 hours. After addition of water (10 mL), the reaction mixture was extracted with ethyl acetate (3×10 mL). The combined organic layers were washed with brine (3×10 mL), dried over anhydrous sodium sulfate, and filtered. Concentration of the filtrate and purification of the residue by preparative reverse phase HPLC using acetonitrile in water containing 0.2% formic acid as eluent provided the title compound as a colorless solid (0.037 g, 0.070 mmol, 10% yield): $^1$H NMR (400 MHz, CD$_3$OD) δ8.70 (d, J=2.2 Hz, 1H), 8.46 (br s, 1H), 8.09 (s, 1H), 7.69 (s, 1H), 7.47-7.36 (m, 1H), 7.27-7.15 (m, 2H), 7.02 (d, J=1.6 Hz, 1H), 4.59 (s, 2H), 4.19 (s, 2H), 3.77 (t, J=7.6 Hz, 4H), 2.32 (quin, J=7.6 Hz, 2H), 2.23 (s, 3H), NH and COOH not observed; MS (ES+) m/z 448.1 (M+1).

Example 8

Synthesis of 5-((2-((2,2-dimethylazetidin-1-yl)methyl)-6-fluorobenzyl)amino)-6-methyl-N-(thiazol-4-yl)pyridine-2-sulfonamide trifluoroacetic acid salt

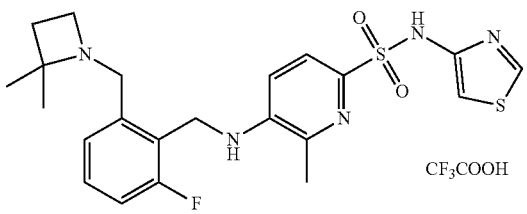 [SMILES: Cc1nc(S(=O)(=O)Nc2cscn2)ccc1NCc1c(F)cccc1CN1CCC1(C)C ; "CF3COOH"]

Step 1. Preparation of 6-(benzylthio)-3-fluoro-2-methylpyridine

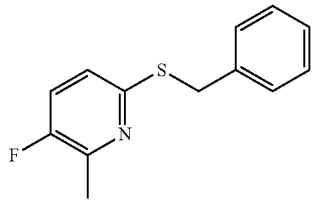 [SMILES: Cc1nc(SCc2ccccc2)ccc1F]

To a degassed solution of 6-bromo-3-fluoro-2-methylpyridine (5.79 g, 30.47 mmol) and N,N-diisopropylethylamine (10.6 mL, 60.9 mmol) in anhydrous dioxane (250 mL) was added 4,5-bis(diphenylphosphino)-9,9-dimethylxanthene (1.41 g, 2.44 mmol), tris(dibenzylideneacetone)dipalladium(0) (1.11 g, 1.22 mmol), and benzyl mercaptan (3.22 ml, 27.4 mmol). The reaction mixture was refluxed under nitrogen for 18 hours and then concentrated in vacuo. Purification of the residue by column chromatography, eluting with a gradient of 0 to 15% of ethyl acetate in heptane, provided the title compound as a yellowish oil (6.20 g, 87% yield): $^1$H NMR (400 MHz, CDCl$_3$) δ 7.46-7.40 (m, 2H), 7.35-7.23 (m, 3H), 7.16 (t, J=8.7 Hz, 1H), 6.98 (dd, J=8.5, 3.4 Hz, 1H), 4.42 (s, 2H), 2.54 (d, J=3.0 Hz, 3H); MS (ES+) m/z 234.1 (M+1).

Step 2. Preparation of 5-fluoro-6-methylpyridine-2-sulfonyl chloride

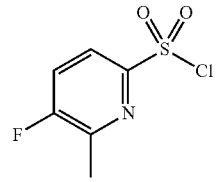

To a solution of 6-(benzylthio)-3-fluoro-2-methylpyridine (6.20 g, 26.57 mmol) in acetonitrile (110 mL), acetic acid (7.60 mL), and water (6.22 mL) was added 1,3-dichloro-5,5-dimethylhydantoin (10.47 g, 53.15 mmol) at 0° C. The reaction mixture was stirred at 0° C. for 1 hour and then diluted with ethyl acetate (550 mL). The mixture was washed with ice cold brine (4×100 mL), dried over anhydrous sodium sulfate, and filtered. Concentration of the filtrate in vacuo and purification of the residue by column chromatography, eluting with a gradient of 0 to 40% of ethyl acetate in heptane, afforded the title compound as a colorless solid (4.29 g, 77% yield): ¹H NMR (400 MHz, CDCl₃) δ 8.02 (ddd, J=8.5, 3.5, 0.5 Hz, 1H), 7.63 (t, J=8.3 Hz, 1H), 2.69 (d, J=3.0 Hz, 3H); MS (ES+) m/z 210.0 (M+1), 212.0 (M+1).

Step 3. Preparation of tert-butyl ((5-fluoro-6-methyl pyridin-2-yl)sulfonyl)(thiazol-4-yl)carbamate

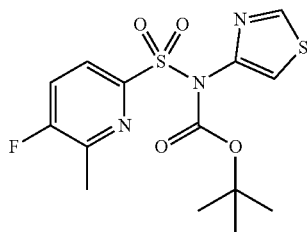 [SMILES: Cc1nc(S(=O)(=O)N(C(=O)OC(C)(C)C)c2cscn2)ccc1F]

To a solution tert-butyl thiazol-4-ylcarbamate (4.51 g, 22.51 mmol) anhydrous tetrahydrofuran (125 mL) was added a 1 M solution of lithium bis(trimethylsilyl)amide in tetrahydrofuran (22.5 mL, 22.5 mmol) at 0° C. The reaction mixture was stirred at 0° C. for 1 h, cooled to −78° C., and a solution of 5-fluoro-6-methylpyridine-2-sulfonyl chloride (4.29 g, 20.47 mmol) in anhydrous tetrahydrofuran (60 mL) was added dropwise. The reaction mixture was stirred at −78° C. for 1.5 h, allowed to warm to ambient temperature, and stirred for 18 hours. The reaction mixture was concentrated in vacuo and the residue was dissolved in ethyl acetate (100 mL). The mixture was washed with saturated ammonium chloride (2×60 mL), brine (60 mL), dried over anhydrous sodium sulfate, and filtered. Concentration of the filtrate in vacuo and purification of the residue by column chromatography, eluting with a gradient of 10 to 65% of ethyl acetate in heptane, afforded the title compound as a colorless solid (7.46 g, 98% yield): ¹H NMR (400 MHz, CDCl₃) δ 8.83 (d, J=2.3 Hz, 1H), 8.15 (dd, J=8.5, 3.6 Hz, 1H), 7.71 (d, J=2.3 Hz, 1H), 7.57 (t, J=8.5 Hz, 1H), 2.66 (d, J=3.0 Hz, 3H), 1.33 (s, 9H); MS (ES+) m/z 374.2 (M+1).

Step 4. Preparation of 5-fluoro-N-(4-methoxybenzyl)-6-methyl-N-(thiazol-4-yl)pyridine-2-sulfonamide

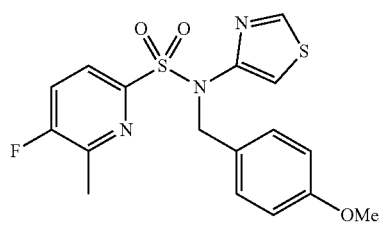 [SMILES: COc1ccc(CN(c2cscn2)S(=O)(=O)c2ccc(F)c(C)n2)cc1]

To a solution of tert-butyl ((5-fluoro-6-methylpyridin-2-yl)sulfonyl)(thiazol-4-yl)carbamate (7.46 g, 19.98 mmol) in dichloromethane (40 mL) was added trifluoroacetic acid (15 mL). The reaction mixture was stirred at ambient temperature for 3 hours and then concentrated in vacuo. To the residue was added anhydrous N,N-dimethylformamide (60 mL), sodium bicarbonate (8.39 g, 99.9 mmol), and 4-methoxybenzyl chloride (5.42 mL, 39.96 mmol). The reaction mixture was heated to 65° C. for 3 hours and then diluted with ethyl acetate (120 mL). The mixture was washed with saturated ammonium chloride (3×75 mL), brine (2×75 mL), dried over anhydrous sodium sulfate, and filtered. Concentration of the filtrate in vacuo and purification of the residue by column chromatography, eluting with a gradient of 10 to 50% of ethyl acetate in heptane, afforded the title compound as a colorless solid (7.86 g, quantitative yield): ¹H NMR (400 MHz, CDCl₃) δ 8.52 (d, J=2.3 Hz, 1H), 7.67 (ddd, J=8.4, 3.6, 0.5 Hz, 1H), 7.40 (t, J=8.5 Hz, 1H), 7.32-7.27 (m, 2H), 7.25-7.20 (m, 2H), 7.19 (d, J=2.3 Hz, 1H), 5.10 (s, 2H), 3.81 (s, 3H), 2.59 (d, J=3.0 Hz, 3H); MS (ES+) m/z 394.2 (M+1).

Step 5. Preparation of 2-((2,2-dimethylazetidin-1-yl)methyl)-6-fluorobenzonitrile

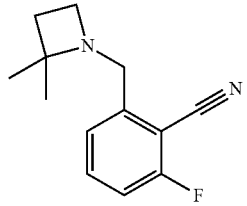 [SMILES: CC1(C)CCN1Cc1cccc(F)c1C#N]

To a solution of 2,2-dimethylazetidine (4.29 g, 50.38 mmol) and N,N-diisopropylethylamine (13.16 mL, 75.57 mmol) in anhydrous N,N-dimethylformamide (100 mL) was added 2-(bromomethyl)-6-fluorobenzonitrile (9.80 g, 45.80 mmol) at 0° C. The reaction mixture was stirred at 0° C. for 1.5 hours and then diluted with ethyl acetate (170 mL). The mixture was washed with saturated ammonium chloride solution (2×100 mL), brine (100 mL), dried over anhydrous sodium sulfate, and filtered. Concentration of the filtrate in vacuo afforded the title compound as a yellow oil (9.97 g, quantitative yield): ¹H NMR (400 MHz, CDCl₃) δ 7.52 (td, J=8.1, 5.7 Hz, 1H), 7.40-7.36 (m, 1H), 7.10-7.04 (m, 1H), 3.73 (s, 2H), 3.18 (t, J=7.0 Hz, 2H), 1.94 (t, J=7.0 Hz, 2H), 1.26 (s, 6H); MS (ES+) m/z 219.3 (M+1).

Step 6. Preparation of (2-((2,2-dimethylazetidin-1-yl)methyl)-6-fluorophenyl)methanamine

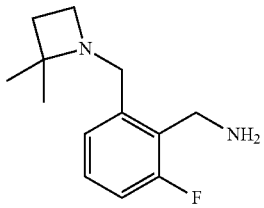 [SMILES: CC1(C)CCN1Cc1cccc(F)c1CN]

To a slurry of Raney-Nickel (1.7 g, 28.9 mmol) in water (1.7 mL) was added ethanol (20 mL) followed by a mixture of 2-((2,2-dimethylazetidin-1-yl)methyl)-6-fluorobenzonitrile (9.00 g, 41.23 mmol) and concentrated ammonium hydroxide (25 mL) in ethanol (230 mL). The reaction mixture was stirred under an atmosphere of 1 atm of hydrogen for 24 hours. The mixture was filtered through diatomaceous earth and rinsed with methanol (200 mL). Concentration of the filtrate in vacuo afforded the title compound as a brown oil (8.08 g, 88% yield): MS (ES+) m/z 223.3 (M+1).

Step 7. Preparation of 5-((2-((2,2-dimethylazetidin-1-yl)methyl)-6-fluorobenzyl)amino)-N-(4-methoxybenzyl)-6-methyl-N-(thiazol-4-yl)pyridine-2-sulfonamide

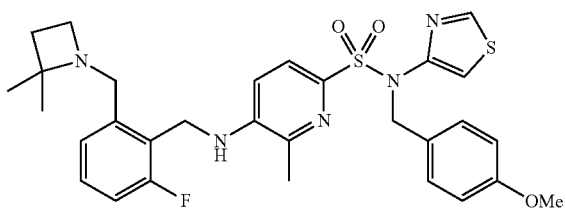 [SMILES: COc1ccc(CN(c2cscn2)S(=O)(=O)c2ccc(NCc3c(F)cccc3CN3CCC3(C)C)c(C)n2)cc1]

To a solution of 5-fluoro-N-(4-methoxybenzyl)-6-methyl-N-(thiazol-4-yl)pyridine-2-sulfonamide (1.80 g, 4.57 mmol) and (2-((2,2-dimethylazetidin-1-yl)methyl)-6-fluorophenyl)methanamine (1.02 g, 4.57 mmol) in anhydrous dimethyl sulfoxide (20 mL) was added N,N-diisopropylethylamine (1.59 mL, 9.14 mmol). The reaction mixture was heated to 110° C. for 16 hours and then allowed to cool to ambient temperature.

After dilution with ethyl acetate (80 mL), the mixture was washed with saturated ammonium chloride solution (2×40 mL), brine (40 mL), dried over anhydrous sodium sulfate, and filtered. Concentration of the filtrate in vacuo and purification of the residue by column chromatography, eluting with a gradient of 10 to 55% of ethyl acetate (containing 20% 20% ethanol and 0.2% ammonium hydroxide) in heptane, afforded the title compound as a colorless oil (0.90 g, 33% yield): $^1$H NMR (400 MHz, CDCl$_3$) δ 8.52 (d, J=2.3 Hz, 1H), 7.61 (d, J=8.5 Hz, 1H), 7.27-7.19 (m, 4H), 7.12-7.00 (m, 3H), 6.79-6.74 (m, 2H), 6.27-6.23 (m, 1H), 5.11 (s, 2H), 4.43 (s, 2H), 3.75 (s, 3H), 3.64 (s, 2H), 3.08 (t, J=7.0 Hz, 2H), 2.45 (s, 3H), 1.91 (t, J=7.0 Hz, 2H), 1.26 (s, 6H); MS (ES+) m/z 596.3 (M+1).

Step 7. Preparation of 5-((2-((2,2-dimethylazetidin-1-yl)methyl)-6-fluorobenzyl)amino)-6-methyl-N-(thiazol-4-yl)pyridine-2-sulfonamide trifluroacetic acid salt

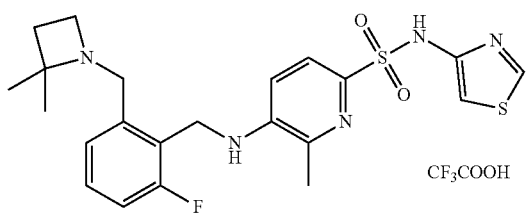 [SMILES: Cc1nc(S(=O)(=O)Nc2cscn2)ccc1NCc1c(F)cccc1CN1CCC1(C)C ; "CF3COOH"]

To a solution of 5-((2-((2,2-dimethylazetidin-1-yl)methyl)-6-fluorobenzyl)amino)-N-(4-methoxybenzyl)-6-methyl-N-(thiazol-4-yl)pyridine-2-sulfonamide in dichloromethane (8 mL) was added trifluroacetic acid (8 mL). The reaction mixture was heated under refluxed for 2 hours and then concentrated in vacuo. After addition of methanol (30 mL), the mixture was filtered and the filtrate concentrated in vacuo. Purification of the residue by preparative reverse phase HPLC, using acetonitrile in water containing 0.1% trifluoroacetic acid as eluent, afforded the title compound as a colorless solid (0.16 g, 20% yield): $^1$H NMR (300 MHz, DMSO-d$_6$) δ 10.98 (s, 1H), 9.79 (s, 1H), 8.84 (d, J=2.2 Hz, 1H), 7.71 (d, J=8.5 Hz, 1H), 7.51-7.43 (m, 1H), 7.39-7.29 (m, 2H), 7.04 (d, J=8.6 Hz, 1H), 6.93 (d, J=2.2 Hz, 1H), 6.30-6.24 (m, 1H), 4.50-4.42 (m, 2H), 4.36-4.16 (m, 3H), 3.90-3.82 (m, 1H), 2.32 (d, J=14.3 Hz, 4H), 2.16-2.08 (m, 1H), 1.60 (s, 3H), 1.46 (s, 3H); $^{19}$F NMR (282 MHz, DMSO-d$_6$) δ −74.1 (s, 3F), −115.2 (s, 1F); MS (ES+) m/z 476.3 (M+1).

Example 9

Synthesis of 5-((2-(azetidin-1-ylmethyl)-6-fluorobenzyl)amino)-N-(6-fluoropyridin-2-yl)-4-methylpyridine-2-sulfonamide

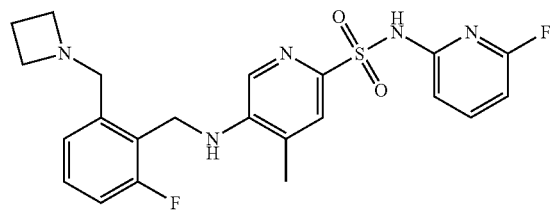 [SMILES: Cc1cc(S(=O)(=O)Nc2cccc(F)n2)ncc1NCc1c(F)cccc1CN1CCC1]

Step 1. Preparation of N-(2,4-dimethoxybenzyl)-6-fluoropyridin-2-amine

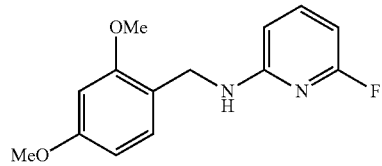 [SMILES: COc1ccc(CNc2cccc(F)n2)c(OC)c1]

To a mixture of (2,4-dimethoxyphenyl)methanamine (117.5 mL, 782.0 mmol) and N,N-diisopropylethylamine (147.6 mL, 847.2 mmol) in anhydrous dimethyl sulfoxide (500 mL) was added 2,6-difluoropyridine (75.0 g, 651.7 mmol). The resulting mixture was heated to 100° C. for 5 hours and then cooled to ambient temperature. The mixture was diluted with ethyl acetate (600 mL), washed with water (1000 mL), saturated ammonium chloride (2×200 mL), brine (100 mL), and dried over anhydrous sodium sulfate. Filtration and concentration of the filtrate in vacuo provided a residue, which was triturated in methanol (250 mL) to afford the title compound as a colorless solid (140.0 g, 82% yield): $^1$H-NMR (300 MHz, CDCl$_3$) δ 7.44 (q, J=8.2 Hz, 1H), 7.22 (d, J=8.2 Hz, 1H), 6.49 (d, J=2.3 Hz, 1H), 6.44 (dd, J=8.2, 2.4 Hz, 1H), 6.21 (dd, J=8.0, 2.4 Hz, 1H), 6.12 (dd, J=7.7, 2.3 Hz, 1H), 5.17-5.07 (m, 1H), 4.40 (d, J=6.0 Hz, 2H), 3.84 (s, 3H), 3.81 (s, 3H); MS (ES+) m/z 263.2 (M+1).

Step 2. Preparation of N-(2,4-dimethoxybenzyl)-5-fluoro-N-(6-fluoropyridin-2-yl)-4-methylpyridine-2-sulfonamide

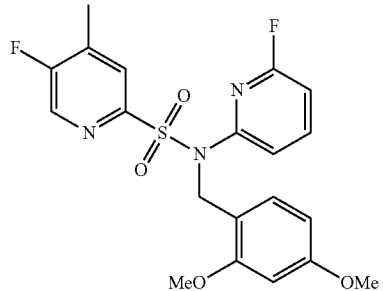 [SMILES: COc1ccc(CN(c2cccc(F)n2)S(=O)(=O)c2cc(C)c(F)cn2)c(OC)c1]

To a solution of N-(2,4-dimethoxybenzyl)-6-fluoropyridin-2-amine (2.50 g, 9.54 mmol) in anhydrous tetrahydrofuran (25 mL) was added a 1 M solution of lithium bis(trimethylsilyl)amide in tetrahydrofuran (10.5 mL, 10.5 mmol) at −78° C. and the reaction mixture was stirred at −78° C. for 30 minutes. To this mixture was then slowly added a solution of 5-fluoro-4-methylpyridine-2-sulfonyl chloride (2.00 g, 9.54 mmol) in anhydrous tetrahydrofuran (5.50 mL). The reaction mixture was stirred at −78° C. for 1 hour, allowed to warm to ambient temperature, and stirred for at ambient temperature for 16 hours. After dilution with ethyl acetate (100 mL), the mixture was washed with brine (2×50 mL). The organic layer was dried over anhydrous magnesium sulfate, filtered and the filtrate concentrated in vacuo. Purification of the residue by column chromatography, eluting with a gradient of 15 to 75% of ethyl acetate (containing 20% of ethanol and 1% ammonium hydroxide) in heptanes, afforded the title compound as a yellow solid (2.90 g, 70% yield): ¹H NMR (300 MHz, CDCl₃) δ 8.37 (s, 1H), 7.73 (t, J=7.0 Hz, 2H), 7.48-7.45 (m, 1H), 7.27 (dd, J=6.8, 1.6 Hz, 1H), 6.69-6.65 (m, 1H), 6.38 (dd, J=8.4, 2.4 Hz, 1H), 6.27 (d, J=2.4 Hz, 1H), 5.16 (s, 2H), 3.76 (d, J=1.9 Hz, 3H), 3.60 (s, 3H), 2.34 (d, J=1.3 Hz, 3H). ¹⁹F NMR (282 MHz, CDCl₃) δ −68.3 (1F), −125.7 (1F).

Step 3. Preparation of 5-((2-(azetidin-1-ylmethyl)-6-fluorobenzyl)amino)-N-(2,4-dimethoxybenzyl)-N-(6-fluoropyridin-2-yl)-4-methylpyridine-2-sulfonamide

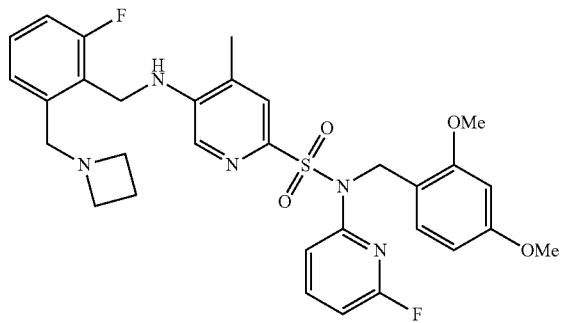 [SMILES: COc1ccc(CN(c2cccc(F)n2)S(=O)(=O)c2cc(C)c(NCc3c(F)cccc3CN3CCC3)cn2)c(OC)c1]

To a solution of (2-(azetidin-1-ylmethyl)-6-fluorophenyl)methanamine (0.30 g, 1.34 mmol) in anhydrous N,N-dimethylformamide (5 mL) was added a 1 M solution of potassium bis(trimethylsilyl)amide in tetrahydrofuran (1.47 mL, 1.47 mmol) at 0° C. and the reaction mixture was stirred for 30 minutes at 0° C. To the mixture was then added a solution of N-(2,4-dimethoxybenzyl)-5-fluoro-N-(6-fluoropyridin-2-yl)-4-methylpyridine-2-sulfonamide (0.53 g, 1.22 mmol) in anhydrous N, N-dimethylformamide (1.1 mL). The reaction mixture was allowed to warm to ambient temperature, stirred for 4 h, and then heated to 90° C. for 4 hours. The reaction mixture was allowed to cool to ambient temperature and diluted with ethyl acetate (120 mL). The organic phase was washed with water (3×50 mL) and brine (50 mL), dried over anhydrous magnesium sulfate and filtered. Concentration of the filtrate in vacuo provided a residue which was purified by column chromatography, eluting with a gradient of 15 to 75% of ethyl acetate (containing 20% of ethanol and 1% of ammonium hydroxide) in heptanes, to afford the title compound as a yellow oil (0.20 g, 27% yield): MS (ES+) m/z 610 (M+1).

Step 4. Preparation of 5-((2-(azetidin-1-ylmethyl)-6-fluorobenzyl)amino)-N-(6-fluoropyridin-2-yl)-4-methylpyridine-2-sulfonamide

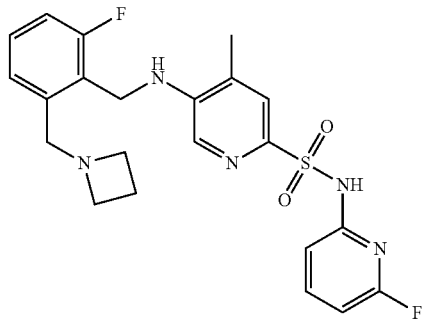 [SMILES: Cc1cc(S(=O)(=O)Nc2cccc(F)n2)ncc1NCc1c(F)cccc1CN1CCC1]

To a solution of tert-butyl 5-((2-(azetidin-1-ylmethyl)-6-fluorobenzyl)amino)-N-(2,4-dimethoxybenzyl)-N-(6-fluoropyridin-2-yl)-4-methylpyridine-2-sulfonamide (0.20 g, 0.327 mmol) in dichloromethane (3 mL) was added trifluoroacetic acid (3 mL) and the reaction mixture was stirred at ambient temperature for 1 hour. The reaction mixture was concentrated in vacuo and the residue triturated with methanol (2×20 mL).

Filtration and concentration of the filtrate in vacuo provided an oily residue. Purification of the residue by column chromatography, eluting with a gradient of 5 to 100% of ethyl acetate (containing 20% of ethanol and 1% of ammonium hydroxide) in heptanes, followed by purification of the residue by preparative reverse phase HPLC, eluting with a gradient of 5 to 100% of acetonitrile (containing 0.1% of ammonium hydroxide) in water, afforded the title compound as a colorless solid (0.037 g, 21% yield): ¹H-NMR (300 MHz, DMSO-d₆) δ 11.35-11.04 (m, 1H), 8.14 (s, 1H), 7.84-7.76 (m, 2H), 7.32 (td, J=7.8, 5.8 Hz, 1H), 7.21-7.11 (m, 2H), 6.98 (dd, J=7.9, 2.2 Hz, 1H), 6.89-6.83 (m, 1H), 6.65 (dd, J=7.9, 2.5 Hz, 1H), 4.50-4.48 (m, 2H), 3.67 (s, 2H), 3.19-3.12 (m, 4H), 2.21 (s, 3H), 2.02-1.93 (m, 2H); ¹⁹F-NMR (282 MHz, DMSO-d₆) δ −69.2 (1F), −116.8 (1F); MS (ES+) m/z 460.4 (M+1).

Example 10

Synthesis of 6-((2-((tert-butyl(methyl)amino)methyl)-6-fluorobenzyl)amino)-2-methyl-N-(thiazol-4-yl)pyridine-3-sulfonamide formic acid salt

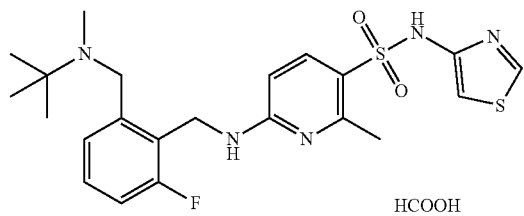 [SMILES: Cc1nc(NCc2c(F)cccc2CN(C)C(C)(C)C)ccc1S(=O)(=O)Nc1cscn1 ; "HCOOH"]

Step 1. Preparation of 3-(benzylthio)-6-fluoro-2-methylpyridine

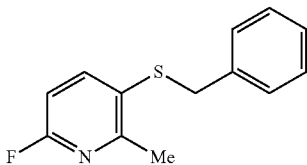 [SMILES: Cc1nc(F)ccc1SCc1ccccc1]

To a solution of 3-bromo-6-fluoro-2-methylpyridine (10.0 g, 52.6 mmol) in anhydrous 1,4-dioxane (105 mL) was added N,N-diisopropylethylamine (11.0 mL, 63.2 mmol) and the mixture was degassed with argon. To the mixture was then added tris(dibenzylideneacetone)dipalladium(0) (1.20 g, 1.30 mmol), 4,5-bis(diphenylphosphino)-9,9-dimethylxanthene (1.83 g, 3.20 mmol) and benzyl mercaptan (7.3 mL, 61.9 mmol). The reaction mixture was degassed with argon and then heated to 100° C. for 16 hours. The reaction mixture was allowed to cool to ambient temperature and filtered. Concentration of the filtrate in vacuo and purification of the residue by column chromatography, eluting with 5% of ethyl acetate in heptane, afforded the title compound as a colorless oil (12.3 g, >99% yield): $^1$H-NMR (300 MHz, CDCl$_3$) δ 7.58 (t, J=8.1 Hz, 1H), 7.34-7.24 (m, 3H), 7.19-7.16 (m, 2H), 6.68-6.64 (m, 1H), 3.99 (s, 2H), 2.49 (s, 3H); MS (ES+) m/z 234.2 (M+1).

Step 2. Preparation of 6-fluoro-2-methylpyridine-3-sulfonyl chloride

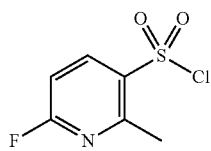

To a solution of 3-(benzylthio)-6-fluoro-2-methylpyridine (12.3 g, 52.9 mmol) in a mixture of acetonitrile (378 mL) and water (13 mL) was added 1,3-dichloro-5,5-dimethyl-imidazolidine-2,4-dione (20.8 g, 106 mmol). The reaction mixture was cooled to 0° C. and acetic acid (18 mL) was added dropwise. The reaction mixture was stirred at 0° C. for 30 minutes. Water (150 mL) was added to the mixture, and the mixture was extracted with ethyl acetate (3×100 mL). The combined organic layers were washed with brine (50 mL), dried over anhydrous sodium sulfate, and filtered. Concentration of the filtrate in vacuo and purification of the residue by column chromatography, eluting with 20% of ethyl acetate in heptane, afforded the title compound as a pale yellow oil (4.28 g, 39% yield): $^1$H-NMR (300 MHz, CDCl$_3$) δ 8.46-8.41 (m, 1H), 7.02-6.98 (m, 1H), 2.96 (s, 3H).

Step 3. Preparation of tert-butyl ((6-fluoro-2-methylpyridin-3-yl)sulfonyl)(thiazol-4-yl)carbamate

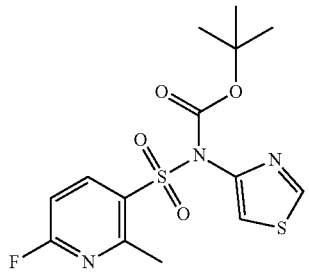 [SMILES: Cc1nc(F)ccc1S(=O)(=O)N(C(=O)OC(C)(C)C)c1cscn1]

To a solution of tert-butyl thiazol-4-ylcarbamate (2.10 g, 10.5 mmol) in anhydrous tetrahydrofuran (48 mL) was added a 1 M solution of lithium bis(trimethylsilyl)amide in tetrahydrofuran (10.5 mL, 10.5 mmol) at −78° C. The reaction mixture was stirred at −78° C. for 15 minutes, allowed to warm to ambient temperature and stirred for 1 hour. The reaction mixture was cooled to −78° C., and a solution of 6-fluoro-2-methylpyridine-3-sulfonyl chloride (2.00 g, 9.50 mmol) in anhydrous tetrahydrofuran (48 mL) was then added dropwise. The reaction mixture was stirred at −78° C. for 30 minutes, allowed to warm to ambient temperature, and stirred for 16 hours. After addition of saturated aqueous ammonium chloride (50 mL), the mixture was extracted with ethyl acetate (3×50 mL). The combined organic phases were washed with brine (50 mL), dried over anhydrous sodium sulfate, and filtered. Concentration of the filtrate in vacuo and purification of the residue by column chromatography, eluting with 25% of ethyl acetate in heptane, afforded the title compound as a yellow solid (0.56 g, 16% yield): $^1$H-NMR (300 MHz, CDCl$_3$) δ 8.80 (d, J=2.3 Hz, 1H), 8.69-8.64 (m, 1H), 7.56 (d, J=2.2 Hz, 1H), 6.97-6.93 (m, 1H), 2.82 (s, 3H), 1.33 (s, 9H); MS (ES+) m/z 374.1 (M+1).

Step 4. Preparation of tert-butyl ((6-((2-((tert-butyl(methyl)amino)methyl)-6-fluorobenzyl)amino)-2-methylpyridin-3-yl)sulfonyl)(thiazol-4-yl)carbamate

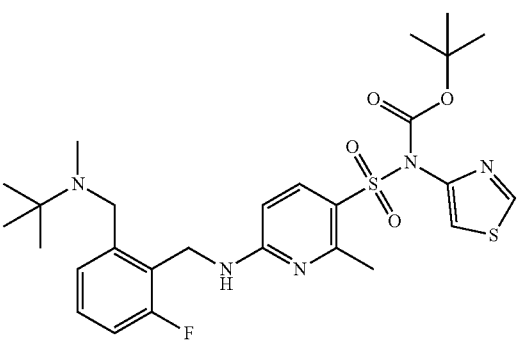 [SMILES: Cc1nc(NCc2c(F)cccc2CN(C)C(C)(C)C)ccc1S(=O)(=O)N(C(=O)OC(C)(C)C)c1cscn1]

To a solution of tert-butyl ((6-fluoro-2-methylpyridin-3-yl)sulfonyl)(thiazol-4-yl)carbamate (0.218 g, 0.750 mmol) and N-(2-(aminomethyl)-3-fluorobenzyl)-N,2-dimethylpropan-2-amine (0.177 g, 0.790 mmol) in anhydrous dimethyl sulfoxide (8 mL) was added potassium carbonate (0.208 g, 1.50 mmol) and the reaction mixture stirred at ambient temperature for 16 hours. After addition of water (30 mL), the reaction mixture was extracted with ethyl acetate (3×30 mL). The combined organic layers were washed with brine (20 mL), dried over anhydrous sodium sulfate, and filtered. Concentration of the filtrate in vacuo and purification of the residue by column chromatography, eluting with 40% of ethyl acetate (containing 10% of triethylamine and 10% of 2-propanol) in heptane, provided the title compound as a yellow oil (0.395 g, 91% yield): MS (ES+) m/z 578.3 (M+1).

Step 5. Preparation of 6-((2-(((tert-butyl(methyl)amino)methyl)-6-fluorobenzyl)amino)-2-methyl-N-(thiazol-4-yl)pyridine-3-sulfonamide formic acid salt

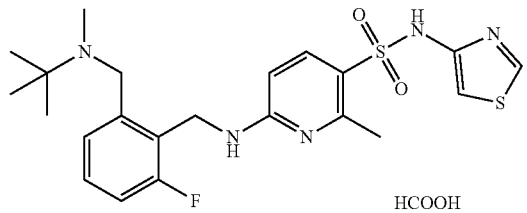 [SMILES: Cc1nc(NCc2c(F)cccc2CN(C)C(C)(C)C)ccc1S(=O)(=O)Nc1cscn1 ; "HCOOH"]

HCOOH

To tert-butyl ((6-((2-(((tert-butyl(methyl)amino)methyl)-6-fluorobenzyl)amino)-2-methylpyridin-3-yl)sulfonyl)(thiazol-4-yl)carbamate (0.395 g, 0.684 mmol) in dichloromethane (8 mL) was added trifluoroacetic acid (1.6 mL, 21.5 mmol) and the reactopm mixture was stirred at ambient temperature for 16 hours. Concentration in vacuo and purification of the residue by preparative reverse phase HPLC, using acetonitrile in water containing 0.5% of formic acid as eluent, afforded the title compound as a colorless solid (0.149 g, 46% yield): $^1$H-NMR (300 MHz, DMSO-$d_6$) δ 8.86 (d, J=2.2 Hz, 1H), 8.15 (s, 1H), 7.74-7.64 (m, 2H), 7.35-7.23 (m, 2H), 7.14-7.08 (m, 1H), 6.83 (d, J=2.2 Hz, 1H), 6.35 (d, J=8.9 Hz, 1H), 4.59 (s, 2H), 3.74 (s, 2H), 2.57 (s, 3H), 2.00 (s, 3H), 1.06 (s, 9H), sulfonamide NH and COOH not observed; MS (ES+) m/z 478.4 (M+1); MS (ES-) m/z 476.4 (M-1).

Example 11

Synthesis of 6-((2-(((tert-butyl(methyl)amino)methyl)-6-fluorobenzyl)amino)-5-chloro-N-(thiazol-4-yl)pyridine-3-sulfonamide formic acid salt

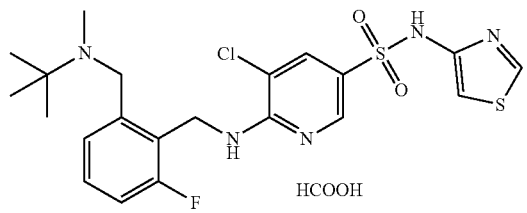 [SMILES: CN(Cc1cccc(F)c1CNc1ncc(S(=O)(=O)Nc2cscn2)cc1Cl)C(C)(C)C ; "HCOOH"]

HCOOH

Step 1. Preparation of 5-(benzylthio)-3-chloro-2-fluoropyridine

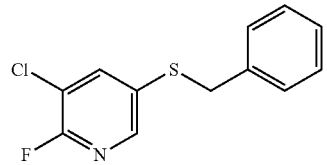 [SMILES: Fc1ncc(SCc2ccccc2)cc1Cl]

To a solution of 5-bromo-3-chloro-2-fluoropyridine (10.0 g, 47.5 mmol) in anhydrous 1,4-dioxane (95 mL) was added N,N-diisopropylethylamine (10.0 mL, 57.0 mmol) and the mixture was degassed with argon. To the resulting mixture was added tris(dibenzylideneacetone)dipalladium(0) (1.09 g, 1.20 mmol), 4,5-bis(diphenylphosphino)-9,9-dimethylxanthene (1.65 g, 2.90 mmol) and benzyl mercaptan (6.6 mL, 55.9 mmol). The reaction mixture was degassed with argon and then heated to 100° C. for 16 hours. The reaction mixture was allowed to cool to ambient temperature and filtered. Concentration of the filtrate in vacuo and purification of the residue by column chromatography, eluting with 5% of ethyl acetate in heptane, afforded the title compound as a yellow oil (9.54 g, 79% yield): $^1$H-NMR (300 MHz, CDCl$_3$) δ 7.92 (dd, J=2.2, 1.3 Hz, 1H), 7.61 (dd, J=8.4, 2.2 Hz, 1H), 7.32-7.24 (m, 3H), 7.19-7.16 (m, 2H), 4.02 (s, 2H); MS (ES+) m/z 254.1 (M+1).

Step 2. Preparation of 5-chloro-6-fluoropyridine-3-sulfonyl chloride

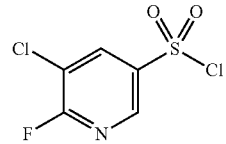 [SMILES: O=S(=O)(Cl)c1cnc(F)c(Cl)c1]

To a solution of 5-(benzylthio)-3-chloro-2-fluoropyridine (9.54 g, 37.6 mmol) in a mixture of acetonitrile (269 mL) and water (9 mL) was added 1,3-dichloro-5,5-dimethylimidazolidine-2,4-dione (20.8 g, 106 mmol). The reaction mixture was cooled to 0° C. and acetic acid (13 mL) was added dropwise. The reaction mixture was stirred at 0° C. for 30 minutes. Water (130 mL) was added to the mixture, and the mixture was extracted with ethyl acetate (3×80 mL). The combined organic layers were washed with brine (40 mL), dried over anhydrous sodium sulfate, and filtered. Concentration of the filtrate in vacuo and purification of the residue by column chromatography, eluting with 10% of ethyl acetate in heptane, afforded the title compound as a pale yellow oil (3.29 g, 38% yield): $^1$H-NMR (300 MHz, CDCl$_3$) δ 8.79 (dd, J=2.3, 1.1 Hz, 1H), 8.44 (dd, J=7.7, 2.4 Hz, 1H).

Step 3. Preparation of tert-butyl ((5-chloro-6-fluoropyridin-3-yl)sulfonyl)(thiazol-4-yl)carbamate

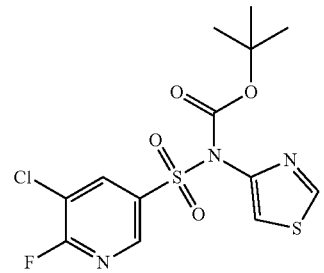 [SMILES: CC(C)(C)OC(=O)N(c1cscn1)S(=O)(=O)c1cnc(F)c(Cl)c1]

To a solution of tert-butyl thiazol-4-ylcarbamate (3.15 g, 15.7 mmol) in anhydrous tetrahydrofuran (72 mL) was added a 1 M solution of lithium bis(trimethylsilyl)amide in tetrahydrofuran (15.7 mL, 15.7 mmol) at −78° C. The reaction mixture was stirred at −78° C. for 15 minutes, allowed to warm to ambient temperature and stirred for 1 hour. The reaction mixture was cooled to −78° C., and a solution of 5-chloro-6-fluoropyridine-3-sulfonyl chloride (3.29 g, 14.3 mmol) in anhydrous tetrahydrofuran (72 mL) was then added dropwise. The reaction mixture was stirred at −78° C. for 30 minutes, allowed to warm to ambient temperature, and stirred for 16 hours. After addition of saturated aqueous ammonium chloride (50 mL), the mixture was extracted with ethyl acetate (3×50 mL). The combined organic phases were washed with brine (50 mL), dried over anhydrous sodium sulfate, and filtered. Concentration of the filtrate in vacuo and purification of the residue by column chromatography, eluting with 20% of ethyl acetate in heptane, afforded the title compound as a yellow solid (1.40 g, 25% yield): $^1$H-NMR (300 MHz, CDCl$_3$) δ 8.81 (dd, J=2.3, 1.1 Hz, 1H), 8.79 (d, J=2.2 Hz, 1H), 8.60 (dd, J=8.1, 2.3 Hz, 1H), 7.56 (d, J=2.2 Hz, 1H), 1.38 (s, 9H); MS (ES+) m/z 394.0, 396.1 (M+1).

Step 4. Preparation of tert-butyl ((6-((2-((tert-butyl (methyl)amino)methyl)-6-fluorobenzyl)amino)-5-chloropyridin-3-yl)sulfonyl)(thiazol-4-yl)carbamate

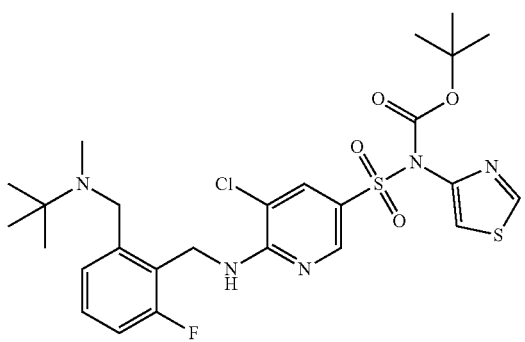 [SMILES: CN(Cc1cccc(F)c1CNc1ncc(S(=O)(=O)N(C(=O)OC(C)(C)C)c2cscn2)cc1Cl)C(C)(C)C]

To a solution of tert-butyl ((5-chloro-6-fluoropyridin-3-yl)sulfonyl)(thiazol-4-yl)carbamate (0.836 g, 2.12 mmol) and N-(2-(aminomethyl)-3-fluorobenzyl)-N,2-dimethylpropan-2-amine (0.500 g, 2.23 mmol) in anhydrous dimethyl sulfoxide (21 mL) was added potassium carbonate (0.587 g, 4.25 mmol) and the reaction mixture stirred at ambient temperature for 16 hours. After addition of water (50 mL), the reaction mixture was extracted with ethyl acetate (3×50 mL). The combined organic layers were washed with brine (50 mL), dried over anhydrous sodium sulfate, and filtered. Concentration of the filtrate in vacuo and purification of the residue by column chromatography, eluting with 25% of ethyl acetate (containing 10% of triethylamine and 10% of 2-propanol) in heptane, provided the title compound as a yellow oil (1.02 g, 80% yield): $^1$H-NMR (300 MHz, CDCl$_3$) δ 8.77 (d, J=2.3 Hz, 1H), 8.70 (d, J=2.2 Hz, 1H), 8.03 (d, J=2.2 Hz, 1H), 7.57-7.52 (m, 1H), 7.49 (d, J=2.2 Hz, 1H), 7.24-7.17 (m, 1H), 7.05-6.97 (m, 2H), 4.94 (dd, J=5.7, 1.6 Hz, 2H), 3.73 (s, 2H), 2.08 (s, 3H), 1.41 (s, 9H), 1.23 (s, 9H); MS (ES+) m/z 598.2 (M+1), 600.2 (M+1).

Step 5. Preparation of 6-((2-((tert-butyl(methyl) amino)methyl)-6-fluorobenzyl)amino)-5-chloro-N-(thiazol-4-yl)pyridine-3-sulfonamide formic acid salt

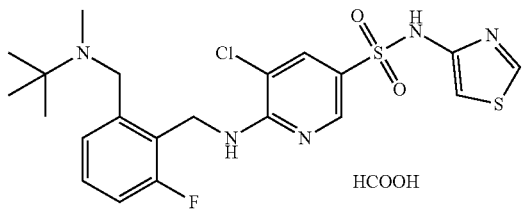 [SMILES: CN(Cc1cccc(F)c1CNc1ncc(S(=O)(=O)Nc2cscn2)cc1Cl)C(C)(C)C ; "HCOOH"]

To tert-butyl ((6-((2-((tert-butyl(methyl)amino)methyl)-6-fluorobenzyl)amino)-5-chloropyridin-3-yl)sulfonyl)(thiazol-4-yl)carbamate (0.205 g, 0.343 mmol) in dichloromethane (4 mL) was added trifluoroacetic acid (0.9 mL, 11.9 mmol) and the reaction mixture was stirred at ambient temperature for 16 hours. Concentration in vacuo and purification of the residue by preparative reverse phase HPLC, using acetonitrile in water containing 0.5% formic acid as eluent, afforded the title compound as a colorless solid (0.130 g, 76% yield): $^1$H-NMR (300 MHz, DMSO-d$_6$) δ 8.90 (d, J=2.1 Hz, 1H), 8.40 (d, J=2.1 Hz, 1H), 8.15 (s, 1H), 7.87 (d, J=2.1 Hz, 1H), 7.73 (s, 1H), 7.33-7.26 (m, 1H), 7.19-7.17 (m, 1H), 7.13-7.07 (m, 2H), 4.78 (s, 2H), 3.73 (s, 2H), 2.00 (s, 3H), 1.13 (s, 9H), sulfonamide NH and COOH not observed; MS (ES+) m/z 498.4 (M+1), 500.4 (M+1); MS (ES−) m/z 496.3 (M−1), 498.3 (M−1).

Example 12

Synthesis of 5-((2-(azetidin-1-ylmethyl)-6-fluorobenzyl)amino)-N-(isothiazol-3-yl)-4-methylpyridine-2-sulfonamide trifluoroacetic acid salt

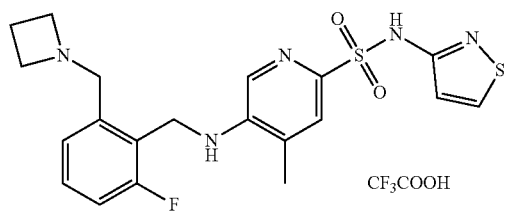 [SMILES: Cc1cc(S(=O)(=O)Nc2ccsn2)ncc1NCc1c(F)cccc1CN1CCC1 ; "CF3COOH"]

Step 1. Preparation of 2-(benzylthio)-5-fluoro-4-methylpyridine

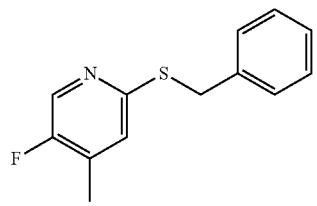 [SMILES: Cc1cc(SCc2ccccc2)ncc1F]

To a mixture of 2-bromo-5-fluoro-4-methylpyridine (25.0 g, 131.5 mmol), tris(dibenzylideneacetone)dipalladium(0)

(3.0 g, 3.3 mmol) and 4,5-bis(diphenylphosphino)-9,9-dimethylxanthene (3.8 g, 6.6 mmol) in anhydrous 1,4-dioxane (260 mL) was added N,N-diisopropylethylamine (34.4 mL, 197 mmol) and benzyl mercaptan (14.6 mL, 125 mmol). The reaction mixture was carefully degassed with nitrogen and then heated at 100° C. for 16 hours. After cooling to ambient temperature, the reaction mixture was concentrated under reduced pressure. After addition of water (50 mL) to the residue, the mixture was extracted with ethyl acetate (2×100 mL). The combined organic layers were washed with brine (50 mL), dried over anhydrous sodium sulfate, and filtered. Concentration of the filtrate under reduced pressure and purification of the residue by column chromatography, eluting with a gradient of 0 to 30% of ethyl acetate in heptane, afforded the title compound as colorless oil (28.0 g, 91% yield): $^1$H NMR (300 MHz, DMSO-$d_6$) δ 8.38 (d, J=1.5 Hz, 1H), 7.38 (dd, J=8.1, 1.5 Hz, 2H), 7.27-7.22 (m, 4H), 4.38 (s, 2H), 2.22 (d, J=0.9 Hz, 3H); MS (ES+) m/z 234.2 (M+1).

Step 2. Preparation of
5-fluoro-4-methylpyridine-2-sulfonyl chloride

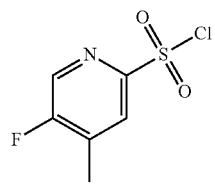

To a solution of 2-(benzylthio)-5-fluoro-4-methylpyridine (26.6 g, 114 mmol) in a mixture of acetonitrile (325 mL) and water (10 mL) was added acetic acid (13 mL, 228 mmol) at 0° C. followed by 1,3-dichloro-5,5-dimethyl-imidazolidine-2,4-dione (44.9 g, 228 mmol). The reaction mixture was stirred at 0° C. for 30 minutes, and then quenched by addition of saturated sodium bicarbonate solution until pH 7 was reached.

The mixture was extracted with ethyl acetate (3×70 mL). The combined organic layers were washed with brine (20 mL), dried over anhydrous sodium sulfate, and filtered. Concentration of the filtrate under reduced pressure and purification of the residue by column chromatography, eluting with a gradient of 0 to 30% of ethyl acetate in heptane, afforded the title compound as colorless oil (11.5 g, 48% yield): $^1$H NMR (300 MHz, CDCl$_3$) δ 8.52 (s, 1H), 8.03 (dd, J=5.5, 0.2 Hz, 1H), 2.49 (dd, J=1.9, 0.6 Hz, 3H).

Step 3. Preparation of Tert-butyl
Isothiazol-3-ylcarbamate

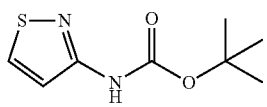

To a slurry of isothiazole-3-carboxylic acid (5.0 g, 38.7 mmol) in tert-butanol (194 mL) was added triethylamine (4.3 g, 42.6 mmol) followed by diphenyl phosphoryl azide (11.9 g, 43.3 mmol). The reaction mixture was heated to reflux for 9 hours. After cooling the ambient temperature, the reaction mixture was concentrated in vacuo and the residue dissolved in ethyl acetate (300 mL). The organic layer was washed with water (100 mL), 1 N sodium hydroxide solution (50 mL), water (100 mL), brine (50 mL), and dried over anhydrous magnesium sulfate. Filtration and concentration of the filtrate in vacuo afforded a residue. Purification of the residue by column chromatography, eluting with a gradient of 0 to 10% of ethyl acetate in heptane, provided the title compound as a colorless solid (6.16 g, 79% yield): $^1$H NMR (300 MHz, CDCl$_3$) δ 9.03-8.98 (m, 1H), 8.58 (d, J=4.9 Hz, 1H), 7.70 (d, J=4.9 Hz, 1H), 1.53 (d, J=0.7 Hz, 9H).

Step 4. Preparation of tert-butyl ((5-fluoro-4-methyl pyridin-2-yl)sulfonyl)(isothiazol-3-yl)carbamate

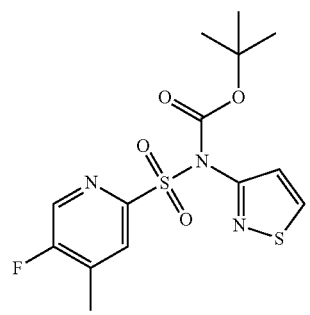 [SMILES: Cc1cc(S(=O)(=O)N(C(=O)OC(C)(C)C)c2ccsn2)ncc1F]

To a solution of tert-butyl isothiazol-3-ylcarbamate (0.95 g, 4.78 mmol) in anhydrous tetrahydrofuran (16 mL) was added a 1 M solution of lithium bis(trimethylsilyl)amide in tetrahydrofuran (5.25 mL, 5.25 mmol) at −78° C. The reaction mixture was stirred at −78° C. for 10 minutes, allowed to warm to 0° C., and stirred at this temperature for 10 minutes. The reaction mixture was then cooled to −78° C., and a solution of 5-fluoro-4-methylpyridine-2-sulfonyl chloride (1.00 g, 4.78 mmol) anhydrous tetrahydrofuran (5 mL) was added to the reaction mixture. The reaction mixture was stirred at −78° C. for 1 h, allowed to warm to ambient temperature, and stirred for 16 hours. After addition of water (10 mL), the mixture was extracted with ethyl acetate (2×20 mL). The combined organic layers were washed with brine (10 mL), dried over anhydrous sodium sulfate, and filtered. After concentration of the filtrate under reduced pressure the residue was triturated with methanol (5 mL). The precipitate was filtered off and washed with methanol (3×5 mL) to afford the title compound as a colorless solid (0.73 g, 41% yield): MS (ES+) m/z 274.2 (M−99).

Step 5. Preparation of 5-fluoro-N-(isothiazol-3-yl)-
N-(4-methoxybenzyl)-4-methylpyridine-2-sulfonamide

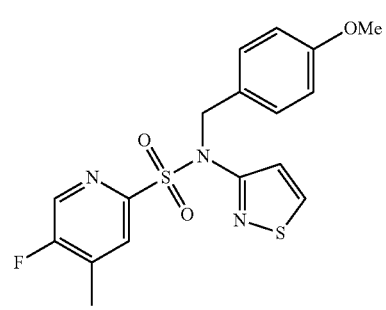 [SMILES: COc1ccc(CN(c2ccsn2)S(=O)(=O)c2cc(C)c(F)cn2)cc1]

To a solution of tert-butyl ((5-fluoro-4-methylpyridin-2-yl)sulfonyl)(isothiazol-3-yl)carbamate (0.73 g, 1.95 mmol) in dichloromethane (5 mL) was added trifluoroacetic acid (5 mL) and the reaction mixture was stirred at ambient temperature for 1 hour.

The reaction mixture was concentrated in vacuo. To the residue was added anhydrous dimethyl sulfoxide (6 mL), sodium bicarbonate (0.82 g, 9.78 mmol) and 4-methoxybenzyl chloride (0.46 g, 2.9 mmol). The reaction mixture was stirred at ambient temperature for 2 hours and then quenched by addition of water (10 mL). The mixture was extracted with ethyl acetate (3×20 mL) and the combined organic layers were washed with brine (20 mL), dried over anhydrous sodium sulfate, and filtered. Concentration of the filtrate under reduced pressure and purification of the residue by column chromatography, eluting with a gradient of 0 to 60% of ethyl acetate in heptane, afforded the title compound as colorless oil (0.77 g, quantitative yield): MS (ES+) m/z 394.2 (M+1).

Step 6. Preparation of 5-((2-(azetidin-1-ylmethyl)-6-fluorobenzyl)amino)-N-(isothiazol-3-yl)-N-(4-methoxybenzyl)-4-methylpyridine-2-sulfonamide

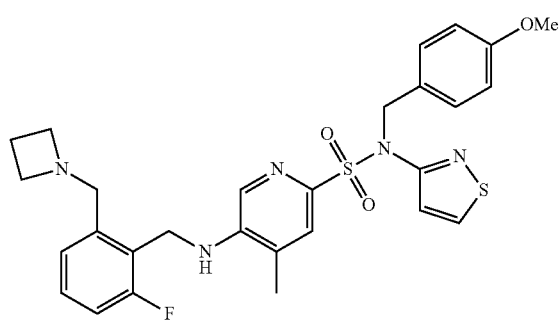 [SMILES: COc1ccc(CN(c2ccsn2)S(=O)(=O)c2cc(C)c(NCc3c(F)cccc3CN3CCC3)cn2)cc1]

To a mixture of (2-(azetidin-1-ylmethyl)-6-fluorophenyl)methanamine (0.39 g, 1.3 mmol) and 5-fluoro-N-(isothiazol-3-yl)-N-(4-methoxybenzyl)-4-methylpyridine-2-sulfonamide (0.40 g, 1.02 mmol) in anhydrous dimethyl sulfoxide (5 mL) was added N,N-diisopropylethylamine (0.26 g, 2.04 mmol) and the reaction mixture was stirred at 110° C. for 8 hours. The reaction mixture was allowed to cool to ambient temperature, water (10 mL) was added to it, and the mixture was extracted with ethyl acetate (3×10 mL). The combined organic layers were washed with brine (3×10 mL), dried over anhydrous sodium sulfate and filtered. Concentration of the filtrate and purification of the residue by column chromatography, eluting with a gradient of 0 to 8% of methanol in dichloromethane afforded the title compound as colorless oil (0.40 g, 69% yield): MS (ES+) m/z 568.2 (M+1).

Step 7. Preparation of 5-((2-(azetidin-1-ylmethyl)-6-fluorobenzyl)amino)-N-(isothiazol-3-yl)-4-methylpyridine-2-sulfonamide trifluoroacetic acid salt

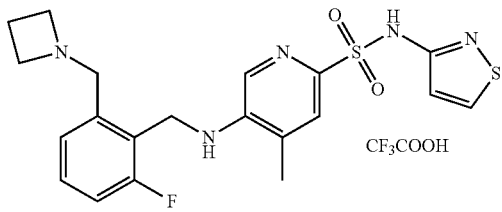

To a solution of 5-((2-(azetidin-1-ylmethyl)-6-fluorobenzyl)amino)-N-(isothiazol-3-yl)-N-(4-methoxybenzyl)-4-methylpyridine-2-sulfonamide (0.40 g, 0.70 mmol) in dichloromethane (5 mL) was added trifluoroacetic acid (5 mL) and the reaction mixture was heated under reflux for 10 hours. The reaction mixture was concentrated under reduced pressure and the residue purified by column chromatography, eluting with a gradient of 0 to 10% of methanol in dichloromethane, providing the title compound as colorless solid (0.31 g, 79% yield): $^1$H-NMR (300 MHz, DMSO-$d_6$) δ 11.52-11.39 (br s, 1H), 10.70-10.53 (br s, 1H), 8.86 (d, J=4.8 Hz, 1H), 7.99 (s, 1H), 7.71 (s, 1H), 7.49-7.43 (m, 1H), 7.31 (t, J=8.7 Hz, 2H), 7.01 (d, J=4.8 Hz, 1H), 6.22 (s, 1H), 4.60-4.44 (m, 4H), 4.19-3.96 (m, 4H), 2.47-2.22 (m, 2H), 2.17 (s, 3H); MS (ES+) m/z 448.2 (M+1).

Example 13

Synthesis of 6-((2-((tert-butyl(methyl)amino)methyl)-6-fluorobenzyl)amino)-5-methyl-N-(thiazol-4-yl)pyridine-3-sulfonamide formic acid salt

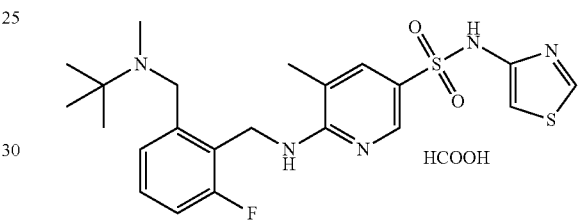

Step 1. Preparation of tert-butyl ((6-((2-((tert-butyl(methyl)amino)methyl)-6-fluorobenzyl)amino)-5-methylpyridin-3-yl)sulfonyl)(thiazol-4-yl)carbamate

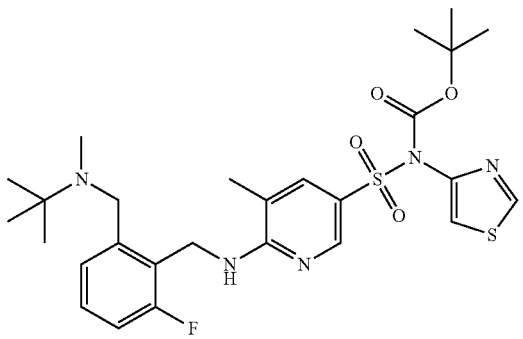 [SMILES: Cc1cc(S(=O)(=O)N(C(=O)OC(C)(C)C)c2cscn2)cnc1NCc1c(F)cccc1CN(C)C(C)(C)C]

To a solution of tert-butyl ((6-((2-((tert-butyl(methyl)amino)methyl)-6-fluorobenzyl)amino)-5-chloropyridin-3-yl)sulfonyl)(thiazol-4-yl)carbamate (0.40 g, 0.670 mmol) in anhydrous 1,2-dimethoxyethane (13 mL) was added methyl boronic acid (0.32 g, 5.35 mmol) and potassium phosphate (0.430 g, 2.01 mmol) and the mixture was degassed with argon. To the mixture was then added palladium (II) acetate (0.023 g, 0.100 mmol) and tricyclohexyl phosphonium tetrafluoroborate (0.074 g, 0.200 mmol). The reaction mixture was degassed with argon and then heated to 85° C. for 2 hours in a microwave. The reaction mixture was allowed to cool to ambient temperature and filtered through diatomaceous earth. Concentration of the filtrate in vacuo and purification of the residue by column chromatography, eluting with 40% of ethyl acetate (containing 10% of triethylamine and 10% of 2-propanol) in heptane, afforded the title compound as a brown solid (0.294 g, 76% yield): ¹H-NMR (300 MHz, CDCl₃) δ 8.76 (d, J=2.2 Hz, 1H), 8.70 (d, J=2.3 Hz, 1H), 7.76-7.75 (m, 1H), 7.49 (d, J=2.3 Hz, 1H), 7.24-7.16 (m, 1H), 7.07-6.96 (m, 2H), 6.48-6.43 (m, 1H), 4.95-4.93 (m, 2H), 3.74 (s, 2H), 2.08 (s, 3H), 2.05 (s, 3H), 1.39 (s, 9H), 1.21 (s, 9H); MS (ES+) m/z 578.3 (M+1).

Step 2. Preparation of 6-((2-(((tert-butyl(methyl)amino)methyl)-6-fluorobenzyl)amino)-5-methyl-N-(thiazol-4-yl)pyridine-3-sulfonamide formic acid salt

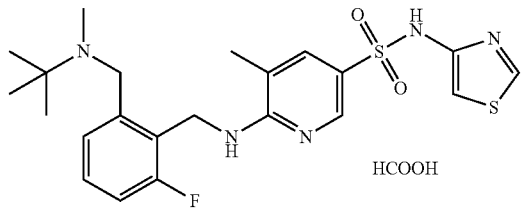 [SMILES: Cc1cc(S(=O)(=O)Nc2cscn2)cnc1NCc1c(F)cccc1CN(C)C(C)(C)C ; "HCOOH"]

To tert-butyl ((6-((2-(((tert-butyl(methyl)amino)methyl)-6-fluorobenzyl)amino)-5-methylpyridin-3-yl)sulfonyl)(thiazol-4-yl)carbamate (0.294 g, 0.510 mmol) in dichloromethane (10 mL) was added trifluoroacetic acid (0.8 mL, 10.2 mmol) and the reaction mixture was stirred at ambient temperature for 16 hours. Concentration in vacuo and purification of the residue by preparative reverse phase HPLC, using acetonitrile in water containing 0.5% of formic acid as eluent, afforded the title compound as a colorless solid (0.090 g, 37% yield): ¹H-NMR (300 MHz, DMSO-d₆) δ 8.87 (d, J=2.1 Hz, 1H), 8.31 (d, J=2.4 Hz, 1H), 8.16 (s, 1H), 7.56-7.55 (m, 1H), 7.32-7.21 (m, 2H), 7.11-7.05 (m, 1H), 7.01 (d, J=2.1 Hz, 1H), 6.97-6.91 (m, 1H), 4.71 (s, 2H), 3.75 (s, 2H), 2.02-2.01 (m, 6H), 1.07 (s, 9H), sulfonamide NH and COOH not observed; MS (ES+) m/z 478.4 (M+1); MS (ES-) m/z 476.3 (M-1).

Example 14

Synthesis of 5-((2-fluoro-6-((3-fluoro-3-methylazetidin-1-yl)methyl)benzyl)amino)-6-methyl-N-(thiazol-4-yl)pyridine-2-sulfonamide

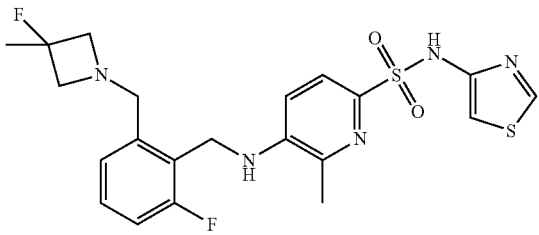 [SMILES: Cc1nc(S(=O)(=O)Nc2cscn2)ccc1NCc1c(F)cccc1CN1CC(C)(F)C1]

Step 1. Preparation of 2-fluoro-6-((3-fluoro-3-methylazetidin-1-yl)methyl)benzonitrile

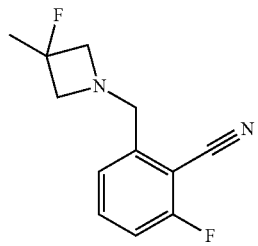 [SMILES: CC1(F)CN(Cc2cccc(F)c2C#N)C1]

To a solution of 2-(bromomethyl)-6-fluorobenzonitrile (0.35 g, 1.64 mmol) and 3-fluoro-3-methylazetidine hydrochloride (0.27 g, 2.13 mmol) in anhydrous N,N-dimethylformamide (10 mL) was added potassium carbonate (0.90 g, 6.54 mmol). The mixture was stirred at ambient temperature for 12 h, and then diluted with water (30 mL) and extracted with ethyl acetate (3×30 mL). The combined organic extracts were washed with brine (20 mL), dried over anhydrous sodium sulfate, and filtered. Concentration of the filtrate in vacuo and purification of the residue by column chromatography, eluting with a gradient of 20 to 35% of ethyl acetate in petroleum ether, provided 2-fluoro-6-((3-fluoro-3-methylazetidin-1-yl)methyl)benzonitrile as a colorless oil (0.36 g, 99% yield): ¹H NMR (400 MHz, CDCl₃) δ 7.48 (td, J=8.2, 5.6 Hz, 1H), 7.24 (d, J=7.6 Hz, 1H), 7.03 (t, J=8.4 Hz, 1H), 3.80 (s, 2H), 3.40-3.23 (m, 4H), 1.64-1.54 (m, 3H); MS (ES+) m/z 223.3 (M+1).

Step 2. Preparation of (2-fluoro-6-((3-fluoro-3-methylazetidin-1-yl)methyl)phenyl)methanamine

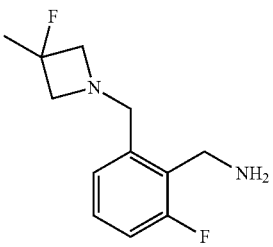 [SMILES: CC1(F)CN(Cc2cccc(F)c2CN)C1]

To a solution of 2-fluoro-6-((3-fluoro-3-methylazetidin-1-yl)methyl)benzonitrile (0.31 g, 1.39 mmol) in methanol (20 mL) and ammonium hydroxide (4 mL) was added Raney-Nickel (0.024 g, 0.28 mmol). The mixture was stirred under a hydrogen atmosphere (50 psi) at ambient temperature for 12 hours. The mixture was filtered and the filtrate concentrated in vacuo. The residue was purified by preparative reverse-phase HPLC, using a gradient of acetonitrile in water (containing ammonium carbonate, 0.010 M), to provide the title compound as a colorless oil (0.11 g, 35% yield): ¹H NMR (400 MHz, CDCl₃) δ 7.14-7.07 (m, 1H), 6.98-6.91 (m, 2H), 3.84 (d, J=1.6 Hz, 2H), 3.66 (s, 2H), 3.31-3.13 (m, 4H), 1.58-1.48 (m, 3H), NH not observed; MS (ES+) m/z 227.3 (M+1).

Step 3. Preparation of Synthesis of 5-((2-fluoro-6-((3-fluoro-3-methylazetidin-1-yl)methyl)benzyl)amino)-6-methyl-N-(thiazol-4-yl)pyridine-2-sulfonamide

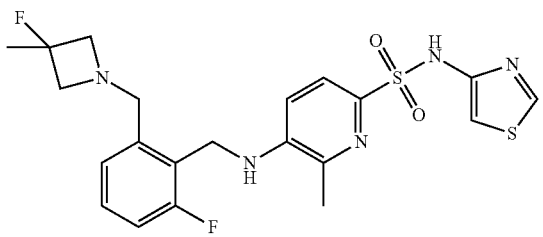 [SMILES: Cc1nc(S(=O)(=O)Nc2cscn2)ccc1NCc1c(F)cccc1CN1CC(C)(F)C1]

To a solution of tert-butyl (5-bromo-6-methylpyridin-2-yl)sulfonyl(thiazol-4-yl)carbamate (0.15 g, 0.35 mmol) and (2-fluoro-6-((3-fluoro-3-methylazetidin-1-yl)methyl)phenyl)methanamine (0.101 g, 0.45 mmol) in anhydrous dioxane (2 mL) was added [(2-di-tert-butylphosphino-2',4',6'-triisopropyl-1,1'-biphenyl)-2-(2'-amino-1,1'-biphenyl)]palladium(II) methanesulfonate (0.027 g, 0.035 mmol) and a 2 M solution of sodium tert-butoxide in tetrahydrofuran (0.52 mL, 1.04 mmol). The reaction mixture was degassed and stirred at ambient temperature for 12 hours. The mixture was diluted with water (50 mL) and extracted with ethyl acetate (3×40 mL). The combined organic phase was washed with brine (20 mL), dried over anhydrous sodium sulfate, and filtered. Concentration of the filtrate under reduced pressure provided a residue which was purified by preparative reverse phase HPLC using acetonitrile in water containing 0.23% formic acid as eluent to give the title compound as a colorless solid (0.051 g, 29% yield): $^1$H NMR (400 MHz, CD$_3$OD) δ8.70 (d, J=2.2 Hz, 1H), 7.73 (d, J=8.4 Hz, 1H), 7.37-7.29 (m, 1H), 7.18 (dd, J=14.0, 8.0 Hz, 2H), 7.13-7.06 (m, 1H), 7.01 (d, J=2.2 Hz, 1H), 4.50 (s, 2H), 3.84 (br d, J=8.8 Hz, 2H), 3.50-3.35 (m, 4H), 2.38 (s, 3H), 1.53 (d, J=22 Hz, 3H), NH not observed; MS (ES+) m/z 479.9 (M+1).

Example 15

Synthesis of 5-((2-(((cyclopropylmethyl)(methyl)amino)methyl)-6-fluorobenzyl)amino)-6-methyl-N-(thiazol-4-yl)pyridine-2-sulfonamide formic acid salt

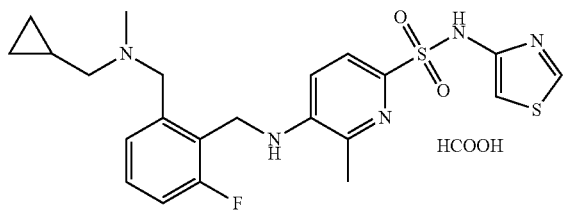 [SMILES: Cc1nc(S(=O)(=O)Nc2cscn2)ccc1NCc1c(F)cccc1CN(C)CC1CC1 ; "HCOOH"]

Step 1. Preparation of 2-(((cyclopropylmethyl)(methyl)amino)methyl)-6-fluorobenzonitrile

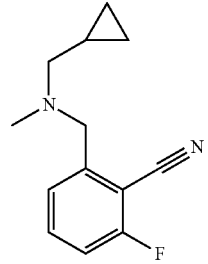 [SMILES: CN(Cc1cccc(F)c1C#N)CC1CC1]

To a solution of 2-(bromomethyl)-6-fluorobenzonitrile (0.97 g, 4.52 mmol) in anhydrous dichloromethane (1 mL) was added 1-cyclopropyl-N-methyl-methanamine hydrochloride (0.5 g, 4.11 mmol) and triethylamine (0.83 g, 8.22 mmol) and the reaction mixture was stirred at ambient temperature for 12 hours. The reaction mixture was diluted with saturated ammonium chloride (20 mL) and extracted with ethyl acetate (3×20 mL). The combined organic phase was washed with brine (3×20 mL), dried over anhydrous sodium sulfate, and filtered. Concentration of the filtrate in vacuo and purification of the residue by column chromatography, eluting with 10-30% of ethyl acetate in petroleum ether, afforded the title compound as a yellow oil (0.4 g, 44% yield): $^1$H NMR (400 MHz, CDCl$_3$) δ 7.54 (dt, J=8.2, 8.2 Hz, 1H), 7.39 (d, J=7.8 Hz, 1H), 7.10 (t, J=8.6 Hz, 1H), 3.74 (s, 2H), 2.37 (d, J=6.6 Hz, 2H), 2.31 (s, 3H), 0.98-0.89 (m, 1H), 0.58-0.51 (m, 2H), 0.16-0.11 (m, 2H).

Step 2. Preparation of N-(2-(aminomethyl)-3-fluorobenzyl)-1-cyclopropyl-N-methylmethanamine

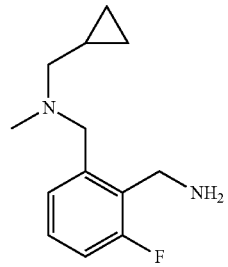 [SMILES: CN(Cc1cccc(F)c1CN)CC1CC1]

To a mixture of 2-(((cyclopropylmethyl)(methyl)amino)methyl)-6-fluorobenzonitrile (0.4 g, 1.83 mmol) in methanol (10 mL) and concentrated ammonium hydroxide (2 mL) was added Raney-Nickel (0.16 g, 1.83 mmol). The reaction mixture was stirred under an atmosphere of hydrogen (50 psi) at ambient temperature 12 hours. Filtration of the reaction mixture and concentration of the filtrate under reduced pressure afforded the title compound as a yellow oil (0.35 g, 85% yield).

Step 3. Preparation of 5-((2-(((cyclopropylmethyl)(methyl)amino)methyl)-6-fluorobenzyl)amino)-6-methyl-N-(thiazol-4-yl)pyridine-2-sulfonamide formic acid salt

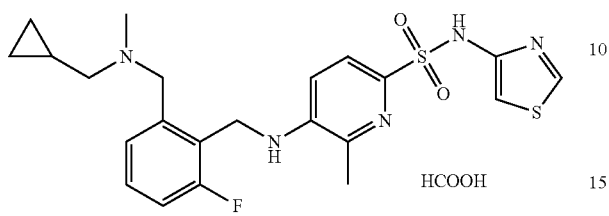

Following the procedure as described for EXAMPLE 14, Step 3 and making non-critical variations as required to replace (2-fluoro-6-((3-fluoro-3-methylazetidin-1-yl)methyl)phenyl)methanamine with N-(2-(aminomethyl)-3-fluorobenzyl)-1-cyclopropyl-N-methylmethanamine, the title compound was obtained as a colorless solid (0.012 g, 6% yield): $^1$H NMR (400 MHz, CD$_3$OD) δ 8.68 (d, J=2.2 Hz, 1H), 8.37 (br s, 1H), 7.73 (d, J=8.6 Hz, 1H), 7.38 (dt, J=7.8, 5.8 Hz, 1H), 7.27-7.14 (m, 3H), 6.99 (d, J=2.2 Hz, 1H), 4.50 (s, 2H), 3.97 (s, 2H), 2.60 (br d, J=6.8 Hz, 2H), 2.43 (s, 3H), 2.32 (s, 3H), 1.01-0.87 (m, 1H), 0.56-0.44 (m, 2H), 0.15 (q, J=5.0 Hz, 2H), NH and COOH not observed; MS (ES+) m/z 476.3 (M+1).

Example 16

Synthesis of 5-((isoquinolin-8-ylmethyl)amino)-6-methyl-N-(thiazol-4-yl)pyridine-2-sulfonamide formic acid salt

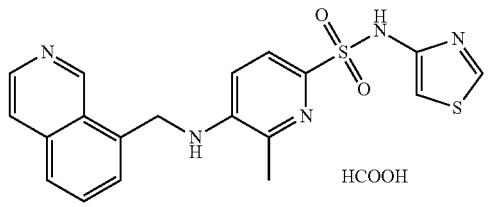 [SMILES: Cc1nc(S(=O)(=O)Nc2cscn2)ccc1NCc1cccc2ccncc12 ; "HCOOH"]

Following the procedure as described for EXAMPLE 14, Step 3 and making non-critical variations as required to replace (2-fluoro-6-((3-fluoro-3-methylazetidin-1-yl)methyl)phenyl)methanamine with isoquinolin-8-ylmethanamine, the title compound was obtained as a yellow solid (0.038 g, 23% yield): $^1$H NMR (400 MHz, CD30D) δ 9.58 (s, 1H), 8.69 (d, J=2.2 Hz, 1H), 8.51 (d, J=5.6 Hz, 1H), 8.26 (br s, 1H), 7.93-7.86 (m, 2H), 7.72 (t, J=7.6 Hz, 1H), 7.65-7.58 (m, 2H), 6.99 (d, J=2.0 Hz, 1H), 6.83 (d, J=8.4 Hz, 1H), 5.08 (s, 2H), 2.49 (s, 3H), NH and COOH not observed; MS (ES+) m/z 411.9 (M+1).

Example 17

Synthesis of 4-(difluoromethyl)-5-((2-fluoro-6-(pyrrolidin-1-ylmethyl)benzyl)amino)-N-(thiazol-4-yl)pyridine-2-sulfonamide formic acid salt

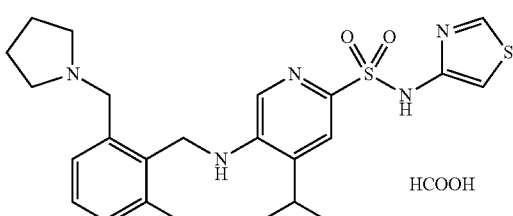

Step 1. Preparation of 2-(benzylthio)-5-fluoroisonicotinaldehyde

To a mixture of 2-bromo-5-fluoroisonicotinaldehyde (5.04 g, 24.7 mmol) in anhydrous dioxane (100 mL) was added N,N-diisopropylethylamine (8.62 mL, 49.4 mmol), benzyl mercaptan (2.76 mL, 23.5 mmol), 4,5-bis(diphenylphosphino)-9,9-dimethylxanthene (1.43 g, 2.47 mmol) and tris(dibenzylideneacetone)dipalladium(0) (1.13 g, 1.24 mmol). The reaction mixture was heated under reflux for 20 hours. After cooling to ambient temperature, the reaction mixture was filtered and the filter cake washed with ethyl acetate (100 mL). Concentration of the combined filtrate under reduced pressure and purification of the residue by column chromatography, eluting with a gradient of 0-40% of ethyl acetate in heptane, provided the title compound as a brownish oil (5.23 g, 90% yield): $^1$H NMR (300 MHz, CDCl$_3$) δ 10.33 (s, 1H), 8.56 (dd, J=1.5, 0.6 Hz, 1H), 7.52 (dd, J=5.0, 0.6 Hz, 1H), 7.47-7.39 (m, 2H), 7.35-7.23 (m, 3H), 4.43 (s, 2H); MS (ES+) m/z 248.2 (M+1).

Step 2. Preparation of 2-(benzylthio)-4-(difluoromethyl)-5-fluoropyridine

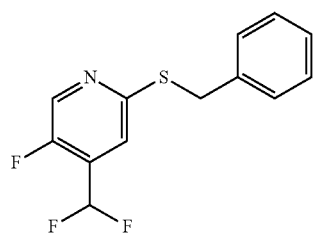 [SMILES: Fc1cnc(SCc2ccccc2)cc1C(F)F]

To a mixture of 2-(benzylthio)-5-fluoroisonicotinaldehyde (3.67 g, 14.8 mmol) in anhydrous dichloromethane (50 ml) was added (diethylamino)sulfur trifluoride (3.92 mL, 29.7 mmol) at 0° C. The reaction mixture stirred for 2.5 hours at 0° C., and then quenched by slow addition of 2 M sodium carbonate until pH 9 was obtained. The mixture was extracted with ethyl acetate (100 mL). The organic phase was washed with 2 M sodium carbonate (50 mL), saturated ammonium chloride (50 mL), brine (50 mL), and dried over anhydrous sodium sulfate. Filtration and concentration of the filtrate under reduced pressure gave a residue. Purification of the residue by column chromatography, eluting with a gradient of 0-20% of ethyl acetate in heptane, provided the title compound as an orange oil (3.04 g, 71% yield): $^1$H NMR (300 MHz, CDCl$_3$) δ 8.45-8.44 (m, 1H), 7.44-7.40 (m, 2H), 7.37-7.25 (m, 4H), 6.82 (t, J=54.2 Hz, 1H), 4.45 (s, 2H); MS (ES+) m/z 270.2 (M+1).

Step 3. Preparation of 4-(difluoromethyl)-5-fluoropyridine-2-sulfonyl chloride

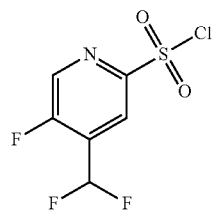

To a mixture of 2-(benzylthio)-4-(difluoromethyl)-5-fluoropyridine (3.04 g, 11.2 mmol) in acetonitrile (60 mL) was added water (2.6 mL) and acetic acid (3.2 mL). The mixture was cooled to 0° C., and 1,3-dichloro-5,5-dimethylhydantoin (4.44 g, 22.6 mmol) was added to it. The reaction mixture was stirred at 0° C. for 1.5 hours and was then diluted with ethyl acetate (200 mL). The mixture was washed with cold brine (4×75 mL), dried over anhydrous sodium sulfate, and filtered. Concentration of the filtrate under reduced pressure and purification of the residue by column chromatography, eluting with a gradient of 0-30% of ethyl acetate in heptane, provided the title compound as a colorless oil (2.39 g, 87% yield): $^1$H NMR (300 MHz, CDCl$_3$) δ 8.79-8.77 (m, 1H), 8.38 (d, J=5.0 Hz, 1H), 6.99 (t, J=53.6 Hz, 1H).

Step 4. Preparation of tert-butyl ((4-(difluoromethyl)-5-fluoropyridin-2-yl)sulfonyl)(thiazol-4-yl) carbamate

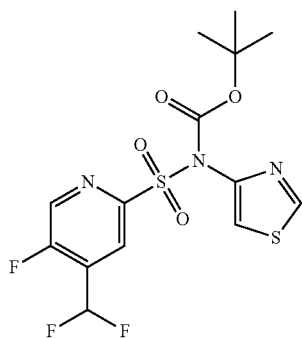

To a mixture of tert-butyl thiazol-4-ylcarbamate (2.14 g, 10.7 mmol) in anhydrous tetrahydrofuran (50 mL) was added a 1 M solution of lithium bis(trimethylsilyl)amide in tetrahydrofuran (10.7 mL, 10.7 mmol) at 0° C. The reaction mixture was stirred at 0° C. for 1 hours and then cooled to −78° C. To it was then added a solution of 4-(difluoromethyl)-5-fluoropyridine-2-sulfonyl chloride (2.39 g, 9.73 mmol) in anhydrous tetrahydrofuran (25 mL) at −78° C. The reaction was allowed to warm to ambient temperature, stirred for 2 h, and then concentrated in vacuo. To the residue was added ethyl acetate (80 mL), and the mixture was washed with concentrated ammonium chloride (2×50 mL), and brine (50 mL). The organic phase was dried over anhydrous sodium sulfate and filtered. Concentration of the filtrate under reduced pressure and purification of the residue by column chromatography, eluting with a gradient of 0-80% of ethyl acetate in heptane, provided the title compound as a colorless oil (2.82 g, 71% yield): $^1$H NMR (300 MHz, CDCl$_3$) δ 8.84 (d, J=2.3 Hz, 1H), 8.75 (br s, 1H), 8.53 (d, J=5.2 Hz, 1H), 7.67 (d, J=2.3 Hz, 1H), 6.98 (t, J=53.7 Hz, 1H), 1.34 (s, 9H); MS (ES+) m/z 410.3 (M+1).

Step 5. Preparation of 4-(difluoromethyl)-5-fluoro-N-(4-methoxybenzyl)-N-(thiazol-4-yl)pyridine-2-sulfonamide

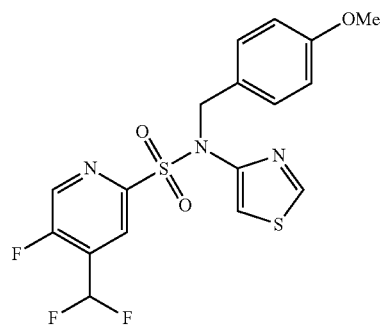 [SMILES: COc1ccc(CN(c2cscn2)S(=O)(=O)c2cc(C(F)F)c(F)cn2)cc1]

To a solution of tert-butyl ((4-(difluoromethyl)-5-fluoropyridin-2-yl)sulfonyl)(thiazol-4-yl)carbamate (2.11 g, 6.84 mmol) in dichloromethane (10 mL) was added trifluoroacetic acid (5 mL) and the reaction mixture was stirred at ambient temperature for 1 hour. The reaction mixture was concentrated in vacuo. To the residue was added anhydrous dimethyl sulfoxide (20 mL), sodium bicarbonate (2.8 g, 34.2 mmol) and 4-methoxybenzyl chloride (1.60 g, 10.3 mmol). The reaction mixture was stirred at ambient temperature for 16 hours and then quenched by addition of water (20 mL). The mixture was extracted with ethyl acetate (3×50 mL) and the combined organic layers were washed with brine (2×20 mL), dried over anhydrous sodium sulfate, and filtered. Concentration of the filtrate under reduced pressure and purification of the residue by column chromatography, eluting with a gradient of 0-60% of ethyl acetate in heptane, afforded the title compound as a colorless oil (2.80 g, 95% yield): MS (ES+) m/z 430.2 (M+1).

Step 6. Preparation of (2-fluoro-6-(pyrrolidin-1-ylmethyl)phenyl)methanamine

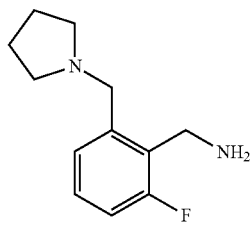 [SMILES: NCc1c(F)cccc1CN1CCCC1]

To a solution of 2-(bromomethyl)-6-fluorobenzonitrile (10.0 g, 46.7 mmol) in dichloromethane (234 mL) was added pyrrolidine (4.29 mL), 51.4 mmol), and N,N-diisopropylethylamine (10.6 mL, 60.7 mmol). The resulting mixture was stirred at ambient temperature for 18 hours. The reaction mixture was washed with saturated ammonium chloride (100 mL) and the aqueous layer was extracted with dichloromethane (75 mL). The organic layers were combined, washed with water (50 mL), brine (50 mL), dried over anhydrous magnesium sulfate, and filtered. The filtrate was concentrated in vacuo and the residue was dissolved in methanol (234 mL). To the solution was added concentrated ammonium hydroxide (30 mL) and Raney-Nickel (3.0 g, 51.1 mmol). The mixture was sparged with hydrogen gas for 20 minutes, then held under 1 atm of hydrogen gas for 3 days. The mixture was filtered through diatomaceous earth and the filtrate was concentrated in vacuo to a total volume of 50 mL. The mixture was extracted with dichloromethane (3×100 mL). The combined the organic layers were washed with water (30 mL), and brine (30 mL), dried over anhydrous magnesium sulfate, and filtered. Concentration of the filtrate in vacuo afforded the title compound as a yellow oil (9.73 g, quantitative yield): $^1$H NMR (300 MHz, CDCl$_3$) δ 7.20-7.12 (m, 1H), 7.05-6.97 (m, 2H), 4.95 (s, 2H), 3.90 (d, J=1.9 Hz, 2H), 3.67 (s, 2H), 3.47-3.47 (m, 2H), 2.41-2.34 (m, 4H), 1.77-1.73 (m, 2H); MS (ES+) m/z 209.2 (M+1).

Step 7. Preparation of 4-(difluoromethyl)-5-((2-fluoro-6-(pyrrolidin-1-ylmethyl)benzyl)amino)-N-(thiazol-4-yl)pyridine-2-sulfonamide formic acid salt

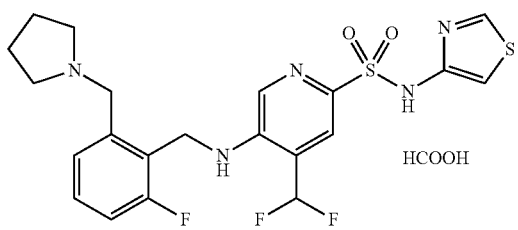 [SMILES: O=S(=O)(Nc1cscn1)c1cc(C(F)F)c(NCc2c(F)cccc2CN2CCCC2)cn1 ; "HCOOH"]

To a solution of 4-(difluoromethyl)-5-fluoro-N-(4-methoxybenzyl)-N-(thiazol-4-yl)pyridine-2-sulfonamide (0.38 g, 0.89 mmol), (2-fluoro-6-(pyrrolidin-1-ylmethyl)phenyl)methanamine (0.19 g, 0.89 mmol) in anhydrous dimethyl sulfoxide (6 mL) was added N,N-diisopropylethylamine (0.16 mL, 0.89 mmol). The mixture was stirred for 18 hours at ambient temperature and then diluted with ethyl acetate (50 mL). The mixture was washed with saturated ammonium chloride (2×30 mL), brine (20 mL), dried over anhydrous sodium sulfate, and filtered. The filtrate was concentrated in vacuo and the residue was dissolved in dichloromethane (10 mL). To the mixture was added trifluoroacetic acid and the mixture was refluxed for 4 hours. The reaction mixture was quenched by addition of methanol (20 mL), filtered, and the filtrate concentrated in vacuo. The residue was dissolved in ethyl acetate (50 mL), washed with saturated sodium bicarbonate (35 mL), saturated ammonium chloride (30 mL), brine (30 mL), dried over anhydrous sodium sulfate, and filtered. The filtrate was concentrated in vacuo and the residue was purified by preparative reverse phase HPLC, using acetonitrile in water containing 0.5% formic acid as eluent, to give the title compound as a colorless solid (0.122 g, 25% yield): $^1$H NMR (300 MHz, DMSO-d$_6$) δ 8.85 (d, J=2.1 Hz, 1H), 8.46 (s, 1H), 8.17 (s, 1H), 7.82 (s, 1H), 7.37-7.09 (m, 4H), 6.95 (d, J=2.1 Hz, 1H), 6.73 (s, 1H), 4.65 (d, J=0.2 Hz, 2H), 3.71 (s, 2H), 2.44-2.35 (m, 4H), 1.71-1.55 (m, 4H), sulfonamide NH and COOH not observed; MS (ES+) m/z 498.2 (M+1).

Example 18

Synthesis of 6-(difluoromethyl)-5-((2-fluoro-6-(pyrrolidin-1-ylmethyl)benzyl)amino)-N-(thiazol-4-yl)pyridine-2-sulfonamide formic acid salt

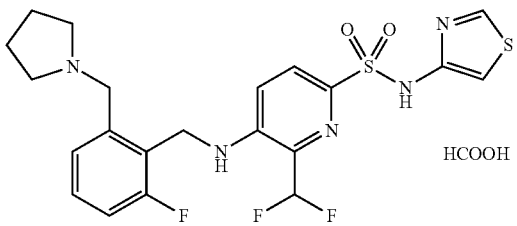 [SMILES: O=S(=O)(Nc1cscn1)c1ccc(NCc2c(F)cccc2CN2CCCC2)c(C(F)F)n1 ; "HCOOH"]

Step 1. Preparation of 6-(benzylthio)-3-fluoropicolinaldehyde

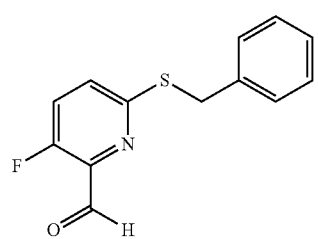 [SMILES: O=Cc1nc(SCc2ccccc2)ccc1F]

Following the procedure as described for EXAMPLE 17, Step 1 and making non-critical variations as required to replace 2-bromo-5-fluoroisonicotinaldehyde with 6-bromo-3-fluoropicolinaldehyde, the title compound was obtained as a yellow oil (3.77 g, 95% yield): MS (ES+) m/z 248.2 (M+1).

Step 2. Preparation of 6-(benzylthio)-2-(difluoromethyl)-3-fluoropyridine

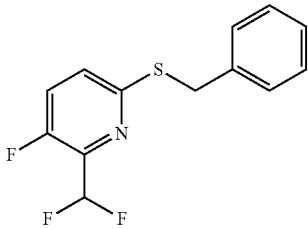

Following the procedure as described for EXAMPLE 17, Step 2 and making non-critical variations as required to replace 2-(benzylthio)-5-fluoroisonicotinaldehyde with 6-(benzylthio)-3-fluoropicolinaldehyde, the title compound was obtained as a orange oil (2.53 g, 71% yield): ¹H NMR (300 MHz, CDCl₃) δ 7.47-7.43 (m, 2H), 7.38-7.24 (m, 5H), 6.81 (t, J=53.7 Hz, 1H), 4.45 (s, 2H); MS (ES+) m/z 270.2 (M+1).

Step 3. Preparation of 6-(difluoromethyl)-5-fluoropyridine-2-sulfonyl chloride

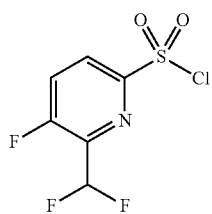 [SMILES: O=S(=O)(Cl)c1ccc(F)c(C(F)F)n1]

Following the procedure as described for EXAMPLE 17, Step 3 and making non-critical variations as required to replace 2-(benzylthio)-4-(difluoromethyl)-5-fluoropyridine with 6-(benzylthio)-2-(difluoromethyl)-3-fluoropyridine, the title compound was obtained as a colorless oil (2.31 g, quantitative yield): ¹H NMR (300 MHz, CDCl₃) δ 8.33 (dd, J=8.7, 3.4 Hz, 1H), 7.93 (t, J=8.6 Hz, 1H), 6.84 (t, J=52.9 Hz, 1H).

Step 4. Preparation of tert-butyl ((6-(difluoromethyl)-5-fluoropyridin-2-yl)sulfonyl)(thiazol-4-yl)carbamate

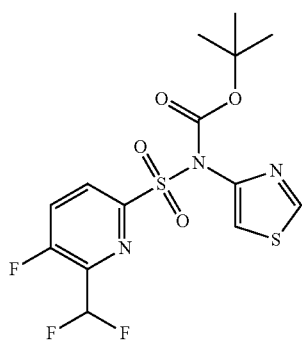 [SMILES: CC(C)(C)OC(=O)N(c1cscn1)S(=O)(=O)c1ccc(F)c(C(F)F)n1]

Following the procedure as described for EXAMPLE 17, Step 4 and making non-critical variations as required to replace 4-(difluoromethyl)-5-fluoropyridine-2-sulfonyl chloride with 6-(difluoromethyl)-5-fluoropyridine-2-sulfonyl chloride, the title compound was obtained as a colorless solid (0.40 g, 50% yield): ¹H NMR (300 MHz, CDCl₃) δ 8.83 (d, J=2.3 Hz, 1H), 8.46 (dd, J=8.7, 3.5 Hz, 1H), 7.84 (t, J=8.7 Hz, 1H), 7.74 (d, J=2.3 Hz, 1H), 6.88 (t, J=52.9 Hz, 1H), 1.32 (s, 9H); MS (ES+) m/z 410.2 (M+1).

Step 5. Preparation of 6-(difluoromethyl)-5-((2-fluoro-6-(pyrrolidin-1-ylmethyl)benzyl)amino)-N-(thiazol-4-yl)pyridine-2-sulfonamide formic acid salt

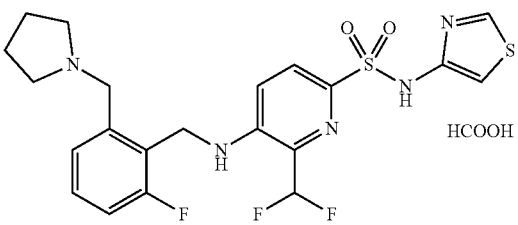 [SMILES: O=S(=O)(Nc1cscn1)c1ccc(NCc2c(F)cccc2CN2CCCC2)c(C(F)F)n1 ; "HCOOH"]

To a solution of tert-butyl ((6-(difluoromethyl)-5-fluoropyridin-2-yl)sulfonyl)(thiazol-4-yl)carbamate (0.40 g, 0.98 mmol) in anhydrous dimethyl sulfoxide (6 mL) was added (2-fluoro-6-(pyrrolidin-1-ylmethyl)phenyl)methanamine (0.20 g, 0.98 mmol). The reaction mixture was stirred at ambient temperature for 1 hour and then diluted with ethyl acetate (50 mL). The mixture was washed with saturated ammonium chloride (30 mL), brine (30 mL), dried over anhydrous sodium sulfate, and filtered. The filtrate was concentrated in vacuo and the residue was dissolved in dichloromethane (10 mL). To the solution was added trifluoroacetic acid and the mixture was stirred for 1 hour. The reaction mixture was concentrated in vacuo and the residue was dissolved in ethyl acetate (50 mL). The mixture was washed with saturated sodium bicarbonate (30 mL), saturated ammonium chloride (30 mL), brine (30 mL), dried over anhydrous sodium sulfate, and filtered. The filtrate was concentrated in vacuo and the residue was purified by preparative reverse phase HPLC, using acetonitrile in water containing 0.5% formic acid as eluent, to give the title compound as a colorless solid (0.147 g, 28% yield): ¹H NMR (300 MHz, DMSO-d₆) δ 8.85 (d, J=2.1 Hz, 1H), 8.18 (s, 1H), 7.91 (d, J=8.9 Hz, 1H), 7.57 (d, J=9.0 Hz, 1H), 7.39-7.31 (m, 1H), 7.25-7.10 (m, 2H), 7.01 (d, J=2.1 Hz, 1H), 6.85 (t, J=53.3 Hz, 1H), 6.68 (s, 1H), 4.55-4.51 (m, 2H), 3.83-3.76 (m, 2H), 2.60-2.52 (m, 4H), 1.76-1.62 (m, 4H), sulfonamide NH and COOH not observed; MS (ES+) m/z 498.2 (M+1).

Example 19

Synthesis of 5-((2-(((tert-butyl(methyl)amino)methyl)-6-fluorobenzyl)amino)-N-(isothiazol-3-yl)-6-methylpyridine-2-sulfonamide trifluoroacetic acid salt

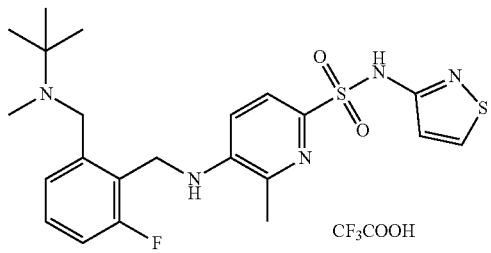 [SMILES: Cc1nc(S(=O)(=O)Nc2ccsn2)ccc1NCc1c(F)cccc1CN(C)C(C)(C)C ; "CF3COOH"]

Step 1. Preparation of tert-butyl ((5-fluoro-6-methyl pyridin-2-yl)sulfonyl)(isothiazol-3-yl)carbamate

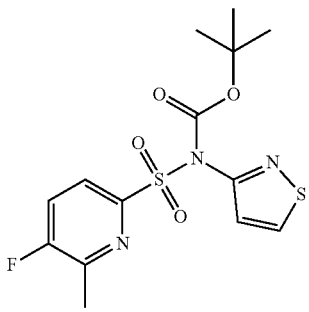 [SMILES: Cc1nc(S(=O)(=O)N(C(=O)OC(C)(C)C)c2ccsn2)ccc1F]

To a solution of tert-butyl isothiazol-3-ylcarbamate (1.99 g, 10.0 mmol) in anhydrous tetrahydrofuran (20 mL) was added a 1 M solution of lithium bis(trimethylsilyl)amide in tetrahydrofuran (10.5 mL, 10.5 mmol) at −78° C. The reaction mixture was stirred for 10 minutes at −78° C., and then allowed to warm to ambient temperature and stirred for 1 hour. After cooling the reaction mixture to −78° C., a solution of 5-fluoro-6-methylpyridine-2-sulfonyl chloride (1.89 g, 10.0 mmol) in anhydrous tetrahydrofuran (5 mL) was added to it. The reaction mixture was allowed to warm to ambient temperature and stirred for 12 hours. The reaction mixture was quenched by the addition of saturated ammonium chloride solution (30 mL), and the aqueous layer was extracted with ethyl acetate (3×30 mL). The combined organic layers were washed with water (20 mL), brine (20 mL), dried over sodium sulfate, and filtered. Concentration of the filtrate in vacuo and trituration of the residue in methanol (15 mL) afforded the title compound as a colorless solid (1.95 g, 52% yield): MS (ES+) m/z 274.2 (M−99).

Step 2. Preparation of 5-fluoro-N-(isothiazol-3-yl)-N-(4-methoxybenzyl)-6-methylpyridine-2-sulfonamide

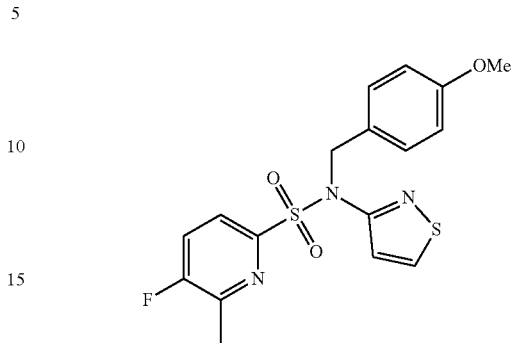

To a solution of tert-butyl ((5-fluoro-6-methylpyridin-2-yl)sulfonyl)(isothiazol-3-yl)carbamate (1.95 g, 5.2 mmol) in dichloromethane (5 mL) was added trifluoroacetic acid (5 mL). The reaction mixture was stirred at ambient temperature for 1 hour and then concentrated in vacuo. To the residue was added anhydrous dimethyl sulfoxide (10 mL), sodium bicarbonate (2.18 g, 26.0 mmol) and 4-methoxybenzyl chloride (1.22 g, 7.8 mmol). The reaction mixture was stirred at ambient temperature for 2 hours and then quenched by addition of water (20 mL). The mixture was extracted with ethyl acetate (3×30 mL) and the combined organic layers were washed with brine (20 mL), dried over anhydrous sodium sulfate, and filtered. Concentration of the filtrate under reduced pressure and purification of the residue by column chromatography, eluting with a gradient of 0 to 60% of ethyl acetate in heptane, afforded the title compound as colorless oil (2.0 g, quantitative yield): MS (ES+) m/z 394.2 (M+1).

Step 3. Preparation of-((2-(((tert-butyl(methyl)amino)methyl)-6-fluorobenzyl)amino)-N-(isothiazol-3-yl)-6-methylpyridine-2-sulfonamide trifluoroacetic acid salt

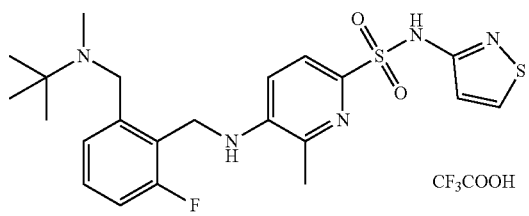 [SMILES: Cc1nc(S(=O)(=O)Nc2ccsn2)ccc1NCc1c(F)cccc1CN(C)C(C)(C)C ; "CF3COOH"]

To a mixture of 5-fluoro-N-(isothiazol-3-yl)-N-(4-methoxybenzyl)-6-methylpyridine-2-sulfonamide (0.66 g, 1.68 mmol) and N-(2-(aminomethyl)-3-fluorobenzyl)-N,2-dimethylpropan-2-amine (0.37 mg, 1.68 mmol) in anhydrous dimethyl sulfoxide (6 mL) was added N,N-diisopropylethylamine (0.88 mL, 5.04 mmol) and the reaction mixture was heated at 100° C. for 16 hours. The reaction mixture was allowed cooled to ambient temperature, diluted with saturated aqueous ammonium chloride solution (10 mL), and extracted with ethyl acetate (3×20 mL). The combined organic layers were washed with water (30 mL), brine (30 mL), dried over anhydrous sodium sulfate, and filtered. Concentration in vacuo and purification of the residue by column chromatography, eluting with a gradient of 0% to 60% of ethyl acetate in heptane, afforded a colorless solid (0.24 g), which was dissolved in a mixture of 1,2-dichloroethane (2.5 mL) and trifluoroacetic acid (2.5 mL). The reaction mixture was stirred at 40° C. for 2 hours and then concentrated in vacuo. Purification of the residue by column chromatography, eluting with a gradient of 0 to 15% of methanol in dichloromethane, afforded the title compound as colorless solid (0.50 g, 50% yield): $^1$H NMR (300 MHz, DMSO-$d_6$) δ 11.44 (s, 1H), 9.16-9.14 (br s, 1H), 8.86 (d, J=4.8 Hz, 1H), 7.79 (d, J=8.5 Hz, 1H), 7.55-7.50 (m, 1H), 7.45-7.38 (m, 2H), 7.06 (d, J=8.7 Hz, 1H), 7.00 (d, J=4.8 Hz, 1H), 6.31 (d, J=2.3 Hz, 1H), 4.71-4.66 (m, 1H), 4.42-4.39 (m, 2H), 4.13-4.05 (m, 1H), 2.61 (d, J=4.6 Hz, 3H), 2.30 (s, 3H), 1.37 (s, 9H); MS (ES+) m/z 478.2 (M+1).

Example 20

Synthesis of 5-((2-(azetidin-1-ylmethyl)-6-fluorobenzyl)amino)-N-(isothiazol-3-yl)-6-methylpyridine-2-sulfonamide trifluoroacetic acid salt

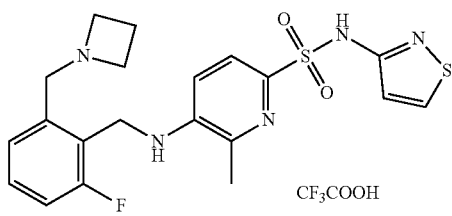 [SMILES: Cc1nc(S(=O)(=O)Nc2ccsn2)ccc1NCc1c(F)cccc1CN1CCC1 ; "CF3COOH"]

Following the procedure as described for EXAMPLE 19, Step 3 and making non-critical variations as required to replace N-(2-(aminomethyl)-3-fluorobenzyl)-N,2-dimethylpropan-2-amine with (2-(azetidin-1-ylmethyl)-6-fluorophenyl)methanamine, the title compound was obtained as a colorless solid (0.26 g, 25% yield): $^1$H NMR (300 MHz, DMSO-$d_6$) δ 11.46-11.40 (m, 1H), 10.25-10.14 (m, 1H), 8.85 (d, J=4.8 Hz, 1H), 7.79 (d, J=8.5 Hz, 1H), 7.52-7.45 (m, 1H), 7.32 (t, J=9.2 Hz, 2H), 7.05 (d, J=8.7 Hz, 1H), 7.00 (d, J=4.8 Hz, 1H), 6.28 (s, 1H), 4.52 (s, 2H), 4.41 (d, J=4.1 Hz, 2H), 4.19-3.98 (m, 4H), 2.46-2.20 (m, 5H); MS (ES+) m/z 448.0 (M+1).

Example 21

Synthesis of 5-((2-((tert-butyl(methyl)amino)methyl)-3,6-difluorobenzyl)amino)-6-methyl-N-(thiazol-4-yl)pyridine-2-sulfonamide trifluoroacetic acid salt

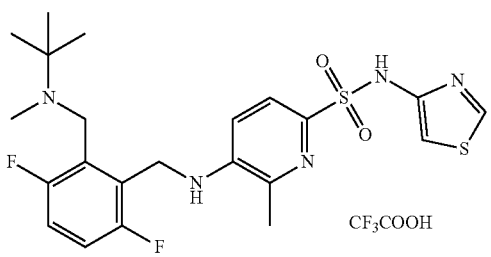 [SMILES: Cc1nc(S(=O)(=O)Nc2cscn2)ccc1NCc1c(F)ccc(F)c1CN(C)C(C)(C)C ; "CF3COOH"]

Step 1. Preparation of N-(2-bromo-3,6-difluorobenzyl)-N,2-dimethylpropan-2-amine

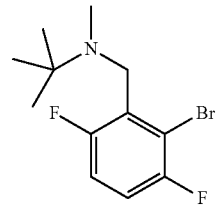 [SMILES: CN(Cc1c(F)ccc(F)c1Br)C(C)(C)C]

To a solution of 2-bromo-3,6-difluorobenzaldehyde (4.42 g, 20.1 mmol) in dichloromethane (100 mL) was added N,2-dimethylpropan-2-amine (2.40 mL, 20.1 mmol) followed by sodium triacetoxyborohydride (11.0 g, 52.0 mmol) and the reaction mixture was stirred at ambient temperature for 16 hours. The reaction was quenched by addition of 2 M sodium hydroxide (100 mL) and stirred for 20 minutes. The aqueous layer was extracted with dichloromethane (2×100 mL). The combined organic phase was washed with brine (40 mL), dried over anhydrous sodium sulfate and filtered. Concentration of the filtrate in vacuo and purification of the residue by column chromatography, eluting with a gradient of 0-30% ethyl acetate in heptane, afforded the title compound as a colorless solid (3.70 g, 63% yield): MS (ES+) m/z 292.1 (M+1), 294.1 (M+1).

Step 2. Preparation of 2-((tert-butyl(methyl)amino)methyl)-3,6-difluorobenzaldehyde oxime

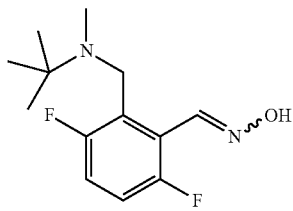 [SMILES: CN(Cc1c(F)ccc(F)c1C=NO)C(C)(C)C]

To a solution of N-(2-bromo-3,6-difluorobenzyl)-N,2-dimethylpropan-2-amine (1.60 g, 5.50 mmol) in anhydrous tetrahydrofuran (30 mL) was added dropwise a 1.3 M solution of isopropylmagnesium chloride lithium chloride in tetrahydrofuran (12.7 mL, 16.5 mmol) at 0° C. The reaction mixture was stirred at 0° C. for 2 hours and then N,N-dimethylformamide (0.85 mL, 11.0 mmol) was added to it. The reaction mixture was stirred at 0° C. for 1 hour and then allowed to warm to ambient temperature. To it was then added a solution of hydroxylamine hydrochloride (1.90 g, 27.5 mmol) in water (3 mL), and the reaction mixture was stirred at ambient temperature for 16 hours. The reaction mixture was concentrated under reduced pressure and water (30 mL) was added to it. The mixture was extracted with dichloromethane (2×20 mL). The combined organic phase was washed with brine (20 mL), dried over anhydrous sodium sulfate and filtered. Concentration of the filtrate in vacuo afforded the title compound as a colorless solid (1.70 g, quantitative yield): MS (ES+) m/z 257.2 (M+1).

Step 3. Preparation of N-(2-(aminomethyl)-3,6-difluorobenzyl)-N,2-dimethylpropan-2-amine

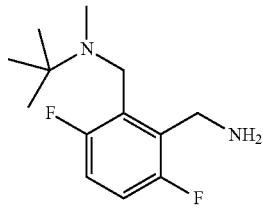 [SMILES: CN(Cc1c(F)ccc(F)c1CN)C(C)(C)C]

To a solution of 2-((tert-butyl(methyl)amino)methyl)-3,6-difluorobenzaldehyde oxime (1.70 g, 6.6 mmol) in anhydrous tetrahydrofuran (25 mL) was added a 1 M of solution of lithium aluminum hydride in tetrahydrofuran (13.2 mL, 13.2 mmol) at 0° C.

The reaction mixture was allowed to warm to ambient temperature and stirred for 16 hours. After cooling the reaction mixture to 0° C., sodium sulfate decahydrate (13 g) was added to it in small portions. The mixture was stirred at 0° C. for 30 minutes, allowed to warm to ambient temperature, and stirred for 2 hours. The mixture was filtered and the filtrate was dried over anhydrous magnesium sulfate. Filtration and concentration of the filtrate in vacuo afforded the title compound as a pale brown oil (1.10 g, 68% yield): MS (ES+) m/z 243.3 (M+1).

Step 4. Preparation of 5-((2-((tert-butyl(methyl)amino)methyl)-3,6-difluorobenzyl)amino)-6-methyl-N-(thiazol-4-yl)pyridine-2-sulfonamide trifluoroacetic acid salt

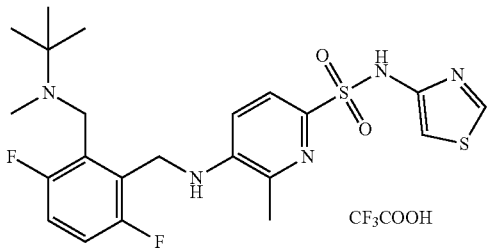 [SMILES: Cc1nc(S(=O)(=O)Nc2cscn2)ccc1NCc1c(F)ccc(F)c1CN(C)C(C)(C)C ; "CF3COOH"]

To a mixture of 5-fluoro-N-(4-methoxybenzyl)-6-methyl-N-(thiazol-4-yl)pyridine-2-sulfonamide (0.48 g, 2.00 mmol) and N-(2-(aminomethyl)-3,6-difluorobenzyl)-N,2-dimethylpropan-2-amine (0.52 g, 1.32 mmol) in anhydrous dimethyl sulfoxide (4 mL) was added N,N-diisopropylethylamine (0.70 mL, 3.96 mmol) and the reaction mixture was heated at 100° C. for 16 hours. The reaction mixture was allowed cooled to ambient temperature, diluted with saturated aqueous ammonium chloride solution (20 mL), and extracted with ethyl acetate (3×30 mL). The combined organic layers were washed with water (40 mL), brine (40 mL), dried over anhydrous sodium sulfate, and filtered. Concentration in vacuo and purification of the residue by column chromatography, eluting with a gradient of 0% to 60% of ethyl acetate in heptane, afforded a colorless solid (0.24 g), which was dissolved in a mixture of 1,2-dichloroethane (2.5 mL) and trifluoroacetic acid (2.5 mL). The reaction mixture was stirred at 40° C. for 2 hours and then concentrated in vacuo. Purification of the residue by column chromatography, eluting with a gradient of 0 to 15% of methanol in dichloromethane, afforded the title compound as colorless solid (0.192 g, 20% yield): $^1$H NMR (300 MHz, DMSO-$d_6$) δ 10.97 (s, 1H), 9.12-9.00 (m, 1H), 8.83 (d, J=2.2 Hz, 1H), 7.70 (d, J=8.5 Hz, 1H), 7.54-7.41 (m, 2H), 6.96 (d, J=8.6 Hz, 1H), 6.92 (d, J=2.2 Hz, 1H), 6.41-6.35 (m, 1H), 4.72 (d, J=13.2 Hz, 1H), 4.56-4.38 (m, 2H), 4.19-4.08 (m, 1H), 2.64 (dd, J=4.4, 0.5 Hz, 3H), 2.31 (s, 3H), 1.41 (s, 9H); MS (ES+) m/z 496.2 (M+1).

Example 22

Synthesis of 5-((2-((tert-butyl(methyl)amino)methyl)-6-fluorobenzyl)amino)-N-(6-fluoropyridin-2-yl)-6-methylpyridine-2-sulfonamide trifluoroacetic acid salt

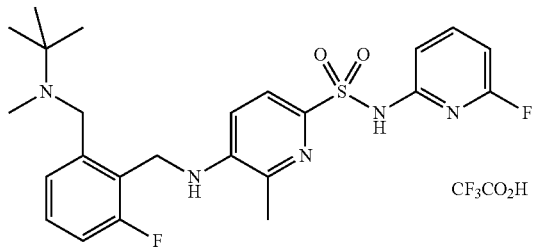 [SMILES: Cc1nc(S(=O)(=O)Nc2cccc(F)n2)ccc1NCc1c(F)cccc1CN(C)C(C)(C)C ; "CF3CO2H"]

Step 1. Preparation of N-(2,4-dimethoxybenzyl)-5-fluoro-N-(6-fluoropyridin-2-yl)-6-methylpyridine-2-sulfonamide

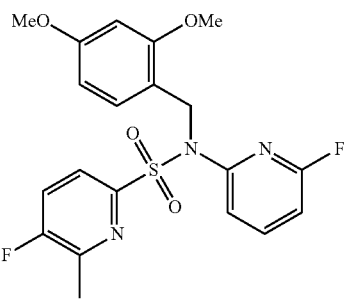 [SMILES: COc1ccc(CN(c2cccc(F)n2)S(=O)(=O)c2ccc(F)c(C)n2)c(OC)c1]

To a solution of N-(2,4-dimethoxybenzyl)-6-fluoropyridin-2-amine (1.26 g, 4.77 mmol) in anhydrous tetrahydrofuran (12.6 mL) was added a 1 M solution of lithium bis(trimethylsilyl)amide in tetrahydrofuran (5.24 mL, 5.24 mmol) at −78° C. and the reaction mixture was stirred at −78° C. for 30 minutes. To it was then added dropwise a solution of 5-fluoro-6-methylpyridine-2-sulfonyl chloride (1.00 g, 4.77 mmol) in anhydrous tetrahydrofuran (2.7 mL) at −78° C. The reaction mixture was allowed to warm to ambient temperature and stirred for 18 hours. The reaction mixture was diluted with ethyl acetate (150 mL), and the organic layer was washed with brine (3×50 mL), dried over magnesium sulfate, and filtered. Concentration of the filtrate in vacuo and purification of the residue by column chromatography, eluting with a gradient of 5-50% of ethyl acetate in heptane, afforded the title compound as a yellow oil (1.1 g, 53% yield): $^1$H NMR (300 MHz, CDCl$_3$) δ 7.81 (dd, J=8.5, 3.7 Hz, 1H), 7.71 (q, J=8.1 Hz, 1H), 7.45-7.39 (m, 2H), 7.30-7.27 (m, 1H), 6.67 (dd, J=8.0, 3.0 Hz, 1H), 6.38 (dd, J=8.4, 2.4 Hz, 1H), 6.33 (d, J=2.3 Hz, 1H), 5.15 (s, 2H), 3.77-3.76 (m, 3H), 3.65 (d, J=2.9 Hz, 3H), 2.55 (t, J=3.4 Hz, 3H).

Step 2. Preparation of 5-((2-((tert-butyl(methyl) amino)methyl)-6-fluorobenzyl)amino)-N-(2,4-dimethoxybenzyl)-N-(6-fluoropyridin-2-yl)-6-methylpyridine-2-sulfonamide

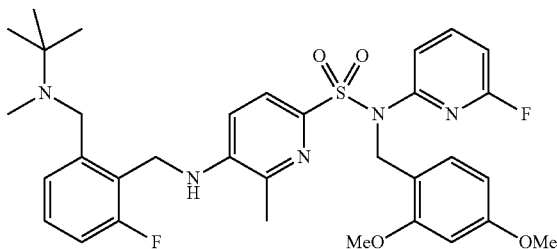 [SMILES: COc1ccc(CN(c2cccc(F)n2)S(=O)(=O)c2ccc(NCc3c(F)cccc3CN(C)C(C)(C)C)c(C)n2)c(OC)c1]

To a solution of N-(2,4-dimethoxybenzyl)-5-fluoro-N-(6-fluoropyridin-2-yl)-6-methylpyridine-2-sulfonamide (0.45 g, 1.05 mmol) and N-(2-(aminomethyl)-3-fluorobenzyl)-N,2-dimethylpropan-2-amine (0.24 g, 1.05 mmol) in anhydrous dimethyl sulfoxide (6.0 mL) was added N,N-diisopropylethylamine (0.36 mL, 2.10 mmol). The mixture was heated to 120° C. for 18 h, cooled to ambient temperature, and diluted with ethyl acetate (80 mL). The mixture was washed with saturated ammonium chloride (2×40 mL), brine (30 mL), dried over anhydrous sodium sulfate, and filtered. The filtrate was concentrated in vacuo and the residue was purified by by column chromatography, eluting with a gradient of 0-55% of ethyl acetate (containing 20% of ethanol and 0.1% of ammonium hydroxide) in heptane, to afford the title compound as a yellow oil (0.67 g, quantitative yield): MS (ES+) m/z 640.6 (M+1).

Step 3. Preparation of 5-((2-((tert-butyl(methyl) amino)methyl)-6-fluorobenzyl)amino)-N-(6-fluoropyridin-2-yl)-6-methylpyridine-2-sulfonamide trifluoroacetic acid salt

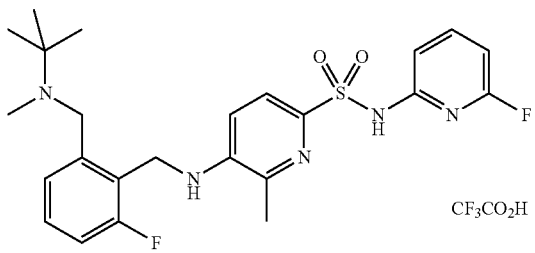 [SMILES: Cc1nc(S(=O)(=O)Nc2cccc(F)n2)ccc1NCc1c(F)cccc1CN(C)C(C)(C)C ; "CF3CO2H"]

To a solution of 5-((2-((tert-butyl(methyl)amino)methyl)-6-fluorobenzyl)amino)-N-(2,4-dimethoxybenzyl)-N-(6-fluoropyridin-2-yl)-6-methylpyridine-2-sulfonamide (0.67 g, 1.05 mmol) in dichloromethane (30 mL) was added trifluoroacetic acid (3 mL). The mixture was stirred at ambient temperature for 1.5 hours and then concentrated in vacuo. To the residue was added methanol (20 mL), the mixture was filtered, and the filtrate was concentrated in vacuo. The residue was purified by preparative reverse phase HPLC, using acetonitrile in water containing 0.1% trifluoroacetic acid as eluent, to afford the title compound as a colorless solid (0.10 g, 16% yield): $^1$H NMR (300 MHz, DMSO-$d_6$) δ 11.24 (s, 1H), 9.26 (s, 1H), 7.87-7.77 (m, 2H), 7.57-7.50 (m, 1H), 7.46-7.35 (m, 2H), 7.11 (d, J=8.6 Hz, 1H), 6.97 (dd, J=8.0, 2.0 Hz, 1H), 6.67 (dd, J=7.9, 2.4 Hz, 1H), 6.33 (s, 1H), 4.72-4.68 (m, 1H), 4.43 (s, 2H), 4.13-4.05 (m, 1H), 2.61 (d, J=4.5 Hz, 3H), 2.30 (s, 3H), 1.37 (s, 9H), COOH not observed; MS (ES+) m/z 490.2 (M+1).

Example 23

Synthesis of 4-((2-bromo-6-fluorobenzyl)amino)-N-(6-fluoropyridin-2-yl)-5-methylthiophene-2-sulfonamide

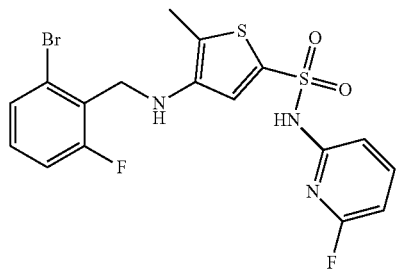 [SMILES: Cc1sc(S(=O)(=O)Nc2cccc(F)n2)cc1NCc1c(F)cccc1Br]

Step 1. Preparation of N-(6-fluoropyridin-2-yl)-5-methyl-4-nitrothiophene-2-sulfonamide

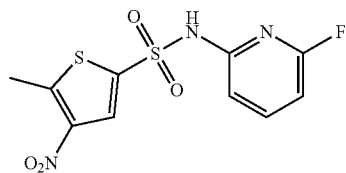 [SMILES: Cc1sc(S(=O)(=O)Nc2cccc(F)n2)cc1[N+](=O)[O-]]

To a solution of 5-methyl-4-nitrothiophene-2-sulfonyl chloride (0.500 g, 2.07 mmol) and 2-amino 6-fluoropyridine (0.256 g, 2.28 mmol) in dichloromethane (11 mL) was added pyridine (0.25 mL, 3.1 mmol). The reaction mixture was stirred at ambient temperature for 72 hours. The reaction mixture was diluted with dichloromethane (10 mL) and water (10 mL). The layers were separated and the aqueous phase was extracted with dichloromethane (3×10 mL). The combined organic phases were washed with a solution of 5% hydrochloric acid (3×10 mL) and brine (10 mL), dried over anhydrous magnesium sulfate, and filtered. Concentration of the filtrate in vacuo and purification of the residue by column chromatography, eluting with a gradient of 10 to 80% of ethyl acetate in hexanes, afforded the title compound as a yellow oil (0.465 g, 71% yield): MS (ES-) m/z 316.0 (M-1).

Step 2. Preparation of 4-amino-N-(6-fluoropyridin-2-yl)-5-methylthiophene-2-sulfonamide

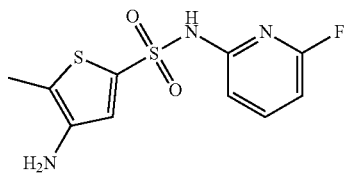

To a solution of N-(6-fluoropyridin-2-yl)-5-methyl-4-nitrothiophene-2-sulfonamide (0.465 g, 1.47 mmol) in acetic acid (5 mL) was added iron powder (0.412 g, 7.35 mmol) and the reaction mixture was stirred at 60° C. for 1 hour. The acetic acid was then removed in vacuo. Saturated sodium bicarbonate was added until a pH 8 was reached and the mixture extracted with ethyl acetate (3×10 mL). The combined organic phases were washed with brine (10 mL), dried over anhydrous magnesium sulfate, and filtered. Concentration of the filtrate in vacuo and purification of the residue by column chromatography, eluting with a gradient of 10 to 80% of ethyl acetate in hexanes, afforded the title compound as a colorless oil (0.260 g, 62% yield): $^1$H-NMR (300 MHz, CDCl$_3$) δ 7.77 (q, J=8.0 Hz, 1H), 7.31-7.29 (m, 1H), 7.17 (s, 1H), 6.65 (ddd, J=8.0, 2.5, 0.5 Hz, 1H), 3.42 (broad singlet, 2H), 2.23 (s, 3H), one exchangeable proton not observed; MS (ES-) m/z 286.0 (M−1).

Step 3. Preparation of 4-((2-bromo-6-fluorobenzyl)amino)-N-(6-fluoropyridin-2-yl)-5-methylthiophene-2-sulfonamide

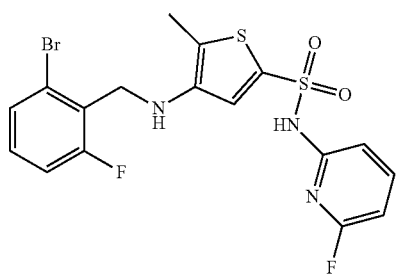 [SMILES: Cc1sc(S(=O)(=O)Nc2cccc(F)n2)cc1NCc1c(F)cccc1Br]

To a solution of 4-amino-N-(6-fluoropyridin-2-yl)-5-methylthiophene-2-sulfonamide (0.266 g, 0.931 mmol) and 2-bromo-3-fluorobenzaldehyde (0.188 g, 0.933 mmol) in trifluoroacetic acid (5 mL) was added sodium triacetoxyborohydride (0.589 g, 2.79 mmol) and the reaction mixture was stirred at ambient temperature for 1 hour. The mixture concentrated in vacuo. After dilution with ethyl acetate (10 mL), the solution was washed with a solution of 5.0N sodium hydroxide until pH 10 was reached. The layers were separated and the aqueous phase was extracted with ethyl acetate (3×10 mL). The combined organic phases were washed with brine (10 mL), dried over anhydrous magnesium sulfate, and filtered. Concentration of the filtrate in vacuo and purification of the residue by column chromatography, eluting with a gradient of 10 to 80% of ethyl acetate in hexanes, afforded the title compound as a colorless solid (0.265 g, 60% yield): $^1$H NMR (300 MHz, DMSO-d$_6$) δ 11.39 (s, 1H), 7.88 (q, J=8.3 Hz, 1H), 7.49-7.45 (m, 1H), 7.42 (s, 1H), 7.33-7.20 (m, 2H), 6.98 (dd, J=8.0, 2.2 Hz, 1H), 6.78 (dd, J=7.9, 2.5 Hz, 1H), 5.16-5.12 (m, 1H), 4.32-4.29 (m, 2H), 2.19-2.14 (m, 3H); MS (ES+) m/z 473.9 (M+1), 475.9 (M+1).

Example 24

Synthesis of 5-((2-fluoro-6-((3-methylazetidin-1-yl)methyl)benzyl)amino)-6-methyl-N-(thiazol-4-yl)pyridine-2-sulfonamide

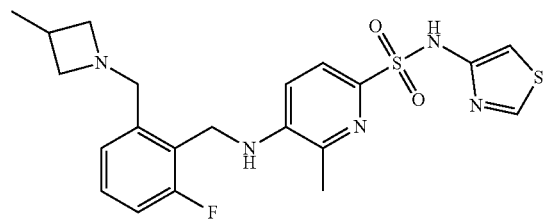 [SMILES: Cc1nc(S(=O)(=O)Nc2cscn2)ccc1NCc1c(F)cccc1CN1CC(C)C1]

Step 1. Preparation of 2-fluoro-6-((3-methylazetidin-1-yl)methyl)benzonitrile

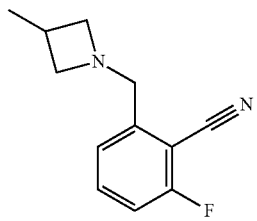

To a solution of 2-(bromomethyl)-6-fluorobenzonitrile (4.50 g 21.0 mmol) in anhydrous dichloromethane (50 mL) was added 3-methylazetidine hydrochloride (2.26 g, 21.0 mol) and N,N-diisopropylethylamine (8.15 g, 62.1 mmol) and the reaction mixture was stirred at ambient temperature for 16 hours. The reaction mixture was concentrated under reduced pressure and the residue was triturated in a mixture of heptane and ethyl acetate (2:1, 150 mL). After filtration, the filtrate was concentrated under reduced pressure to give the title compound as crude yellowish oil which was used without further purification: MS (ES+) m/z 205.0 (M+1).

Step 2. Preparation of (2-fluoro-6-((3-methylazetidin-1-yl)methyl)phenyl)methanamine

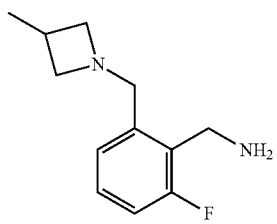

To a mixture of 2-fluoro-6-((3-methylazetidin-1-yl)methyl)benzonitrile (crude product from step 1) in methanol (100 mL) and concentrated ammonium hydroxide solution (15 mL) was added Raney-Nickel (0.594 g). The suspension was degassed and purged with hydrogen three times. The reaction mixture was stirred 16 hours under an atmosphere of hydrogen at ambient temperature. Filtration of the reaction mixture and concentration of the filtrate under reduced pressure afforded the title compound as a yellowish solid (4.20 g, 96% yield over two steps): $^1$H-NMR (300 MHz, CDCl$_3$) δ 7.20-7.08 (m, 1H), 7.02-6.96 (m, 2H), 4.74-4.52 (m, 2H), 3.95 (s, 2H), 3.63 (s, 2H), 3.38 (s, 2H), 2.75 (t, J=7.1 Hz, 2H), 2.56-2.45 (m, 1H), 1.13 (d, J=6.7 Hz, 3H); MS (ES+) m/z 209.2 (M+1).

Step 3. Preparation of 5-((2-fluoro-6-((3-methylazetidin-1-yl)methyl)benzyl)amino)-N-(4-methoxybenzyl)-6-methyl-N-(thiazol-4-yl)pyridine-2-sulfonamide

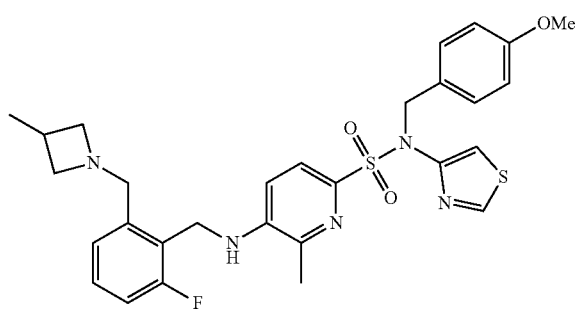 [SMILES: COc1ccc(CN(c2cscn2)S(=O)(=O)c2ccc(NCc3c(F)cccc3CN3CC(C)C3)c(C)n2)cc1]

To a solution of (2-fluoro-6-((3-methylazetidin-1-yl)methyl)phenyl)methanamine (0.08 g, 0.37 mmol) in anhydrous dimethyl sulfoxide (3 mL) was added N,N-diisopropylethylamine (0.3 mL, 1.92 mmol) and 5-fluoro-N-(4-methoxybenzyl)-6-methyl-N-(thiazol-4-yl)pyridine-2-sulfonamide (0.15 g, 0.37 mmol). The reaction mixture was heated to 125° C. for 16 hours. After cooling to ambient temperature, the reaction mixture was diluted with ethyl acetate (70 mL) and washed with saturated ammonium chloride (20 mL), brine (20 mL), and dried over anhydrous sodium sulfate.

Filtration and concentration of the filtrate in vacuo provided a residue, which was purified by column chromatography, eluting with a gradient of 10 to 100% of ethyl acetate (containing 20% of ethanol and 0.2% of ammonium hydroxide) in heptane, to afford the title compound as a pale yellow solid (yield not determined): MS (ES+) m/z 582 (M+1); MS (ES-) m/z 580 (M-1).

Step 4. Preparation of 5-((2-fluoro-6-((3-methylazetidin-1-yl)methyl)benzyl)amino)-6-methyl-N-(thiazol-4-yl)pyridine-2-sulfonamide

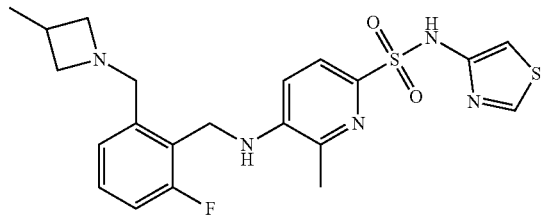 [SMILES: Cc1nc(S(=O)(=O)Nc2cscn2)ccc1NCc1c(F)cccc1CN1CC(C)C1]

To a mixture of 5-((2-fluoro-6-((3-methylazetidin-1-yl)methyl)benzyl)amino)-N-(4-methoxybenzyl)-6-methyl-N-(thiazol-4-yl)pyridine-2-sulfonamide (from previous step) in anhydrous 1,2-dichloroethane (2 mL) was added trifluoroacetic acid (1.0 mL). The reaction mixture was stirred at 65° C. for 16 hours and then concentrated in vacuo. The residue was purified by preparative reverse-phase HPLC, eluting with a gradient of 15% to 60% of acetonitrile in water containing 0.5% of formic acid, to afford the title compound as a colorless solid (0.09 g, 50% yield over 2 steps): $^1$H NMR (300 MHz, DMSO-d$_6$) δ 8.84 (d, J=2.2 Hz, 1H), 8.17 (d, J=0.7 Hz, 1H), 7.71 (d, J=8.5 Hz, 1H), 7.40-7.32 (m, 1H), 7.25-7.10 (m, 3H), 6.93 (d, J=2.2 Hz, 1H), 6.78-6.65 (m, 1H), 4.40 (s, 2H), 3.90 (s, 2H), 3.58 (t, J=7.8 Hz, 2H), 3.04 (t, J=7.8 Hz, 2H), 2.62-2.54 (m, 1H), 2.34 (s, 3H), 1.11 (d, J=6.7 Hz, 3H); MS (ES+) m/z 462.1 (M+1); MS (ES-) m/z 460.1 (M-1).

Example 25

Synthesis of 5-((2-((7-azabicyclo[2.2.1]heptan-7-yl)methyl)-6-fluorobenzyl)amino)-6-methyl-N-(thiazol-4-yl)pyridine-2-sulfonamide trifluoroacetic acid salt

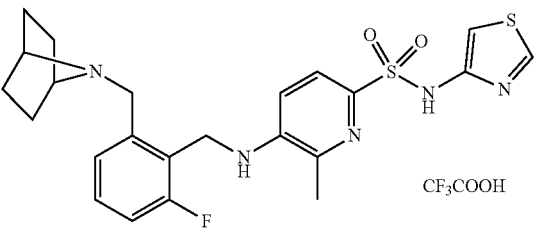 [SMILES: Cc1nc(S(=O)(=O)Nc2cscn2)ccc1NCc1c(F)cccc1CN1C2CCC1CC2 ; "CF3COOH"]

Step 1. Preparation of 2-((7-azabicyclo[2.2.1]heptan-7-yl)methyl)-6-fluorobenzonitrile

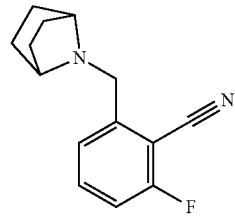 [SMILES: N#Cc1c(F)cccc1CN1C2CCC1CC2]

To a solution of 2-(bromomethyl)-6-fluorobenzonitrile (13.90 g, 65.4 mmol) in anhydrous N,N-dimethylformamide (120 mL) was added 7-azabicyclo[2.2.1]heptane hydrochloride (8.70 g, 65.4 mmol) and potassium carbonate (18.0 g, 130.8 mmol) and the reaction mixture was stirred at ambient temperature for 16 hours. After addition of water (100 mL), the mixture was extracted with ethyl acetate (2×100 mL). The combined organic layers were washed with brine (100 mL), dried over anhydrous sodium sulfate, and filtered. Concentration of the filtrate under reduced pressure and purification of the residue by column chromatography, eluting with a gradient of 0-5% of methanol in dichloromethane, provided the title compound as yellowish oil (5.30 g, 35% yield): MS (ES+) m/z 231.0 (M+1).

Step 2. Preparation of (2-((7-azabicyclo[2.2.1]heptan-7-yl)methyl)-6-fluorophenyl)methanamine

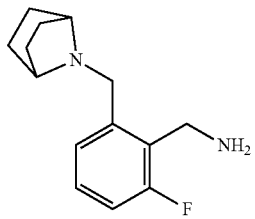 [SMILES: NCc1c(F)cccc1CN1C2CCC1CC2]

To a mixture of 2-(azetidin-1-ylmethyl)-6-fluorobenzonitrile (5.30 g, 23.0 mmol) in methanol (100 mL) and was added Raney-Nickel (4.0 g, 46.7 mmol). The suspension was degassed and purged with hydrogen three times. The reaction mixture was stirred under an atmosphere of hydrogen (50 psi) at ambient temperature for 12 hours. Filtration of the reaction mixture and concentration of the filtrate under reduced pressure afforded the title compound as a yellow oil (5.30 g, 98% yield): $^1$H NMR (400 MHz, CDCl$_3$) δ 7.15-7.07 (m, 1H), 6.95 (t, J=8.8 Hz, 2H), 3.87 (d, J=1.9 Hz, 2H), 3.53 (s, 2H), 3.18 (dt, J=4.5, 2.3 Hz, 2H), 2.47 (s, 2H), 1.73-1.65 (m, 4H), 1.29-1.23 (m, 4H); MS (ES+) m/z 235.0 (M+1).

Step 3. Preparation of 5-((2-((7-azabicyclo[2.2.1]heptan-7-yl)methyl)-6-fluorobenzyl)amino)-N-(4-methoxybenzyl)-6-methyl-N-(thiazol-4-yl)pyridine-2-sulfonamide

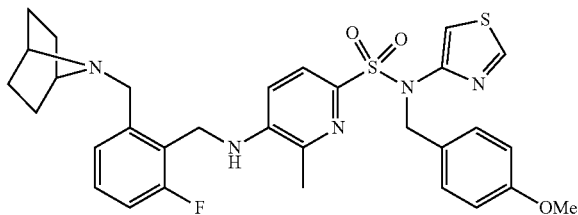 [SMILES: COc1ccc(CN(c2cscn2)S(=O)(=O)c2ccc(NCc3c(F)cccc3CN3C4CCC3CC4)c(C)n2)cc1]

Following the procedure as described in Example 24, Step 2 and making variations as required to replace (2-fluoro-6-((3-methylazetidin-1-yl)methyl)phenyl)methanamine with (2-((7-azabicyclo[2.2.1]heptan-7-yl)methyl)-6-fluorophenyl)methanamine, the title compound was obtained as colorless solid (0.5 g, 90% yield): $^1$H NMR (300 MHz, CDCl$_3$) δ 8.53 (d, J=2.3 Hz, 1H), 7.60 (d, J=8.5 Hz, 1H), 7.28-7.23 (m, 4H), 7.09-7.03 (m, 3H), 6.79-6.75 (m, 2H), 5.40 (dd, J=1.9, 0.8 Hz, 1H), 5.10 (s, 2H), 4.52-4.51 (m, 2H), 3.76 (s, 3H), 3.58 (s, 2H), 3.26-3.23 (m, 2H), 2.35 (s, 3H), 1.84-1.76 (m, 4H), 1.41-1.33 (m, 4H); MS (ES+) m/z 608.3 (M+1), MS (ES−) m/z 606.3 (M−1).

Step 4. Preparation of 5-((2-((7-azabicyclo[2.2.1]heptan-7-yl)methyl)-6-fluorobenzyl)amino)-6-methyl-N-(thiazol-4-yl)pyridine-2-sulfonamide trifluoroacetic acid salt

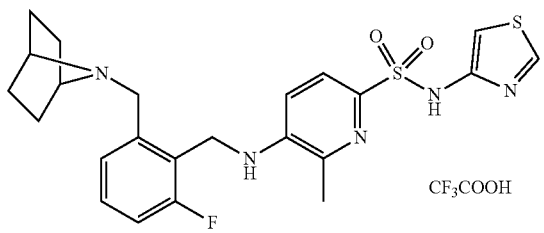 [SMILES: Cc1nc(S(=O)(=O)Nc2cscn2)ccc1NCc1c(F)cccc1CN1C2CCC1CC2 ; "CF3COOH"]

Following the procedure as described in Example 24, Step 3, and making variations as required to replace 5-((2-fluoro-6-((3-methylazetidin-1-yl)methyl)benzyl)amino)-N-(4-methoxybenzyl)-6-methyl-N-(thiazol-4-yl)pyridine-2-sulfonamide with 5-((2-((7-azabicyclo[2.2.1]heptan-7-yl)methyl)-6-fluorobenzyl)amino)-N-(4-methoxybenzyl)-6-methyl-N-(thiazol-4-yl)pyridine-2-sulfonamide, the title compound was obtained as colorless solid (0.27 g, 54% yield): $^1$H NMR (300 MHz, DMSO-d$_6$) δ 10.97 (s, 1H), 9.57-9.50 (m, 1H), 8.84 (d, J=2.2 Hz, 1H), 7.72 (d, J=8.5 Hz, 1H), 7.55-7.33 (m, 3H), 7.05 (d, J=8.6 Hz, 1H), 6.93 (d, J=2.2 Hz, 1H), 6.32-6.25 (m, 1H), 4.47-4.41 (m, 2H), 4.35 (d, J=5.2 Hz, 2H), 4.18-4.13 (m, 2H), 2.31 (s, 3H), 2.22-2.14 (m, 2H), 1.97-1.88 (m, 2H), 1.79-1.64 (m, 4H); MS (ES+) m/z 488 (M+1), MS (ES−) m/z 486.2 (M−1).

Examples 26-30

In a similar manner as described in EXAMPLES 21, 24 and 25, utilizing the appropriately substituted starting materials and intermediates, the following compounds were prepared:

| Example No | Name | MS (ES+) m/z | $^1$H NMR |
|---|---|---|---|
| 26 | 5-((2-(azetidin-1-ylmethyl)benzyl)amino)-6-methyl-N-(thiazol-4-yl)pyridine-2-sulfonamide trifluoroacetic acid salt | 430.1 (M + 1) | (300 MHz, DMSO-d$_6$) δ 10.94 (br s, 1H), 10.12 (br s, 1H), 8.83 (d, J = 2.2 Hz, 1H), 7.57 (d, J = 8.4 Hz, 1H), 7.45-7.37 (m, 1H), 7.35-7.27 (m, 3H), 6.91 (d, J = 2.2 Hz, 1H), 6.75-6.67 (m, 2H), 4.58-4.42 (m, 4H), 4.09 (s, 4H), 2.45-2.27 (m, 5H). |
| 27 | 5-((2-(azetidin-1-ylmethyl)-3-fluorobenzyl)amino)-6-methyl-N-(thiazol-4-yl)pyridine-2-sulfonamide trifluoroacetic acid salt | 448.2 (M + 1) | (300 MHz, DMSO-d$_6$) δ 10.95 (s, 1H), 10.07 (br s, 1H), 8.83 (d, J = 2.2 Hz, 1H), 7.57 (d, J = 8.5 Hz, 1H), 7.47-7.38 (m, 1H), 7.29-7.14 (m, 2H), 6.91 (d, J = 2.2 Hz, 1H), 6.79-6.70 (m, 2H), 4.64-4.49 (m, 4H), 4.29-4.01 (m, 4H), 2.42 (s, 3H), 2.36-2.20 (m, 2H). |

-continued

| Example No | Name | MS (ES+) m/z | $^1$H NMR |
|---|---|---|---|
| 28 | 5-((2-((tert-butyl(methyl)amino)methyl)benzyl)amino)-6-methyl-N-(thiazol-4-yl)pyridine-2-sulfonamide trifluoroacetic acid salt | 460.2 (M + 1) | (300 MHz, DMSO-$d_6$) δ 10.93 (br s, 1H), 8.83 (d, J = 2.2 Hz, 1H), 7.61-7.50 (m, 2H), 7.46-7.12 (m, 4H), 6.92-6.66 (m, 3H), 4.88-4.68 (m, 1H), 4.64-4.48 (m, 2H), 4.16-3.93 (m, 1H), 3.72-3.54 (m, 1H), 2.71-2.57 (m, 1H), 2.42 (s, 3H), 2.06-1.95 (m, 1H), 1.52-1.06 (m, 9H). |
| 29 | 5-((2-fluoro-6-((isopropyl(methyl)amino)methyl)benzyl)amino)-6-methyl-N-(thiazol-4-yl)pyridine-2-sulfonamide trifluoroacetic acid salt | 464.3 (M + 1) | (300 MHz, DMSO-$d_6$) δ 10.97 (s, 1H), 9.22 (br s, 1H), 8.83 (d, J = 2.2 Hz, 1H), 7.71 (d, J = 8.5 Hz, 1H), 7.57-7.43 (m, 2H), 7.41-7.33 (m, 1H), 7.04 (d, J = 8.7 Hz, 1H), 6.92 (d, J = 2.2 Hz, 1H), 6.28-6.22 (m, 1H), 4.59-4.19 (m, 4H), 3.68-3.57 (m, 1H), 2.62 (d, J = 4.9 Hz, 3H), 2.31 (s, 3H), 1.25 (t, J = 7.1 Hz, 6H). |
| 30 | 5-((2-fluoro-6-(pyrrolidin-1-ylmethyl)benzyl)amino)-6-methyl-N-(thiazol-4-yl)pyridine-2-sulfonamide trifluoroacetic acid salt | 462.2 (M + 1) | (300 MHz, DMSO-$d_6$) δ 10.97 (s, 1H), 9.97-9.96 (m, 1H), 8.83 (d, J = 2.1 Hz, 1H), 7.71 (d, J = 8.5 Hz, 1H), 7.55-7.43 (m, 2H), 7.37-7.31 (m, 1H), 7.03 (d, J = 8.5 Hz, 1H), 6.93 (d, J= 2.1 Hz, 1H), 6.25 (dd, J = 0.9, 0.7 Hz, 1H), 4.53-4.51 (m, 2H), 4.43-4.42 (m, 2H), 3.49-3.44 (m, 2H), 3.15-3.09 (m, 2H), 2.30 (s, 3H), 2.03-2.01 (m, 2H), 1.87-1.84 (m, 2H). |

Example 31

Synthesis of 5-((2-(azetidin-1-ylmethyl)-6-fluorobenzyl)amino)-N-(thiazol-4-yl)-4-(trifluoromethyl)pyridine-2-sulfonamide

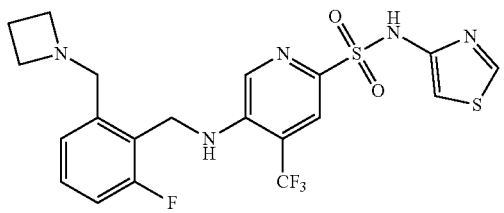 [SMILES: O=S(=O)(Nc1cscn1)c1cc(C(F)(F)F)c(NCc2c(F)cccc2CN2CCC2)cn1]

Step 1. Preparation of 2-(benzylthio)-5-fluoro-4-(trifluoromethyl)pyridine

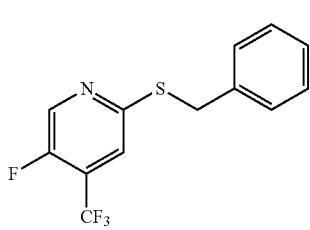 [SMILES: Fc1cnc(SCc2ccccc2)cc1C(F)(F)F]

To a solution of 2-chloro-5-fluoro-4-(trifluoromethyl)pyridine (2.90 g, 14.5 mmol) in anhydrous dioxane (10 mL) and N,N-diisopropylethylamine (5.1 mL, 29.1 mmol) was added tris(dibenzylideneacetone)dipalladium(0) (0.40 g, 0.44 mmol), Xantphos (0.40 g, 0.73 mmol) and benzyl mercaptan (1.71 g, 13.8 mmol). The reaction mixture was degassed with nitrogen and heated to 103° C. for 16 hours. After cooling to ambient temperature, the reaction mixture was diluted with ethyl acetate (100 mL), washed with saturated ammonium chloride (3×30 mL), and dried over anhydrous sodium sulfate. Filtration and concentration of the filtrate in vacuo provided a residue, which was purified by column chromatography, eluting with a gradient of 5 to 40% of ethyl acetate in heptane, to afford the title compound as colorless liquid (2.40 g, 60% yield): $^1$H NMR (300 MHz, CDCl$_3$) δ 8.51 (t, J=0.5 Hz, 1H), 7.43-7.25 (m, 6H), 4.45 (s, 2H); MS (ES+) m/z 288.0 (M+1).

Step 2. Preparation of 5-fluoro-4-(trifluoromethyl)pyridine-2-sulfonyl chloride

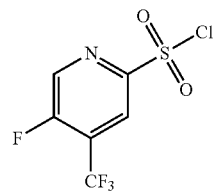

To a cooled solution of 2-(benzylthio)-5-fluoro-4-(trifluoromethyl)pyridine (2.40 g, 8.35 mmol) in acetonitrile (40 mL), acetic acid (10 mL), and water (10 mL) was added 1,3-dichloro-5,5-dimethylhydantoin (3.29 g, 67%, 16.7 mmol) in small portions at 0° C. The reaction mixture was stirred at 0° C. for 2 h, and concentrated in vacuo while keeping the temperature below 30° C. The residue was triturated in diethyl ether (100 mL), and the solid was filtered off and washed with diethyl ether (50 mL). The combined diethyl ether layers were concentrated in vacuo. The obtained residue was purified by column chromatography, eluting with a gradient of 5 to 40% of ethyl acetate in heptane, to afford the title compound as colorless liquid (1.00 g, 45% yield): $^1$H NMR (300 MHz, CDCl$_3$) δ 8.87 (s, 1H), 8.37 (dd, J=5.1, 0.3 Hz, 1H).

Step 3. Preparation of tert-butyl ((5-fluoro-4-(trifluoromethyl)pyridin-2-yl)sulfonyl)(thiazol-4-yl)carbamate

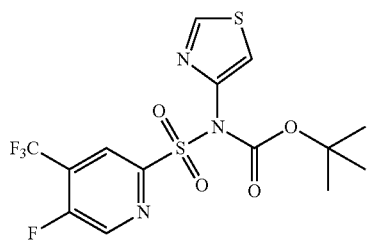 [SMILES: CC(C)(C)OC(=O)N(c1cscn1)S(=O)(=O)c1cc(C(F)(F)F)c(F)cn1]

To a solution of tert-butyl thiazol-4-ylcarbamate (1.09 g, 5.46 mmol) in anhydrous tetrahydrofuran (40 mL) was added a 1 M solution of lithium bis(trimethylsilyl)amide in tetrahydrofuran (5.5 mL, 5.5 mmol) at −78° C. The reaction mixture was stirred at −78° C. for 20 minutes, allowed to warm to ambient temperature and stirred for 1 hour. The reaction mixture was cooled to −78° C., and a solution of 5-fluoro-4-(trifluoromethyl)pyridine-2-sulfonyl chloride (1.20 g, 4.55 mmol) in anhydrous tetrahydrofuran (5 mL) was then added dropwise. The reaction mixture was stirred at −78° C. for 30 minutes, allowed to warm to ambient temperature, and stirred for 16 hours. After addition of saturated aqueous ammonium chloride (50 mL), the mixture was extracted with ethyl acetate (3×50 mL). The combined organic phases were washed with brine (50 mL), dried over anhydrous sodium sulfate, and filtered. Concentration of the filtrate in vacuo and purification of the residue by column chromatography, eluting with a gradient of 5% to 50% of ethyl acetate in heptane, afforded the title compound as a light yellow solid (0.90 g, 46% yield): $^1$H NMR (300 MHz, CDCl$_3$) δ 8.81 (d, J=2.3 Hz, 2H), 8.53 (d, J=5.3 Hz, 1H), 7.64 (d, J=2.3 Hz, 1H), 1.29 (s, 9H); MS (ES+) m/z 328.0 (M−99).

Step 4. Preparation of 5-((2-(azetidin-1-ylmethyl)-6-fluorobenzyl)amino)-N-(thiazol-4-yl)-4-(trifluoromethyl)pyridine-2-sulfonamide

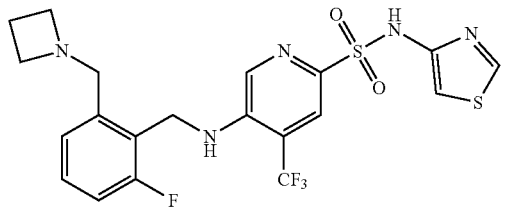 [SMILES: O=S(=O)(Nc1cscn1)c1cc(C(F)(F)F)c(NCc2c(F)cccc2CN2CCC2)cn1]

To a mixture of (2-(azetidin-1-ylmethyl)-6-fluorophenyl)methanamine (0.08 g, 0.39 mmol) in anhydrous N,N-dimethylformamide (3 mL) was added N,N-diisopropylethylamine (0.2 mL, 1.4 mmol) and tert-butyl ((5-fluoro-4-(trifluoromethyl)pyridin-2-yl)sulfonyl)(thiazol-4-yl) carbamate (0.15 g, 0.35 mmol). The reaction mixture was heated to 50° C. for 16 hours. After cooling to ambient temperature, the reaction mixture was diluted with ethyl acetate (70 mL), washed with saturated ammonium chloride (20 mL) and brine (20 mL), and dried over anhydrous sodium sulfate. Filtration and concentration of the filtrate in vacuo provided a residue which was purified by preparative reverse-phase HPLC, eluting with a gradient of 10% to 60% of acetonitrile in water containing 0.4% of formic acid, to afford the title compound as colorless solid (0.01 g, 4% yield): $^1$H NMR (300 MHz, DMSO-d$_6$) δ 11.14 (br s, 1H), 8.86 (d, J=2.2 Hz, 1H), 8.59-8.54 (m, 1H), 7.84 (s, 1H), 7.53-7.18 (m, 4H), 7.01 (d, J=2.2 Hz, 1H), 4.76-4.70 (m, 2H), 4.08-3.92 (m, 2H), 3.55-3.42 (m, 4H), 2.18-2.06 (m, 2H); MS (ES+) m/z 502.0 (M+1), MS (ES-) m/z 500.1 (M−1).

Example 32

Synthesis of 5-((2-((tert-butyl(methyl)amino)methyl)benzyl)amino)-3-fluoro-N-(6-fluoropyridin-2-yl)-6-methylpyridine-2-sulfonamide trifluoroacetic acid salt

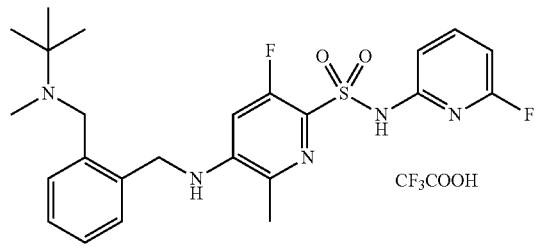 [SMILES: Cc1nc(S(=O)(=O)Nc2cccc(F)n2)c(F)cc1NCc1ccccc1CN(C)C(C)(C)C ; "CF3COOH"]

Step 1. Preparation of tert-butyl (2-chloro-5-fluoropyridin-3-yl)carbamate

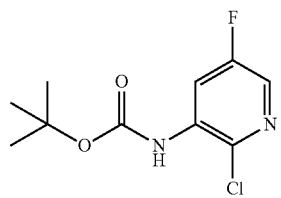 [SMILES: CC(C)(C)OC(=O)Nc1cc(F)cnc1Cl]

To a solution of 2-chloro-5-fluoronicotinic acid (35.11 g, 0.20 mol) in tert-butanol (100 mL) and toluene (100 mL) was added triethylamine (30.0 mL, 0.21 mol) and diphenylphosphoryl azide (48.0 mL, 0.22 mol). The reaction mixture was heated at 90° C. for 4 hours. After cooling to ambient temperature, the reaction mixture was diluted with ethyl acetate (400 mL), and washed with 10% aqueous sodium carbonate solution (3×100 mL) and brine (100 mL). The organic phase was dried over anhydrous sodium sulfate and filtered. The filtrate was concentrated in vacuo and the residue was purified by column chromatography, eluting Step 2. Preparation of tert-butyl (5-fluoro-2-methylpyridin-3-yl)carbamate

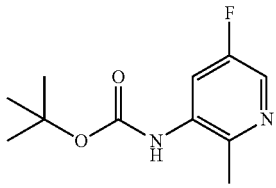 [SMILES: Cc1ncc(F)cc1NC(=O)OC(C)(C)C]

To a mixture of tert-butyl (2-chloro-5-fluoropyridin-3-yl)carbamate (24.67 g, 0.10 mol), methylboronic acid (12.0 g, 0.20 mmol) and potassium phosphate tribasic (89.8 g, 0.40 mol) in toluene (250 mL) was added water (25 mL). The mixture was sparged with nitrogen for 10 minutes and then dichloro[1,1'-bis(diphenylphosphino)-ferrocene]palladium (11)dichloromethane adduct (4.0 g, 4.89 mmol) was added. The reaction mixture was heated to 100° C. for 16 hours. After cooling to ambient temperature, water (150 mL) was added to the mixture. The organic layer was separated, and the aqueous layer was extracted with ethyl acetate (2×100 mL). The combined organic layers were washed with brine (100 mL), dried over anhydrous sodium sulfate, and filtered. The filtrate was concentrated in vacuo and the residue was purified by column chromatography, eluting with a gradient of 5 to 20% of ethyl acetate in heptane, to afford the title compound as colorless solid (16.9 g, 74% yield): $^1$H NMR (300 MHz, CDCl$_3$) δ 8.19-8.15 (m, 1H), 8.04 (d, J=2.7 Hz, 1H), 6.40 (s, 1H), 2.47 (d, J=1.1 Hz, 3H), 1.53 (s, 9H).

Step 3. Preparation of tert-butyl (6-bromo-5-fluoro-2-methylpyridin-3-yl)carbamate

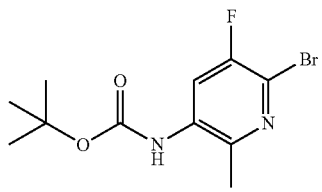 [SMILES: Cc1nc(Br)c(F)cc1NC(=O)OC(C)(C)C]

To a solution of tert-butyl (5-fluoro-2-methylpyridin-3-yl)carbamate (14.5 g, 64.1 mmol) in acetonitrile (300 mL) was added anhydrous N,N-dimethylformamide (0.5 mL) and N-bromosuccinimide (13.7 g, 76.9 mmol) and the reaction mixture was heated to 80° C. for 16 hours. After cooling to ambient temperature, the reaction mixture was diluted with ethyl acetate (100 mL) and washed with saturated ammonium chloride (3×40 mL). The organic phase was dried over anhydrous sodium sulfate, and filtered. The filtrate was concentrated in vacuo and the residue purified by column chromatography, eluting with a gradient of 10 to 50% of ethyl acetate in heptane, to afford the title compound as colorless solid (14.0 g, 72% yield): $^1$H NMR (300 MHz, CDCl$_3$) δ 8.23 (d, J=9.7 Hz, 1H), 6.39 (s, 1H), 2.46 (d, J=1.1 Hz, 3H), 1.54 (s, 9H).

Step 4. Preparation of tert-butyl (6-(benzylthio)-5-fluoro-2-methyl pyridin-3-yl)carbamate

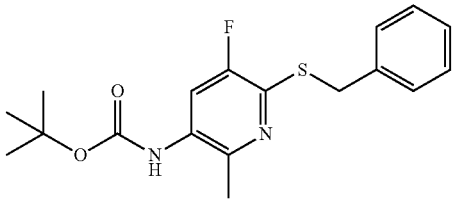 [SMILES: Cc1nc(SCc2ccccc2)c(F)cc1NC(=O)OC(C)(C)C]

To a solution of tert-butyl (6-bromo-5-fluoro-2-methylpyridin-3-yl)carbamate (14.0 g, 45.9 mmol) in anhydrous dioxane (125 mL) was added N,N-diisopropylethylamine (16 mL, 91.8 mmol), tris(dibenzylideneacetone)dipalladium (0) (1.26 g, 1.38 mmol), 4,5-bis(diphenylphosphino)-9,9-dimethylxanthene (0.80 g, 1.38 mmol) and benzyl mercaptan (5.44 g, 43.6 mmol). The reaction mixture was degassed with nitrogen and heated to 103° C. for 16 hours in a sealed tube. After cooling to ambient temperature, the reaction mixture was diluted with ethyl acetate (150 mL), washed with saturated ammonium chloride (3×50 mL), and dried over anhydrous sodium sulfate. Filtration and concentration of the filtrate in vacuo provided a residue, which was purified by column chromatography, eluting with a gradient of 10 to 50% of ethyl acetate in heptane, to afford the title compound as colorless solid (15.1 g, 94% yield): $^1$H NMR (300 MHz, CDCl$_3$) δ 7.99-7.95 (m, 1H), 7.44-7.41 (m, 2H), 7.33-7.24 (m, 3H), 6.30 (s, 1H), 4.44 (s, 2H), 2.47 (d, J=1.1 Hz, 3H), 1.55 (s, 9H); MS (ES+) m/z 349.2 (M+1), MS (ES−) m/z 347.1 (M−1).

Step 5. Preparation of tert-butyl (6-(chlorosulfonyl)-5-fluoro-2-methylpyridin-3-yl)carbamate

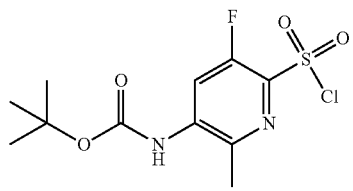 [SMILES: Cc1nc(S(=O)(=O)Cl)c(F)cc1NC(=O)OC(C)(C)C]

To an ice-cold solution of tert-butyl (6-(benzylthio)-5-fluoro-2-methylpyridin-3-yl)carbamate (40.0 g, 0.114 mol) in acetonitrile (1000 mL), acetic acid (250 mL) and water (250 mL) was added portionwise 2,4-dichloro-5,5-dimethylhydantoin (74.0 g, 0.255 mol) over 30 minutes. After addition, the reaction mixture was stirred at 0-5° C. for 1h, and concentrated under vacuum below 30° C. to remove acetonitrile. The solid was collected by filtration and washed with water (3×200 mL); dried under vacuum to give the title compound as a colorless solid (28.0 g, 75% yield): $^1$H NMR (300 MHz, CDCl$_3$) δ 8.56 (d, J=11.9 Hz, 1H), 6.79 (s, 1H), 2.58 (d, J=0.7 Hz, 3H), 1.57 (s, 9H).

with a gradient of 5 to 15% of ethyl acetate in heptane, to afford the title compound as colorless solid (47.0 g, 85% yield): $^1$H NMR (300 MHz, CDCl$_3$) δ 8.42-8.36 (m, 1H), 7.91 (d, J=1.1 Hz, 1H), 7.04 (s, 1H), 1.53 (s, 9H).

Step 6. Preparation of tert-butyl (5-fluoro-6-(N-(6-fluoropyridin-2-yl)sulfamoyl)-2-methylpyridin-3-yl)carbamate

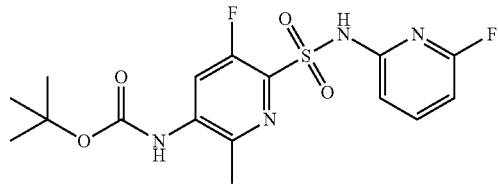 [SMILES: Cc1nc(S(=O)(=O)Nc2cccc(F)n2)c(F)cc1NC(=O)OC(C)(C)C]

To a mixture of tert-butyl (6-(chlorosulfonyl)-5-fluoro-2-methylpyridin-3-yl)carbamate (2.0 g, 6.16 mmol) in anhydrous pyridine (5 mL) was added 6-fluoropyridin-2-amine (0.70 g, 6.16 mmol). The reaction mixture was stirred at ambient temperature for 16 hours and then diluted with ethyl acetate (100 mL). The mixture was washed with 1 N hydrochloric acid (2×20 mL), saturated ammonium chloride (2×30 mL), dried over anhydrous sodium sulfate, and filtered. The filtrate was concentrated in vacuo and the residue was purified by column chromatography, eluting with a gradient of 10 to 70% of ethyl acetate in heptane, to afford the title compound as a beige solid (0.45 g, 18% yield): $^1$H NMR (300 MHz, CDCl$_3$) δ 8.39 (d, J=11.9 Hz, 1H), 7.86 (d, J=0.5 Hz, 1H), 7.70 (q, J=8.0 Hz, 1H), 7.33 (dd, J=8.0, 2.0 Hz, 1H), 6.64-6.60 (m, 2H), 2.45 (d, J=0.7 Hz, 3H), 1.54 (s, 9H); MS (ES+) m/z 401 (M+1), MS (ES−) m/z 399 (M−1).

Step 7. Preparation of 2-((tert-butyl(methyl)amino)methyl)benzonitrile

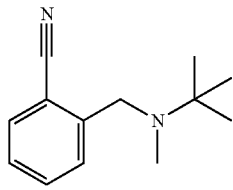

To a solution of 2-(bromomethyl)benzonitrile (19.6 g, 100 mmol) in dimethyl sulfoxide (80 mL) was added potassium carbonate (27.64 g, 200 mmol) and tert-butylmethylamine (15.6 mL, 130 mmol). The resulting mixture was stirred at ambient temperature for 18 hours. The reaction mixture was diluted with diethyl ether (400 mL), washed with water (3×100 mL), brine (100 mL), dried over anhydrous sodium sulfate, and filtered. The filtrate was concentrated in vacuo to give the title compound as pale yellow oil (20.0 g, 98% yield): $^1$HNMR (300 MHz, CDCl$_3$) δ 7.69-7.51 (m, 3H), 7.33-7.27 (m, 1H), 3.74 (s, 2H), 2.11 (s, 3H), 1.17 (s, 9H).

Step 8. Preparation of 2-((tert-butyl(methyl)amino)methyl)benzaldehyde

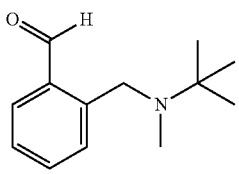

To a solution of 2-((tert-butyl(methyl)amino)methyl)benzonitrile (9.50 g, 46.95 mmol) in anhydrous dichloromethane (100 mL) was added a 1.0 M solution of diisobutylaluminum hydride in toluene (60 mL, 60 mmol) at −78° C. The reaction mixture was slowly warmed to −30° C. over a period of 4 hours and stirred at −30° C. to −20° C. for 5h. To it was then added saturated aqueous sodium bicarbonate solution (50 mL) and the mixture was stirred for 1 hour. The mixture was extracted with diethyl ether (2×200 mL), washed with water (50 mL) and brine (50 mL), and dried over anhydrous sodium sulfate. After filtration, the filtrate was concentrated in vacuo and the residue was purified by column chromatography, eluting with a gradient of 10 to 40% of ethyl acetate (containing 1.0% triethylamine) in heptane, to afford the title compound as pale yellow oil (2.96 g, 30% yield): $^1$H NMR (300 MHz, CDCl$_3$) δ 10.51 (s, 1H), 7.83-7.79 (m, 1H), 7.54-7.45 (m, 2H), 7.39-7.32 (m, 1H), 3.90 (s, 2H), 2.01 (s, 3H), 1.15 (s, 9H).

Step 9. Preparation of 5-((2-((tert-butyl(methyl)amino)methyl)benzyl)amino)-3-fluoro-N-(6-fluoropyridin-2-yl)-6-methylpyridine-2-sulfonamide trifluoroacetic acid salt

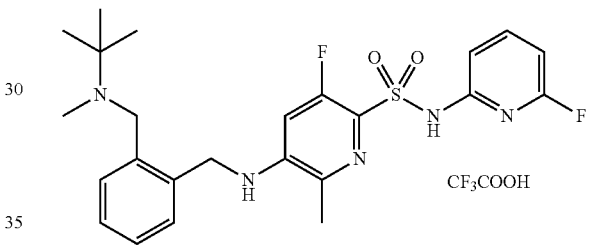

To a solution of tert-butyl (5-fluoro-6-(N-(6-fluoropyridin-2-yl)sulfamoyl)-2-methylpyridin-3-yl)carbamate (0.35 g, 0.88 mmol) in anhydrous dichloromethane (5 mL) was added a 4 M solution of hydrogen chloride in dioxane (5 mL). The reaction mixture was stirred at ambient temperature for 16 h, after which the reaction mixture was concentrated in vacuo. The residue was dissolved in anhydrous tetrahydrofuran (5 mL) and to this mixture was added 2-((tert-butyl(methyl)amino)methyl)benzaldehyde (0.25 g, 1.14 mmol) and titanium(IV) isopropoxide (0.70 g, 2.46 mmol). The reaction mixture was stirred at ambient temperature for 3 h, after which a 1 M solution of sodium cyanoborohydride in tetrahydrofuran (2.32 mL, 2.32 mmol) was added to it. The reaction mixture was stirred at ambient temperature for 16 hours. The reaction mixture was diluted with ethyl acetate (40 mL), washed with saturated ammonium chloride (10 mL), brine (10 mL), and dried over anhydrous sodium sulfate. Filtration and concentration of the filtrate in vacuo provided a residue. Purification of the residue by preparative reverse-phase HPLC, eluting with a gradient of 10% to 60% of acetonitrile in water containing 0.1% of trifluoroacetic acid, afforded the title compound obtained as colorless solid (0.01 g, 1% yield): $^1$H NMR (300 MHz, DMSO-d$_6$) δ 11.42 (s, 1H), 8.98-8.83 (m, 1H), 7.87-7.79 (m, 1H), 7.60-7.51 (m, 1H), 7.47-7.38 (m, 2H), 7.37-7.29 (m, 1H), 7.13-7.02 (m, 1H), 6.95-6.92 (m, 1H), 6.70 (dd, J=8.0, 2.5 Hz, 1H), 6.61 (d, J=13.0 Hz, 1H), 4.84-4.72 (m, 1H), 4.63-4.54 (m, 2H), 4.11-3.98 (m, 1H), 2.65 (d, J=4.9 Hz, 3H), 2.36 (s, 3H), 1.46 (s, 9H); MS (ES+) m/z 490 (M+1), MS (ES−) m/z 488.2 (M−1).

Example 33

Synthesis of 5-((2-((azabicyclo[2.2.1]heptan-7-yl)methyl)-6-fluorobenzyl)amino)-3-fluoro-6-methyl-N-(thiazol-4-yl)pyridine-2-sulfonamide trifluoroacetic acid salt

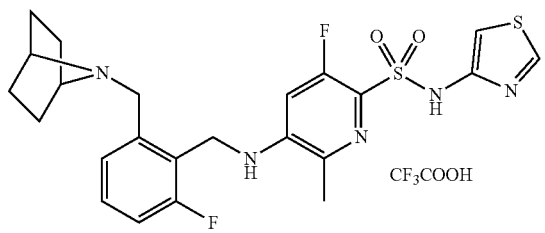

Step 1. Preparation of tert-butyl (5-fluoro-2-methyl-6-(N-(thiazol-4-yl)sulfamoyl)pyridin-3-yl)carbamate

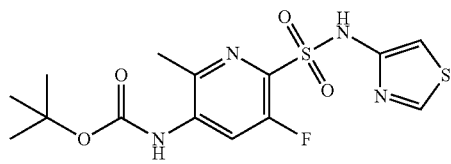 [SMILES: Cc1nc(S(=O)(=O)Nc2cscn2)c(F)cc1NC(=O)OC(C)(C)C]

To a mixture of tert-butyl (6-(chlorosulfonyl)-5-fluoro-2-methylpyridin-3-yl)carbamate (2.45 g, 7.54 mmol) in anhydrous pyridine (5 mL) was added thiazol-4-amine hydrochloride (1.24 g, 9.05 mmol) at 0° C. The reaction mixture was stirred at ambient temperature for 16 h, and then diluted with ethyl acetate (100 mL). The mixture was washed with 1 N hydrochloric acid (2×20 mL) and saturated ammonium chloride (2×30 mL), dried over anhydrous sodium sulfate, and filtered. The filtrate was concentrated in vacuo, and the residue was purified by column chromatography, eluting with a gradient of 10 to 100% of ethyl acetate in heptane, to afford the title compound as a beige color solid (0.95 g, 32% yield): $^1$HNMR (300 MHz, CDCl$_3$), 11.48-11.45 (m, 1H), 8.77 (d, J=2.3 Hz, 1H), 8.31 (d, J=11.9 Hz, 1H), 7.06 (d, J=2.3 Hz, 1H), 6.61 (s, 1H), 2.39 (s, 3H), 1.52 (s, 9H); MS (ES+) m/z 389 (M+1).

Step 2. Preparation of 2-((7-azabicyclo[2.2.1]heptan-7-yl)methyl)-6-fluorobenzaldehyde

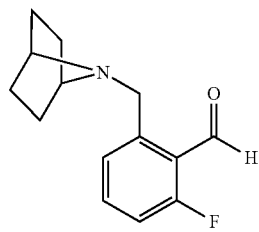 [SMILES: O=Cc1c(F)cccc1CN1C2CCC1CC2]

Following the procedure as described in Example 32, Step 7 and making variations as required to replace 2-((tert-butyl(methyl)amino)methyl)benzonitrile with 2-((7-azabicyclo[2.2.1]heptan-7-yl)methyl)-6-fluorobenzonitrile, the title compound was obtained as pale yellow oil (1.30 g, 21% yield): $^1$H NMR (300 MHz, CDCl$_3$) δ 10.49 (s, 1H), 7.49-7.44 (m, 1H), 7.14-6.89 (m, 2H), 3.88 (s, 2H), 3.24-3.19 (m, 2H), 1.83-1.72 (m, 4H), 1.34-1.20 (m, 4H).

Step 2. Preparation of 5-((2-((azabicyclo[2.2.1]heptan-7-yl)methyl)-6-fluorobenzyl)amino)-3-fluoro-6-methyl-N-(thiazol-4-yl)pyridine-2-sulfonamide trifluoroacetic acid salt

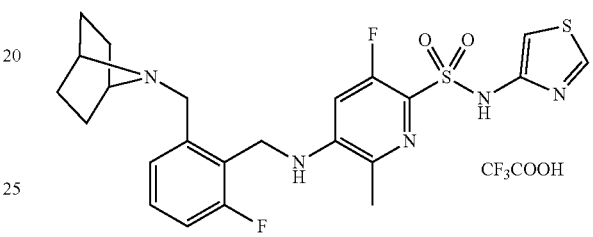

To a solution of tert-butyl (5-fluoro-2-methyl-6-(N-(thiazol-4-yl)sulfamoyl)pyridin-3-yl)carbamate (0.55 g, 1.91 mmol) in anhydrous dichloromethane (5 mL) was added a 4 M solution of hydrogen chloride in dioxane (5 mL). The reaction mixture was stirred at ambient temperature for 16 h, after which the reaction mixture was concentrated in vacuo. The residue was dissolved in anhydrous tetrahydrofuran (5 mL). To this mixture, 2-((7-azabicyclo[2.2.1]heptan-7-yl)methyl)-6-fluorobenzaldehyde (0.58 g, 2.48 mmol)) and titanium(IV) isopropoxide (1.08 g, 3.82 mmol) were added. The reaction mixture was stirred at ambient temperature for 16 h, and a 1 M solution of sodium cyanoborohydride in tetrahydrofuran (6.0 mL, 6.00 mmol) was added to it. The reaction mixture was stirred at ambient temperature for 16 hours and the mixture was diluted with ethyl acetate (40 mL), washed with saturated ammonium chloride (10 mL) and brine (10 mL), and dried over anhydrous sodium sulfate. Filtration and concentration of the filtrate in vacuo provided a residue. Purification of the residue by preparative reverse-phase HPLC, eluting with a gradient of 10% to 60% of acetonitrile in water containing 0.1% of trifluoroacetic acid, afforded the title compound was obtained as colorless solid (0.17 g, 54% yield): $^1$H NMR (300 MHz, DMSO-d$_6$) δ 11.14 (s, 1H), 10.22-10.14 (m, 1H), 8.87 (t, J=2.6 Hz, 1H), 7.53-7.45 (m, 2H), 7.39-7.31 (m, 1H), 6.94-6.88 (m, 2H), 6.83-6.77 (m, 1H), 4.54-4.45 (m, 2H), 4.40-4.29 (m, 2H), 4.17-4.09 (m, 2H), 2.27 (s, 3H), 2.23-2.13 (m, 2H), 2.06-1.95 (m, 2H), 1.80-1.57 (m, 4H); MS (ES+) m/z 506.2 (M+1), MS (ES-) m/z 504.2 (M-1).

Examples 34-37

In a similar manner as described in EXAMPLES 32 and 33, utilizing the appropriately substituted starting materials and intermediates, the following compounds were prepared:

| Example No | Name | MS (ES+) m/z | $^1$H NMR |
|---|---|---|---|
| 34 | 5-((2-((tert-butyl(methyl)amino)methyl)benzyl)amino)-3-fluoro-6-methyl-N-(thiazol-4-yl)pyridine-2-sulfonamide formic acid salt | 478.0 (M + 1) | $^1$H NMR (300 MHz, DMSO-d$_6$) δ 11.06 (br s, 2H), 8.85 (d, J = 2.1 Hz, 1H), 8.13 (s, 1H), 7.35-7.19 (m, 4H), 7.11-7.04 (m, 1H), 6.88 (d, J = 2.1 Hz, 1H), 6.86-6.83 (m, 1H), 4.61-4.58 (m, 2H), 3.89-3.62 (m, 2H), 2.34 (s, 3H), 2.19-2.02 (m, 3H), 1.20 (s, 9H). |
| 35 | 3-fluoro-5-((2-fluoro-6-((isopropyl(methyl)amino)methyl)benzyl)amino)-6-methyl-N-(thiazol-4-yl)pyridine-2-sulfonamide trifluoroacetic acid salt | 482.1 (M + 1) | (300 MHz, DMSO-d$_6$) δ 11.15 (s, 1H), 9.43-9.36 (m, 1H), 8.87 (d, J = 2.2 Hz, 1H), 7.58-7.46 (m, 2H), 7.41-7.35 (m, 1H), 6.93 (dd, J = 13.9, 2.4 Hz, 2H), 6.58-6.54 (m, 1H), 4.56-4.20 (m, 4H), 3.67-3.61 (m, 1H), 2.62 (d, J = 4.8 Hz, 3H), 2.25 (s, 3H), 1.31-1.21 (m, 6H). |
| 36 | 5-((2-bromo-3,6-difluorobenzyl)amino)-3-fluoro-6-methyl-N-(thiazol-4-yl)pyridine-2-sulfonamide trifluoroacetic acid salt | 492.8 (M + 1), 494.8 (M + 1) | (300 MHz, DMSO-d$_6$) δ 11.12 (s, 1H), 8.87 (d, J = 2.2 Hz, 1H), 7.48-7.39 (m, 2H), 6.98 (d, J = 13.2 Hz, 1H), 6.91 (d, J = 2.2 Hz, 1H), 6.62-6.57 (m, 2H), 4.43-4.42 (m, 2H), 2.24 (s, 3H). |
| 37 | 5-((2-((7-azabicyclo[2.2.1]heptan-7-yl)methyl)-3-(trifluoromethyl)benzyl)amino)-3-fluoro-6-methyl-N-(thiazol-4-yl)pyridine-2-sulfonamide trifluoroacetic acid salt | 556.0 (M + 1) | (300 MHz, DMSO-d$_6$) δ 11.19-10.98 (m, 1H), 8.85 (d, J = 2.2 Hz, 1H), 8.14 (s, 1H), 7.56 (dd, J = 19.8, 7.6 Hz, 2H), 7.38 (t, J = 7.8 Hz, 1H), 7.31-7.26 (m, 1H), 6.88 (d, J= 2.2 Hz, 1H), 6.63 (d, J = 13.0 Hz, 1H), 4.83 (d, J = 5.7 Hz, 2H), 3.73 (s, 2H), 3.39-3.28 (m, 2H), 2.41 (s, 3H), 1.76-1.65 (m, 4H), 1.33-1.27 (m, 4H). |

Example 38

Synthesis of 5-((2-fluoro-6-(pyrrolidin-1-ylmethyl)benzyl)amino)-N-(6-fluoropyridin-2-yl)-6-methylpyridine-2-sulfonamide

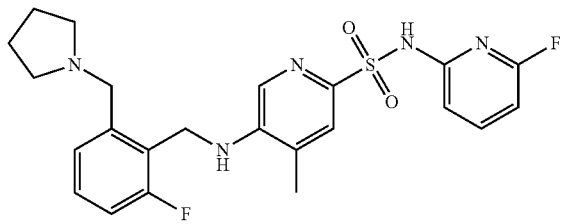 [SMILES: Cc1cc(S(=O)(=O)Nc2cccc(F)n2)ncc1NCc1c(F)cccc1CN1CCCC1]

To a solution of (2-fluoro-6-(pyrrolidin-1-ylmethyl)phenyl)methanamine (0.24 g, 1.17 mmol) in anhydrous N,N-dimethylformamide (3.0 mL) was added solid potassium bis(trimethylsilyl)amide (0.24 g, 1.22 mmol) at ambient temperature. The suspension was stirred for 20 minutes before a solution of N-(2,4-dimethoxybenzyl)-5-fluoro-N-(6-fluoropyridin-2-yl)-4-methylpyridine-2-sulfonamide (0.42 g, 0.97 mmol) in anhydrous N,N-dimethylformamide (1.86 mL) was added to it. The reaction mixture was heated to 80° C. for 6 hours. After cooling to ambient temperature, the reaction mixture was diluted with ethyl acetate (150 mL). The organic phase was washed with water (3×50 mL), brine (50 mL), dried over magnesium sulfate, and filtered. Concentration of the filtrate in vacuo and purification of the residue by column chromatography, eluting with a gradient of 0-50% of ethyl acetate (containing 20% of ethanol and 1% of ammonium hydroxide) in heptane, afforded a mixture of regioisomers as a red oil. The residue was dissolved in dichloromethane (2 mL) and trifluoroacetic acid (2 mL) and stirred at ambient temperature for 1 hour. The reaction mixture was concentrated in vacuo and the residue purified by column chromatography, eluting with a gradient of 20-90% of ethyl acetate (containing 5% of triethylamine) in heptane, followed by column chromatography, eluting with a gradient of 1-15% of ethyl acetate (containing 20% of ethanol and 1% of ammonium hydroxide) in heptane, to afford the title compound as a colorless solid (0.014 g, 3% yield): $^1$H NMR (300 MHz, DMSO-d$_6$) δ 11.20-11.15 (m, 1H), 8.14 (d, J=2.7 Hz, 1H), 7.84-7.75 (m, 2H), 7.36-7.29 (m, 1H), 7.21-7.11 (m, 2H), 6.98 (dd, J=7.9, 2.1 Hz, 1H), 6.66 (dd, J=7.9, 2.4 Hz, 1H), 6.32-6.26 (m, 1H), 4.56-4.53 (m, 2H), 3.70-3.67 (m, 2H), 2.48-2.40 (m, 4H), 2.11-2.09 (m, 3H), 1.71-1.63 (m, 4H); $^{19}$F NMR (282 MHz, DMSO-d$_6$) δ −69.3 (1F), −116.9 (1F); MS (ES+) m/z 474.1 (M+1).

Example 39

Synthesis of 5-((2-fluoro-6-(pyrrolidin-1-ylmethyl)benzyl)amino)-6-methyl-N-(thiazol-4-yl)pyridine-2-sulfonamide trifluoroacetic acid salt

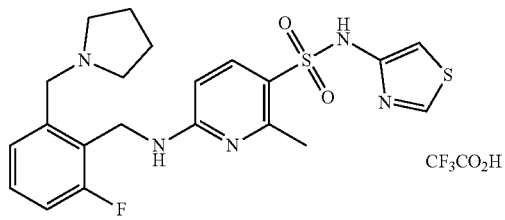 [SMILES: Cc1nc(NCc2c(F)cccc2CN2CCCC2)ccc1S(=O)(=O)Nc1cscn1 ; "CF3CO2H"]

To a solution of tert-butyl ((6-fluoro-2-methylpyridin-3-yl)sulfonyl)(thiazol-4-yl)carbamate (0.21 g, 0.56 mmol) in anhydrous N,N-dimethylformamide (3.0 mL) was added (2-fluoro-6-(pyrrolidin-1-ylmethyl)phenyl)methanamine (0.19 g, 0.89 mmol) and N,N-diisopropylethylamine (0.15 g, 1.12 mmol) and the reaction mixture was stirred at ambient temperature for 2 hours. The reaction mixture was diluted with ethyl acetate (100 mL), washed with water (3×50 mL) and brine (50 mL), and dried over magnesium sulfate. Filtration and concentration of the filtrate in vacuo provided a residue, which was purified by column chromatography, eluting with a gradient of 5-60% of ethyl acetate (containing 20% of ethanol and 1% of ammonium hydroxide) in heptane. The purified residue was dissolved in dichloromethane (3 mL) and trifluoroacetic acid (0.5 mL) and the reaction mixture was stirred at ambient temperature for 18 hours. Concentration in vacuo and purification of the residue by column chromatography, eluting with a gradient of 10-75% of ethyl acetate (containing 20% of ethanol and 1% of ammonium hydroxide) in heptane, afforded the title compound as a colorless solid (0.091 g, 24% yield): $^1$H NMR (300 MHz, DMSO-$d_6$) δ 11.04-11.00 (m, 1H), 10.09-9.87 (m, 1H), 8.87 (d, J=2.2 Hz, 1H), 7.81-7.76 (m, 1H), 7.76-7.72 (m, 1H), 7.46-7.26 (m, 4H), 6.86 (d, J=2.2 Hz, 1H), 6.36 (d, J=8.9 Hz, 1H), 4.72-4.55 (m, 4H), 3.49-3.31 (m, 2H), 3.19-3.05 (m, 2H), 2.58 (s, 3H), 2.03-1.78 (m, 4H); MS (ES+) m/z 462.1 (M+1).

Example 40

Synthesis of 6-((2-fluoro-6-(pyrrolidin-1-ylmethyl)benzyl)amino)-N-(6-fluoropyridin-2-yl)-2-methylpyridine-3-sulfonamide trifluoroacetic acid salt

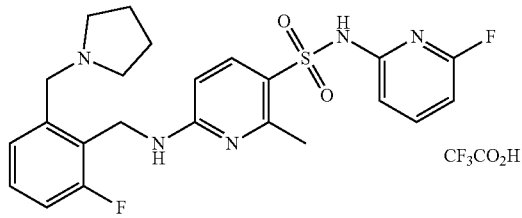

Step 1. Preparation of N-(2,4-dimethoxybenzyl)-6-fluoro-N-(6-fluoropyridin-2-yl)-2-methylpyridine-3-sulfonamide

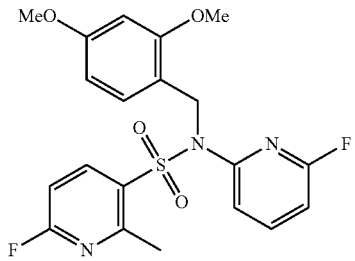 [SMILES: COc1ccc(CN(c2cccc(F)n2)S(=O)(=O)c2ccc(F)nc2C)c(OC)c1]

To a solution of N-(2,4-dimethoxybenzyl)-6-fluoropyridin-2-amine (1.26 g, 4.77 mmol) in anhydrous tetrahydrofuran (12.6 mL) was added a 1 M solution of lithium bis(trimethylsilyl)amide in tetrahydrofuran (5.24 mL, 5.24 mmol) at −78° C. The reaction mixture was stirred at −78° C. for 30 minutes. To it was then added dropwise a solution of 6-fluoro-2-methylpyridine-3-sulfonyl chloride (1.0 g, 4.8 mmol) in anhydrous tetrahydrofuran (2.7 mL) at −78° C. The reaction mixture was allowed to warm to ambient temperature and stirred for 18 hours. The reaction mixture was diluted with ethyl acetate (150 mL), and the organic layer was washed with brine (3×50 mL), dried over magnesium sulfate, and filtered. Concentration of the filtrate in vacuo and purification of the residue by column chromatography, eluting with a gradient of 5-50% of ethyl acetate in heptane, afforded the title compound as a yellow oil (1.2 g, 57% yield): $^1$H NMR (300 MHz, CDCl$_3$) δ 7.81 (dd, J=8.5, 3.7 Hz, 1H), 7.70 (t, J=8.1 Hz, 1H), 7.45-7.39 (m, 2H), 7.30-7.27 (m, 1H), 6.67 (dd, J=8.0, 3.0 Hz, 1H), 6.38 (dd, J=8.4, 2.4 Hz, 1H), 6.33 (d, J=2.3 Hz, 1H), 5.15 (s, 2H), 3.77 (s, 3H), 3.66 (s, 3H), 2.55 (d, J=3.0 Hz, 3H).

Step 2. Preparation of 6-((2-fluoro-6-(pyrrolidin-1-ylmethyl)benzyl)amino)-N-(6-fluoropyridin-2-yl)-2-methylpyridine-3-sulfonamide trifluoroacetic acid salt

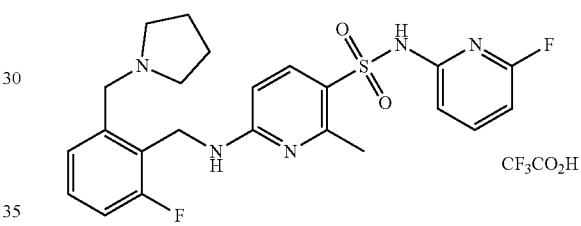

To a solution of N-(2,4-dimethoxybenzyl)-6-fluoro-N-(6-fluoropyridin-2-yl)-2-methylpyridine-3-sulfonamide (0.16 g, 0.37 mmol) in anhydrous N,N-dimethylformamide (2.0 mL) was added (2-fluoro-6-(pyrrolidin-1-ylmethyl)phenyl)methanamine (0.10 g, 0.48 mmol) and N,N-diisopropylethylamine (0.10 g, 0.74 mmol) and the reaction mixture was stirred at ambient temperature for 1 hour. The reaction mixture was then diluted with ethyl acetate (150 mL), washed with water (3×50 mL), brine (50 mL), and dried over anhydrous magnesium sulfate. Filtration and concentration of the filtrate in vacuo provided a residue which was purified by column chromatography, eluting with a gradient of 15-25% of ethyl acetate (containing 20% of ethanol and 1% of ammonium hydroxide) in heptane. The residue was dissolved in a mixture of dichloromethane (2 mL) and trifluoroacetic acid (2 mL) and the reaction mixture was stirred at ambient temperature for 2 hours. The reaction mixture was then concentrated in vacuo. The residue was dissolved in methanol (25 mL), the mixture filtered, and the filtrate concentrated in vacuo. Purification of the residue by column chromatography, eluting with a gradient of 25-100% of ethyl acetate (containing 20% of ethanol and 1% of ammonium hydroxide) in heptane, afforded the title compound as a colorless solid (0.091 g, 36% yield): $^1$H NMR (300 MHz, DMSO-$d_6$) δ 11.37 (s, 1H), 9.92-9.85 (m, 1H), 7.91-7.76 (m, 3H), 7.49-7.29 (m, 3H), 6.82-6.79 (m, 1H), 6.69-6.65 (m, 1H), 6.44 (d, J=9.0 Hz, 1H), 4.72-4.64 (m, 2H), 4.61-4.55 (m, 2H), 3.49-3.38 (m, 2H), 3.19-3.07 (m, 2H), 2.59-2.56 (m, 3H), 2.04-1.79 (m, 4H); MS (ES+) m/z 474.1 (M+1).

Example 41

Synthesis of 5-((2-fluoro-6-(pyrrolidin-1-ylmethyl)benzyl)amino)-N-(6-fluoropyridin-2-yl)-6-methylpyridine-2-sulfonamide trifluoroacetic acid salt

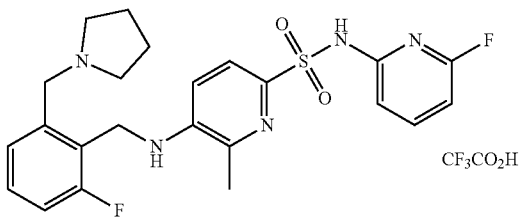

To a solution of N-(2,4-dimethoxybenzyl)-5-fluoro-N-(6-fluoropyridin-2-yl)-6-methylpyridine-2-sulfonamide (0.55 g, 1.26 mmol) in anhydrous dimethyl sulfoxide (6.3 mL) was added (2-fluoro-6-(pyrrolidin-1-ylmethyl)phenyl)methanamine (0.42 g, 2.0 mmol) and N,N-diisopropylethylamine (0.33 g, 2.5 mmol). The reaction mixture was heated to 130° C. for 18 hours. After cooling to ambient temperature, the reaction mixture was diluted with ethyl acetate (100 mL), washed with water (3×50 mL), brine (50 mL), and dried over anhydrous magnesium sulfate. Filtration and concentration of the filtrate in vacuo provided a residue, which was purified by column chromatography, eluting with a gradient of 25-75% of ethyl acetate (containing 20% of ethanol and 1% of ammonium hydroxide) in heptane. The residue was dissolved in a mixture of dichloromethane (5 mL) and trifluoroacetic acid (5 mL). The reaction mixture was stirred at ambient temperature for 2 hours and then concentrated in vacuo. The residue was dissolved in methanol (25 mL), filtered, and the filtrate concentrated in vacuo. Purification of the residue by column chromatography, eluting with a gradient of 25-100% of ethyl acetate (containing 20% of ethanol and 1% of ammonium hydroxide) in heptane, afforded the title compound as a colorless solid (0.17 g, 21% yield): $^1$H NMR (300 MHz, DMSO-$d_6$) δ 11.41-11.05 (m, 1H), 10.24-9.71 (m, 1H), 7.95-7.70 (m, 2H), 7.62-7.23 (m, 3H), 7.21-7.06 (m, 1H), 7.03-6.93 (m, 1H), 6.75-6.60 (m, 1H), 6.41-6.25 (m, 1H), 4.69-4.20 (m, 4H), 3.62-2.82 (m, 4H), 2.32-2.21 (m, 3H), 2.06-1.70 (m, 4H); MS (ES+) m/z 474.1 (M+1).

Example 42

Synthesis of 5-chloro-6-((2-fluoro-6-(pyrrolidin-1-ylmethyl)benzyl)amino)-N-(6-fluoropyridin-2-yl)pyridine-3-sulfonamide trifluoroacetic acid salt

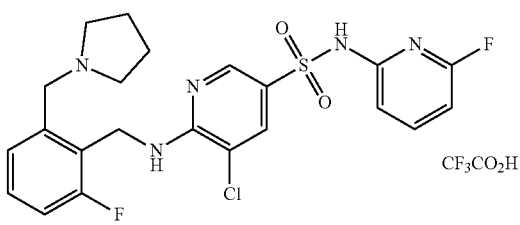

Step 1. Preparation of 5-(benzylthio)-3-chloro-2-fluoropyridine

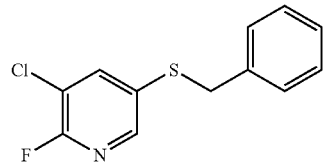 [SMILES: Fc1ncc(SCc2ccccc2)cc1Cl]

To a solution of 5-bromo-3-chloro-2-fluoropyridine (13.9 g, 66.1 mmol) in anhydrous 1,4-dioxane (132 mL) was added N,N-diisopropylethylamine (14 mL, 79.3 mmol) and benzylthiol (10.34 mL, 66.1 mmol). The reaction mixture was sparged with argon for 20 minutes. To it was then added tris(dibenzylideneacetone)bispalladium (0.91 g, 3.61 mmol), and 4,5-bis(diphenylphosphino)-9,9-dimethylxanthene (2.30 g, 3.97 mmol) and the reaction mixture was heated to reflux for 3 hours. After cooling to ambient temperature, the reaction mixture was filtered through a bed of diatomaceous earth. The filter bed was washed with ethyl acetate (2×75 mL), and the combined filtrate concentrated in vacuo. Purification of the residue by column chromatography, eluting with heptane, afforded the title compound as an orange oil (16.1 g, 97% yield): MS (ES+) m/z 254 (M+1).

Step 2. Preparation of 5-chloro-6-fluoropyridine-3-sulfonyl chloride

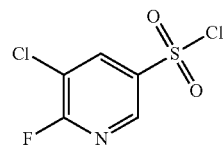 [SMILES: O=S(=O)(Cl)c1cnc(F)c(Cl)c1]

To a solution of 5-(benzylthio)-3-chloro-2-fluoropyridine (16.1 g, 64 mmol) in acetonitrile (391 mL) was added water (22 mL) and acetic acid (28 mL) and the mixture was cooled to 0° C. To it was then added 1,3-dichloro-5,5-dimethylhydantoin (25.2 g, 128 mmol) and the reaction mixture was stirred at 0° C. for 1 hour. The reaction mixture was then allowed to warm to ambient temperature and stirred for 18 hours. After dilution with ethyl acetate (500 mL), the mixture was washed with saturated sodium bicarbonate solution (3×100 mL), water (3×100 mL), and brine (100 mL). The organic phase was dried over anhydrous magnesium sulfate, filtered, and filtrate concentrated in vacuo. The colorless residue was used without further purification (10.2 g, 69% yield): $^1$H NMR (300 MHz, DMSO-$d_6$) δ 8.82-8.79 (m, 1H), 8.48-8.44 (m, 1H).

Step 3. Preparation of 5-chloro-N-(2,4-dimethoxybenzyl)-6-fluoro-N-(6-fluoropyridin-2-yl)pyridine-3-sulfonamide

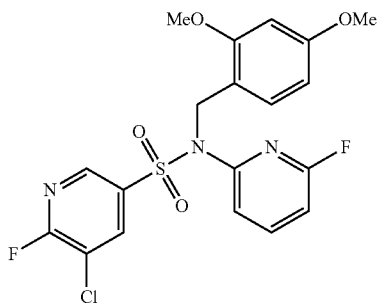 [SMILES: COc1ccc(CN(c2cccc(F)n2)S(=O)(=O)c2cnc(F)c(Cl)c2)c(OC)c1]

To a solution of N-(2,4-dimethoxybenzyl)-6-fluoropyridin-2-amine (2.0 g, 8.69 mmol) in anhydrous tetrahydrofuran (23 mL) was added a 1 M solution of lithium bis(trimethylsilyl)amide in tetrahydrofuran (9.6 mL, 9.6 mmol) at −78° C. and the reaction mixture was stirred at −78° C. for 1 hour. To it was then added dropwise a solution of 5-chloro-6-fluoropyridine-3-sulfonyl chloride (1.0 g, 4.8 mmol) in anhydrous tetrahydrofuran (5.0 mL) at −78° C. The reaction mixture was allowed to warm to ambient temperature and stirred for 18 hours. To the reaction mixture was added water (60 mL) and the mixture was extracted with ethyl acetate (2×100 mL). The organic layers were washed with water (3×50 mL), brine (50 mL), and dried over anhydrous magnesium sulfate. Filtration and concentration of the filtrate in vacuo provided a residue, which was purified by column chromatography, eluting with a gradient of 5-60% of ethyl acetate in heptane, to afford the title compound as an orange oil (0.40 g, 10% yield): MS (ES+) m/z 478.2 (M+23), 480.2 (M+23).

Step 4. Preparation of 5-chloro-6-((2-fluoro-6-(pyrrolidin-1-ylmethyl)benzyl)amino)-N-(6-fluoropyridin-2-yl)pyridine-3-sulfonamide trifluoroacetic acid salt

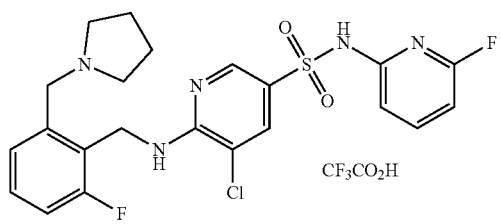 [SMILES: O=S(=O)(Nc1cccc(F)n1)c1cnc(NCc2c(F)cccc2CN2CCCC2)c(Cl)c1 ; "CF3CO2H"]

To a solution of 5-chloro-N-(2,4-dimethoxybenzyl)-6-fluoro-N-(6-fluoropyridin-2-yl)pyridine-3-sulfonamide (0.4 g, 0.88 mmol) in anhydrous N,N-dimethylformamide (4.3 mL) was added (2-fluoro-6-(pyrrolidin-1-ylmethyl)phenyl)methanamine (0.29 g, 1.4 mmol) and N,N-diisopropylethylamine (0.23 g, 1.75 mmol) and the reaction mixture was stirred at ambient temperature for 2 hours. The reaction mixture was diluted with ethyl acetate (125 mL), washed with water (3×50 mL) brine (50 mL), and dried over anhydrous magnesium sulfate. Filtration and concentration of the filtrate in vacuo provided a residue, which was purified by column chromatography, eluting with a gradient of 10-60% of ethyl acetate (containing 20% of ethanol and 1% of ammonium hydroxide) in heptane. The residue was then dissolved in a mixture of dichloromethane (4 mL) and trifluoroacetic acid (3 mL). The reaction mixture was stirred at ambient temperature for 2 hours and then concentrated in vacuo. The residue was triturated with methanol (3×25 mL), the mixture filtered, and the filtrate concentrated in vacuo. Purification of the residue by column chromatography, eluting with a gradient of 10-80% of ethyl acetate (containing 20% of ethanol and 1% of ammonium hydroxide) in heptane, afforded the title compound as a colorless solid (0.27 g, 46% yield): $^1$H NMR (300 MHz, DMSO-$d_6$) δ 11.63-11.08 (m, 1H), 10.18-9.64 (m, 1H), 8.54-8.52 (m, 1H), 8.03-7.82 (m, 3H), 7.46-7.34 (m, 2H), 7.32-7.23 (m, 1H), 6.93-6.89 (m, 1H), 6.77-6.73 (m, 1H), 4.78-4.52 (m, 4H), 3.37-3.03 (m, 4H), 2.08-1.79 (m, 4H); MS (ES+) m/z 494.0 (M+1), 496.0 (M+1).

Example 43

Synthesis of 5-((2-fluoro-6-(pyrrolidin-1-ylmethyl)benzyl)amino)-N-(6-fluoropyridin-2-yl)-4-methylthiophene-2-sulfonamide trifluoroacetic acid salt

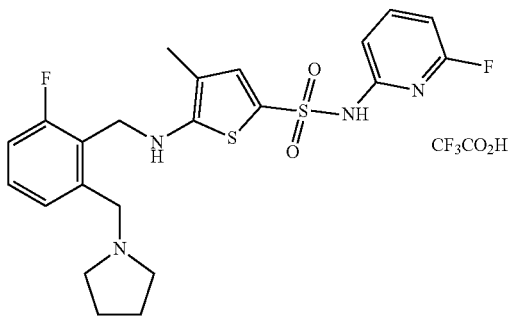 [SMILES: Cc1cc(S(=O)(=O)Nc2cccc(F)n2)sc1NCc1c(F)cccc1CN1CCCC1 ; "CF3CO2H"]

Step 1. Preparation of N-(6-fluoropyridin-2-yl)-4-methyl-5-nitrothiophene-2-sulfonamide

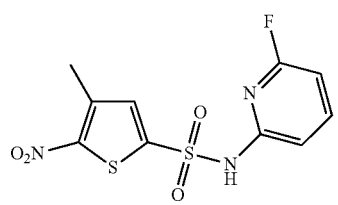 [SMILES: Cc1cc(S(=O)(=O)Nc2cccc(F)n2)sc1[N+](=O)[O-]]

To a solution of 4-methylthiophene-2-sulfonyl chloride (13.9 g, 66.1 mmol) in anhydrous dichloromethane (5.5 mL) was carefully added concentrated nitric acid (5.5 mL) and concentrated sulfuric acid (0.5 mL) at 0° C. The reaction mixture was allowed to warm to ambient temperature and stirred for 2 hours. The reaction mixture was diluted with ethyl acetate (25 mL), and carefully neutralized with saturated sodium bicarbonate solution (100 mL). The aqueous layer was extracted with ethyl acetate (3×50 mL), and the combined organic layers were washed with saturated sodium bicarbonate solution (50 mL), water (50 mL), and brine (50 mL). The combined organic layers were dried over anhydrous magnesium sulfate, filtered, and the filtrate concentrated in vacuo. The residue was dissolved in anhydrous dichloromethane (20 mL) and slowly added to a solution of 6-fluoropyridin-2-amine (1.5 g, 13.5 mmol) in pyridine (20 mL) at 0° C. The reaction mixture was stirred at 0° C. for 3 hours. The reaction mixture was then diluted with ethyl acetate (200 mL) and washed with 1 M hydrochloric acid (3×50 mL), water (50 mL), and brine (50 mL). The organic phase was dried over anhydrous magnesium sulfate, filtered, and the filtrate concentrated in vacuo. Purification of the residue by column chromatography, eluting with ethyl acetate (containing 10% of 2-propanol and 10% of triethylamine) in heptane, afforded the title compound as an orange oil (1.75 g, 45% yield): $^1$H NMR (300 MHz, CDCl$_3$) δ 7.51 (dt, J=9.1, 7.9 Hz, 1H), 7.31 (d, J=0.4 Hz, 1H), 6.96 (ddd, J=8.0, 2.7, 0.5 Hz, 1H), 6.28 (ddd, J=7.8, 2.7, 0.5 Hz, 1H), 2.58 (d, J=0.4 Hz, 3H), NH not observed.

Step 2. Preparation of 5-amino-N-(6-fluoropyridin-2-yl)-4-methylthiophene-2-sulfonamide

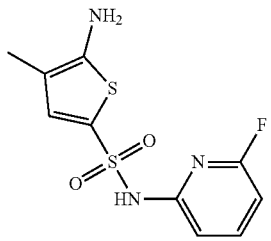 [SMILES: Cc1cc(S(=O)(=O)Nc2cccc(F)n2)sc1N]

To a solution of N-(6-fluoropyridin-2-yl)-4-methyl-5-nitrothiophene-2-sulfonamide (1.75 g, 5.5 mmol) in ethyl acetate (11 mL) was added glacial acetic acid (11 mL) and iron powder (1.5 g, 27.6 mmol) and the reaction mixture was stirred at ambient temperature for 3 hours. The reaction mixture was diluted with ethyl acetate (200 mL) and washed with 10% sodium bicarbonate solution (50 mL), saturated sodium bicarbonate solution (2×100 mL), water (50 mL), and brine (50 mL). The organic phase was dried over anhydrous magnesium sulfate, filtered, and the filtrate concentrated in vacuo. The obtained brownish solid was used without further purification (1.2 g, 76% yield): $^1$H NMR (300 MHz, CDCl$_3$) δ 7.80-7.72 (m, 1H), 7.55-7.47 (m, 1H), 7.27-7.25 (m, 1H), 6.63 (dd, J=8.0, 2.4 Hz, 1H), 4.13-4.07 (m, 2H), 1.99 (s, 3H), NH not observed.

Step 3. Preparation of 5-((2-bromo-6-fluorobenzyl) amino)-N-(6-fluoropyridin-2-yl)-4-methylthiophene-2-sulfonamide

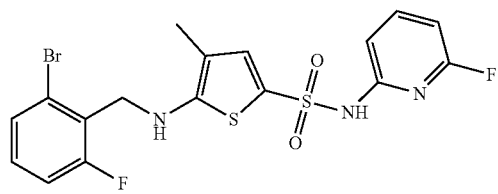 [SMILES: Cc1cc(S(=O)(=O)Nc2cccc(F)n2)sc1NCc1c(F)cccc1Br]

To a solution of 5-amino-N-(6-fluoropyridin-2-yl)-4-methylthiophene-2-sulfonamide (0.62 g, 2.16 mmol) in trifluoroacetic acid (5.5 mL) was added 2-bromo-6-fluorobenzaldehyde (0.66 g, 3.24 mmol) and the reaction mixture was stirred at ambient temperature for 5 minutes. To it was then added sodium triacetoxyborohydride (0.82 g, 3.89 mmol) in portions over 20 minutes. The reaction mixture was stirred for another 20 minutes before being diluted with ethyl acetate (200 mL). The organic phase was washed with saturated sodium bicarbonate solution (3×75 mL), water (50 mL) brine (50 mL), and dried over magnesium sulfate. Filtration and concentration of the filtrate in vacuo provided a residue. Purification of the residue by column chromatography, eluting with ethyl acetate (containing 10% of 2-propanol and 10% of triethylamine) in heptane, afforded the title compound as an orange oil (0.37 g, 36% yield): MS (ES+) m/z 474.0 (M+1), 476.0 (M+1).

Step 4. Preparation of 5-((2-fluoro-6-(pyrrolidin-1-ylmethyl)benzyl)amino)-N-(6-fluoropyridin-2-yl)-4-methylthiophene-2-sulfonamide trifluoroacetic acid salt

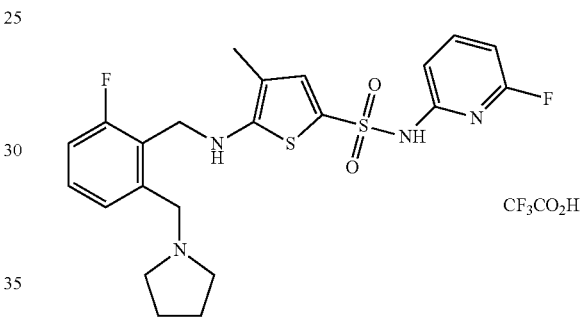

To a solution of 5-((2-bromo-6-fluorobenzyl)amino)-N-(6-fluoropyridin-2-yl)-4-methylthiophene-2-sulfonamide (0.37 g, 0.79 mmol) in anhydrous 1,4-dioxane (6 mL) was added water (1.2 mL) and the mixture was sparged with argon for 10 minutes. To it was then added potassium trifluoro[(pyrrolidin-1-yl)methyl]borate (0.30 g, 1.57 mmol), cesium carbonate (0.77 g, 2.35 mmol), palladium acetate (0.018 g, 0.078 mmol), and di(1-adamantyl)-n-butylphosphine (0.055 g, 0.16 mmol). The reaction mixture was sparged with argon for 5 minutes and then heated to 90° C. for 18 hours. After cooling to ambient temperature, the reaction mixture was diluted with ethyl acetate (200 mL). The organic phase was washed with saturated ammonium chloride solution (3×50 mL), water (50 mL), brine (50 mL), and dried over anhydrous magnesium sulfate. Filtration and concentration of the filtrate in vacuo provided a residue which was purified by preparative reverse-phase HPLC, eluting with a gradient of 5 to 95% of acetonitrile in water containing 0.1% of trifluoroacetic acid, to afford the title compound as a colorless solid (0.062 g, 13% yield): $^1$H NMR (300 MHz, DMSO-d$_6$) δ 11.13 (s, 1H), 9.80-9.74 (m, 1H), 7.86 (q, J=8.3 Hz, 1H), 7.52 (td, J=7.9, 5.7 Hz, 1H), 7.45-7.43 (m, 1H), 7.38-7.32 (m, 2H), 6.97-6.88 (m, 2H), 6.73 (dd, J=7.9, 2.4 Hz, 1H), 4.51-4.47 (m, 2H), 4.36-4.31 (m, 2H), 3.49-3.39 (m, 2H), 3.18-3.07 (m, 2H), 2.07-1.96 (m, 2H), 1.95-1.90 (m, 3H), 1.91-1.81 (m, 2H); MS (ES+) m/z 479.0 (M+1).

Example 44

Synthesis of 5-((3,6-difluoro-2-(pyrrolidin-1-ylmethyl)benzyl)amino)-N-(thiazol-4-yl)imidazo[1,2-a]pyridine-8-sulfonamide trifluoroacetic acid salt

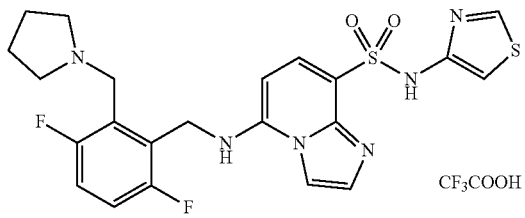 [SMILES: O=S(=O)(Nc1cscn1)c1ccc(NCc2c(F)ccc(F)c2CN2CCCC2)n2ccnc12 ; "CF3COOH"]

Step 1. Preparation of 2,6-difluoropyridine-3-sulfonyl chloride

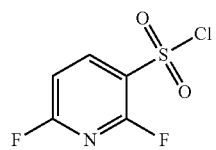 [SMILES: O=S(=O)(Cl)c1ccc(F)nc1F]

To a solution of 2,6-difluoropyridine (3.45 g, 30 mmol) in tetrahydrofuran (60 mL) was added a 1.6 M solution of n-butyllithium in hexanes (18.7 mL, 30 mmol) at −78° C. and the resulting mixture was stirred at −78° C. for 45 minutes. The reaction mixture was then treated with sulfur dioxide gas by bubbling it through the mixture for 5 minutes. The reaction mixture was stirred at −78° C. for 2 h, and N-chlorosuccinimide (4.40 g, 33 mmol) was added to it. The reaction mixture was allowed to warm to ambient temperature, stirred for 16 h, and then quenched by addition of water (75 mL). The mixture was extracted with ethyl acetate (2×100 mL) and the organic layers were washed with brine (50 mL) and concentrated in vacuo. The residue was purified by column chromatography, eluting with a gradient of 0-60% of ethyl acetate in heptane, to afford the title compound as a colorless solid (2.51 g, 39% yield): $^1$H NMR (300 MHz, CDCl$_3$) δ 8.54 (td, J=8.5, 6.7 Hz, 1H), 7.11 (dd, J=8.4, 2.9 Hz, 1H); $^{19}$F-NMR (282 MHz, CDCl$_3$) δ −53.6 (d, J=4.4 Hz), −55.2 (d, J=4.3 Hz).

Step 2. Preparation of tert-butyl ((2,6-difluoropyridin-3-yl)sulfonyl)(thiazol-4-yl)carbamate

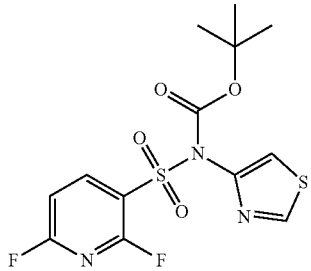 [SMILES: CC(C)(C)OC(=O)N(c1cscn1)S(=O)(=O)c1ccc(F)nc1F]

To a solution of tert-butyl thiazol-4-ylcarbamate (0.46 g, 2.3 mmol) in anhydrous tetrahydrofuran (8 mL) was added a 1.0 M solution of lithium bis(trimethylsilyl)amide in tetrahydrofuran (2.50 mL, 2.50 mmol) at −78° C. The resulting mixture was stirred at −78° C. for 10 minutes and then was then allowed to warm up to 10° C. The reaction mixture was then cooled to −78° C. again and a solution of 2,6-difluoropyridine-3-sulfonyl chloride (0.49 g, 2.3 mmol) in anhydrous tetrahydrofuran (5 mL) was added to it. The reaction mixture was allowed to warm to ambient temperature, stirred for 16 h, and then quenched by addition of a saturated ammonium chloride solution (15 mL). The mixture was extracted with ethyl acetate (2×20 mL) and the organic layers were washed with brine (50 mL) and concentrated in vacuo. The residue was purified by column chromatography, eluting with a gradient of 0-80% of ethyl acetate in heptane, to afford the title compound as a colorless solid (0.16 g, 18% yield): MS (ES+) m/z 378.0 (M+1).

Step 3. Preparation of 1-(2-bromo-3,6-difluorobenzyl)pyrrolidine

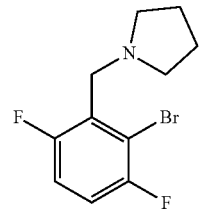 [SMILES: Fc1ccc(F)c(CN2CCCC2)c1Br]

Following the procedure as described for EXAMPLE 21, Step 1 and making non-critical variations as required to replace N,2-dimethylpropan-2-amine with pyrrolidine, the title compound was isolated as a colorless solid (1.30 g, 45% yield): MS (ES+) m/z 276.1 (M+1), 278.1 (M+1).

Step 4. Preparation of 3,6-difluoro-2-(pyrrolidin-1-ylmethyl)benzaldehyde oxime

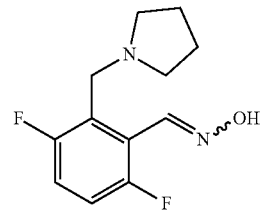 [SMILES: ON=Cc1c(F)ccc(F)c1CN1CCCC1]

Following the procedure as described for EXAMPLE 21, Step 2 and making non-critical variations as required to replace N-(2-bromo-3,6-difluorobenzyl)-N,2-dimethylpropan-2-amine with 1-(2-bromo-3,6-difluorobenzyl)pyrrolidine, the title compound was isolated as a colorless solid (1.30 g, quantitative yield): MS (ES+) m/z 241.2 (M+1).

Step 5. Preparation of (3,6-difluoro-2-(pyrrolidin-1-ylmethyl)phenyl)methanamine

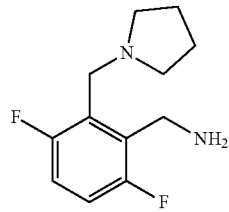 [SMILES: NCc1c(F)ccc(F)c1CN1CCCC1]

Following the procedure as described for EXAMPLE 21, Step 3 and making non-critical variations as required to replace 2-((tert-butyl(methyl)amino)methyl)-3,6-difluorobenzaldehyde oxime with 3,6-difluoro-2-(pyrrolidin-1-ylmethyl)benzaldehyde oxime, the title compound was isolated as a colorless oil (1.10 g, 90% yield): MS (ES+) m/z 227.2 (M+1).

Step 6. Preparation of tert-butyl ((6-((3,6-difluoro-2-(pyrrolidin-1-ylmethyl)benzyl)amino)-2-((2,4-dimethoxybenzyl)amino)pyridin-3-yl)sulfonyl)(thiazol-4-yl)carbamate

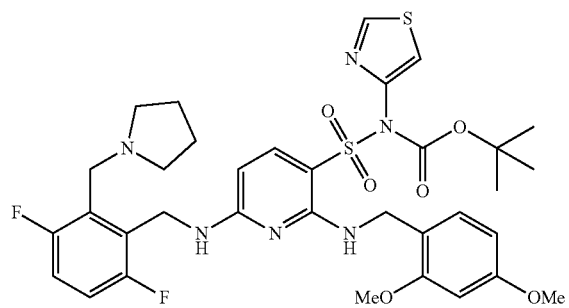 [SMILES: COc1ccc(CNc2nc(NCc3c(F)ccc(F)c3CN3CCCC3)ccc2S(=O)(=O)N(C(=O)OC(C)(C)C)c2cscn2)c(OC)c1]

To a solution of tert-butyl ((2,6-difluoropyridin-3-yl)sulfonyl)(thiazol-4-yl)carbamate (0.16 g, 0.42 mmol) in anhydrous dimethyl sulfoxide (2 mL) was added triethylamine (0.20 mL, 1.45 mmol) followed by 2,4-dimethoxybenzylamine (0.07 g, 0.42 mmol). The reaction mixture was stirred at ambient temperature for 1 hour and (3,6-difluoro-2-(pyrrolidin-1-ylmethyl)phenyl)methanamine (0.09 g, 0.42 mmol) was added to it. The reaction mixture was stirred at ambient temperature for 16 hours and then quenched by addition of water (10 mL). The mixture was extracted with ethyl acetate (2×10 mL) and the organic layers were washed with brine (10 mL) and concentrated in vacuo. The residue was purified by column chromatography, eluting with a gradient of 0-100% of ethyl acetate in heptane, to afford the title compound as a colorless solid (0.18 g, 62% yield): MS (ES+) m/z 731.2 (M+1).

Step 7. Preparation of 2-amino-6-((3,6-difluoro-2-(pyrrolidin-1-ylmethyl)benzyl)amino)-N-(thiazol-4-yl)pyridine-3-sulfonamide

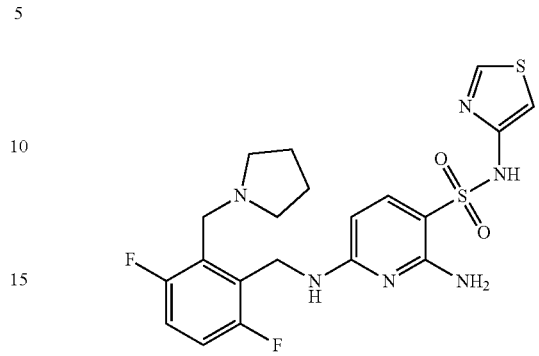

To a solution of tert-butyl ((6-((3,6-difluoro-2-(pyrrolidin-1-ylmethyl)benzyl)amino)-2-((2,4-dimethoxybenzyl)amino)pyridin-3-yl)sulfonyl)(thiazol-4-yl)carbamate (0.18 g, 0.25 mmol) in dichloromethane (1.5 mL) was added trifluoroacetic acid (1.5 mL) and the mixture was stirred at ambient temperature for 2 hours. The reaction mixture was concentrated in vacuo and the residue purified by column chromatography, eluting with a gradient of 0-15% of methanol in dichloromethane, to afford the title compound as a colorless solid (0.09 g, 75% yield): MS (ES+) m/z 481.1 (M+1).

Step 8. Preparation of 5-((3,6-difluoro-2-(pyrrolidin-1-ylmethyl)benzyl)amino)-N-(thiazol-4-yl)imidazo[1,2-a]pyridine-8-sulfonamide trifluoroacetic acid salt

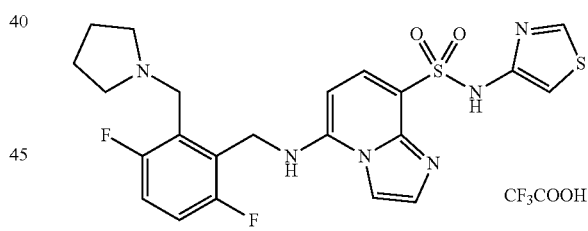

To a solution of 2-amino-6-((3,6-difluoro-2-(pyrrolidin-1-ylmethyl)benzyl)amino)-N-(thiazol-4-yl)pyridine-3-sulfonamide (0.09 g, 0.21 mmol) in ethanol (4 mL) was added 2-chloroacetaldehyde (50% solution in water, 0.2 mL, 1.8 mmol) and the mixture was heated to 90° C. for 16 hours. After cooling to ambient temperature, the reaction mixture was concentrated in vacuo and the residue purified by preparative reverse phase HPLC, using acetonitrile in water containing 0.1% trifluoroacetic acid as eluent. The title compound was obtained as a colorless solid (0.025 g, 24% yield): $^1$H NMR (300 MHz, DMSO-$d_6$) δ 9.98-9.95 (br s, 1H), 8.84 (d, J=2.2 Hz, 1H), 8.33-8.31 (m, 2H), 8.12-8.09 (m, 1H), 7.93-7.92 (m, 1H), 7.56-7.51 (m, 2H), 7.07 (d, J=2.2 Hz, 1H), 6.54-6.51 (m, 1H), 4.75-4.73 (m, 2H), 4.61-4.56 (m, 2H), 3.58-3.51 (m, 2H), 3.21-3.14 (m, 2H), 2.05-1.84 (m, 4H), COOH not observed; MS (ES+) m/z 505.2 (M+1).

Example 45

Synthesis of 3-fluoro-5-((2-fluoro-6-((isopropyl (methyl)amino)methyl)benzyl)amino)-N-(6-fluoropyridin-2-yl)-4-methylpyridine-2-sulfonamide

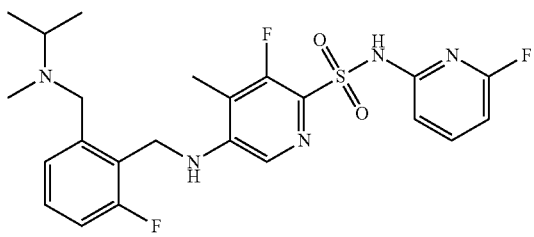 [SMILES: Cc1c(NCc2c(F)cccc2CN(C)C(C)C)cnc(S(=O)(=O)Nc2cccc(F)n2)c1F]

Step 1. Preparation of 2-(benzylthio)-3,5-difluoropyridine

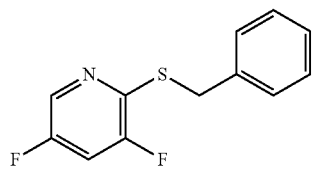 [SMILES: Fc1cnc(SCc2ccccc2)c(F)c1]

To a degassed solution of 2-bromo-3,5-difluoropyridine (1.0 g, 5.15 mmol) in anhydrous 1,4-dioxane (21 mL) was added N,N-diisopropylethylamine (1.9 g, 15.45 mmol), benzylthiol (0.64 g, 5.15 mmol), tris(benzylideneacetone)dipalladium(0) (0.12 g, 0.13 mmol), and 4,5-bis(diphenylphosphino)-9,9-dimethylxanthene (0.15 g, 0.26 mmol) and the reaction mixture was heated to 100° C. for 18 hours. After cooling to ambient temperature, the reaction mixture was filtered through a bed of diatomaceous earth and the filtrate concentrated under reduced pressure. Purification of the residue by column chromatography, eluting with a gradient of 5 to 70% of ethyl acetate in heptane, afforded the title compound as a yellow oil (0.68 g, 55% yield): $^1$H NMR (300 MHz, CDCl$_3$) δ 8.27 (d, J=2.3 Hz, 1H), 7.44-7.40 (m, 2H), 7.35-7.24 (m, 3H), 7.16-7.10 (m, 1H), 4.46 (s, 2H).

Step 2. Preparation of 2-(benzylthio)-3,5-difluoro-4-methylpyridine

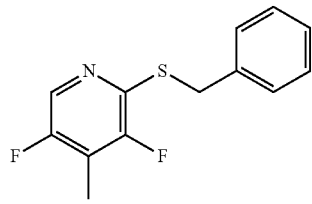

To a solution of anhydrous N,N-diisopropylamine (1.27 g, 12.6 mmol) in anhydrous tetrahydrofuran (36 mL) was added a 1.6 M solution of n-butyl lithium (7.9 mL, 12.6 mmol) at 0° C. The reaction mixture was stirred at 0° C. for 30 minutes, cooled to −78° C., and then added slowly to a solution of 2-(benzylthio)-3,5-difluoropyridine (2.0 g, 8.4 mmol) in anhydrous tetrahydrofuran (10 mL) at −78° C. The reaction mixture was stirred at −78° C. for 30 minutes, and iodomethane (1.252 g, 8.82 mmol) was added to it. The reaction mixture was stirred at −78° C. for 30 minutes, and then allowed to warm to ambient temperature over the course of 3 hours. The reaction mixture was subsequently poured into a 1:1 mixture of saturated ammonium chloride and brine (50 mL). The layers were separated and the aqueous layer was extracted with ethyl acetate (2×50 mL). The combined organic layers were dried over anhydrous magnesium sulfate, filtered, and the filtrate concentrated in vacuo. Purification of the residue by column chromatography, eluting with a gradient of 0 to 10% of ethyl acetate in heptane, afforded the title compound as a yellow oil (2.08 g, 98% yield): $^1$H NMR (300 MHz, CDCl$_3$) δ 8.18 (d, J=2.7 Hz, 1H), 7.47-7.40 (m, 2H), 7.34-7.23 (m, 3H), 4.45 (s, 2H), 2.25 (t, J=1.7 Hz, 3H); MS (ES+) m/z 252.0 (M+1).

Step 3. Preparation of 3,5-difluoro-N-(6-fluoropyridin-2-yl)-4-methylpyridine-2-sulfonamide

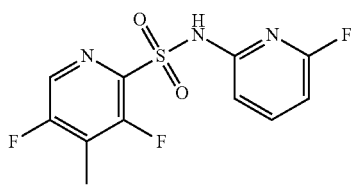 [SMILES: Cc1c(F)cnc(S(=O)(=O)Nc2cccc(F)n2)c1F]

To a mixture of 2-(benzylthio)-3,5-difluoro-4-methylpyridine (3.83 g, 15.2 mmol) in acetonitrile (76 mL), water (4.2 mL), and acetic acid (5.4 mL) was added 1,3-dichloro-5,5-dimethylimidazolidine-2,4-dione (5.69 g, 28.9 mmol) at 0° C. The reaction mixture was stirred for 20 minutes at 0° C. and then diluted with ethyl acetate (250 mL). The organic layer was washed with saturated sodium bicarbonate (4×50 mL), water (50 mL), brine (50 mL), and dried over anhydrous magnesium sulfate. Filtration and concentration of the filtrate under reduced pressure provided a yellow oil, which was dissolved in dichloromethane (25 mL). The mixture was cooled to 0° C. and added dropwise to a mixture of 6-fluoropyridin-2-amine (1.87 g, 16.72 mmol) in pyridine (25 mL) at 0° C. The reaction mixture was stirred at ambient temperature for 2 hours and then diluted with ethyl acetate (250 mL). The mixture was washed with 1 M hydrochloric acid (4×75 mL), water (75 mL), brine (50 mL), and dried over anhydrous magnesium sulfate. Filtration and concentration of the filtrate under reduced pressure provided a residue, which was purified by column chromatography, eluting with a gradient of 10 to 100% of ethyl acetate (containing 10% ethanol and 10% triethylamine) in heptane, to afford the title compound as a yellow solid (2.91 g, 63% yield): $^1$H NMR (300 MHz, CDCl$_3$) δ 8.26 (s, 1H), 7.40 (dt, J=9.2, 7.9 Hz, 1H), 6.99 (ddd, J=8.0, 2.8, 0.5 Hz, 1H), 6.21 (ddd, J=7.8, 2.8, 0.5 Hz, 1H), 2.27 (t, J=1.7 Hz, 3H), NH not observed; MS (ES+) m/z 304.0 (M+1).

Step 4. Preparation of 3,5-difluoro-N-(6-fluoropyridin-2-yl)-N-(4-methoxybenzyl)-4-methylpyridine-2-sulfonamide

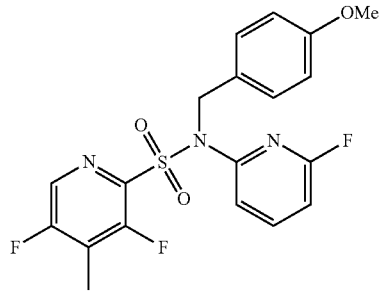 [SMILES: COc1ccc(CN(c2cccc(F)n2)S(=O)(=O)c2ncc(F)c(C)c2F)cc1]

To a mixture of 3,5-difluoro-N-(6-fluoropyridin-2-yl)-4-methylpyridine-2-sulfonamide (6.56 g, 21.65 mmol), and sodium bicarbonate (4.36 g, 51.96 mmol) in anhydrous N,N-dimethylformamide (72 mL) was added para-methoxybenzyl chloride (4.07 g, 25.98 mmol). The reaction mixture was heated to 50° C. for 5 hours. After cooling to ambient temperature, the reaction mixture was diluted with ethyl acetate (300 mL), and the organic phase was washed with saturated ammonium chloride solution (100 mL), water (3×75 mL), and brine (100 mL). The organic phase was dried over anhydrous magnesium sulfate, filtered, and concentrated in vacuo. Purification of the residue by column chromatography, eluting with a gradient of 10-70% of ethyl acetate in heptane, afforded the title compound as a yellow oil (5.02 g, 55% yield): $^1$H NMR (300 MHz, CDCl$_3$) δ 8.30 (s, 1H), 7.69 (q, J=8.1 Hz, 1H), 7.37-7.30 (m, 3H), 6.82-6.79 (m, 2H), 6.70 (dd, J=8.0, 3.0 Hz, 1H), 5.17 (s, 2H), 3.77 (s, 3H), 2.32 (t, J=1.8 Hz, 3H); MS (ES+) m/z 424.0 (M+1).

Step 5. Preparation of 2-fluoro-6-((isopropyl(methyl)amino)methyl)benzonitrile

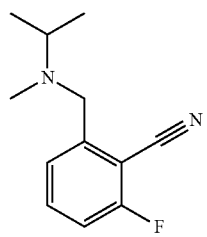

To a solution of 2-(bromomethyl)-6-fluorobenzonitrile (75.0 g, 350 mmol) and N,N-diisopropylethylamine (73.2 mL, 421 mmol) in anhydrous tetrahydrofuran (1000 mL) was added N-methylpropan-2-amine (40.2 mL. 385 mmol) at −42° C. The reaction mixture was stirred at −42° C. for 4 hours and then at ambient temperature for 60 hours. The reaction mixture was diluted with diethyl ether (500 mL) and filtered. The filtrate was concentrated in vacuo and the residue was dissolved in ethyl acetate (250 mL). The mixture was washed with saturated ammonium chloride (2×100 mL), brine (100 mL), and dried over anhydrous sodium sulfate. The mixture was filtered and the filtrate was concentrated in vacuo to afford the title compound as a reddish oil (72.3 g, quantitative yield): $^1$H NMR (300 MHz, CDCl$_3$) δ 7.54 (td, J=8.1, 5.7 Hz, 1H), 7.40-7.38 (m, 1H), 7.11-7.05 (m, 1H), 3.71 (s, 2H), 2.96 (7, J=6.6 Hz, 1H), 2.17 (s, 3H), 1.11 (s, 3H), 1.09 (s, 3H); MS (ES+) m/z 207.1 (M+1).

Step 6. Preparation of N-(2-(aminomethyl)-3-fluorobenzyl)-N-methylpropan-2-amine

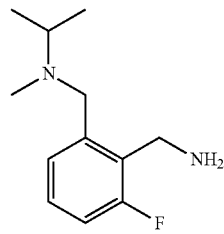

To a flask containing Raney-Nickel (10 g) was added a solution of 2-fluoro-6-((isopropyl(methyl)amino)methyl)benzonitrile (72.3 g, 350 mmol) in methanol (600 mL) and concentrated aqueous ammonium hydroxide (50 mL). The reaction mixture was sparged with nitrogen for 10 minutes and then with hydrogen for 10 minutes. The reaction mixture was then stirred under 1 atm of hydrogen for 72 hours. The mixture was sparged with nitrogen for 10 minutes and filtered through diatomaceous earth. The filtrate was concentrated in vacuo to afford the title compound as a red oil (68.0 g, 92% yield): $^1$H NMR (300 MHz, CDCl$_3$) δ 7.17-7.10 (m, 1H), 7.06-6.91 (m, 2H), 3.86 (s, 2H), 3.58 (s, 2H), 3.00-2.87 (m, 1H), 2.57 (s, 2H), 2.06 (s, 3H), 1.09 (s, 3H), 1.07 (s, 3H); MS (ES+) m/z 211.1 (M+1).

Step 7. Preparation of 3-fluoro-5-((2-fluoro-6-((isopropyl(methyl)amino)methyl)benzyl)amino)-N-(6-fluoropyridin-2-yl)-N-(4-methoxybenzyl)-4-methylpyridine-2-sulfonamide

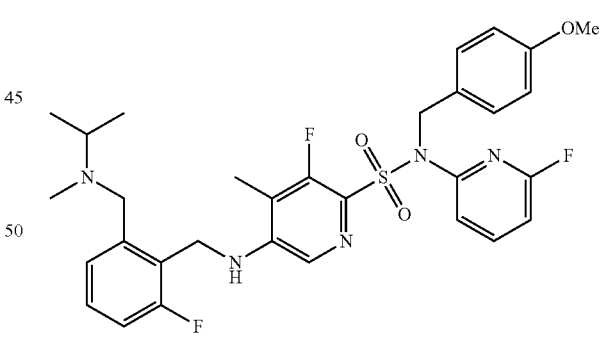

To a mixture of 3,5-difluoro-N-(6-fluoropyridin-2-yl)-N-(4-methoxybenzyl)-4-methylpyridine-2-sulfonamide (1.0 g, 2.36 mmol), N,N-diisopropylethylamine (0.98 g, 7.55 mmol) in anhydrous dimethyl sulfoxide (11.8 mL) was added N-(2-(aminomethyl)-3-fluorobenzyl)-N-methylpropan-2-amine (0.74 g, 3.54 mmol). The reaction mixture was sparged with nitrogen gas for 5 minutes and heated to 130° C. for 18 hours. After cooling to ambient temperature, the reaction mixture was diluted with ethyl acetate (200 mL). The organic phase was washed with water (4×75 mL), saturated ammonium chloride solution (2×75 mL), brine (100 mL), dried over anhydrous sodium sulfate, and filtered.

Concentration of the filtrate in vacuo and purification of the residue by column chromatography, eluting with a gradient of 5-65% of ethyl acetate (with 10% of isopropanol and 10% of triethylamine) in heptane, afforded the title compound as a yellow oil (1.09 g, 75% yield): MS (ES+) m/z 614.0 (M+1).

Step 8. Preparation of 3-fluoro-5-((2-fluoro-6-((isopropyl(methyl)amino)methyl)benzyl)amino)-N-(6-fluoropyridin-2-yl)-4-methylpyridine-2-sulfonamide

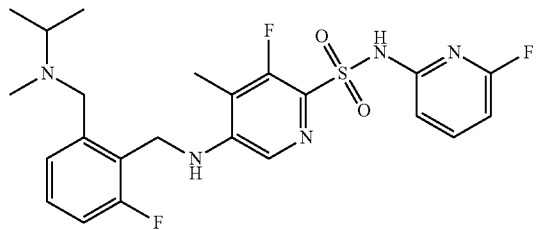 [SMILES: Cc1c(NCc2c(F)cccc2CN(C)C(C)C)cnc(S(=O)(=O)Nc2cccc(F)n2)c1F]

To a solution of 3-fluoro-5-((2-fluoro-6-((isopropyl(methyl)amino)methyl)benzyl)-amino)-N-(6-fluoropyridin-2-yl)-N-(4-methoxybenzyl)-4-methylpyridine-2-sulfonamide (1.09 g, 1.78 mmol) in 1,2-dichloroethane (10 mL) was added trifluoroacetic acid (10 mL) and the solution was stirred at 60° C. for 2 hours. The reaction mixture was concentrated in vacuo, and the residue was dissolved in methanol (50 mL). The methanol solution was filtered through a bed of diatomaceous earth and concentrated in vacuo. The residue was purified by column chromatography, eluting with a gradient of 20-100% of ethyl acetate (with 10% of isopropanol and 10% of triethylamine) in heptane, to give the title compound as a colorless solid (0.42 g, 48% yield): $^1$H NMR (300 MHz, DMSO-$d_6$) δ 11.49-10.85 (m, 1H), 8.00-7.98 (m, 1H), 7.82 (q, J=8.3 Hz, 1H), 7.40-7.32 (m, 1H), 7.28-7.16 (m, 2H), 6.93 (dd, J=7.9, 2.1 Hz, 1H), 6.70 (dd, J=8.0, 2.5 Hz, 1H), 6.62-6.58 (m, 1H), 4.55 (t, J=5.1 Hz, 2H), 3.83-3.69 (m, 2H), 3.06-2.95 (m, 1H), 2.19-2.04 (m, 3H), 2.04-1.96 (m, 3H), 1.06-0.93 (m, 6H); MS (ES+) 494.1 m/z (M+1).

Example 46

Synthesis of 5-((2-((tert-butyl(methyl)amino)methyl)benzyl)amino)-3-fluoro-N-(isoxazol-3-yl)-6-methylpyridine-2-sulfonamide trifluoroacetic acid salt

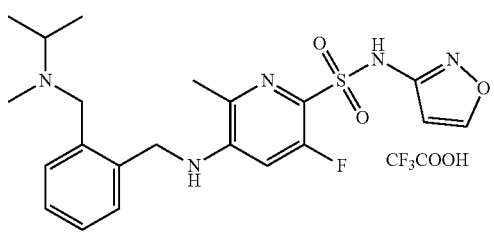 [SMILES: Cc1nc(S(=O)(=O)Nc2ccon2)c(F)cc1NCc1ccccc1CN(C)C(C)C ; "CF3COOH"]

Step 1. Preparation of tert-butyl (5-fluoro-6-(N-(isoxazol-3-yl)sulfamoyl)-2-methylpyridin-3-yl)carbamate

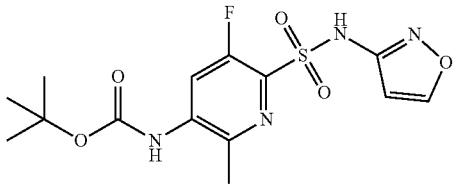 [SMILES: Cc1nc(S(=O)(=O)Nc2ccon2)c(F)cc1NC(=O)OC(C)(C)C]

To a mixture of tert-butyl (6-(chlorosulfonyl)-5-fluoro-2-methylpyridin-3-yl)carbamate (1.0 g, 3.08 mmol) in anhydrous pyridine (5 mL) was added 3-aminoisoxazole (0.39 g, 4.62 mmol). The reaction mixture was stirred at ambient temperature for 16 h, and then diluted with ethyl acetate (100 mL). The mixture was washed with 1 N hydrochloric acid (2×20 mL) and saturated ammonium chloride (2×30 mL), dried over anhydrous sodium sulfate, and filtered. The filtrate was concentrated in vacuo, and the residue was purified by column chromatography, eluting with a gradient of 10 to 100% of ethyl acetate in heptane, to afford the title compound as a beige color solid (yield not determined): MS (ES+) m/z 373 (M+1).

Step 2. Preparation of 5-amino-3-fluoro-N-(isoxazol-3-yl)-6-methylpyridine-2-sulfonamide hydrochloride

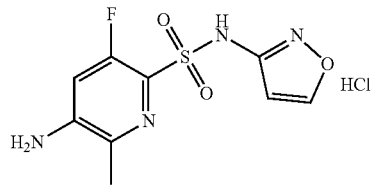 [SMILES: Cc1nc(S(=O)(=O)Nc2ccon2)c(F)cc1N ; Cl]

To tert-butyl (5-fluoro-6-(N-(isoxazol-3-yl)sulfamoyl)-2-methylpyridin-3-yl)carbamate was added 4 N hydrogen chloride in dioxane (30 mL) and the reaction mixture was stirred at ambient temperature for 4 hours. The mixture was concentrated in vacuo to afford the title compound as a brownish solid (0.40 g, 42% yield over two steps): MS (ES+) m/z 273 (M+1).

Step 3. Preparation of 5-((2-((tert-butyl(methyl)amino)methyl)benzyl)amino)-3-fluoro-N-(isoxazol-3-yl)-6-methylpyridine-2-sulfonamide trifluoroacetic acid salt

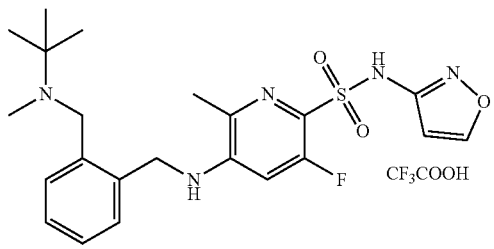 [SMILES: Cc1nc(S(=O)(=O)Nc2ccon2)c(F)cc1NCc1ccccc1CN(C)C(C)(C)C ; "CF3COOH"]

To a mixture of 5-amino-3-fluoro-N-(isoxazol-3-yl)-6-methylpyridine-2-sulfonamide hydrochloride (0.40 g, 1.29 mmol) and 2-((tert-butyl(methyl)amino)methyl)benzaldehyde in tetrahydrofuran (5 mL) was added titanium(IV) isopropoxide (5.0 mL) and the reaction mixture was stirred at ambient temperature for 18 hours. To it was then added a 1 M solution of sodium cyanoborohydride in tetrahydrofuran (5.0 mL, 5.0 mmol) and the reaction mixture was stirred at ambient temperature for 5 hours. The reaction mixture was quenched by addition of saturated aqueous sodium bicarbonate solution (50 mL) and stirred for 30 minutes. The mixture was filtered through a pad of diatomaceous earth and washed with ethyl acetate (100 mL). The filtrate was washed with water (20 mL) and brine (20 mL), and dried over anhydrous sodium sulfate. Filtration and concentration of the filtrate in vacuo provided a residue. Purification of the residue by preparative reverse-phase HPLC, eluting with a gradient of 10% to 60% of acetonitrile in water containing 0.1% of trifluoroacetic acid, afforded the title compound as colorless solid (0.20 g, 27% yield): $^1$H NMR (300 MHz, DMSO-$d_6$) δ 11.65 (s, 1H), 9.05-8.94 (m, 1H), 8.68 (d, J=1.8 Hz, 1H), 7.58-7.54 (m, 1H), 7.44-7.39 (m, 2H), 7.36-7.31 (m, 1H), 7.17-7.11 (m, 1H), 6.61 (d, J=12.9 Hz, 1H), 6.34 (d, J=1.8 Hz, 1H), 4.78 (d, J=13.5 Hz, 1H), 4.67-4.51 (m, 2H), 4.10-4.00 (m, 1H), 2.68-2.61 (m, 3H), 2.38 (s, 3H), 1.46 (s, 9H); MS (ES+) m/z 462.1 (M+1).

Example 47

Synthesis of 5-((2-((7-azabicyclo[2.2.1]heptan-7-yl)methyl)-6-fluorobenzyl)amino)-N-(thiazol-4-yl)-6-(trifluoromethyl)pyridine-2-sulfonamide trifluoroacetic acid salt

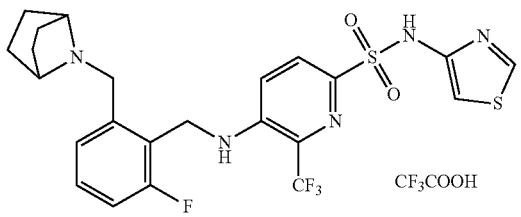 [SMILES: O=S(=O)(Nc1cscn1)c1ccc(NCc2c(F)cccc2CN2C3CCC2CC3)c(C(F)(F)F)n1 ; "CF3COOH"]

Step 1. Preparation of 6-(benzylthio)-3-fluoro-2-(trifluoromethyl)pyridine

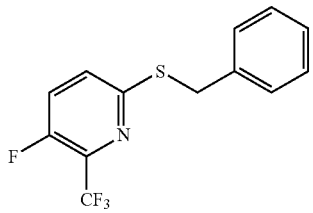 [SMILES: Fc1ccc(SCc2ccccc2)nc1C(F)(F)F]

To a degassed solution of 6-chloro-3-fluoro-2-(trifluoromethyl)pyridine (2.50 g, 12.5 mmol) and N,N-diisopropylethylamine (1.71 mL, 18.8 mmol) in anhydrous dioxane (25 mL) was added 4,5-bis(diphenylphosphino)-9,9-dimethylxanthene (0.361 g, 0.625 mmol), tris(dibenzylideneacetone)dipalladium(0) (0.286 g, 0.312 mmol), and benzyl mercaptan (1.46 ml, 12.5 mmol). The reaction mixture was heated under reflux for 16 h, allowed to cool to ambient temperature, and then concentrated in vacuo. Purification of the residue by column chromatography, eluting with a gradient of 0 to 30% of ethyl acetate in heptane, provided the title compound as a yellowish oil (3.10 g, 86% yield): MS (ES+) m/z 288.0 (M+1).

Step 2. Preparation of 5-fluoro-6-(trifluoromethyl)pyridine-2-sulfonyl chloride

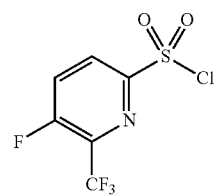 [SMILES: O=S(=O)(Cl)c1ccc(F)c(C(F)(F)F)n1]

To a solution of 6-(benzylthio)-3-fluoro-2-(trifluoromethyl)pyridine (1.50 g, 5.22 mmol) in acetonitrile (20 mL), acetic acid (2.0 mL), and water (2.0 mL) was added 1,3-dichloro-5,5-dimethylhydantoin (3.08 g, 15.7 mmol) at 0° C. The reaction mixture was stirred at 0° C. for 1.5 hours and then diluted with ethyl acetate (550 mL). The mixture was washed with ice cold brine (4×100 mL), dried over anhydrous sodium sulfate, and filtered. Concentration of the filtrate in vacuo and purification of the residue by column chromatography, eluting with a gradient of 0 to 15% of ethyl acetate in heptane, afforded the title compound as a colorless solid (1.40 g, quantitative yield): $^1$H NMR (400 MHz, CDCl$_3$) δ 8.39 (dd, J=8.7, 3.3 Hz, 1H), 7.96 (t, J=8.6 Hz, 1H).

Step 3. Preparation of tert-butyl ((5-fluoro-6-(trifluoromethyl)pyridin-2-yl)sulfonyl)(thiazol-4-yl)carbamate

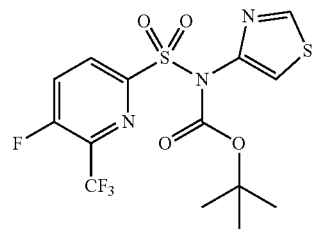 [SMILES: CC(C)(C)OC(=O)N(c1cscn1)S(=O)(=O)c1ccc(F)c(C(F)(F)F)n1]

To a solution 5-fluoro-6-(trifluoromethyl)pyridine-2-sulfonyl chloride (1.30 g, 4.94 mmol) anhydrous tetrahydrofuran (25 mL) was added a 1 M solution of lithium bis(trimethylsilyl)amide in tetrahydrofuran (5.90 mL, 5.90 mmol) at −78° C. The reaction mixture was allowed to warm 0° C., stirred at 0° C. for 1 h, and cooled to −78° C. To it was then added dropwise a solution of 5-fluoro-6-methylpyridine-2-sulfonyl chloride (0.98 g, 4.94 mmol) in anhydrous tetrahydrofuran (10 mL) at −78° C. The reaction mixture was stirred at −78° C. for 1.5 h, allowed to warm to ambient temperature, and stirred for 18 hours. The reaction mixture was concentrated in vacuo and the residue was dissolved in ethyl acetate (50 mL). The mixture was washed with saturated ammonium chloride (2×30 mL), brine (30 mL), dried over anhydrous sodium sulfate, and filtered. Concentration of the filtrate in vacuo and purification of the residue by column chromatography, eluting with a gradient of 0 to 50% of ethyl acetate in heptane, afforded the title compound as a colorless solid (1.30 g, 61% yield): MS (ES+) m/z 428.0 (M+1).

Step 4. Preparation tert-butyl ((5-((2-((7-azabicyclo [2.2.1]heptan-7-yl)methyl)-6-fluorobenzyl)amino)-6-(trifluoromethyl)pyridin-2-yl)sulfonyl) (thiazol-4-yl) carbamate

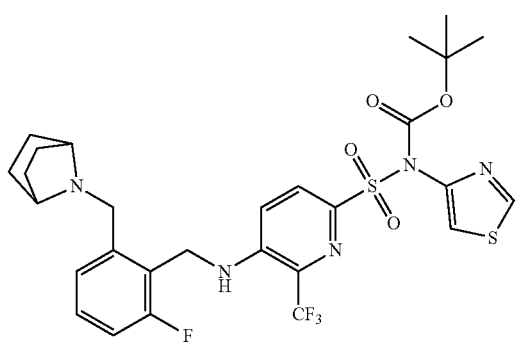 [SMILES: CC(C)(C)OC(=O)N(c1cscn1)S(=O)(=O)c1ccc(NCc2c(F)cccc2CN2C3CCC2CC3)c(C(F)(F)F)n1]

To a solution of tert-butyl ((5-fluoro-6-(trifluoromethyl) pyridin-2-yl)sulfonyl)(thiazol-4-yl)carbamate (0.30 g, 0.70 mmol) and (2-((7-azabicyclo[2.2.1]heptan-7-yl)methyl)-6-fluorophenyl)methanamine (0.197 g, 0.84 mmol) in anhydrous dimethyl sulfoxide (6 mL) was added N,N-diisopropylethylamine (304 µL, 1.75 mmol). The reaction mixture was heated to 110° C. for 16 hours and then allowed to cool to ambient temperature. After dilution with ethyl acetate (20 mL), the mixture was washed with saturated ammonium chloride solution (2×20 mL), brine (20 mL), dried over anhydrous sodium sulfate, and filtered. Concentration of the filtrate in vacuo and purification of the residue by column chromatography, eluting with a gradient of 10 to 80% of ethyl acetate (containing 20% of ethanol and 0.2% of ammonium hydroxide) in heptane, afforded the title compound as a colorless oil (0.15 g, 33% yield): MS (ES+) m/z 642.1 (M+1).

Step 5. Preparation of 5-((2-((7-azabicyclo[2.2.1] heptan-7-yl)methyl)-6-fluorobenzyl)amino)-N-(thiazol-4-yl)-6-(trifluoromethyl)pyridine-2-sulfonamide trifluoroacetic acid salt

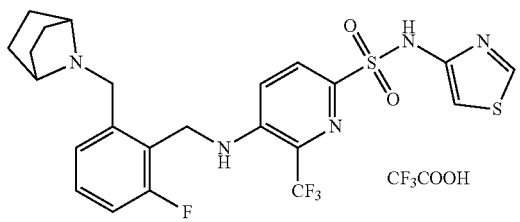 [SMILES: O=S(=O)(Nc1cscn1)c1ccc(NCc2c(F)cccc2CN2C3CCC2CC3)c(C(F)(F)F)n1 ; "CF3COOH"]

To a solution of tert-butyl ((5-((2-((7-azabicyclo[2.2.1] heptan-7-yl)methyl)-6-fluorobenzyl)amino)-6-(trifluoromethyl)pyridin-2-yl)sulfonyl) (thiazol-4-yl)carbamate (0.15 g, 0.23 mmol) in dichloromethane (3 mL) was added trifluoroacetic acid (2 mL). The reaction mixture was stirred at ambient temperature for 0.5 hour and then concentrated in vacuo. After addition of methanol (30 mL), the mixture was filtered and the filtrate concentrated in vacuo. Purification of the residue by preparative reverse phase HPLC, eluting with a gradient of 10 to 50% of acetonitrile in water (containing 0.1% trifluoroacetic acid), afforded the title compound as a colorless solid (0.056 g, 42% yield): $^1$H NMR (300 MHz, DMSO-$d_6$) δ 11.16 (s, 1H), 9.43 (s, 1H), 8.86 (d, J=2.2 Hz, 1H), 8.01 (d, J=8.9 Hz, 1H), 7.53-7.32 (m, 4H), 7.02 (t, J=1.9 Hz, 1H), 6.95-6.90 (m, 1H), 4.63-4.61 (m, 2H), 4.39-4.36 (m, 2H), 4.16-4.15 (m, 2H), 2.23-2.17 (m, 2H), 1.95-1.88 (m, 2H), 1.80-1.65 (m, 4H); MS (ES+) m/z 542.1 (M+1).

Example 48

Synthesis of 5-((2-((tert-butyl(methyl)amino)-methyl)-6-fluorobenzyl)amino)-3-fluoro-6-methyl-N-(thiazol-4-yl)pyridine-2-sulfonamide

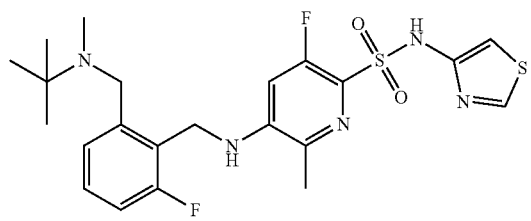 [SMILES: Cc1nc(S(=O)(=O)Nc2cscn2)c(F)cc1NCc1c(F)cccc1CN(C)C(C)(C)C]

Step 1. Preparation of 2-((tert-butyl(methyl)amino) methyl)-6-fluorobenzaldehyde

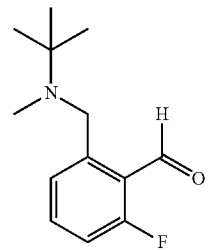 [SMILES: CN(Cc1cccc(F)c1C=O)C(C)(C)C]

To a solution of 2-((tert-butyl(methyl)amino)methyl)-6-fluorobenzonitrile (26 g, 0.118 mol) in formic acid (120 mL) and water (120 mL) was added Raney-Nickel (50 g, 0.85 mol). The reaction was heated at 45° C. for 16 hours. The reaction mixture was allowed to cool to ambient temperature, filtered through diatomaceous earth, and rinsed with 2-propanol (3×50 mL). The filtrate was concentrated in vacuo. The residue was neutralized with saturated sodium carbonate solution to pH 10 and extracted with diethyl ether (3×500 mL). The combined organics were washed with brine (100 mL), dried over anhydrous sodium sulfate, filtered, and concentrated in vacuo. Upon standing at −25° C. for 16 h, the pale yellow oil solidified and the resulting solid was triturated in heptane (50 mL) and filtered to afford 2-((tert-butyl(methyl)amino)methyl)-6-fluorobenzaldehyde as a colorless solid (8.7 g, 33% yield). The mother liquor was concentrated and purified by flash chromatography eluting with 10 to 20% ethyl acetate (containing 20% of ethanol and 0.2% of ammonium hydroxide) in heptane, to provide additional 2-((tert-butyl(methyl)amino)methyl)-6-fluorobenzaldehyde as a colorless solid (4.5 g, 17% yield): $^1$H NMR (300 MHz, CDCl$_3$) δ 10.53 (s, 1H), 7.57-7.45 (m, 2H), 7.06-6.99 (m, 1H), 3.91 (s, 2H), 2.09 (s, 3H), 1.15 (s, 9H).

Step 2. Preparation of Thiazol-4-amine Hydrogen Chloride Salt

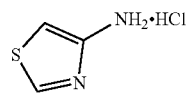

To a solution of tert-butyl thiazol-4-ylcarbamate (100 g, 0.50 mol) in dichloromethane (700 mL) was added 4.0 M hydrogen chloride in dioxane (550 mL). After stirring at ambient temperature for 18 h, the solid filtered off and washed with dichloromethane (5×100 ml) to give thiazol-4-amine hydrogen chloride as a colorless solid (64.6 g, 94% yield): $^1$H NMR (300 MHz, DMSO-d$_6$) δ 11.57-11.40 (m, 3H), 9.18 (d, J=2.2 Hz, 1H), 7.70 (d, J=2.2 Hz, 1H).

Step 3. Preparation of tert-butyl (5-fluoro-2-methyl-6-(N-(thiazol-4-yl)sulfamoyl)pyridin-3-yl)carbamate

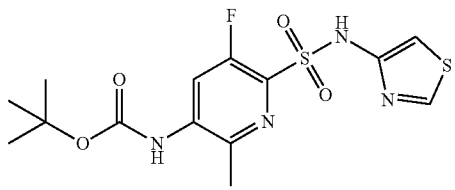 [SMILES: Cc1nc(S(=O)(=O)Nc2cscn2)c(F)cc1NC(=O)OC(C)(C)C]

To a solution of tert-butyl (6-(chlorosulfonyl)-5-fluoro-2-methylpyridin-3-yl)carbamate (28.0 g, 86.22 mmol) in anhydrous pyridine (180 mL) was added portionwise thiazol-4-amine hydrogen chloride salt (15.3 g, 112.0 mmol) over 30 minutes at ambient temperature. The reaction mixture was then stirred for 17 hours at ambient temperature. After concentration in vacuo, the residue was dissolved in N,N-dimethylformamide (100 mL) and added slowly to 10% ammonium chloride solution (1000 mL) with stirring. The solid was filtered off and washed with water (3×200 mL). The solid was then triturated in methanol (200 mL) to afford tert-butyl (5-fluoro-2-methyl-6-(N-(thiazol-4-yl)sulfamoyl)pyridin-3-yl)carbamate as a brown solid (21.1 g, 63% yield): $^1$H NMR (300 MHz, DMSO-d$_6$) δ 9.26 (s, 1H), 8.88 (d, J=2.1 Hz, 1H), 8.08 (d, J=12.3 Hz, 1H), 6.99 (d, J=2.1 Hz, 1H), 2.41 (d, J=0.6 Hz, 3H), 1.48 (s, 9H); NH not observed.

Step 4. Preparation of 5-amino-3-fluoro-6-methyl-N-(thiazol-4-yl)pyridine-2-sulfonamide hydrogen chloride salt

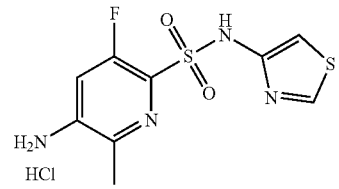 [SMILES: Cc1nc(S(=O)(=O)Nc2cscn2)c(F)cc1N ; Cl]

To tert-butyl (5-fluoro-2-methyl-6-(N-(thiazol-4-yl)sulfamoyl)pyridin-3-yl)carbamate (35.6 g, 91.65 mmol) was added 4.0 M hydrogen chloride in dioxane (230 mL) and the reaction mixture was stirred at ambient temperature for 18 hours. After concentration in vacuo, the residue was triturated in toluene (200 mL) to afford 5-amino-3-fluoro-6-methyl-N-(thiazol-4-yl)pyridine-2-sulfonamide hydrogen chloride salt as a brown solid (29.2 g, 98% yield): $^1$H NMR (300 MHz, DMSO-d$_6$) δ 11.02 (s br, 1H), 8.85 (d, J=2.1 Hz, 1H), 6.94 (s br, 3H), 6.87 (d, J=2.1 Hz, 1H), 6.78 (d, J=12.6 Hz, 1H), 2.20 (s, 3H).

Step 5. Preparation of 5-((2-((tert-butyl(methyl) amino)methyl)-6-fluorobenzyl)amino)-3-fluoro-6-methyl-N-(thiazol-4-yl)pyridine-2-sulfonamide

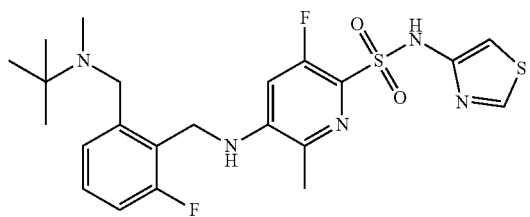 [SMILES: Cc1nc(S(=O)(=O)Nc2cscn2)c(F)cc1NCc1c(F)cccc1CN(C)C(C)(C)C]

To a suspension of 5-amino-3-fluoro-6-methyl-N-(thiazol-4-yl)pyridine-2-sulfonamide hydrogen chloride salt (29.0 g, 89.27 mmol) in anhydrous tetrahydrofuran (140 mL) was added 2-((tert-butyl(methyl)amino)methyl)-6-fluorobenzaldehyde (31.9 g, 142.86 mmol) and titanium(IV) isopropoxide (132 mL, 445.85 mmol). After stirring at ambient temperature for 18 h, sodium cyanoborohydride (1 M solution in tetrahydrofuran, 270 mL, 270 mmol,) was added to the reaction mixture over 30 minutes. The reaction mixture was stirred at ambient temperature for 5 h, and then quenched by addition of saturated sodium bicarbonate solution (100 mL). After stirring for 1 h, the mixture was filtered and the solid was washed with ethyl acetate (5×300 mL). The combined filtrate was washed with saturated ammonium chloride (200 mL), brine (100 mL), dried over anhydrous sodium sulfate, and filtered. The filtrate was concentrated in vacuo and the residue was dissolved in N,N-dimethylformamide (100 mL) and added slowly to water (2000 mL) with stirring. After filtration, the obtained solid and charcoal (~12 g) were heated in anhydrous ethanol (2200 mL) at reflux for 1 hour. The mixture was filtered and the residue washed with hot ethanol (200 mL). The combined filtrate was kept at ambient temperature for 20 h, and then filtered. The obtained solid was heated at reflux in anhydrous ethanol (450 mL) for 16 h, after which the mixture was allowed to cool to ambient temperature and filtered. The title compound was obtained as a colorless solid (11.0 g, 25% yield): m.p. 188-190 (ethanol); $^1$H NMR (300 MHz, DMSO-d$_6$) δ 11.09 (s, 1H), 8.86 (d, J=2.2 Hz, 1H), 7.32-7.11 (m, 4H), 6.89 (d, J=2.2 Hz, 1H), 6.47 (d, J=0.6 Hz, 1H), 4.47 (d, J=4.7 Hz, 2H), 3.64 (s, 2H), 2.22 (s, 3H), 1.99 (s, 3H), 1.07 (s, 9H); $^{13}$C NMR (151 MHz {$^1$H, $^{19}$F}, DMSO-d$_6$,) δ 161.4, 157.4, 153.1, 148.6, 147.8, 142.6, 139.5, 129.4, 127.7, 127.1, 124.0, 114.7, 103.3, 102.1, 55.0, 53.1, 37.7, 34.8, 26.1, 20.7; MS (ES+) m/z 496.1 (M+1); MS (ES−) m/z 494.2 (M−1).

Example 49

Synthesis of 5-((2-((tert-butyl(methyl)amino)methyl)-6-fluorobenzyl)amino)-6-cyclopropyl-3-fluoro-N-(thiazol-4-yl)pyridine-2-sulfonamide

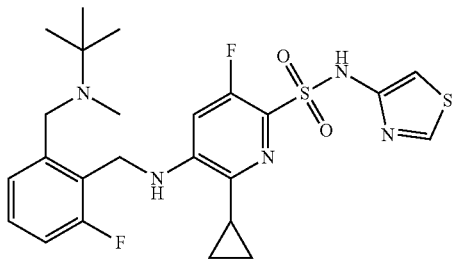 [SMILES: CN(Cc1cccc(F)c1CNc1cc(F)c(S(=O)(=O)Nc2cscn2)nc1C1CC1)C(C)(C)C]

Step 1. Preparation of tert-butyl (2,6-dichloro-5-fluoropyridin-3-yl)carbamate

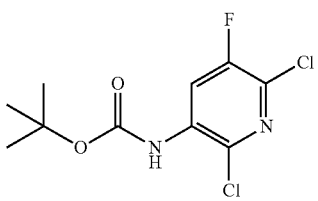 [SMILES: CC(C)(C)OC(=O)Nc1cc(F)c(Cl)nc1Cl]

To a solution of 2,6-dichloro-5-fluoronicotinic acid (78.0 g, 0.37 mol) in tert-butanol (300 mL) and toluene (200 mL) was added triethylamine (67.0 mL, 0.48 mol) and diphenylphosphoryl azide (88.0 mL, 0.40 mmol). The reaction mixture was heated at 50° C. for 16 hours. After cooling to ambient temperature, the reaction mixture was diluted with diethyl ether (800 mL), washed with 10% aqueous sodium carbonate solution (3×100 mL), and brine (100 mL). The organic phase was dried over anhydrous sodium sulfate and filtered. The filtrate was concentrated in vacuo and the residue was recrystallized from methanol (200 mL) to afford the title compound as colorless solid (71.0 g, 68% yield): $^1$H NMR (300 MHz, DMSO-d$_6$) δ 9.23 (s, 1H), 8.27 (d, J=9.6 Hz, 1H), 1.47 (s, 9H).

Step 2. Preparation of tert-butyl (6-chloro-2-cyclopropyl-5-fluoropyridin-3-yl)carbamate

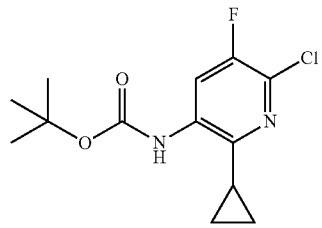 [SMILES: CC(C)(C)OC(=O)Nc1cc(F)c(Cl)nc1C1CC1]

A mixture of tert-butyl (2,6-dichloro-5-fluoropyridin-3-yl)carbamate (24.2 g, 0.086 mol), cyclopropylboronic acid (8.9 g, 0.104 mmol) and potassium phosphate tribasic (58.4 g, 0.26 mol) in toluene (400 mL) and water (40 mL) was purged with nitrogen for 10 minutes, after which dichloro [1,1'-bis(diphenylphosphino)-ferrocene]palladium(II) dichloromethane adduct (3.5 g, 4.2 mmol) was added. The reaction mixture was heated to 90° C. for 16 hours. After cooling to ambient temperature, water (150 mL) was added to the mixture. The organic layer was separated, and the aqueous layer was extracted with ethyl acetate (2×150 mL). The combined organic layers were washed with brine (100 mL), dried over anhydrous sodium sulfate, and filtered. The filtrate was concentrated in vacuo, and the residue was purified by column chromatography, eluting with a gradient of 5 to 10% of ethyl acetate in heptane, to afford the title compound as colorless solid (15.7 g, 63% yield): $^1$H NMR (300 MHz, CDCl$_3$) δ 8.24 (d, J=9.9 Hz, 1H), 6.84 (s, 1H), 1.87-1.74 (m, 1H), 1.53 (s, 9H), 1.05-0.86 (m, 4H); MS (ES+) m/z 287.1 (M+1), 289.1 (M+1).

Step 3. Preparation of tert-butyl (6-(benzylthio)-2-cyclopropyl-5-fluoropyridin-3-yl)carbamate

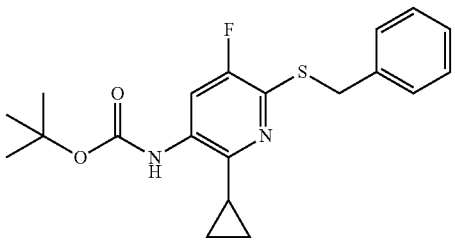 [SMILES: CC(C)(C)OC(=O)Nc1cc(F)c(SCc2ccccc2)nc1C1CC1]

To a solution of tert-butyl (6-chloro-2-cyclopropyl-5-fluoropyridin-3-yl)carbamate (15.7 g, 0.0547 mol) in anhydrous dioxane (100 mL) and N,N-diisopropylethylamine (19.1 mL, 0.109 mol) was added tris(dibenzylideneacetone) dipalladium(0) (2.5 g, 2.73 mmol), 4,5-bis(diphenylphosphino)-9,9-dimethylxanthene (3.16 g, 5.46 mmol) and benzyl mercaptan (6.2 mL, 0.052 mol). The reaction mixture was sparged with nitrogen for 10 minutes, and then heated to 110° C. for 50 hours in a sealed tube. After cooling to ambient temperature, the reaction mixture was diluted with ethyl acetate (400 mL), washed with saturated ammonium chloride (3×100 mL), and dried over anhydrous sodium sulfate. Filtration and concentration of the filtrate in vacuo provided a residue, which was purified by recrystallization from ethyl acetate and heptane to afford the title compound as pale yellow solid (14.6 g, 71% yield): $^1$H NMR (300

MHz, CDCl₃) δ 8.01-7.86 (m, 1H), 7.41-7.21 (m, 5H), 6.67 (s, 1H), 4.41 (s, 2H), 1.94-1.84 (m, 1H), 1.55 (s, 9H), 1.08-0.95 (m, 4H); MS (ES+) m/z 375.1 (M+1).

Step 4. Preparation of tert-butyl (6-(chlorosulfonyl)-2-cyclopropyl-5-fluoropyridin-3-yl)carbamate

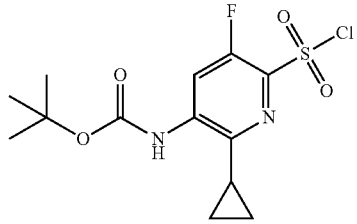 [SMILES: CC(C)(C)OC(=O)Nc1cc(F)c(S(=O)(=O)Cl)nc1C1CC1]

To a cooled solution of tert-butyl (6-(benzylthio)-2-cyclopropyl-5-fluoropyridin-3-yl)carbamate (14.6 g, 38.9 mmol) in acetonitrile (360 mL), acetic acid (100 mL), and water (100 mL) was added 1,3-dichloro-5,5-dimethylhydantoin (23.0 g, 67% purity, 78.2 mmol) in small portions at 0° C. over 20 minutes. After stirring at 0° C. for 30 minutes, the reaction mixture was concentrated in vacuo to remove acetonitrile while keeping the temperature below 30° C. The solid was filtered off, washed with water water (3×100 mL), and dried under vacuum to afford the title compound as colorless solid (11.7 g, 85%): ¹H NMR (300 MHz, CDCl₃) δ 8.50 (d, J=11.7 Hz, 1H), 7.24 (s, 1H), 1.90-1.81 (m, 1H), 1.56 (s, 9H), 1.16-1.10 (m, 4H).

Step 5. Preparation of tert-butyl (2-cyclopropyl-5-fluoro-6-(N-(thiazol-4-yl)sulfamoyl)pyridin-3-yl)carbamate

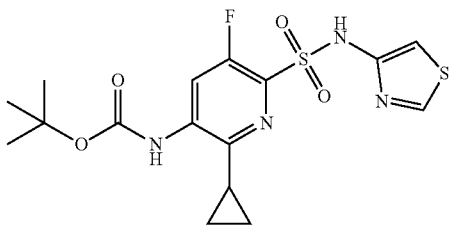 [SMILES: CC(C)(C)OC(=O)Nc1cc(F)c(S(=O)(=O)Nc2cscn2)nc1C1CC1]

To a solution of tert-butyl (6-(chlorosulfonyl)-2-cyclopropyl-5-fluoro-pyridin-3-yl)carbamate (11.7 g, 33.35 mmol) in anhydrous pyridine (100 mL) was added portionwise thiazol-4-amine hydrogen chloride salt (6.0 g, 43.52 mmol) over 30 minutes at ambient temperature. After addition, the reaction mixture was stirred for 6 h, and concentrated under vacuum to near dryness. The residue was dissolved in N,N-dimethylformamide (100 mL) and added slowly to 10% ammonium chloride solution (800 mL) with stirring. The solid was collected by filtration, washed with water (3×200 mL), and dried under vacuum to afford the title compound as a brown solid (11.6 g, 83% yield): ¹H NMR (300 MHz, DMSO-d₆) δ 11.4 (s, 1H), 9.52 (s, 1H), 8.91 (d, J=2.1 Hz, 1H), 8.03 (d, J=12.0 Hz, 1H), 6.90 (d, J=2.1 Hz, 1H), 2.35-2.25 (m, 1H), 1.48 (s, 9H), 0.86-0.79 (m, 2H), 0.67-0.61 (m, 2H).

Step 6. Preparation of 5-amino-6-cyclopropyl-3-fluoro-N-(thiazol-4-yl)pyridine-2-sulfonamide hydrogen chloride salt

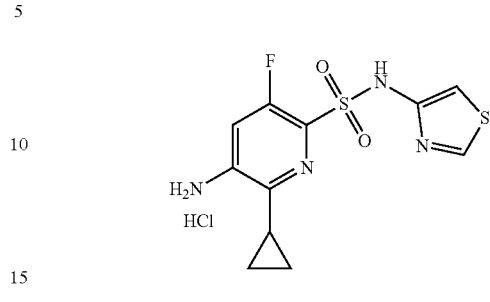

To tert-butyl (6-(chlorosulfonyl)-2-cyclopropyl-5-fluoropyridin-3-yl)carbamate (11.6 g, 27.98 mmol) was added 4.0 M hydrogen chloride in dioxane (80 mL) and the reaction mixture was stirred at ambient temperature for 18 hours. Concentration in vacuo and trituration of the residue in toluene (100 mL) afforded the title compound as a brown solid (9.8 g, 99% yield): ¹H NMR (300 MHz, DMSO-d₆) δ 11.1 (s, 1H), 10.01-8.98 (m, 3H), 7.29-7.10 (m, 1H), 6.81-6.74 (m, 2H), 3.55-1.94 (m, 1H), 0.96-55 (m, 4H).

Step 7. Preparation of 5-((2-((tert-butyl(methyl)amino)methyl)-6-fluorobenzyl)amino)-6-cyclopropyl-3-fluoro-N-(thiazol-4-yl)pyridine-2-sulfonamide

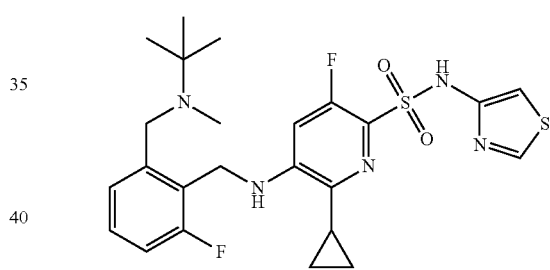

To a suspension of 5-amino-6-cyclopropyl-3-fluoro-N-(thiazol-4-yl)pyridine-2-sulfonamide hydrogen chloride salt (1.75 g, 4.98 mmol) in anhydrous tetrahydrofuran (20 mL) was added 2-((tert-butyl(methyl)amino)methyl)-6-fluorobenzaldehyde (1.87 g, 8.01 mmol) and titanium(IV) isopropoxide (8.0 mL, 27.3 mmol). After stirring at ambient temperature for 20 h, sodium cyanoborohydride (1 M solution in tetrahydrofuran, 16 mL, 16.0 mmol) was added over 30 minutes. The reaction mixture was stirred for 5 h, and then quenched by addition of saturated sodium bicarbonate solution (10 mL). After stirring for 1 h, the mixture was filtered and the solid was washed with ethyl acetate (5×50 mL). The combined filtrate was concentrated in vacuo. The residue was then dissolved in N,N-dimethylformamide (30 mL) and added slowly to saturated saturated ammonium chloride (200 mL) under stirring. The obtained solid was collected by filtration. The solid was heated at reflux in anhydrous ethanol (200 mL) with charcoal (3.0 g) for 3 h, followed by filtration. The residue was washed with hot ethanol (100 mL) and the combined filtrate was kept at ambient temperature for 20 hours. After filtration, the title compound was obtained as a colorless solid (0.86 g, 33% yield): ¹H NMR (300 MHz, DMSO-d₆) δ 11.10 (s br, 1H), 8.87 (d, J=2.1 Hz, 1H), 7.36-7.08 (m, 4H), 6.81-6.72 (m, 2H), 4.45 (d, J=6.0 Hz, 2H), 3.64 (s, 2H), 2.01-1.88 (m, 4H), 1.05 (s, 9H), 0.77-0.70 (m, 2H), 0.66-0.61 (m, 2H); MS (ES+) m/z 522.2 (M+1).

BIOLOGICAL ASSAYS

Various techniques are known in the art for testing the activity of the compound of the invention or determining their solubility in known pharmaceutically acceptable excipients. In order that the invention described herein may be more fully understood, the following biological assays are set forth. It should be understood that these examples are for illustrative purposes only and are not to be construed as limiting this invention in any manner.

Biological Example 1

Electrophysiological Assay (In Vitro Assay)

Patch voltage clamp electrophysiology allows for the direct measurement and quantification of block of voltage-gated sodium channels ($Na_v$'s), and allows the determination of the time- and voltage-dependence of block which has been interpreted as differential binding to the resting, open, and inactivated states of the sodium channel (Hille, B., *Journal of General Physiology* (1977), 69: 497-515).

The following patch voltage clamp electrophysiology studies were performed on representative compounds of the invention using human embryonic kidney cells (HEK), permanently transfected with an expression vector containing the full-length cDNA coding for the desired human sodium channel a-subunit, grown in culture media containing 10% FBS, 1% PSG, and 0.5 mg/mL G418 at 37° C. with 5% $CO_2$. HEK cells used for the electrophysiology (EP) recordings had a passage number of less than 40 for all studies and were used within three days from the time of plating. $Na_v1.1$, $Na_v1.5$ and $Na_v1.6$ cDNAs (NM_001165964 (SCN1A), NM_000335 (SCN5A) and NM_014191 (SCN8A), respectively) were stably expressed in HEK-293 cells.

Sodium currents were measured using the patch clamp technique in the whole-cell configuration using either a PatchXpress automated voltage clamp or manually using an Axopatch 200B (Axon Instruments) or Model 2400 (A-M systems) amplifier. The manual voltage clamp protocol was as follows: Borosilicate glass micropipettes were fire-polished to a tip diameter yielding a resistance of 2-4 Mohms in the working solutions. The pipette was filled with a solution comprised of: 5 mM NaCl, 10 mM CsCl, 120 mM CsF, 0.1 mM $CaCl_2$, 2 mM $MgCl_2$, 10 mM HEPES, 10 mM EGTA; and adjusted to pH 7.2 with CsOH. The external solution had the following composition: 140 mM NaCl, 5 mM KCl, 2 mM $CaCl_2$, 1 mM $MgCl_2$, 10 mM HEPES; and adjusted to pH 7.4 with NaOH. In some studies, the external sodium was reduced by equimolar replacement with choline. Osmolarity in the CsF internal and NaCl external solutions was adjusted to 300 mOsm/kg and 310 mOsm/kg with glucose, respectively. All recordings were performed at ambient temperature in a bath chamber with a volume of 150 µL. Control sodium currents were measured in 0.5% DMSO. Controls and representative compounds of the invention were applied to the recording chamber through a 4-pinch or 8-pinch valve bath perfusion system manufactured by ALA Scientific Instruments.

Currents were recorded at 40 kHz sampling frequency, filtered at 5 Hz, and stored using a Digidata-1322A analogue/digital interface with the pClamp software (Axon Instruments). Series resistance compensation was applied (60-80%). Cells were rejected if currents showed inadequate voltage control (as judged by the IV relationship during stepwise activation). All statistics in this study are given as mean±SD.

The membrane potential was maintained at a voltage where inactivation of the channel is complete. The voltage is then stepped back to a very negative (Vhold=−150 mV) voltage for 20 ms and then a test pulse is applied to quantify the compound block. The 20 ms brief repolarization was long enough for compound-free channels to completely recover from fast inactivation, but the compound-bound channels recovered more slowly such that negligible recovery could occur during this interval. The percent decrease in sodium current following wash-on of compound was taken as the percent block of sodium channels.

Representative compounds of the invention, when tested in this assay, demonstrated the $IC_{50}$'s as set forth below in Table 1 following Biological Example 2.

Biological Example 2

Sodium Influx Assay (In Vitro Assay)

This sodium influx assay employs the use of the cell permeable, sodium sensitive dye ANG2 to quantify sodium ion influx through sodium channels which are maintained in an open state by use of sodium channel modulators. This high throughput sodium influx assay allows for rapid profiling and characterization of sodium channel blockers.

In general, Trex HEK293 cells were stably transfected with an inducible expression vector containing the full-length cDNA coding for the desired human sodium channel α-subunit and with an expression vector containing full length cDNA coding for the β1-subunit. Sodium channel expressing cell lines were induced with tetracycline (1 µg/mL) and plated on 384-well PDL-coated plates at a density of 25K-30K cells/well in culture media (DMEM, containing 10% FBS and 1% L-glutamine). After overnight incubation (37° C., 5% $CO_2$), culture media was removed and cells were loaded with 5 uM ANG2 dye for 1-1.5h in Buffer 1 (155 mM NMDG, 5 mM KCl, 2 mM $CaCl_2$, 1 mM $MgCl_2$, 10 mM HEPES, 10 mM glucose, adjusted with Tris to pH 7.4). Access dye was removed and cells were incubated with test compounds for 1 hr in buffer 1 containing sodium channel modulator(s) at room temperature. Hamamatsu FDSS µCell was used to perform a 1:1 addition of Na/K challenge buffer (140 mM NaCl, 20 mM HEPES, 1 mM $CaC_2$, 15 mM KCl, 1 mM $MgCl_2$, 10 mM glucose, adjusted with Tris to pH 7.4) and simultaneously read plates at excitation wavelength of 530 nm and emission wavelength set at 558 nm. Percent inhibition of sodium ion influx was calculated for each test compound at each test concentration to determine the $IC_{50}$ values.

Representative compounds of the invention, when tested in this assay, demonstrated affinities for the inactivated state of $Na_v1.6$, $Na_v1.5$ and $Na_v1.1$ as set forth below in Table 1.

The Example numbers provided in Table 1 correspond to the Examples herein, "Flux" refers to the Sodium Influx Assay and "EP" refers to the Electrophysiological Assay.

TABLE 1

Inhibition of Nav1.1, Nav1.5, and $Na_V1.6$

| Ex. No. | Flux $Na_V1.6$ $IC_{50}$ (μM) | Flux $Na_V1.5$ $IC_{50}$ (μM) | Flux $Na_V1.1$ $IC_{50}$ (μM) | EP $Na_V1.6$ $IC_{50}$ (μM) |
|---|---|---|---|---|
| 1 | 2.820 | 5.573 | 5.003 | |
| 2 | 13.207 | 20.432 | 25.780 | |
| 3 | 4.743 | 30.000 | 30.000 | |
| 4 | 0.111 | 28.207 | 28.751 | 0.026 |
| 5 | 8.472 | 26.530 | 30.000 | |
| 6 | 0.398 | 30.000 | 30.000 | 0.069 |
| 7 | 5.821 | 30.000 | 30.000 | |
| 8 | 0.719 | 30.000 | 30.000 | |
| 9 | 0.917 | 21.134 | 30.000 | |
| 10 | 5.311 | 7.757 | 23.605 | |
| 11 | 8.367 | 8.865 | 11.742 | |
| 12 | 3.427 | 30.000 | 30.000 | |
| 13 | 11.325 | 6.019 | 14.879 | |
| 14 | 0.382 | 24.521 | 13.005 | |
| 15 | 0.286 | 21.605 | 30.000 | |
| 16 | 1.271 | 30.000 | 30.000 | |
| 17 | 1.460 | 30.000 | 30.000 | |
| 18 | 0.015 | 21.378 | 15.458 | |
| 19 | 0.221 | 30.000 | 30.000 | 0.038 |
| 20 | 0.067 | 25.020 | 30.000 | 0.023 |
| 21 | 0.102 | 30.000 | 30.000 | 0.043 |
| 22 | 0.221 | 30.000 | 30.000 | |
| 23 | 9.543 | 30.000 | 7.676 | |
| 24 | 0.074 | 30.000 | 30.000 | |
| 25 | 0.154 | 30.000 | 30.000 | |
| 26 | 0.242 | 30.000 | 30.000 | |
| 27 | 0.296 | 30.000 | 30.000 | |
| 28 | 0.782 | 30.000 | 30.000 | |
| 29 | 0.082 | 30.000 | 30.000 | 0.039 |
| 30 | 0.111 | 30.000 | 30.000 | |
| 31 | 1.499 | 30.000 | 30.000 | |
| 32 | 0.272 | 30.000 | 16.735 | |
| 33 | 0.037 | 30.000 | 11.803 | |
| 34 | 0.037 | 30.000 | 30.000 | |
| 35 | 0.024 | 30.000 | 10.486 | |
| 36 | 0.863 | 30.000 | 0.245 | |
| 37 | 5.922 | 30.000 | 8.696 | |
| 38 | 3.143 | 28.785 | 30.000 | |
| 39 | 2.683 | 6.176 | 8.162 | |
| 40 | 2.231 | 3.267 | 5.541 | |
| 41 | 0.056 | 30.000 | 11.085 | |
| 42 | 4.468 | 9.114 | 6.289 | |
| 43 | 2.108 | 10.292 | 8.205 | |
| 44 | 0.171 | 8.846 | 20.157 | |
| 45 | 1.925 | 30.000 | 30.000 | |
| 46 | 1.781 | 30.000 | 30.000 | |
| 47 | 0.021 | 30.000 | 13.566 | |
| 48 | 0.084 | 30.000 | 30.000 | 0.017 |
| 49 | 0.078 | 7.500 | 3.751 | |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

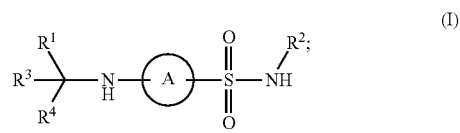

as an individual stereoisomer, enantiomer, or tautomer thereof, or a mixture thereof; or a pharmaceutically acceptable salt or solvate thereof, wherein:

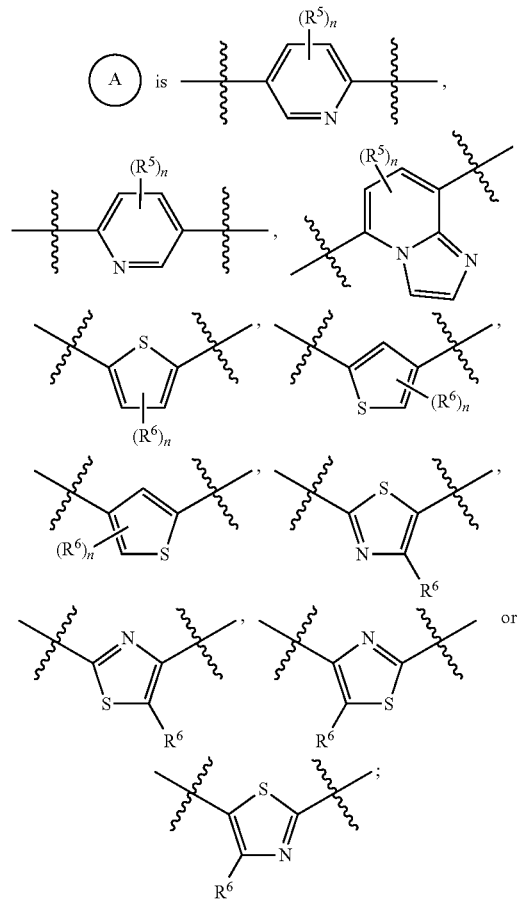

each n is 1 or 2;

$R^1$ is an optionally substituted aryl, an optionally substituted monocyclic heteroaryl or an optionally substituted bicyclic heteroaryl;

$R^2$ is an optionally substituted 5-membered N-heteroaryl or an optionally substituted 6-membered N-heteroaryl;

$R^3$ and $R^4$ are each independently hydrogen or alkyl;

each $R^5$ is independently alkyl, halo, haloalkyl, optionally substituted cycloalkyl, cyano or —$OR^7$;

each $R^6$ is independently hydrogen, alkyl, halo, haloalkyl, optionally substituted cycloalkyl, cyano or —$OR^7$; and $R^7$ is hydrogen, alkyl or haloalkyl.

2. The compound of claim 1, as an individual stereoisomer, enantiomer, or tautomer thereof, or a mixture thereof; or a pharmaceutically acceptable salt or solvate thereof, wherein:
R¹ is aryl optionally substituted by one or more substituents selected from alkyl, halo, haloalkyl, —R⁸—N(R⁹)R¹⁰ and optionally substituted N-heterocyclylalkyl;
R³ and R⁴ are each hydrogen or alkyl;
R⁸ is a direct bond or an optionally substituted straight or branched alkylene chain; and
R⁹ and R¹⁰ are each independently hydrogen, alkyl, haloalkyl, optionally substituted cycloalkyl, optionally substituted cycloalkylalkyl, optionally substituted heterocyclyl, or optionally substituted heterocyclylalkyl.

3. The compound of claim 2, as an individual stereoisomer, enantiomer, or tautomer thereof; or a mixture thereof; or a pharmaceutically acceptable salt or solvate thereof, wherein:
R¹ is phenyl optionally substituted by one or more substituents selected from halo, —R⁸—N(R⁹)R¹⁰ and optionally substituted N-heterocyclylalkyl;
R³ and R⁴ are each hydrogen or alkyl;
R⁸ is an optionally substituted straight or branched alkylene chain;
R⁹ is hydrogen or alkyl; and
R¹⁰ is hydrogen or alkyl.

4. The compound of claim 3, as an individual stereoisomer, enantiomer or tautomer thereof or a mixture thereof: or a pharmaceutically acceptable salt or solvate thereof, wherein the compound has the following formula (Ia):

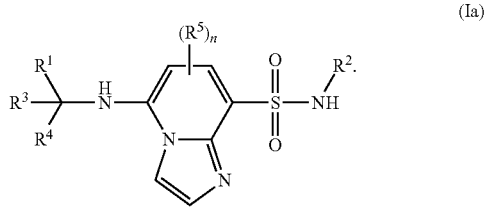

(Ia)

5. A compound, which is 5-((3,6-difluoro-2-(pyrrolidin-1-ylmethyl)benzyl)amino)-N-(thiazol-4-yl)imidazo[1,2-α]pyridine-8-sulfonamide; as an individual stereoisomer, enantiomer or tautomer thereof or a mixture thereof; or a pharmaceutically acceptable salt or solvate thereof.

6. The compound of claim 3, as an individual stereoisomer, enantiomer, or tautomer thereof, or a mixture thereof; or a pharmaceutically acceptable salt or solvate thereof, wherein the compound has the following formula (Ib):

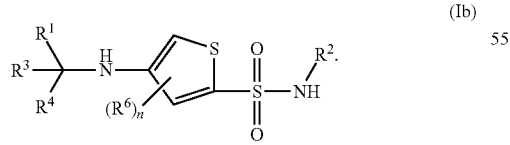

(Ib)

7. The compound of claim 6, which is 4-((2-bromo-6-fluorobenzyl)amino)-N-(6-fluoropyridin-2-yl)-5-methylthiophene-2-sulfonamide; as an individual stereoisomer, enantiomer or tautomer thereof or a mixture thereof; or a pharmaceutically acceptable salt or solvate thereof.

8. The compound of claim 3, as an individual stereoisomer, enantiomer, or tautomer thereof, or a mixture thereof; or a pharmaceutically acceptable salt or solvate thereof, wherein the compound has the following formula (Ic):

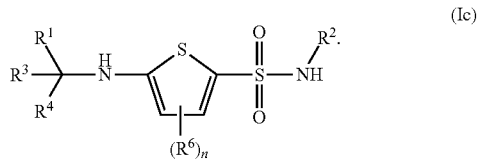

(Ic)

9. The compound of claim 8, which is 5-((2-fluoro-6-(pyrrolidin-1-ylmethyl)benzyl)amino)-N-(6-fluoropyridin-2-yl)-4-methylthiophene-2-sulfonamide; as an individual stereoisomer, enantiomer or tautomer thereof or a mixture thereof; or a pharmaceutically acceptable salt or solvate thereof.

10. The compound of claim 3, as an individual stereoisomer, enantiomer, or tautomer thereof, or a mixture thereof; or a pharmaceutically acceptable salt or solvate thereof, wherein the compound has the following formula (Id):

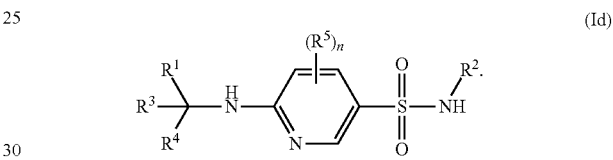

(Id)

11. The compound of claim 10, as an individual stereoisomer, enantiomer, or tautomer thereof, or a mixture thereof; or a pharmaceutically acceptable salt or solvate thereof, wherein R² is an optionally substituted 5-membered N-heteroaryl.

12. The compound of claim 11, as an individual stereoisomer, enantiomer, or tautomer thereof; or a mixture thereof; or a pharmaceutically acceptable salt or solvate thereof, wherein the compound has the following structure (Id1):

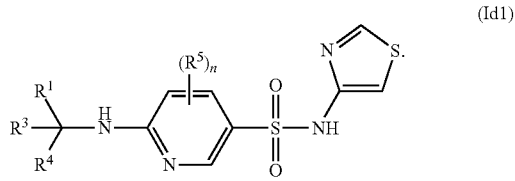

(Id1)

13. The compound of claim 12, selected from:
(S)-5-chloro-((1-(5-chloro-2-fluorophenyl)ethyl)amino)-N-(thiazol-4-yl)pyridine-3-sulfonamide;
(S)-5-chloro-6-((1-(2-fluorophenyl)ethyl)amino)-N-(thiazol-4yl)pyridine-3-sulfonamide;
6((2-((tert-(butyl(methyl)amino)methyl)-6-fluorobenzyl)amino)-2-methyl-N-(thiazol-4-yl)pyridine-3-sulfonamide;
6-((2-((tert-butyl(methyl)amino)methyl)-6-fluorobenzyl)amino)-5-methyl-N-(thiazol-4-yl)pyridine-3-sulfonamide;
6((2-((tert-butyl(methyl)amino)methyl)-6-fluorobenzyl(amino)-5-chloro-N-(thiazol-4-yl)pyridine-3-sulfonamide; and
6((2-fluoro-6-(pyrrolidin-1-ylmethyl)benzyl)amino)-2-methyl-N(thiazol-4-yl)pyridine-3-sulfonamide;

as an individual stereoisomer, enantiomer or tautomer thereof or a mixture thereof;
or a pharmaceutically acceptable salt or solvate thereof.

14. The compound of claim 10, as an individual stereoisomer, enantiomer, or tautomer thereof, or a mixture thereof; or a pharmaceutically acceptable salt or solvate thereof, wherein $R^2$ is an optionally substituted 6-membered N-heteroaryl.

15. The compound of claim 14, as an individual stereoisomer, enantiomer, or tautomer thereof, or a mixture thereof, or a pharmaceutically acceptable salt or solvate thereof, wherein the compound has the following structure (Id2):

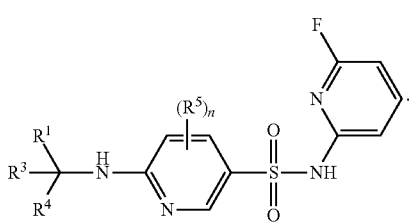

16. The compound of claim 15, selected from:
6((2-fluoro-6-(pyrrolidin-1-ylmethyl)benzyl)amino)-N-(6-fluoropyridin-2-yl)-2-methylpyridine-3-sulfonamide; and
5-chloro-6-((2-fluoro-6-(pyrrolidin-1-ylmethyl)benzyl)amino)-N-(6-fluoropyridin-2-yl)pyridine-3-sulfonamide;
as an individual stereoisomer, enantiomer or tautomer thereof or a mixture thereof;
or a pharmaceutically a acceptable salt or solvate thereof.

17. The compound of claim 3, as an individual stereoisomer, enantiomer, or tautomer thereof, or a mixture thereof; or a pharmaceutically acceptable salt or solvate thereof, wherein the compound has the following formula (Ie):

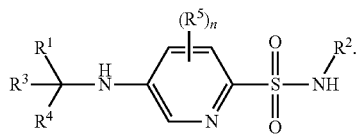

18. The compound of claim 17, as an individual stereoisomer, enantiomer, or tautomer thereof, or a mixture thereof; or a pharmaceutically acceptable salt or solvate thereof, wherein $R^2$ is an optionally substituted 5-membered N-heteroaryl.

19. The compound of claim 18, as an individual stereoisomer, enantiomer, or tautomer thereof, or a mixture thereof; or a pharmaceutically acceptable salt or solvate thereof, wherein the compound has the following structure (Ie1):

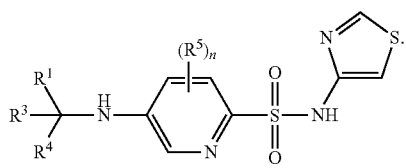

20. The compound of claim 19, selected from:
(S)-5((1-(2-fluorophenyl)ethyl)amino)-6-methyl-N-(thiazol-4-yl)pyridine-2-sulfonamide;

5-((2-(azetidin-1-ylmethyl)-6-fluorobenzyl)amino)-6-methyl-N-(thiazol-4-yl)pyridine-2-sulfonamide;
5((2-(azetidin-1-ylmethyl)-6-fluorobenzyl)amino)-4-methyl-N-(thiazol-4-yl)pyridine-2-sulfonamide;
5-((2-(((tert-butyl(methyl)amino)methyl)-6-fluorobenzyl)amino)-6-methyl-N-(thiazol-4-yl)pyridine-2-sulfonamide;
5-((2-((2,2-dimethylazetidin-1-yl)methyl)-6-fluorobenzyl)amino)-6-methyl-N-(thiazol-4-yl)pyridine-2-sulfonamide;
5-((2-fluoro-6-((isopropyl(methyl)amino)methyl)benzyl)amino-6-methyl-N-(thiazol-4-yl)pyridine-2-sulfonamide;
5-((2-(azetidin-1-ylmethyl)-3-fluorobenzyl)amino)-6-methyl-N-(thiazol-4-yl)pyridine-2-sulfonamide;
4-(difluoromethyl)-5-((2-fluoro-6-(pyrrolidin-1-ylmethyl)benzyl)amino)-N-(thiazol-4-yl)pyridine-2-sulfonamide;
6-(difluoromethyl)-5((2-fluoro-6-(pyrrolidin-1-ylmethyl)benzyl)amino)-N-(thiazol-4-yl)pyridine-2-sulfonamide;
5-((fluoro-6-(3-methylazetidin-1-yl)methyl)benzyl)amino)-6-methyl-N-(thiazol-4--yl)pyridine-2-sulfonamide;
5-((2-(tert-butyl(methyl)amino)methyl)benzyl)amino)-6-methyl-N-(thiazol-4-yl)pyridine-2-sulfonamide;
5-((2-(azetidin-1-ylmethyl)benzyl)amino)-6-methyl-N-(thiazol-4-yl)pyridine-2-sulfonamide;
5((2-fluoro-6-(pyrrolidi 1-ylmethyl)benzyl)amino)-6-methyl-N-(thiazol-4-yl)pyridine-2-sulfonamide;
5-((2-(((cyclopropylmethyl)(methyl)amino)methyl)-6-fluorobenzyl)amino)-6-methyl-N-(thiazol-4-yl)pyridine-2-sulfonamide;
5-((2-fluoro-6-((3-fluoro-3-methylazetidin-1-yl)methyl)benzyl)amino)-6-methyl-N-(thiazol-4-yl)pyridine-2-sulfonamide;
5((2-(tert-butyl(methyl)amino)methyl)-3,6-difluorobenzyl)amino)-6-methyl-N-(thiazol-4-yl)pyridine-2-sulfonamide;
5((2-(azetidin-1-ylmethyl)-6-fluorobenzyl)amino)-N-(thiazol-4yl)-4-(trifluoromethyl)pyridine-2-sulfonamide;
5((2-(((1s,4s)-7-azabicyclo[2.2.1]heptan-7-yl)methyl)-6-fluorobenzyl))amino)-6-methyl-N-(thiazol-4-yl)pyridine-2-sulfonamide;
5-((2-(((1s,4s)-7-azabicyclo[2.2.1]heptan-7-ylmethyl)-6-fluorobenzyl)amino)-3-fluoro-6-methyl-N-(thiazol-4-yl)pyridine-2-sulfonamide;
3-fluoro-5((2-fluoro-6-((isopropyl(methyl)amino)methy)benzyl)amino)-6-methyl-N-(thiazol-4-yl)pyridine-2-sulfonamide;
5-((2-(((tert-butyl(methyl)amino)methyl)-6-fluorobenzyl)amino)-3-fluoro-6-methyl-N-(thiazol-4-yl)pyridine-2-sulfonamide;
5((2-bromo-3,6-difluorobenzyl)amino)-3-fluoro-6-methyl-N-(thiazol-4-yl)pyridine-2-sulfonamide;
5-((2-((7-azabicyclo[2.2.1]heptan-7-yl)methyl)-3-(trifluoromethyl)benzyl)amino)-3-fluoro-6-methyl-N-(thiazol-4-yl)pyridine-2-sulfonamide;
5((2-((7-azabicyclo[2.2.1]heptan-7-yl)methyl)-6-fluorobenzyl)amino)-N-(thiazol-14-yl)-6-(trifluoromethyl)pyridine-2-sulfonamide;
5-((2-((tert-butyl(methyl)amino)methyl)benzyl)amino)-3-fluoro-6-methyl-N-(thiazol-4-yl)pyridine-2-sulfonamide; and 5-((2-(((tert-butyl(methyl)amino)methyl)-6-fluorobenzyl)
amino)-6-cyclopropyl-3-fluoro-N-(thiazol-4-yl)pyri-
dine-2-sulfonamide;

as an individual stereoisomer, enantiomer or tautomer
thereof or a mixture thereof;

or a pharmaceutically acceptable salt or solvate thereof.

21. The compound of claim 18, as an individual stereoisomer, enantiomer, or tautomer thereof, or a mixture thereof; or a pharmaceutically acceptable salt or solvate thereof, wherein the compound has the following structure (Ie2):

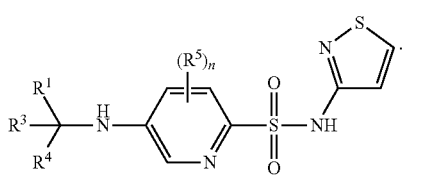

(Ie2)

22. The compound of claim 21, selected from:

5-((2-(azetidin-1-ylmethyl)-6-fluorobenzyl)amino)-N-(isothiazol-3-yl)-4-methylpyridine-2-sulfonamide;

5((2-(azetidin-1-ylmethyl)-6-fluorobenzyl)amino)-N-(isothiazol-3-yl)-6-methyl pyridine-2-sulfonamide; and 5-((2-(((tert-butyl(methy)amino)methyl)-6-fluorobenzyl) amino)-N-(isothiazol-3-yl)-6-methylpyridine-2-sulfonamide;

as an individual stereoisomer, enantiomer or tautomer thereof or a mixture thereof;

or a pharmaceutically acceptable salt or solvate thereof.

23. The compound of claim 18, as an individual stereoisomer, enantiomer, or tautomer thereof, or a mixture thereof; or a pharmaceutically acceptable salt or solvate thereof, wherein the compound has the following structure (Ie3):

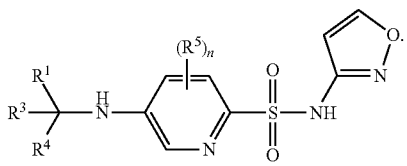

(Ie3)

24. The compound of claim 23, which is 5-((2-(((tert-butyl (methyl)amino)methyl)benzyl)amino)-3-fluoro-N-(isoxazol-3-yl)-6-methylpyridine-2-sulfonamide; as an individual stereoisomer, enantiomer or tautomer thereof or a mixture thereof, or a pharmaceutically acceptable salt solvate thereof.

25. The compound of claim 17, as an individual stereoisomer, enantiomer, or tautomer thereof, or a mixture thereof, or a pharmaceutically acceptable salt or solvate thereof, wherein $R^2$ is an optionally substituted 6-membered N-heteroaryl.

26. The compound of claim 25, as an individual stereoisomer, enantiomer, or tautomer thereof, or a mixture thereof, or a pharmaceutically acceptable salt or solvate thereof, wherein the compound has the following structure (Ie4):

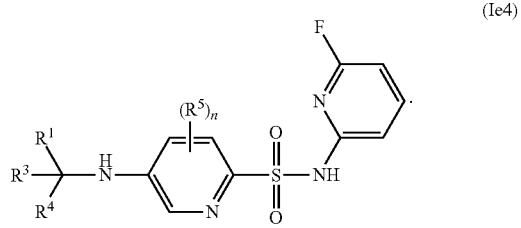

(Ie4)

27. The compound of claim 24, selected from:

5((2-(azetidin-1-ylmethyl)-6-fluorobenzyl)amino)-N-(6-fluoropyridin-2-yl)-4-methylpyridine-2-sulfonamide;

5((2-fluoro-6-(pyrrolidin-1-ylmethyl)benzyl)amino)-N-(6-fluoropyridin-2-yl)-4-methylpyridine 2-sulfonamide;

5-((2-fluoro-6-(pyrrolidin-1-ylmethyl)benzyl)amino)-N-(6-fluoropyridin-2-yl)-6-methylpyridine-2-sulfonamide;

5((2-(((tert-butyl(methyl)amino)methyl)-6-fluorobenzyl) amino)-N-(6-(fluoropyridin-2-yl)-6-methylpyridine-2-sulfonamide;

5((2-(((tert-butyl(methyl)amino)methyl)benzyl)amino)-3-fluoro-N-(6-fluoropyridin-2-yl)-6-methylpyridine-2-sulfonamide; and 3-fluoro-5-((2-fluoro-6-((isopropyl(methyl)amino) methyl)benzyl)amino)-N-(6-fluoropyridin-2-yl)-4-methylpyridine-2-sulfonamide;

as an individual stereoisomer, enantiomer or tautomer thereof or a mixture thereof;

or a pharmaceutically acceptable salt or solvate thereof.

28. The compound of claim 1, as an individual stereoisomer, enantiomer, or tautomer thereof, or a mixture thereof; or a pharmaceutically acceptable salt or solvate thereof, wherein:

$R^1$ is a bicyclic heteroaryl optionally substituted by one or more substituents selected from alkyl, halo, haloalkyl, $—R^8—N(R^9)R^{10}$ and optionally substituted N-heterocyclylalkyl;

$R^3$ and $R^4$ are each hydrogen or alkyl;

$R^8$ is a direct bond or an optionally substituted straight or branched alkylene chain; and $R^9$ and $R^{10}$) are each independently hydrogen, alkyl, haloalkyl, optionally substituted cycloalkyl, optionally substituted cycloalkylalkyl, optionally substituted heterocyclyl, or optionally substituted heterocyclylalkyl.

29. The compound of claim 2, as an individual stereoisomer, enantiomer, or tautomer thereof, or a mixture thereof; or a pharmaceutically acceptable salt or solvate thereof wherein:

$R^1$ is isoquinolinyl optionally substituted by one or more substituents selected from halo, $—R^8—N(R^9)R^{10}$ and optionally substituted N-heterocyclylalkyl;

$R^3$ and $R^4$ are each hydrogen or alkyl;

$R^8$ is an optionally substituted straight or branched alkylene chain;

$R^9$ is hydrogen or alkyl; and $R^{10}$ is hydrogen or alkyl.

30. The compound of claim 29, as an individual stereoisomer, enantiomer, or tautomer thereof, or a mixture thereof; or a pharmaceutically acceptable salt or solvate thereof, wherein the compound has the following formula (Ie):

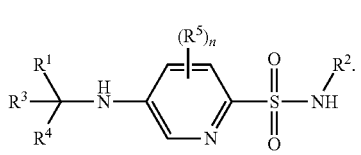

(Ie)

31. The compound of claim 30, as an individual stereoisomer, enantiomer, or tautomer thereof, or a mixture thereof; or a pharmaceutically acceptable salt or solvate thereof, wherein $R^2$ is an optionally substituted 5-membered N-heteroaryl.

32. The compound of claim 31, as an individual stereoisomer, enantiomer, or tautomer thereof, or a mixture thereof; or a pharmaceutically acceptable salt or solvate thereof, wherein the compound has the following structure (Ie1):

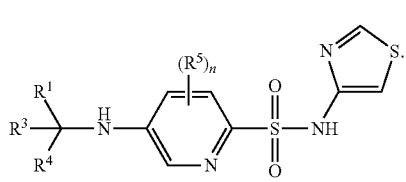

(Ie1)

33. The compound of claim 32, which is 5-(isoquinolin-8-ylmethyl)amino)-6-methyl-N-(thiazol-4-yl)pyridine-2-sulfonamide; as an individual stereoisomer, enantiomer or tautomer thereof or a mixture thereof; or a pharmaceutically acceptable salt or solvate thereof.

34. A pharmaceutical composition comprising a pharmaceutically acceptable excipient and a compound of claim 1, as a stereoisomer, enantiomer or tautomer thereof or a mixture thereof; or a pharmaceutically acceptable salt or solvate thereof.

35. A method of treating a disease or a condition associated with $Na_v1.6$ activity in a mammal wherein the disease or condition is epilepsy or epileptic seizure disorder, and wherein the method comprises administering to the mammal in need thereof a therapeutically effective amount of a compound of claim 1, as a stereoisomer, enantiomer or tautomer thereof or a mixture thereof; or a pharmaceutically acceptable salt or solvate thereof.

36. A method of decreasing ion flux through $Na_v1.6$ in a mammalian cell, wherein the method comprises contacting the cell with a compound of claim 1, as a stereoisomer, enantiomer or tautomer thereof or a mixture thereof; or a pharmaceutically acceptable salt or solvate thereof.

37. A method of selectively inhibiting a first voltage-gated sodium channel over a second voltage-gated sodium channel in a mammal, wherein the method comprises administering to the mammal a modulating amount of a compound of claim 1, as a stereoisomer, enantiomer or tautomer thereof or a mixture thereof; or a pharmaceutically acceptable salt or solvate thereof.

38. The method of claim 37 wherein the first voltage-gated sodium channel is $Na_v1.6$.

39. The method of claim 37 wherein the second voltage-gated sodium channel is $Na_v1.5$.

40. The method of claim 37 wherein the second voltage-gated sodium channel is $Na_v1.1$.

41. A compound, which is 6-((2-(azetidin-1-ylmethyl)-6-fluorobenzyl)amino)-N-(thiazol-4-yl)pyridine-3-sulfonamide, represented by the formula:

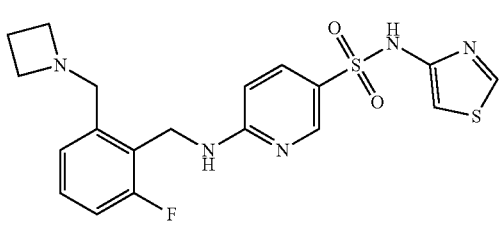 [SMILES: O=S(=O)(Nc1cscn1)c1ccc(NCc2c(F)cccc2CN2CCC2)nc1]

as an individual stereoisomer, enantiomer or tautomer thereof or a mixture thereof; or a pharmaceutically acceptable salt or solvate thereof.

42. A compound, which is 6-((2-(azetidin-1-ylmethyl)-6-fluorobenzyl)amino)-N-(thiazol-4-yl)pyridine-3-sulfonamide, represented by the formula:

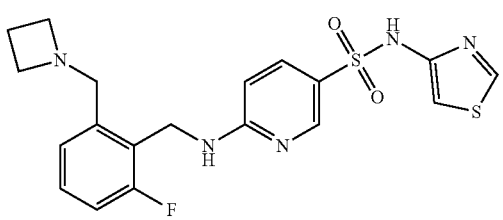 [SMILES: O=S(=O)(Nc1cscn1)c1ccc(NCc2c(F)cccc2CN2CCC2)nc1]

or a pharmaceutically acceptable salt thereof.

43. The compound of claim 1, which is 5-((2-((tert-butyl (methyl)amino)methyl)-6-fluorobenzyl)amino)-N-(6-fluoropyridin-2-yl)-6-methylpyridine-2-sulfonamide, represented by the formula:

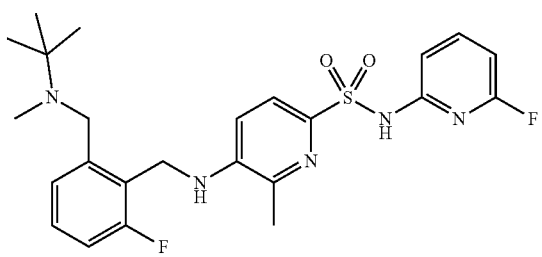 [SMILES: Cc1nc(S(=O)(=O)Nc2cccc(F)n2)ccc1NCc1c(F)cccc1CN(C)C(C)(C)C]

as an individual stereoisomer, enantiomer or tautomer thereof or a mixture thereof; or a pharmaceutically acceptable salt or solvate thereof.

44. The compound of claim 1, which is 5-((2-((tert-butyl (methyl)amino)methyl)-6-fluorobenzyl)amino)-N-(6-fluoropyridin-2-yl)-6-methyl pyri dine-2-sulfonamide, represented by, the formula:

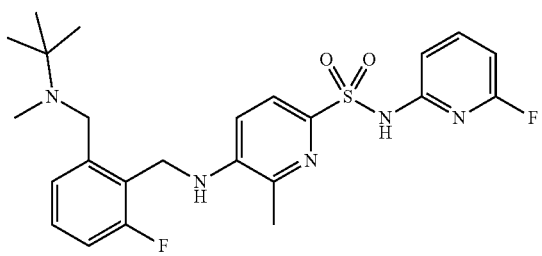 [SMILES: Cc1nc(S(=O)(=O)Nc2cccc(F)n2)ccc1NCc1c(F)cccc1CN(C)C(C)(C)C]

or a pharmaceutically acceptable salt thereof.

45. The compound of claim 1, which is 5((2-fluoro-6-((isopropyl(methyl)-amino)methyl)benzyl)amino)-6-methyl-N-(thiazol-4-yl)pyridine-2-sulfonamide, represented by the formula:

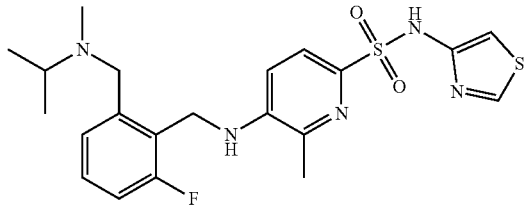 [SMILES: Cc1nc(S(=O)(=O)Nc2cscn2)ccc1NCc1c(F)cccc1CN(C)C(C)C]

as an individual stereoisomer, enantiomer or tautomer thereof or a mixture thereof; or a pharmaceutically acceptable salt or solvate thereof.

46. The compound of claim 1, which is 5-((2-fluoro-6-((isopropyl(methyl)-amino)methyl)benzyl)amino)-6-methyl-N-(thiazol-4-yl)pyridine-2-sulfonamide, represented by the formula:

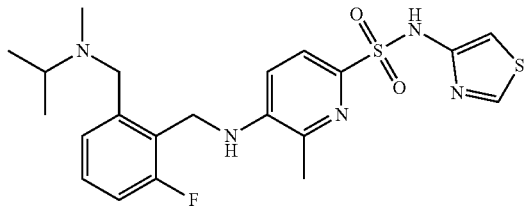 [SMILES: Cc1nc(S(=O)(=O)Nc2cscn2)ccc1NCc1c(F)cccc1CN(C)C(C)C]

or a pharmaceutically acceptable salt thereof.

47. The compound of claim 1, which is 5-((2-((azabicyclo[2.2.1]heptan-7-yl)methyl)-6-fluorobenzyl)amino)-3-fluoro-6-methyl-N-(thiazol-4-yl)pyridine-2-sulfonamide, represented by the formula:

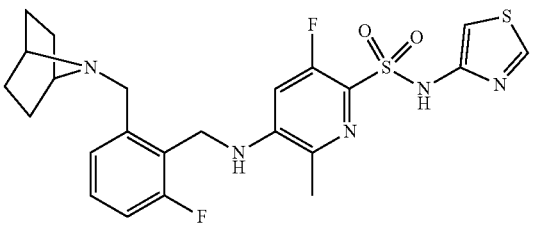 [SMILES: Cc1nc(S(=O)(=O)Nc2cscn2)c(F)cc1NCc1c(F)cccc1CN1C2CCC1CC2]

as an individual stereoisomer, enantiomer or tautomer thereof or a mixture thereof; or a pharmaceutically acceptable salt or solvate thereof.

48. The compound of claim 1, which is 5-((2-((azabicyclo[2.2.1]heptan-7-yl)(methyl)-6-fluorobenzyl)amino)-3-fluoro-6-methyl-N-(thiazol-4-yl)pyridine-2-sulfonamide, represented by the formula:

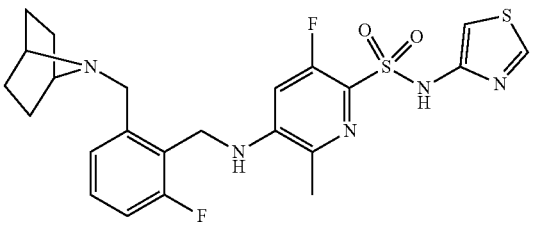 [SMILES: Cc1nc(S(=O)(=O)Nc2cscn2)c(F)cc1NCc1c(F)cccc1CN1C2CCC1CC2]

or a pharmaceutically acceptable salt thereof.

49. The compound of claim 1, which is 3-fluoro-5-((2-fluoro-6-((isopropyl(methyl)-amino)methyl(benzyl)amino)-6-methyl-N-(thiazol-4-yl)pyridine-2-sulfonamide, represented by the formula:

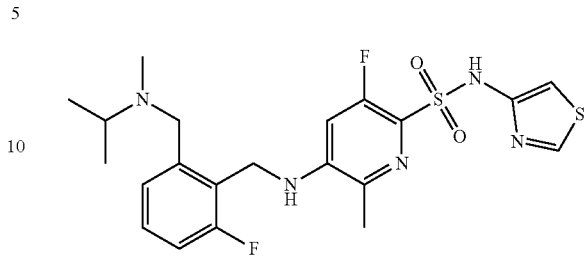

as an individual stereoisomer, enantiomer or tautomer thereof or a mixture thereof; or a pharmaceutically acceptable salt or solvate thereof.

50. The compound of claim 1, which is 3-fluoro-5-((2-fluoro-6-((isopropyl(methyl)-amino)methyl)benzyl)amino)-6-methyl-N-(thiazol-4-yl)pyridine-2-sulfonamide, represented by the formula:

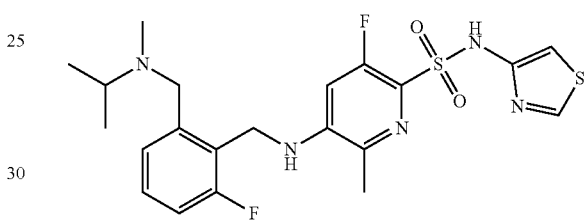

or a pharmaceutically acceptable salt thereof.

51. The compound of claim 1, which is 5-((2-(7-azabicyclo[2.2.1]heptan-7-yl)methy)-6-fluorobenzyl)amino)-N-(thiazol-4-yl)-6-(trifluoromethyl)pyridine-2-sulfonamide, represented by the formula:

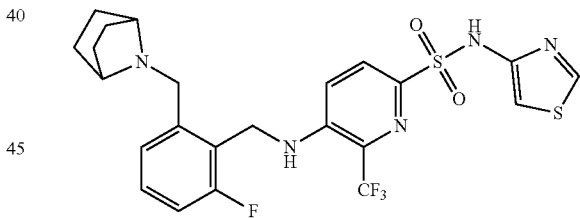

as an individual stereoisomer, enantiomer or tautomer thereof or a mixture thereof; or a pharmaceutically acceptable salt or solvate thereof.

52. The compound of claim 1, which is 5-((2-((7-azabicyclo[2.2.1heptan-7-yl)methy 1)-6fluorobenzyl)amino)-N-(thiazol-4-yl)-6-(trifluoromethyl)pyridine-2-sulfonamide, represented by the formula:

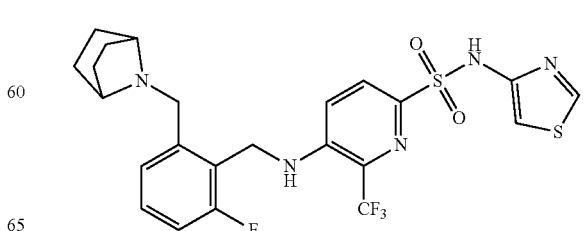

or a pharmaceutically acceptable salt thereof.

53. The compound of claim 1, which is 5-((2-(((tert-butyl)methyl)amino)-methyl)-6-fluorobenzyl)amino)-3-fluoro-6-methyl-N-(thiazol-4-yl)pyridine-2-sulfonamide, represented by the formula:

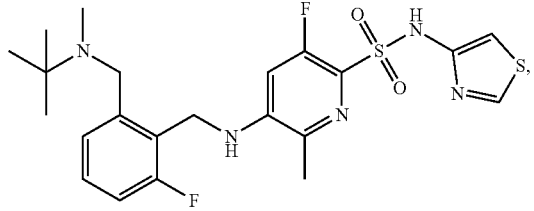 [SMILES: Cc1nc(S(=O)(=O)Nc2cscn2)c(F)cc1NCc1c(F)cccc1CN(C)C(C)(C)C]

as an individual stereoisomer, enantiomer or tautomer thereof or a mixture thereof; or a pharmaceutically acceptable salt or solvate thereof.

54. The compound of claim 1, which is 5((2-(((tert-butyl(methyl)amino)-methyl)-6-fluorobenzyl)amino)-3-fluoro-6-methyl-N-(thiazol-4-yl)pyridine-2-sulfonamide, represented by the formula:

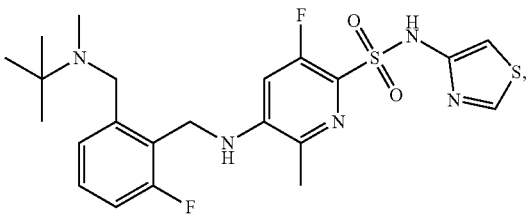 [SMILES: Cc1nc(S(=O)(=O)Nc2cscn2)c(F)cc1NCc1c(F)cccc1CN(C)C(C)(C)C]

or a pharmaceutically acceptable salt thereof.

* * * * *

UNITED STATES PATENT AND TRADEMARK OFFICE
CERTIFICATE OF CORRECTION

Page 1 of 3

PATENT NO. : 10,981,905 B2
APPLICATION NO. : 16/556055
DATED : April 20, 2021
INVENTOR(S) : Andrez et al.

It is certified that error appears in the above-identified patent and that said Letters Patent is hereby corrected as shown below:

In the Claims

Column 161, Line 16, Claim 3, delete "thereof; or" and insert -- thereof, or --, Column 161, Line 29, Claim 4, delete "thereof," and insert -- thereof; --, Column 162, Line 39, Claim 12, delete "thereof; or" and insert -- thereof, or --, Column 162, Line 53, Claim 13, delete "-chloro-" and insert -- -chloro-6- --, first occurrence, Column 162, Line 56, Claim 13, delete "-4yl)" and insert -- -4-yl) --, Column 162, Line 57, Claim 13, delete "6((2-" and insert -- 6-((2- --, Column 162, Line 63, Claim 13, delete "6((2-" and insert -- 6-((2- --, Column 162, Line 66, Claim 13, delete "6((2-" and insert -- 6-((2- --, Column 163, Line 10, Claim 15, delete "mixture thereof," and insert -- mixture thereof; --, Column 163, Line 25, Claim 16, delete "6((2-" and insert -- 6-((2- --, Column 163, Line 33, Claim 16, delete "a acceptable" and insert -- acceptable --, Column 164, Line 3, Claim 20, delete "5((2-" and insert -- 5-((2- --, Column 164, Line 13, Claim 20, delete "amino-" and insert -- amino)- --, Column 164, Line 16, Claim 20, delete ")pyri dine-" and insert -- )pyridine- --, Signed and Sealed this
Seventh Day of September, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,981,905 B2

Column 164, Line 20, Claim 20, delete "5((2-" and insert -- 5-((2- --,

Column 164, Line 23, Claim 20, delete "-(3-" and insert -- -((3- --,

Column 164, Line 26, Claim 20, delete "-(tert-" and insert -- -((tert- --,

Column 164, Line 30, Claim 20, delete "5((2-" and insert -- 5-((2- --,

Column 164, Line 30, Claim 20, delete "-(pyrrolidi 1" and insert -- -(pyrrolidin-1 --, Column 164, Line 39, Claim 20, delete "5((2-(tert-" and insert -- 5-((2-((tert- --, Column 164, Line 42, Claim 20, delete "5((2-" and insert -- 5-((2- --, Column 164, Line 43, Claim 20, delete "-4yl)" and insert -- -4-yl) --, Column 164, Line 45, Claim 20, delete "5((2-" and insert -- 5-((2- --, Column 164, Line 51, Claim 20, delete "5((2-" and insert -- 5-((2- --, Column 164, Line 51, Claim 20, delete "methy)" and insert -- methyl) --, Column 164, Line 57, Claim 20, delete "5((2-" and insert -- 5-((2- --, Column 164, Line 62, Claim 20, delete "5((2-" and insert -- 5-((2- --, Column 165, Line 4, Claim 20, delete "art" and insert -- an --, Column 165, Line 27, Claim 22, delete "5((2-" and insert -- 5-((2- --, Column 165, Line 28, Claim 22, delete "-methyl pyridine-" and insert -- -methylpyridine- --, Column 165, Line 29, Claim 22, delete "(methy)" and insert -- (methyl) --, Column 165, Line 56, Claim 24, delete "thereof," and insert -- thereof; --, Column 165, Line 56, Claim 24, delete "salt solvate" and insert -- salt or solvate --, Column 165, Line 59, Claim 25, delete "mixture thereof," and insert -- mixture thereof; --, Column 165, Line 65, Claim 26, delete "mixture thereof," and insert -- mixture thereof; --, Column 166, Line 13, Claim 27, delete "24" and insert -- 26 --, Column 166, Line 14, Claim 27, delete "5((2-" and insert -- 5-((2- --,

CERTIFICATE OF CORRECTION (continued)
U.S. Pat. No. 10,981,905 B2

Column 166, Line 16, Claim 27, delete "5((2-" and insert -- 5-((2- --,

Column 166, Line 17, Claim 27, delete "methylpyridine 2" and insert -- methylpyridine-2 --, Column 166, Line 22, Claim 27, delete "5((2-" and insert -- 5-((2- --, Column 166, Line 25, Claim 27, delete "5((2-" and insert -- 5-((2- --, Column 166, Line 25, Claim 27, delete "amino-" and insert -- amino)- --, Column 166, Line 47, Claim 28, delete "$R^{10})$" and insert -- $R^{10}$ --, Column 166, Line 53, Claim 29, delete "thereof" and insert -- thereof, --, Column 167, Line 65, Claim 41, delete "6((2-" and insert -- 6-((2- --, Column 168, Line 52, Claim 44, delete "-methyl pyri dine-" and insert -- -methylpyridine- --, Column 168, Line 53, Claim 44, delete "by," and insert -- by --, Column 169, Line 1, Claim 45, delete "5((2-" and insert -- 5-((2- --, Column 170, Line 34, Claim 51, delete "-(7-" and insert -- -((7- --, Column 170, Line 35, Claim 51, delete "methy)" and insert -- methyl) --, Column 170, Line 53, Claim 52, delete "[2.2.1" and insert -- [2.2.1] --, Column 170, Line 53, Claim 52, delete ")methy 1)" and insert -- )methyl) --, Column 171, Line 2, Claim 53, delete "methyl)amino)" and insert -- (methyl)amino) --, Column 172, Line 1, Claim 54, delete "5((2-" and insert -- 5-((2- --.